US009890176B2

(12) United States Patent
Dietrich et al.

(10) Patent No.: US 9,890,176 B2
(45) Date of Patent: Feb. 13, 2018

(54) MANNOSE DERIVATIVES FOR TREATING BACTERIAL INFECTIONS

(71) Applicant: Vertex Pharmaceuticals Incorporated, Boston, MA (US)

(72) Inventors: Evelyne Dietrich, Laval (CA); Carl Poisson, Montreal (CA); Michel Gallant, Pierrefonds (CA); Stephanie Lessard, St-Jean-sur-Richelieu (CA); Bingcan Liu, Montreal (CA); Sanjoy Kumar Das, Pierrefonds (CA); Yeeman Ramtohul, Pierrefonds (CA); Thumkunta Jagadeeswar Reddy, Pierrefonds (CA); Julien Martel, Montreal (CA); Frederic Vallee, Montreal (CA); Jean-Francois Lévesque, Laval (CA)

(73) Assignee: Vertex Pharmaceuticals Incorporated, Boston, MA (US)

( * ) Notice: Subject to any disclaimer, the term of this patent is extended or adjusted under 35 U.S.C. 154(b) by 302 days.

(21) Appl. No.: 14/206,303

(22) Filed: Mar. 12, 2014

(65) Prior Publication Data

US 2014/0274930 A1 Sep. 18, 2014

Related U.S. Application Data

(60) Provisional application No. 61/777,398, filed on Mar. 12, 2013.

(51) Int. Cl.

| C07H 15/203 | (2006.01) |
| C07H 15/20 | (2006.01) |
| C07H 15/207 | (2006.01) |
| C07H 15/22 | (2006.01) |
| C07D 493/10 | (2006.01) |
| C07H 15/18 | (2006.01) |

(52) U.S. Cl.
CPC .......... *C07D 493/10* (2013.01); *C07H 15/18* (2013.01); *C07H 15/20* (2013.01); *C07H 15/203* (2013.01); *C07H 15/207* (2013.01); *C07H 15/22* (2013.01)

(58) Field of Classification Search
None
See application file for complete search history.

(56) References Cited

U.S. PATENT DOCUMENTS

| 6,878,690 | B2 | 4/2005 | Cowden et al. |
| 2010/0015600 | A1 | 1/2010 | Barnich et al. |
| 2012/0231518 | A1* | 9/2012 | Cai ........................ A61K 45/00 435/180 |
| 2012/0309701 | A1 | 12/2012 | Janetka et al. |
| 2013/0261077 | A1 | 10/2013 | Bennani et al. |
| 2014/0107049 | A1 | 4/2014 | Bennani et al. |
| 2014/0243283 | A1 | 8/2014 | Ramtohul et al. |

FOREIGN PATENT DOCUMENTS

| EP | 0619317 A1 | 10/1994 |
| EP | 1800134 B1 | 11/2008 |
| WO | 98/31697 A1 | 7/1998 |
| WO | 2004/091499 A2 | 10/2004 |
| WO | 2005/089733 A2 | 9/2005 |
| WO | 2006/077364 A1 | 7/2006 |
| WO | 2006/077365 A1 | 7/2006 |
| WO | 2006/077366 A1 | 7/2006 |
| WO | 2006/077367 A1 | 7/2006 |
| WO | 2006/135667 A1 | 12/2006 |
| WO | 2007/095124 A2 | 8/2007 |
| WO | 2011/050323 A1 | 4/2011 |
| WO | 2011/073112 A2 | 6/2011 |
| WO | 2012/109263 A1 | 8/2012 |
| WO | 2012/125576 A1 | 9/2012 |
| WO | 2012/164074 A1 | 12/2012 |
| WO | 20121/63478 A1 | 12/2012 |
| WO | 2013/134415 A1 | 9/2013 |
| WO | 2014/055474 A1 | 4/2014 |
| WO | 2014/100158 A1 | 6/2014 |

OTHER PUBLICATIONS

Zissis et al., Journal of the American Chemical Society, 1957, 79, pp. 2593-2597.*
Alzeer, J., and Vasella, A., Oligosaccharide analogs of polysaccharides. Part2. Regioselective deprotection of monosaccharide-derived monomers and dimers, Helvetica Chimica Acta, 1995, vol. 78, pp. 177-193.
Cendret, V., et al., "Design and synthesis of a "click" high-mannose oligosaccharide mimic emulating Man8 binding affinity towards Con A", Chem Commun (Camb) 48(31) : 3733-5 2012.
Dondoni, A., et al., Synthesis of all carbon-linked glycoside clusters round benzene scaffold via Sonogashira-Heck-Cassar cross-coupling of iodobenzenes with ethynyl C-glycosides, Synlett, 2002, No. 11, pp. 1850-1854.
Espinosa, J.F., et al., "Conformational Differences Between C-and O-Glycosides: The alpha-C-Mannobiose/alpha-O-Mannobiose Case", Chemistry A European Journal, vol. 5, No. 2, 1999, pp. 1-32 (XP002716254).
Gottschaldt, M., et al., "Silver(I) complexes based on novel tripodal thioglycosides: synthesis, structure and antimicrobial activity", Tetrahedron, vol. 62, Issue 48, Nov. 27, 2006, pp. 11073-11080.
Han, J., et al., "Characterization of flavonoids in the traditional Chinese herbal medicine-Huangqin by liquid chromatography coupled with electrospray ionization mass spectrometry", J. Chromatography B., 2007, vol. 848, No. 2, pp. 355-362.
Han, Z., et al., "Structure-Based Drug Design and Optimization of Mannoside Bacterial FimH Antagonists", Journal of Medicinal Chemistry, American Chemical Society, vol. 53, No. 12, 2010, pp. 4779-4792 (XP002620405).
International Search Report for PCT/US2014/024411 dated Jan. 14, 2015.

(Continued)

*Primary Examiner* — Traviss C McIntosh, III
(74) *Attorney, Agent, or Firm* — Banner & Witcoff, Ltd.

(57) ABSTRACT

The present invention relates to compounds useful for the treatment or prevention of bacteria infections. These compounds have formula I:

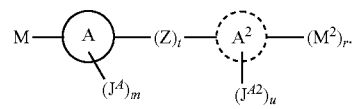

The invention also provides processes for making the compounds described herein. Furthermore, the present invention provides a composition comprising the compounds described herein, and a pharmaceutically acceptable carrier, adjuvant, or vehicle. The present invention also provides methods of treating or preventing bacteria infection in a subject, comprising administering to the subject an effective amount of the compound or the composition described herein.

22 Claims, No Drawings

(56) References Cited

OTHER PUBLICATIONS

Klein, T., et al., "FimH Antagonists for the Oral Treatment of Urinary Tract Infections: From Design and Synthesis to in Vitro and in Vivo Evaluation", Journal of Medicinal Chemistry, American Chemical Society, vol. 53, No. 24, 2010, pp. 8627-8864 (XP002620404).

Lövyova, Z., et al., "Stereoselective preparation of four 3-C-mannosylated d-and l-glucals from a single starting compound", Tetrahedron, vol. 67, No. 27-28, 2011, pp. 4967-4979 (XP055087761).

Mikkelsen, L.M., et al., "Application of the anomeric samarium route for the convergent synthesis of the C-linked trisaccharide alpha-D-Man-(1-3)-[alpha-D-Man-(1-6)]-D-Man and the disaccharides alpha-D-Man-(1-3)-D-Man and alpha-D-Man-(1-6)-D-Man", J Org Chem 67(18) : 6297-308 2002.

Mikkelsen, L.M., et al., "Conformation of Glycomimetics in the Free and Protein-Bound State: Structural and Binding Features of the C-glycosyl Analogue of the Core Trisaccharide alpha-D-Man-(1-3)-[alpha-D-Man-(1-6)]-D-Man", Journal of the American Chemical Society, vol. 124, No. 50, 2002, pp. 14940-14951 (XP055087758).

Pang, L., et al., "FimH Antagonists: Structure-Activity and Structure-Property Relationships of Biphenyl [alpha]-D-Mannopyranosides", Chemmedchem, vol. 7, No. 8, 2012, pp. 1404-1422 (XP055087656).

Papadopoulos A., et al., "Diazo Transfer and Click Chemistry in the Solid Phase Syntheses of Lysine-Based Glycodendrimers as Antagonists against *Escherichia coli* FimH", Mol Pharm 9(3) : 394-403 2012.

Perez-Balderas, F., et al., "Click Multivalent Homogeneous Neoglycoconjugates—Synthesis and Evaluation of Their Binding Affinities", European Journal of Organic Chemistry 2009(15) : 2441-2453 2009.

Schmidt, R.R. and Beyerbach, A., AN1992:592188, Liebigs Annalen der Chemie, 1992, (9), 983-986.

Touaibia M., et al., "Mannosylated G(0) Dendrimers with Nanomolar Affinities to*Escherichia coli* FimH", ChemMedChem 2(8) : 1190-1201 2007.

Zhang P., et al., "Synthesis and biological activities of novel isoxazoline-linked pseudodisaccharide derivatives", Carbohydr Res 351( ) : 7-16 2012.

Office Action issued for corresponding Chinese Patent Application No. 201480024363.7, dated Mar. 31, 2017.

\* cited by examiner

MANNOSE DERIVATIVES FOR TREATING BACTERIAL INFECTIONS

CROSS REFERENCE TO RELATED APPLICATIONS

This present invention claims the benefit, under 35 U.S.C. §119, of U.S. Provisional Application No. 61/777,398, filed Mar. 12, 2013; the entire contents of which are incorporated herein by reference.

BACKGROUND OF THE INVENTION

Inflammatory bowel disease (IBD) is a complex chronic inflammatory disorder, with the two more common forms being ulcerative colitis (UC) and Crohn's disease (CD). IBD is a multifactorial disease that results from a combination of predisposing genetic factors, environmental triggers, dysbiosis of the gastrointestinal microbiota and an inappropriate inflammatory response (Man et al., 2011, Nat Rev Gastroenterol Hepatol, March, 8(3):152-68).

Several studies on fecal and mucosa-associated bacterial communities have shown that the microbiota of patients with Crohn's disease (CD) differ from those of healthy controls, as well as those of patients with ulcerative colitis (UC). Although the reported changes are not always consistent, numbers of *Escherichia coli* are generally increased, whereas Firmicutes are scarcer in CD patients (Peterson et al., 2008, Cell Host Microbe, 3: 17-27; Frank et al., 2007, Proc. Natl. Acad. Sci., 104:13780-13785). Whether these changes are causative factors or consequences of inflammation, it remains controversial. To date, several pathogens have been proposed as causative agents. In particular, adherent-invasive *E. coli* (AIEC) has been reported to be more prevalent in CD patients than in controls in several countries (United Kingdom, France and the USA) (Darfeuille-Michaud et al., 2004, Gastroenterology, 127:412-421; Martinez-Medina et al., 2009, Inflamm Bowel Dis., 15:872-882). AIEC strains have been isolated from ileal lesions in ~35% of CD patients compared to ~5% of healthy subjects. One of the features of AIEC is their ability to adhere and invade epithelial cells. It is known from various models that the binding of adhesins expressed on the bacterial cell surface to defined glycosylated receptors on the host tissue surface is considered to be an initial and critical step in pathogenesis, then opening a new avenue for therapy such as blocking the interaction between type 1 pili and CEACAM6, a known host receptor for FimH (Barnich et al., 2007, J. Clin. Invest., 117:1566-1574; Carvalho et al., 2009, *JEM*, vol. 206, no. 10, 2179-2189). Therefore, inhibition of adhesion, and consequently intracellular replication of AIEC in epithelial cells, may prevent establishment of a sub-mucosal infection leading to mucosal inflammation and epithelial barrier disruption.

It has also been demonstrated recently that FimH antagonists are potentially effective in treating urinary tract infections (J. Med. Chem. 2010, 53, 8627-8641).

SUMMARY OF THE INVENTION

The present invention provides compounds useful for the treatment or prevention of bacteria infections, such as urinary tract infection (UTI) and inflammatory bowel diseases (IBD).

The compounds of the present invention are represented by the following structure of Formula Ia, or a pharmaceutically acceptable salt thereof:

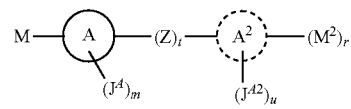

wherein M, $M^2$, Ring A, Ring $A^2$, Z, $J^A$, $J^B$, m, r, t, and u are described herein.

The compounds of the invention have modified mannose moieties which have an unexpected increase in stability compared to compounds with unmodified mannose moieties.

The present invention also provides processes for making the compounds described herein. Furthermore, the present invention provides a composition comprising the compounds described herein, and a pharmaceutically acceptable carrier, adjuvant, or vehicle. The present invention also provides methods of treating or preventing bacteria infection in a subject, comprising administering to the subject an effective amount of the compound or the composition described herein.

DETAILED DESCRIPTION OF THE INVENTION

The present invention relates to compounds useful for the treatment or prevention of bacteria infections, such as urinary tract infection (UTI) and inflammatory bowel diseases (IBD).

In one embodiment, the compounds of the present invention are represented by the following structure of Formula I:

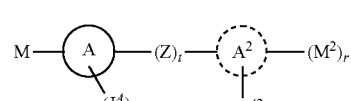

or a pharmaceutically acceptable salt thereof, wherein each M and $M^2$ is independently

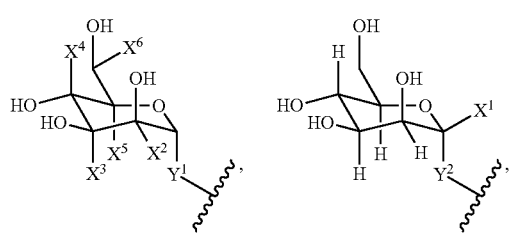

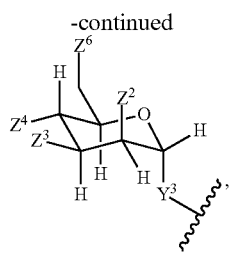

or M together with Ring A form a spiro-fused tricyclic ring as shown below:

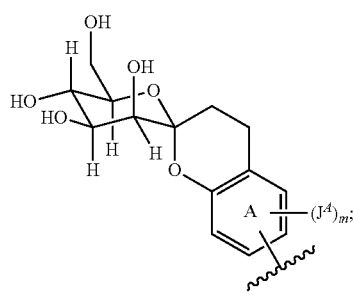

or $M^2$ together with Ring $A^2$ form a spiro-fused tricyclic ring as shown below:

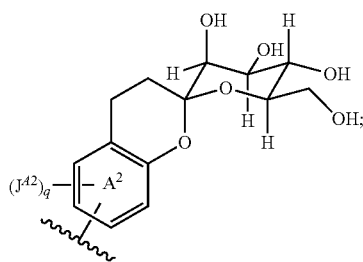

wherein:
$Y^1$ is —O—, —O($C_1$-$C_4$ aliphatic)-, —O(halo$C_1$-$C_4$ aliphatic)-, —S—, —S($C_1$-$C_4$ aliphatic)-, —S(O)$_p$—, —S(O)$_p$($C_1$-$C_4$ aliphatic)-, or —($C_1$-$C_6$)aliphatic;
$Y^2$ is —O($C_1$-$C_4$ aliphatic)-, —S($C_1$-$C_4$ aliphatic)-, —SO$_2$ ($C_1$-$C_4$ aliphatic)-, or —($C_1$-$C_6$) aliphatic;
$Y^3$ is —O—, —O($C_1$-$C_4$ aliphatic)-, —O(halo$C_1$-$C_4$ aliphatic)-, —S—, —S($C_1$-$C_4$ aliphatic)-, —S(O)$_p$—, —S(O)$_p$($C_1$-$C_4$ aliphatic)-, or —($C_1$-$C_6$)aliphatic;
each $Z^2$, $Z^3$, $Z^4$, and $Z^6$ is independently OH or F; provided that at least one of $Z^2$, $Z^3$, $Z^4$, and $Z^6$ is F;
$X^1$ is —$U^1$—$V^1$; $X^1$ is optionally substituted with 1-4 occurrences of halo;
$U^1$ is —(CH$_2$)$_q$— or —C(O)—;
$V^1$ is a $C_1$-$C_{10}$ aliphatic wherein up to four methylene units can be optionally replaced with —O—, —NR—, —S—, —C(O)—, —S(O)—, —S(O)$_2$—, or P(O);
$X^2$ is H, $C_1$-$C_{10}$ aliphatic, —$U^2$—$V^2$, or —$U^2$—$V^2$-Q;
$U^2$ is —(CH$_2$)$_q$— or —C(O)—;
$V^2$ is a $C_1$-$C_{10}$ aliphatic wherein up to four methylene units can be optionally replaced with —O—, —NR$^2$—, —S—, —C(O)—, —S(O)—, —S(O)$_2$—, or P(O);
Q is a 3-8 membered saturated, partially unsaturated, or aromatic ring having 0-4 heteroatoms selected from oxygen, nitrogen, or sulfur;

wherein $X^2$ is optionally substituted with 1-4 occurrences of halo, CN, NO$_2$, or $C_1$-$C_{10}$aliphatic wherein up to three methylene units of the $C_1$-$C_{10}$aliphatic can be optionally replaced with —NR—, —O—, —S—, —C(O)—, or —S(O)—, or —S(O)$_2$;
each $X^3$, $X^4$, $X^5$, and $X^6$ is independently H or $C_{1-3}$alkyl;
provided that only one of $X^2$, $X^3$, $X^4$, $X^5$, and $X^6$ is not H;
Ring A is $C_3$-$C_{10}$ cycloalkyl, 3-12 membered heterocyclyl, $C_{6-10}$ aryl, or 5-14 membered heteroaryl; wherein the heterocyclyl or heteroaryl independently has 1-6 heteroatoms selected from oxygen, nitrogen, or sulfur;
Ring $A^2$ is optionally absent, $C_3$-$C_{10}$ cycloalkyl, 3-12 membered heterocyclyl, $C_{6-10}$ aryl, or 5-14 membered heteroaryl;
Z is —CH=CH—, —C≡C—, or Ring B;
Ring B is $C_3$-$C_{10}$ cycloalkyl, 3-12 membered heterocyclyl, $C_{6-10}$ aryl, or 5-14 membered heteroaryl; wherein said heterocyclyl or heterocyclyl independently has 1-6 heteroatoms selected from oxygen, nitrogen, or sulfur;
each $J^A$, $J^{A2}$, and $J^B$ is independently halogen, CN, NO$_2$, oxo, $C_{3-8}$ cycloalkyl, 3-8 membered heterocyclyl, $C_{6-10}$ aryl, 5-10 membered heteroaryl, ($C_{6-10}$ aryl)-($C_1$-$C_6$alkyl)-, (5-10 membered heteroaryl)-($C_1$-$C_6$alkyl)-, ($C_{3-8}$ cycloalkyl)-($C_1$-$C_6$alkyl)-, (3-8 membered heterocyclyl)-($C_1$-$C_6$alkyl)-, or a $C_1$-$C_{12}$ aliphatic; wherein up to four methylene units of the $C_1$-$C_{12}$ aliphatic or up to three methylene units of the $C_1$-$C_6$alkyl can be optionally replaced with —NR—, —O—, —S—, —C(O)—, —S(O)—, —S(O)$_2$—, or P(O); each $J^A$, $J^{A2}$, and $J^B$ is independently and optionally substituted with 1-5 occurrences of halo, CN, NO$_2$, or $C_1$-$C_{10}$aliphatic wherein up to three methylene units of the $C_1$-$C_{10}$aliphatic can be optionally replaced with —NR—, —O—, —S—, —C(O)—, or —S(O)—, or —S(O)$_2$—;
R and $R^2$ are each independently H, $C_1$-$C_6$ aliphatic, or $C_{3-6}$cycloalkyl;
each m, n, and u is independently 0, 1, 2, 3, or 4;
each t and r is independently 0 or 1; and
each p and q is independently 1 or 2.

In one embodiment, the compounds of the present invention are represented by the following structure of Formula Ia, or a pharmaceutically acceptable salt thereof:

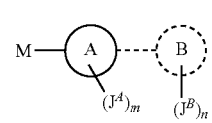

Ia or a pharmaceutically acceptable salt thereof, wherein M is

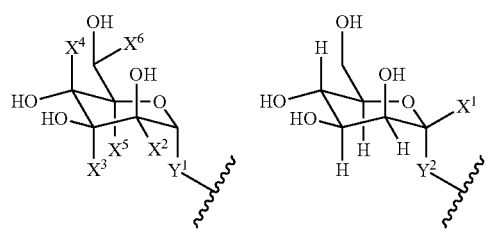

-continued

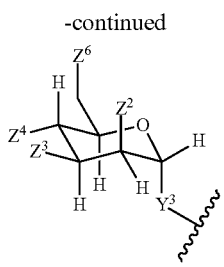

or M and one occurrence of $J^A$, together with Ring A, form a spiro-fused tricyclic ring optionally bonded to Ring B as shown in Formula D:

Formula D

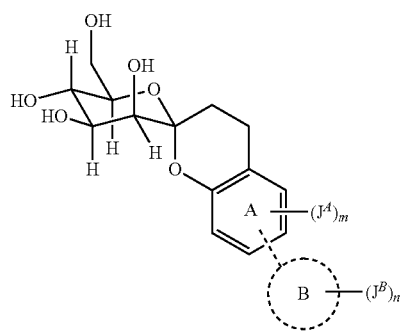

wherein:
$Y^1$ is —O—, —O($C_1$-$C_4$alkyl)-, —S—, —S($C_1$-$C_4$alkyl)-, —S(O)$_p$—, —S(O)$_p$($C_1$-$C_4$alkyl)-, or —($C_1$-$C_6$)alkyl;

$Y^2$ is —O($C_1$-$C_4$alkyl)-, —S($C_1$-$C_4$alkyl)-, —SO$_2$($C_1$-$C_4$alkyl)-, or —($C_1$-$C_6$)alkyl;

$Y^3$ is —O—, —O($C_1$-$C_4$alkyl)-, —S—, —S($C_1$-$C_4$alkyl)-, —S(O)$_p$—, —S(O)$_p$($C_1$-$C_4$alkyl)-, or —($C_1$-$C_6$)alkyl;

wherein the alkyl groups in $Y^1$, $Y^2$, and $Y^3$ are each optionally and independently substituted with 1-4 halo;

each $Z^2$, $Z^3$, $Z^4$, and $Z^6$ is independently OH or F; provided that at least one of $Z^2$, $Z^3$, $Z^4$, and $Z^6$ is F;

each $X^3$, $X^4$, and $X^6$ is H or $C_{1-3}$alkyl;

$X^1$ is —$U^1$—$V^1$; $X^1$ is optionally substituted with 1-4 occurrences of halo;

$U^1$ is —(CH$_2$)$_q$— or —C(O)—;

$V^1$ is a $C_1$-$C_{10}$ aliphatic wherein up to four methylene units can be optionally replaced with —O—, —NR$^2$—, —S—, —C(O)—, —S(O)—, —S(O)$_2$—, or P(O);

$X^2$ is H or —$U^2$—$V^2$; $X^2$ is optionally substituted with 1-4 occurrences of halo;

$U^2$ is —(CH$_2$)$_q$— or —C(O)—;

$V^2$ is a $C_1$-$C_{10}$ aliphatic wherein up to four methylene units can be optionally replaced with —O—, —NR$^2$—, —S—, —C(O)—, —S(O)—, —S(O)$_2$—, or P(O);

$X^5$ is H or $C_{1-3}$alkyl;

provided that at least one of $X^2$, $X^3$, $X^4$, $X^5$, and $X^6$ is not H; and when $X^2$ is other than H, then $X^3$, $X^4$, and $X^6$ are all H;

Ring A is $C_3$-$C_8$ cycloalkyl, 3-8 membered heterocyclyl, $C_{6-10}$ aryl, or 5-10 membered heteroaryl; Ring A is optionally bonded to Ring B;

Ring B is absent or is $C_3$-$C_8$ cycloalkyl, 3-8 membered heterocyclyl, $C_{6-10}$ aryl, ($C_{6-10}$ aryl)-($C_1$-$C_6$alkyl)-, or 5-10 membered heteroaryl;

each $J^A$ and $J^B$ is independently halogen, CN, NO$_2$, $C_{3-8}$ cycloalkyl, 3-8 membered heterocyclyl, $C_{6-10}$ aryl, 5-10 membered heteroaryl, ($C_{6-10}$ aryl)-($C_1$-$C_6$alkyl)-, (5-10 membered heteroaryl)-($C_1$-$C_6$alkyl)-, or a $C_1$-$C_{12}$ aliphatic wherein up to four methylene units of the $C_1$-$C_{12}$ aliphatic can be optionally replaced with —NR, —O, —S—, —C(O)—, —S(O)—, —SO$_2$—, or P(O); each $J^A$ and $J^B$ is independently and optionally substituted with 1-5 occurrences of halo, CN, or NO$_2$;

R and $R^2$ are each independently H, $C_1$-$C_6$ aliphatic, or $C_{3-6}$cycloalkyl;

$R^1$ is H or $C_{1-3}$alkyl;

each m, n, and q is independently 0, 1, 2, 3, or 4; and each p and q is independently 1 or 2.

It shall be understood that when a ring or a bond is drawn with a dotted line, this means that the ring or bond is optionally present. It shall also be understood that rings described as $C_3$-$C_{10}$ cycloalkyl, 3-12 membered heterocyclyl, $C_{6-10}$ aryl, or 5-14 membered heteroaryl include monocyclic, bicyclic, and tricyclic rings. For example, a $C_3$-$C_{10}$ cycloalkyl includes saturated or partially unsaturated monocyclic $C_{3-8}$cycloalkyl and saturated or partially unsaturated $C_{8-12}$ cycloalkyl bicyclic rings. A 3-12 membered heterocyclyl includes monocyclic saturated or partially unsaturated 3-8 membered heterocyclyl rings having 1-4 heteroatoms selected from oxygen, nitrogen, or sulfur; bicyclic saturated or partially unsaturated 8-12 membered heterocyclyl rings having 1-6 heteroatoms selected from oxygen, nitrogen, or sulfur; and tricyclic saturated or partially unsaturated 10-14 membered heterocyclyl rings having 1-6 heteroatoms selected from oxygen, nitrogen, or sulfur. A $C_{6-10}$ aryl includes phenyl and naphthyl. A 5-14 membered heteroaryl includes a monocyclic 5-6 membered heteroaryl having 1-4 heteroatoms selected from oxygen, nitrogen, or sulfur; a bicyclic 8-10 membered heteroaryl having 1-6 heteroatoms selected from oxygen, nitrogen, or sulfur; and a tricyclic 10-14 membered heteroaryl having 1-6 heteroatoms selected from oxygen, nitrogen, or sulfur. A multicyclic ring is considered aryl or heteroaryl if at least one ring is aromatic.

In some embodiments, Ring $A^2$ is absent; r and q are 0; t is 1; and Z is Ring B as shown in Formula Ia:

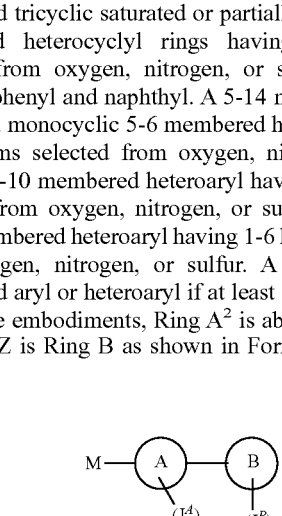

In some embodiments, the compound is not one of the following:

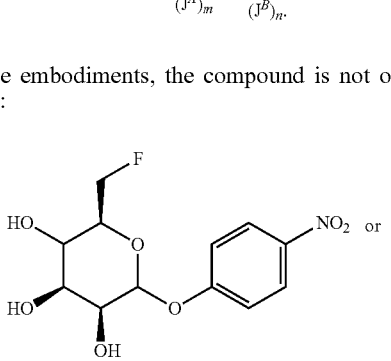

-continued

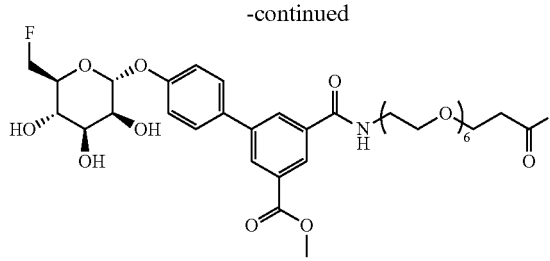

In some embodiments, Ring A is $C_{6-10}$ aryl or 5-10 membered heteroaryl. In some embodiments, Ring A is phenyl or naphthyl. In some embodiments, Ring A is phenyl. In some embodiments, Ring A is bonded to Ring B; and Ring B is $C_{6-10}$ aryl or 5-10 membered heteroaryl. In some embodiments, Ring B is phenyl.

In some embodiments, Ring A is bonded to Ring B as represented in Formula II:

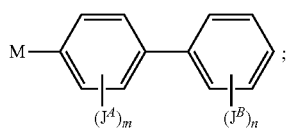

Formula II wherein Ring M, $J^A$, $J^B$, m, and n are as defined herein.

In some embodiments, $J^A$ is halo, $haloC_{1-4}$aliphatic, $C_{1-4}$aliphatic, $-O(C_{1-4}$aliphatic), and $J^B$ is $NO_2$, $C(O)N(R)_2$, $C(O)OR$, or $CONH-(CH_2)_2-O-(CH_2)_2-O-(CH_2)_2-NH_2$.

In some embodiments, $Y^1$, $Y^2$, and $Y^3$ are $-O-$. In some embodiments, $Y^1$, $Y^2$ or $Y^3$ is $C_{1-6}$aliphatic, wherein the aliphatic groups in $Y^1$, $Y^2$, and $Y^3$ are each optionally and independently substituted with 1-4 halo. In some embodiments, the In other embodiments, M is

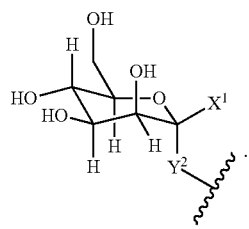

In yet other embodiments, $Y^2$ is O. In some embodiments, $X^1$ is $C_{1-3}$alkyl. In certain embodiments, $X^1$ is methyl.

Another embodiment provides a compound of formula A:

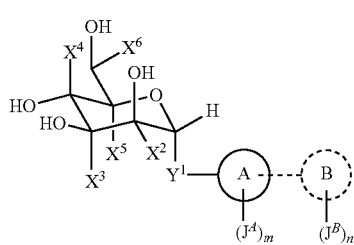

Formula A wherein
$Y^1$ is $-O-$, $-O(C_1-C_4 alkyl)-$, $-S-$, $-S(C_1-C_4 alkyl)-$, $-S(O)_p-$, $-SO_p(C_1-C_4 alkyl)-$, or $-(C_1-C_6)aliphatic$;
$X^2$ is H, $C_1-C_{10}$ aliphatic, $-U^2-V^2$, or $-U^2-V^2-Q$;
$U^2$ is $-(CH_2)_q-$ or $-C(O)-$;
$V^2$ is a $C_1-C_{10}$ aliphatic wherein up to four methylene units can be optionally replaced with $-O-$, $-NR^2-$, $-S-$, $-C(O)-$, $-S(O)-$, $-S(O)_2-$, or $P(O)$;
Q is a 3-8 membered saturated, partially unsaturated, or aromatic ring having 0-4 heteroatoms selected from oxygen, nitrogen, or sulfur;
wherein $X^2$ is optionally substituted with 1-4 occurrences of halo, CN, $NO_2$, or $C_1-C_{10}$aliphatic wherein up to three methylene units of the $C_1-C_{10}$aliphatic can be optionally replaced with $-NR-$, $-O-$, $-S-$, $-C(O)-$, or $-S(O)-$, or $-S(O)_2-$;
$R^2$ is H, $C_1-C_6$ aliphatic, or $C_{3-6}$cycloalkyl;
each $X^3$, $X^4$, and $X^6$ is independently H or $C_{1-3}$alkyl;
$X^5$ is H;
provided that only one of $X^2$, $X^3$, $X^4$, $X^5$, and $X^6$ is not H;
Ring A is $C_3-C_{10}$ cycloalkyl, 3-12 membered heterocyclyl, $C_{6-10}$ aryl, or 5-14 membered heteroaryl; wherein the heterocyclyl or heteroaryl independently has 1-6 heteroatoms selected from oxygen, nitrogen, or sulfur; Ring A is optionally bonded to Ring B;
Ring B is absent, $C_3-C_{10}$ cycloalkyl, 3-12 membered heterocyclyl, $C_{6-10}$ aryl, or 5-14 membered heteroaryl; wherein said heterocyclyl or heterocyclyl independently has 1-6 heteroatoms selected from oxygen, nitrogen, or sulfur;
each $J^A$ and $J^B$ is independently halogen, CN, $NO_2$, $C_{3-8}$ cycloalkyl, 3-8 membered heterocyclyl, $C_{6-10}$ aryl, 5-10 membered heteroaryl, $(C_{6-10}$ aryl)-$(C_1-C_6 alkyl)$-, (5-10 membered heteroaryl)-$(C_1-C_6 alkyl)$-, or a $C_1-C_{12}$ aliphatic wherein up to four methylene units of the $C_1-C_{10}$ aliphatic can be optionally replaced with $-NR$, $-O-$, $-S-$, $-C(O)-$, $-S(O)-$; $-SO_2-$, or $P(O)$; each $J^A$ and $J^B$ is independently and optionally substituted with 1-5 occurrences of halo, CN, or $NO_2$;
R is H, $C_1-C_6$ aliphatic, $C_{3-6}$cycloalkyl, C(O)OH, C(O)O$(C_{1-4} alkyl)$, or $C(O)(C_{1-4} alkyl)$;
each m and n is independently 0, 1, 2, 3, or 4; and
each p and q is independently 1 or 2.
In some embodiments,
$Y^1$ is $-O-$, $-O(C_1-C_4 alkyl)-$, $-S-$, $-S(C_1-C_4 alkyl)-$, $-S(O)_p-$, $-S(O)_p(C_1-C_4 alkyl)-$, or $-(C_1-C_6)alkyl$;
$X^2$ is H or $-U^2-V^2$; $X^2$ is optionally substituted with 1-4 occurrences of halo;
$U^2$ is $-(CH_2)_q-$ or $-C(O)-$;
$V^2$ is a $C_1-C_{10}$ aliphatic wherein up to four methylene units can be optionally replaced with $-O-$, $-NR^2-$, $-S-$, $-C(O)-$, $-S(O)-$, $-S(O)_2-$, or $P(O)$;
$R^2$ is H, $C_1-C_6$ aliphatic, or $C_{3-6}$cycloalkyl;
each $X^3$, $X^4$, and $X^6$ is independently H or $C_{1-3}$alkyl;
$X^5$ is H;
provided that at least one of $X^2$, $X^3$, $X^4$, $X^5$, and $X^6$ is not H; and when $X^2$ is other than H, then $X^3$, $X^4$, and $X^6$ are all H;
Ring A is $C_3-C_8$ cycloalkyl, 3-8 membered heterocyclyl, $C_{6-10}$ aryl, or 5-10 membered heteroaryl; wherein the heterocyclyl or heteroaryl independently has 1-6 heteroatoms selected from oxygen, nitrogen, or sulfur; Ring A is optionally bonded to Ring B;
Ring B is $C_3-C_8$ cycloalkyl, 3-8 membered heterocyclyl, $C_{6-10}$ aryl, $(C_{6-10}$ aryl)-$(C_1-C_6 alkyl)$-, or 5-10 membered heteroaryl; wherein said heterocyclyl or heterocyclyl independently has 1-6 heteroatoms selected from oxygen, nitrogen, or sulfur;

each $J^A$ and $J^B$ is independently halogen, CN, $NO_2$, $C_{3-8}$ cycloalkyl, 3-8 membered heterocyclyl, $C_{6-10}$ aryl, 5-10 membered heteroaryl, $(C_{6-10}$ aryl)-$(C_1$-$C_6$alkyl)-, (5-10 membered heteroaryl)-$(C_1$-$C_6$alkyl)-, or a $C_1$-$C_{12}$ aliphatic wherein up to four methylene units of the $C_1$-$C_{10}$ aliphatic can be optionally replaced with —NR, —O—, —S—, —C(O)—, —S(O)—, —$SO_2$—, or P(O); each $J^A$ and $J^B$ is independently and optionally substituted with 1-5 occurrences of halo, CN, or $NO_2$;

R is H, $C_1$-$C_6$ aliphatic, $C_{3-6}$cycloalkyl, C(O)OH, C(O)O ($C_{1-4}$alkyl), or C(O)($C_{1-4}$alkyl);

each m, n, and q is independently 0, 1, 2, 3, or 4;

each p and q is independently 1 or 2.

According to another embodiment, $X^2$ is H, $C_1$-$C_{10}$ aliphatic, —$U^2$—$V^2$, or —$U^2$—$V^2$-Q;

$U^2$ is —$(CH_2)_q$— or —C(O)—;

$V^2$ is a $C_1$-$C_{10}$ aliphatic wherein up to four methylene units can be optionally replaced with —O—, —NR—, —S—, —C(O)—, —S(O)—, —$S(O)_2$—, or P(O);

Q is a 3-8 membered saturated, partially unsaturated, or aromatic ring having 0-4 heteroatoms selected from oxygen, nitrogen, or sulfur;

wherein $X^2$ is optionally substituted with 1-4 occurrences of halo, CN, $NO_2$, or $C_1$-$C_{10}$aliphatic wherein up to three methylene units of the $C_1$-$C_{10}$aliphatic can be optionally replaced with —NR—, —O—, —S—, —C(O)—, or —S(O)—, or —$S(O)_2$—;

wherein each $R^3$ and $R^5$ is independently H, $C_{1-3}$alkyl, or —($C_{1-3}$alkyl)-(phenyl).

In some embodiments, $Y^2$ is —O—.

In some embodiments, $X^2$ is H; $C_{1-6}$alkyl; or —$U^1$—$V^1$; wherein $U^2$ is —$(CH_2)_q$— and $V^2$ is —$OR^3$—; —$OC(O)N(R^2)_2$—, —$N(R^2)_2$, —$N(R^2)C(O)R^3$, —NHC(O)$OR^5$, —NHC(O) $NHR^2$, —$NHSO_2R^3$, —$NHSO_2NHR^2$, —C(O)$OR^3$, C(O) $N(R^2)_2$, —$SO_2R^3$, —$S(O)R^3$, —$SO_2NHR^3$, —$SR^3$, —$P(O)(OR^3)_2$, —$OP(O)(OR^3)_2$;

or $U^2$ is C(O) and $V^2$ is —$OR^3$ or $N(R^2)_2$;

wherein each $R^3$ and $R^5$ is independently H, $C_{1-3}$alkyl, or —($C_{1-3}$alkyl)-(phenyl).

In some embodiments, $U^1$ is —$(CH_2)_q$—. In other embodiments, $U^2$ is —$(CH_2)_q$—. In some embodiments q is 1. In other embodiments, $X^2$ is H, $C_{1-6}$alkyl or —$(CH_2)_q$ $OR^3$. In yet other embodiments, $X^2$ is methyl, $CH_2OH$, $CH_2N_3$, $CH_2NH_2$, $CH_2OCH_2CH_2OCH_2Ph$, $CH_2OCH_2CH_2OH$,

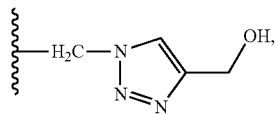 [SMILES: *Cn1cc(CO)nn1]

$CH_2NHC(O)CH_3$, or $CH_2OCH_2Ph$. In yet other embodiments, $X^2$ is methyl, $CH_2OH$, or $CH_2OCH_2Ph$. In some embodiments, $X^2$ is $C_{1-4}$alkyl. In other embodiments, $X^2$ is methyl.

In some embodiments, $X^6$ is $C_{1-6}$alkyl. In other embodiments, $X^6$ is methyl, ethyl, or isopropyl. In some embodiments, $X^3$ is methyl. In some embodiments, one of $X^2$, $X^3$, $X^4$, $X^5$, and $X^6$ is —$U^1$—$V^1$ and the other five of $X^2$, $X^3$, $X^4$, $X^5$, and $X^6$ are H.

In some embodiments, $J^A$ and $J^B$ are each independently halo, CN, $C_{1-10}$aliphatic, C(O)($C_{3-6}$cycloalkyl), or C(O)(3-8 membered heterocyclyl having 1-2 heteroatoms selected from O, NH, N($C_{1-4}$alkyl), or S); wherein up to three methylene units of the $C_{1-10}$aliphatic group are optionally replaced with O, NH, N($C_{1-4}$alkyl), S, C(O), S(O), or $S(O)_2$; each $J^A$ and $J^B$ is independently and optionally substituted with 1-3 occurrences of halo.

In some embodiments, $J^A$ is chloro, fluoro, CN, $CH_3$, $CH_2CH_3$, $CH(CH_3)_2$, $OCH_3$, or $OCF_3$. In other embodiments, $J^B$ is halo, CN, $OCH_3$, C(O)NH($CH_3$), C(O)N($CH_3)_2$, $NO_2$, C(O)OH, C(O)$OCH_3$, C(O)NH($CH_2)_2$—O —$(CH_2)_2$—O—$(CH_2)_2NH_2$, C(O)NH($CH_2)_2OCH_3$, C(O) NH(cyclopropyl), C(O)NH($CH_2)_2$(4-methylpiperazinyl), C(O)NHCH($CH_2OH$)CH(OH)$CH_3$, C(O)NHC($CH_2OH)_3$, C(O)NHC($CH_2OH)_2CH_3$, C(O)NHCH($CH_2OH)_2$, C(O)NH $(CH_2)_2$(morpholinyl), C(O)NHCH$_2$(tetrahydropyranyl), C(O)NH(tetrahydropyranyl), C(O)NHCH$_2$(4-BOCpiperidinyl), C(O)NH($CH_2)_2N(CH_3)_2$, C(O)(4-methylpiperazinyl), C(O)NHCH($CH_2OH$)COOH, C(O)pyrrolidinyl, N($CH_2CH_2OH$)C($CH_2OH)_3$, C(O)NHCH($CH_2OH$)CH (OH)$CH_3$, $S(O)_2NH_2$, $S(O)_2NC(CH_3)_3$, O(tetrahydropyranyl), wherein said tetrahydropyranyl is optionally substituted with $C_{1-4}$alkyl, fluoro, OH, or $CH_2OH$. In some embodiments, the tetrahydropyranyl is a sugar molecule, such as a glycosyl or mannosyl group.

Another embodiment provides a compound of formula B:

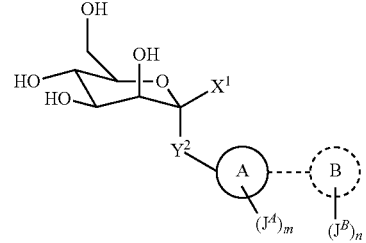

Formula B wherein $Y^2$ is —O($C_1$-$C_4$alkyl)-, —S($C_1$-$C_4$alkyl)-, —S(O)—, —$SO_2$($C_1$-$C_4$alkyl)-, or —($C_1$-$C_6$)alkyl;

$X^1$ is —$U^1$—$V^1$; $X^1$ is optionally substituted with 1-4 occurrences of halo;

$U^1$ is —$(CH_2)_q$— or —C(O)—;

$V^1$ is a $C_1$-$C_{10}$ aliphatic wherein up to four methylene units can be optionally replaced with —O—, —$NR^2$—, —S—, —C(O)—, —S(O)—, —$S(O)_2$—, or P(O);

Ring A is $C_3$-$C_{10}$ cycloalkyl, 3-12 membered heterocyclyl, $C_{6-10}$ aryl, or 5-14 membered heteroaryl; wherein the heterocyclyl or heteroaryl independently has 1-6 heteroatoms selected from oxygen, nitrogen, or sulfur; Ring A is optionally bonded to Ring B;

Ring B is absent, $C_3$-$C_{10}$ cycloalkyl, 3-12 membered heterocyclyl, $C_{6-10}$ aryl, or 5-14 membered heteroaryl; wherein said heterocyclyl or heterocyclyl independently has 1-6 heteroatoms selected from oxygen, nitrogen, or sulfur;

each $J^A$ and $J^B$ is independently halogen, CN, $NO_2$, $C_{3-8}$ cycloalkyl, 3-8 membered heterocyclyl, $C_{6-10}$ aryl, 5-10 membered heteroaryl, ($C_{6-10}$ aryl)-($C_1$-$C_6$alkyl)-, (5-10 membered heteroaryl)-($C_1$-$C_6$alkyl)-, or a $C_1$-$C_{12}$ aliphatic wherein up to four methylene units of the $C_1$-$C_{10}$ aliphatic can be optionally replaced with —NR, —O—, —S—, —C(O)—, —S(O)—, —$SO_2$—, or P(O); each $J^A$ and $J^B$ is independently and optionally substituted with 1-5 occurrences of halo, CN, or $NO_2$;

R is H, $C_1$-$C_6$ aliphatic, $C_{3-6}$cycloalkyl, C(O)OH, C(O)O ($C_{1-4}$alkyl), or C(O)($C_{1-4}$alkyl);

each m and n is independently 0, 1, 2, 3, or 4;

each q is independently 1 or 2.

In some embodiments, $Y^2$ is —O($C_1$-$C_4$alkyl)-, —S($C_1$-$C_4$alkyl)-, —S(O)—, —$SO_2$($C_1$-$C_4$alkyl)-, or —($C_1$-$C_6$)alkyl;

$X^1$ is —$U^1$—$V^1$; $X^1$ is optionally substituted with 1-4 occurrences of halo;

$U^1$ is —$(CH_2)_q$— or —C(O)—;

$V^1$ is a $C_1$-$C_{10}$ aliphatic wherein up to four methylene units can be optionally replaced with —O—, —$NR^2$—, —S—, —C(O)—, —S(O)—, —$S(O)_2$—, or P(O);

Ring A is $C_3$-$C_8$ cycloalkyl, 3-8 membered heterocyclyl, $C_{6-10}$ aryl, or 5-10 membered heteroaryl; Ring A is optionally bonded to Ring B;

Ring B is $C_3$-$C_8$ cycloalkyl, 3-8 membered heterocyclyl, $C_{6-10}$ aryl, ($C_{6-10}$ aryl)-($C_1$-$C_6$alkyl)-, or 5-10 membered heteroaryl;

each $J^A$ and $J^B$ is independently halogen, CN, $NO_2$, $C_{3-8}$ cycloalkyl, 3-8 membered heterocyclyl, $C_{6-10}$ aryl, 5-10 membered heteroaryl, ($C_{6-10}$ aryl)-($C_1$-$C_6$alkyl)-, (5-10 membered heteroaryl)-($C_1$-$C_6$alkyl)-, or a $C_1$-$C_{12}$ aliphatic wherein up to four methylene units of the $C_1$-$C_{10}$ aliphatic can be optionally replaced with —NR, —O—, —S—, —C(O)—, —S(O)—, —$SO_2$—, or P(O); each $J^A$ and $J^B$ is independently and optionally substituted with 1-5 occurrences of halo, CN, or $NO_2$;

R is H, $C_1$-$C_6$ aliphatic, $C_{3-6}$cycloalkyl, C(O)OH, C(O)O ($C_{1-4}$alkyl), or C(O)($C_{1-4}$alkyl);

each m and n is independently 0, 1, 2, 3, or 4.

In some embodiments, $X^1$ is $C_{1-6}$alkyl; or —$U^1$—$V^1$; wherein $U^2$ is —$(CH_2)_q$— and $V^2$ is —$OR^3$—; —OC(O)N$(R^2)_2$—, —N$(R^2)_2$, —N$(R^2)$C(O)$R^3$, —NHC(O)$OR^5$, —NHC(O)NH$R^2$, —NHS$O_2R^3$, —NHS$O_2$NH$R^2$, —C(O)$OR^3$, C(O)N$(R^2)_2$, —S$O_2R^3$, —S(O)$R^3$, —S$O_2$NH$R^3$, —S$R^3$, —P(O)$(OR^3)_2$, —OP(O)$(OR^3)_2$; or $U^2$ is C(O) and $V^2$ is —$OR^3$ or N$(R^2)_2$;

R is H, $C_1$-$C_6$ aliphatic, $C_{3-6}$cycloalkyl, C(O)OH, C(O)O ($C_{1-4}$alkyl), or C(O)($C_{1-4}$alkyl);

$R^2$ is H, $C_1$-$C_6$ aliphatic, or $C_{3-6}$cycloalkyl; and $R^3$ is H, $C_{1-3}$alkyl, or —($C_{1-3}$alkyl)-(phenyl).

In other embodiments, $X^1$ is $C_{1-6}$alkyl; or —$U^1$—$V^1$; wherein $U^2$ is —$(CH_2)_q$— and $V^2$ is —$OR^3$—; —OC(O)N$(R^2)_2$—, —N$(R^2)_2$, —N$(R^2)$C(O)$R^3$, —NHC(O)$OR^5$, —NHC(O)NH$R^2$, —NHS$O_2R^3$, —NHS$O_2$NH$R^2$, —C(O)$OR^3$, C(O)N$(R^2)_2$, —S$O_2R^3$, —S(O)$R^3$, —S$O_2$NH$R^3$, —S$R^3$, —P(O)$(OR^3)_2$, —OP(O)$(OR^3)_2$; or $U^2$ is C(O) and $V^2$ is —$OR^3$ or N$(R^2)_2$;

R is H, $C_1$-$C_6$ aliphatic, $C_{3-6}$cycloalkyl, C(O)OH, C(O)O ($C_{1-4}$alkyl), or C(O)($C_{1-4}$alkyl);

$R^2$ is H, $C_1$-$C_6$ aliphatic, or $C_{3-6}$cycloalkyl; and $R^3$ is H, $C_{1-3}$alkyl, or —($C_{1-3}$alkyl)-(phenyl).

In some embodiments, $X^1$ is $C_{1-6}$alkyl. In some embodiments, $X^1$ is methyl. In yet other embodiments, $Y^2$ is —O($C_1$-$C_4$alkyl)-. IN other embodiments, $Y^2$ is —O(halo$C_1$-$C_4$ alkyl)-. In some embodiments, $Y^2$ is —O($C_1$-$C_4$alkyl)-, Ring A is phenyl, Ring B is absent, and $J^A$ is C(O)NH($C_{1-4}$alkyl).

Another embodiment provides a compound of formula C:

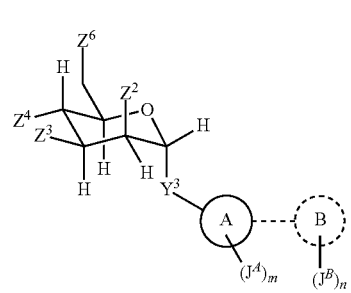

Formula C wherein each $Z^1$, $Z^2$, $Z^3$, and $Z^4$ is independently H or F; provided that at least one of $Z^1$, $Z^2$, $Z^3$, and $Z^4$ is F;

$Y^3$ is —O—, —O($C_1$-$C_4$alkyl)-, —S—, —S($C_1$-$C_4$alkyl)-, —$S(O)_p$—, —$SO_p$ ($C_1$-$C_4$alkyl)-, or —($C_1$-$C_6$)alkyl;

Ring A is $C_3$-$C_{10}$ cycloalkyl, 3-12 membered heterocyclyl, $C_{6-10}$ aryl, or 5-14 membered heteroaryl; wherein the heterocyclyl or heteroaryl independently has 1-6 heteroatoms selected from oxygen, nitrogen, or sulfur; Ring A is optionally bonded to Ring B;

Ring B is absent, $C_3$-$C_{10}$ cycloalkyl, 3-12 membered heterocyclyl, $C_{6-10}$ aryl, or 5-14 membered heteroaryl; wherein said heterocyclyl or heterocyclyl independently has 1-6 heteroatoms selected from oxygen, nitrogen, or sulfur;

each $J^A$ and $J^B$ is independently halogen, CN, $NO_2$, $C_{3-8}$ cycloalkyl, 3-8 membered heterocyclyl, $C_{6-10}$ aryl, 5-10 membered heteroaryl, ($C_{6-10}$ aryl)-($C_1$-$C_6$alkyl)-, (5-10 membered heteroaryl)-($C_1$-$C_6$alkyl)-, or a $C_1$-$C_{12}$ aliphatic wherein up to four methylene units of the $C_1$-$C_{10}$ aliphatic can be optionally replaced with NR, —O—, —S—, —C(O)—, —S(O)—, —$SO_2$—, or P(O); each $J^A$ and $J^B$ is independently and optionally substituted with 1-5 occurrences of halo, CN, or $NO_2$;

R is H, $C_1$-$C_6$ aliphatic, $C_{3-6}$cycloalkyl, C(O)OH, C(O)O ($C_{1-4}$alkyl), or C(O)($C_{1-4}$alkyl);

each m and n is independently 0, 1, 2, 3, or 4;

p is 1 or 2.

In another embodiment, each $Z^1$, $Z^2$, $Z^3$, and $Z^4$ is independently H or F; provided that at least one of $Z^1$, $Z^2$, $Z^3$, and $Z^4$ is F;

$Y^3$ is —O—, —O($C_1$-$C_4$alkyl)-, —S—, —S($C_1$-$C_4$alkyl)-, —$S(O)_p$—, —$SO_p$ ($C_1$-$C_4$alkyl)-, or —($C_1$-$C_6$)alkyl;

Ring A is $C_3$-$C_8$ cycloalkyl, 3-8 membered heterocyclyl, $C_{6-10}$ aryl, or 5-10 membered heteroaryl; Ring A is optionally bonded to Ring B;

Ring B is $C_3$-$C_8$ cycloalkyl, 3-8 membered heterocyclyl, $C_{6-10}$ aryl, ($C_{6-10}$ aryl)-($C_1$-$C_6$alkyl)-, or 5-10 membered heteroaryl;

each $J^A$ and $J^B$ is independently halogen, CN, $NO_2$, $C_{3-8}$ cycloalkyl, 3-8 membered heterocyclyl, $C_{6-10}$ aryl, 5-10 membered heteroaryl, ($C_{6-10}$ aryl)-($C_1$-$C_6$alkyl)-, (5-10 membered heteroaryl)-($C_1$-$C_6$alkyl)-, or a $C_1$-$C_{12}$ aliphatic wherein up to four methylene units of the $C_1$-$C_{10}$ aliphatic can be optionally replaced with —NR, —O—, —S—, —C(O)—, —S(O)—, —$SO_2$—, or P(O); each $J^A$ and $J^B$ is independently and optionally substituted with 1-5 occurrences of halo, CN, or $NO_2$;

R is H, $C_1$-$C_6$ aliphatic, $C_{3-6}$cycloalkyl, C(O)OH, C(O)O($C_{1-4}$alkyl), or C(O)($C_{1-4}$alkyl);

each m and n is independently 0, 1, 2, 3, or 4.

In some embodiments, only one of $Z^1$, $Z^2$, $Z^3$, and $Z^4$ is F and the other three are H. In some embodiments, $Z^1$ is F. In some embodiments, $Z^2$ is F. In some embodiments, $Z^3$ is F. In some embodiments, $Z^4$ is F.

In some embodiments, $Y^3$ is —O—.

According to another embodiment, Ring A is phenyl. In some embodiments, $J^A$ is halo, $C_{1-4}$aliphatic, or —O($C_{1-4}$aliphatic); wherein said $C_{1-4}$aliphatic, or —O($C_{1-4}$aliphatic) is optionally substituted with 1-4 halo.

According to another embodiment, Ring B is a 5-10 membered heteroaryl.

Another embodiment provides a compound of formula D:

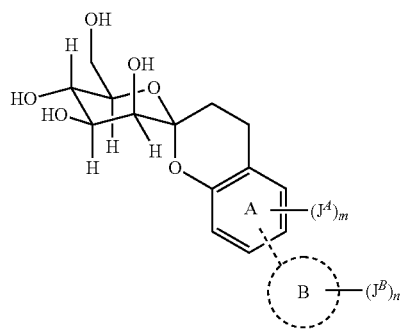

Formula D wherein

Ring B is absent, $C_3$-$C_{10}$ cycloalkyl, 3-12 membered heterocyclyl, $C_{6-10}$ aryl, or 5-14 membered heteroaryl; wherein said heterocyclyl or heterocyclyl independently has 1-6 heteroatoms selected from oxygen, nitrogen, or sulfur;

each $J^A$ and $J^B$ is independently halogen, CN, $NO_2$, $C_{3-8}$ cycloalkyl, 3-8 membered heterocyclyl, $C_{6-10}$ aryl, 5-10 membered heteroaryl, ($C_{6-10}$ aryl)-($C_1$-$C_6$alkyl)-, (5-10 membered heteroaryl)-($C_1$-$C_6$alkyl)-, or a $C_1$-$C_{12}$ aliphatic wherein up to four methylene units of the $C_1$-$C_{10}$ aliphatic can be optionally replaced with —NR, —O—, —S—, —C(O)—, —S(O)—, —$SO_2$—, or P(O); each $J^A$ and $J^B$ is independently and optionally substituted with 1-5 occurrences of halo, CN, or $NO_2$;

R is H, $C_1$-$C_6$ aliphatic, $C_{3-6}$cycloalkyl, C(O)OH, C(O)O($C_{1-4}$alkyl), or C(O)($C_{1-4}$alkyl);

each m and n is independently 0, 1, 2, 3, or 4.

According to another embodiment,

Ring B is $C_3$-$C_8$ cycloalkyl, 3-8 membered heterocyclyl, $C_{6-10}$ aryl, ($C_{6-10}$ aryl)-($C_1$-$C_6$alkyl)-, or 5-10 membered heteroaryl;

each $J^A$ and $J^B$ is independently halogen, CN, $NO_2$, $C_{3-8}$ cycloalkyl, 3-8 membered heterocyclyl, $C_{6-10}$ aryl, 5-10 membered heteroaryl, ($C_{6-10}$ aryl)-($C_1$-$C_6$alkyl)-, (5-10 membered heteroaryl)-($C_1$-$C_6$alkyl)-, or a $C_1$-$C_{12}$ aliphatic wherein up to four methylene units of the $C_1$-$C_{10}$ aliphatic can be optionally replaced with —NR, —O—, —S—, —C(O)—, —S(O)—, —$SO_2$—, or P(O); each $J^A$ and $J^B$ is independently and optionally substituted with 1-5 occurrences of halo, CN, or $NO_2$;

R is H, $C_1$-$C_6$ aliphatic, $C_{3-6}$cycloalkyl, C(O)OH, C(O)O($C_{1-4}$alkyl), or C(O)($C_{1-4}$alkyl);

each m and n is independently 0, 1, 2, 3, or 4.

In some embodiments, Ring B is phenyl and $J^B$ is C(O)$NHCH_3$, $OCH_3$, or $NO_2$.

Another embodiment provides a compound as represented by formula III:

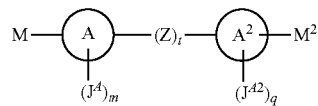

In some embodiments, M and $M^2$ are the same. In other embodiments, M and $M^2$ are different.

In some embodiments, M is

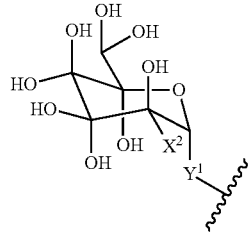

In other embodiments, $M^2$ is

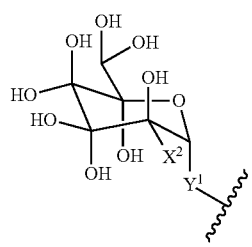

In yet other embodiments, $M^2$ together with Ring $A^2$ form

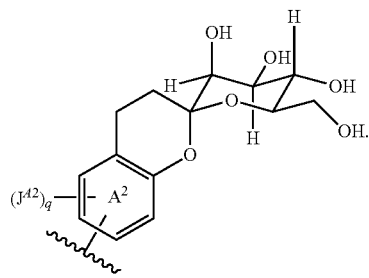

In some embodiments, $Y^1$ is 0 and $X^2$ is methyl. In other embodiments, t is 1 and Z is phenyl or pyridyl. In yet other embodiments, t is 0.

Another embodiment provides a compound as represented by formula E:

Formula E

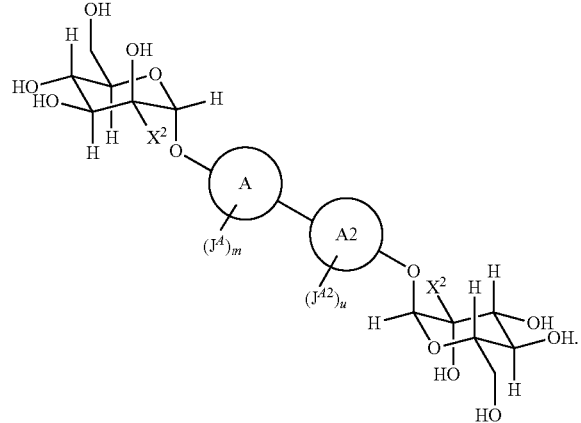

In some embodiments, Ring A and Ring $A^2$ are phenyl. In other embodiments, $X^2$ is $C_{1-4}$alkyl. In some embodiments, $X^2$ is methyl.

In some embodiments, $J^A$ and $J^{A2}$ are each independently CN, halo, $C_{1-6}$alkyl, wherein up to one methylene unit of said $C_{1-6}$alkyl is optionally replaced with O, S, NH, N($C_{1-6}$ alkyl), C(O), S(O), or S(O)$_2$ substituted with 1-3 occurrences of halo. In other embodiments, $J^A$ and $J^{A2}$ are each independently CN, methyl, ethyl, isopropyl, fluoro, chloro, OCH$_3$, or OCF$_3$.

Another embodiment provides a compound as represented by formula F:

Formula F

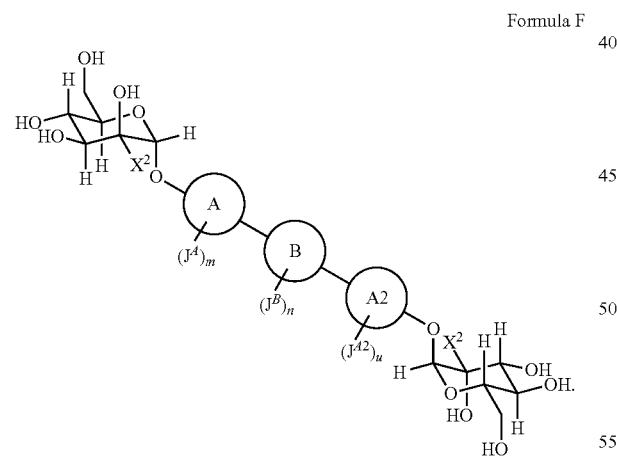

In some embodiments, Ring A and Ring $A^2$ are phenyl. In some embodiments, Ring B is $C_{3-6}$cycloalkyl, phenyl, or pyridyl. In some embodiments, $J^A$ and $J^{A2}$ are each independently CN, halo, $C_{1-6}$alkyl, wherein up to one methylene unit of said $C_{1-6}$alkyl is optionally replaced with O, S, NH, N($C_{1-6}$alkyl), C(O), S(O), or S(O)$_2$ substituted with 1-3 occurrences of halo. In other embodiments, $J^A$ and $J^{A2}$ are each independently methyl; m is 1; and u is 1. In yet other embodiments, $J^B$ is phenyl optionally substituted with methyl and

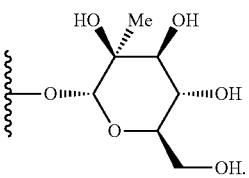 [SMILES: *O[C@H]1O[C@H](CO)[C@@H](O)[C@H](O)[C@]1(C)O]

Another embodiment provides a compound as represented by formula G:

Formula G

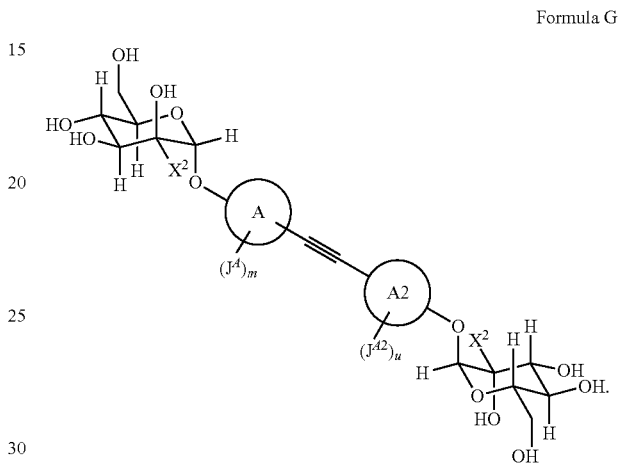

In some embodiments, $X^2$ is methyl, Ring A and Ring $A^2$ are phenyl; $J^A$ and $J^B$ are each independently methyl; m is 1; and n is 1.

Another embodiment provides a compound as represented by formula H:

Formula H

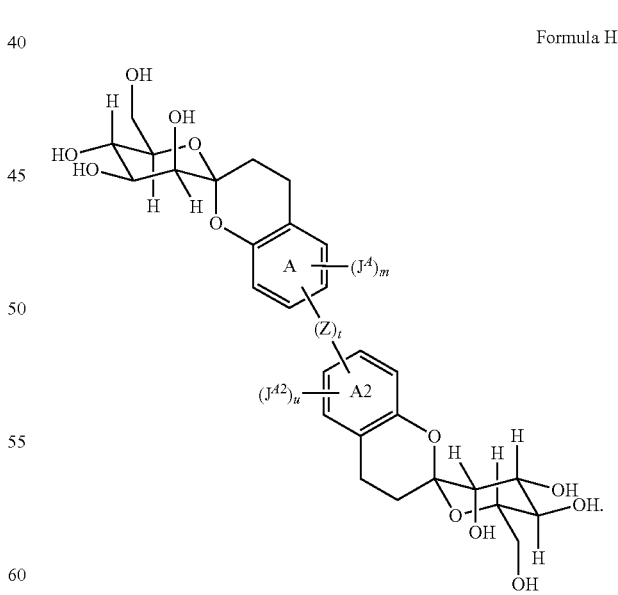

In some embodiments, t is 1 and Z is phenyl or pyridyl. In other embodiments, t is 0. In yet another embodiment, Ring A and Ring $A^2$ are phenyl.

Another embodiment provides a compound is selected from one or more of the following tables:

TABLE 1
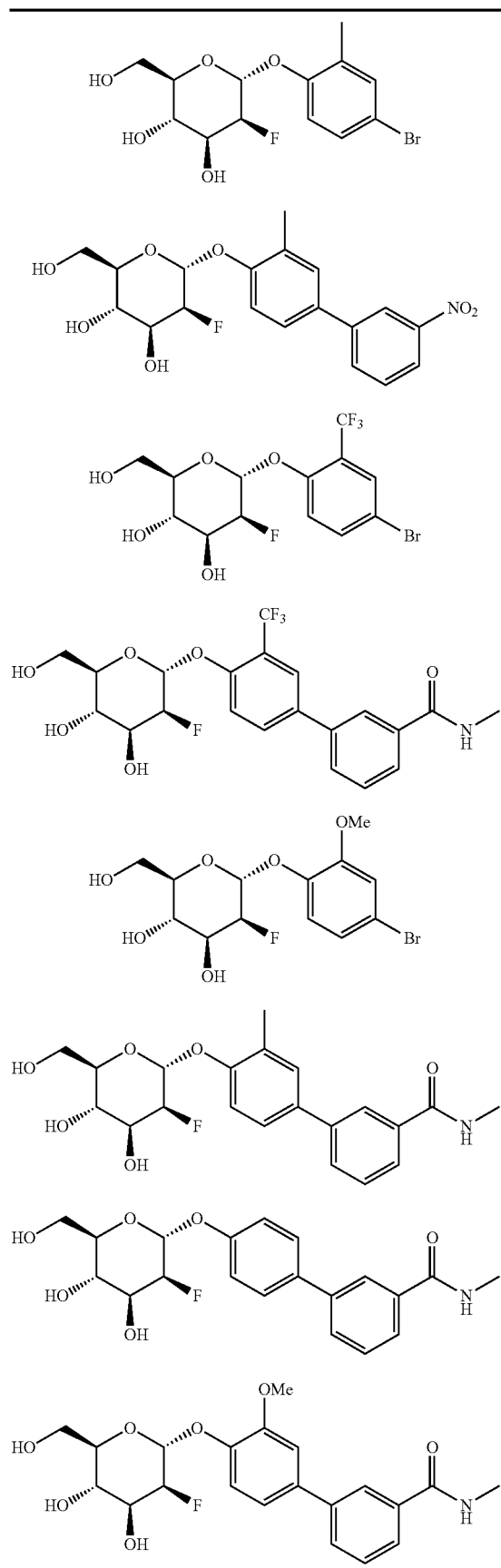
TABLE 1-continued
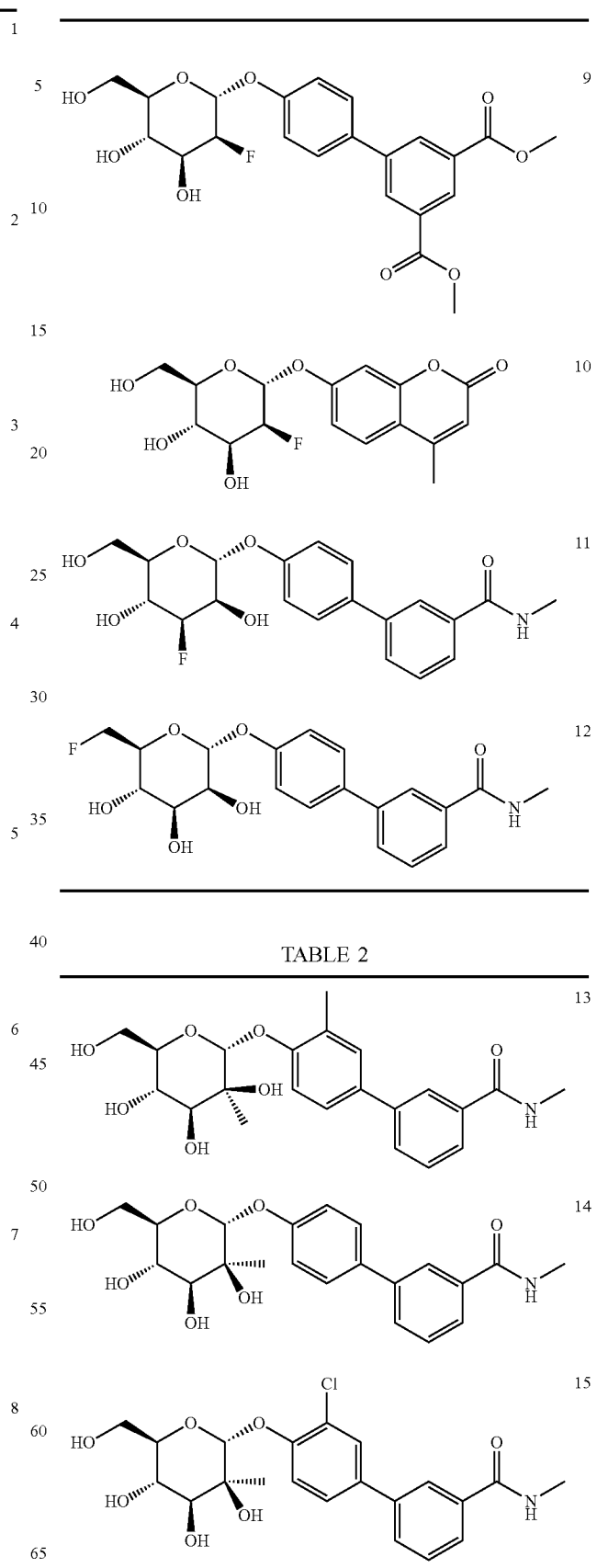
TABLE 2

TABLE 2-continued
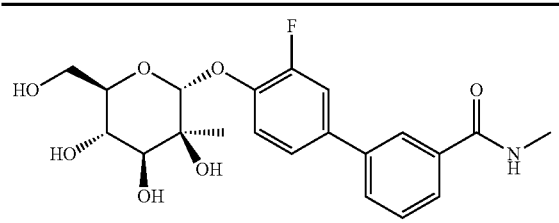 16
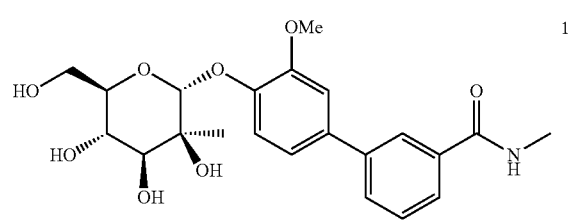 17
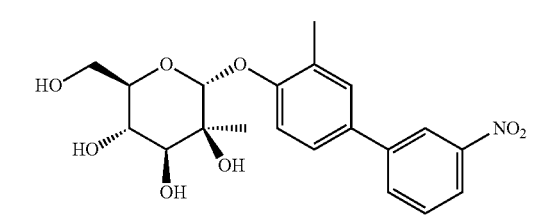 [SMILES: Cc1cc(-c2cccc([N+](=O)[O-])c2)ccc1O[C@H]1O[C@H](CO)[C@@H](O)[C@H](O)[C@]1(C)O] 18
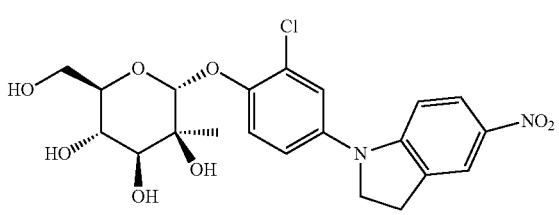 [SMILES: C[C@@]1(O)[C@@H](Oc2ccc(N3CCc4cc([N+](=O)[O-])ccc43)cc2Cl)O[C@H](CO)[C@@H](O)[C@@H]1O] 19
 20
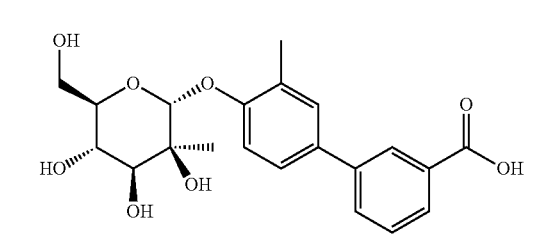 [SMILES: Cc1cc(-c2cccc(C(=O)O)c2)ccc1O[C@H]1O[C@H](CO)[C@@H](O)[C@H](O)[C@]1(C)O] 21
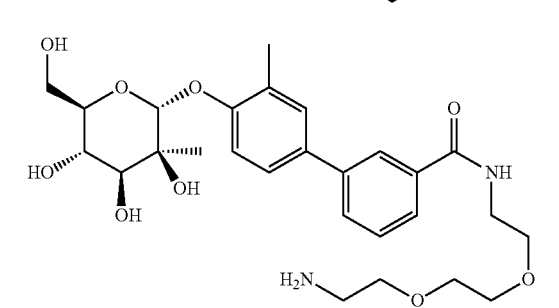 22
TABLE 2-continued
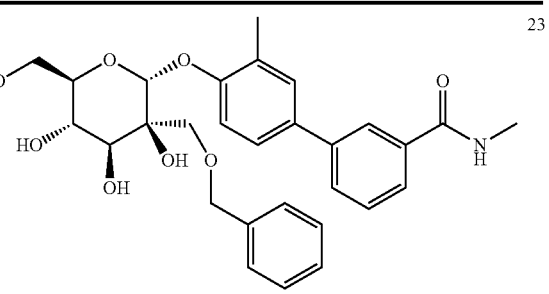 23
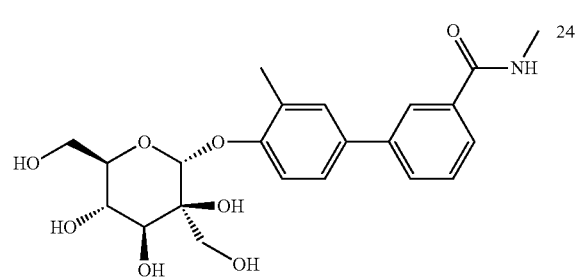 24
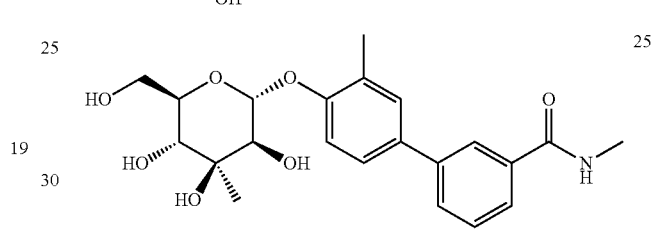 25
 26
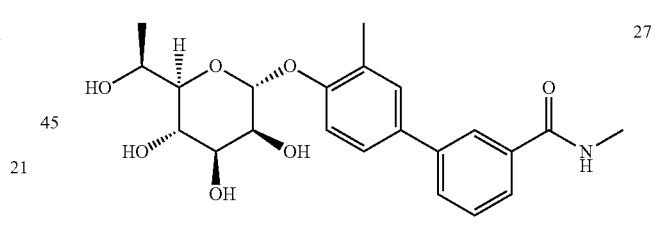 27
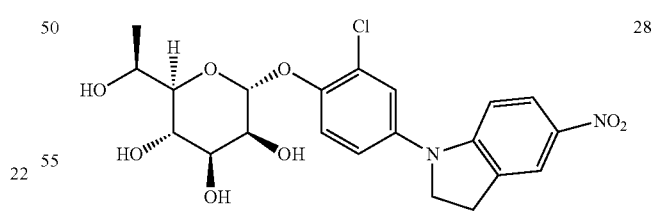 28
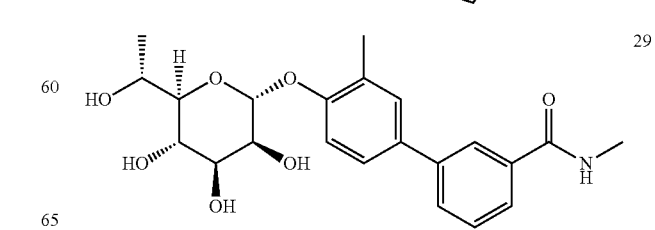 29

TABLE 2-continued
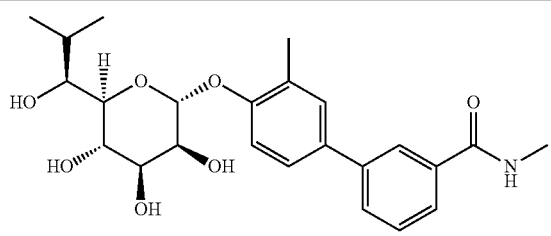 [SMILES: CNC(=O)c1cccc(-c2ccc(O[C@H]3O[C@H]([C@@H](O)C(C)C)[C@@H](O)[C@H](O)[C@@H]3O)c(C)c2)c1]
30
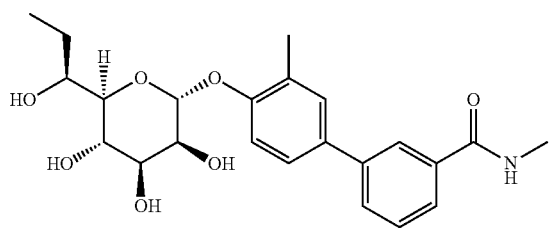 [SMILES: CC[C@H](O)[C@H]1O[C@H](Oc2ccc(-c3cccc(C(=O)NC)c3)cc2C)[C@@H](O)[C@@H](O)[C@@H]1O]
31
TABLE 3
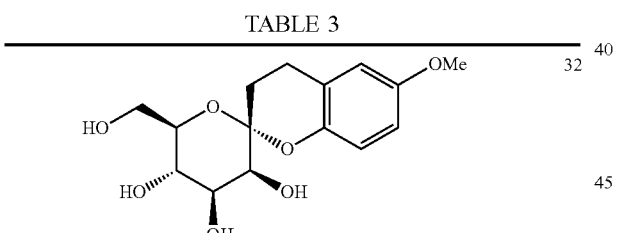
32
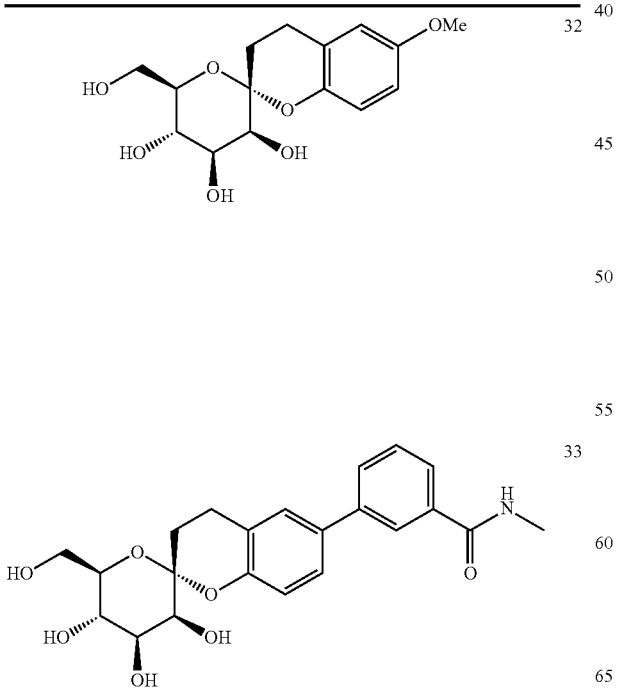
33
TABLE 3-continued
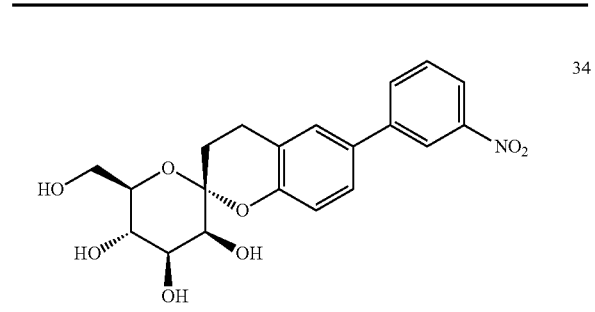
34
TABLE 4
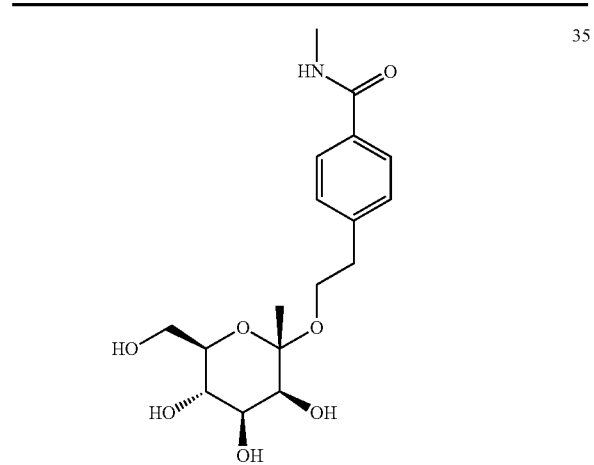
35, 36
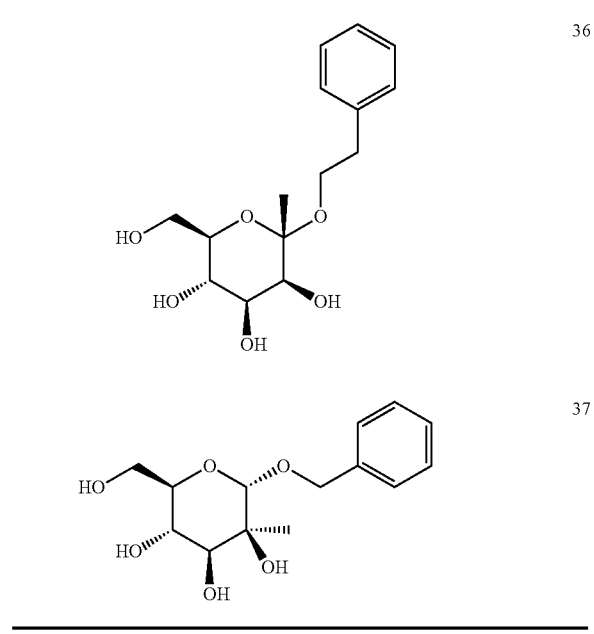
37

TABLE 5
| Cmpd. | Structure |
|---|---|
| 38 | 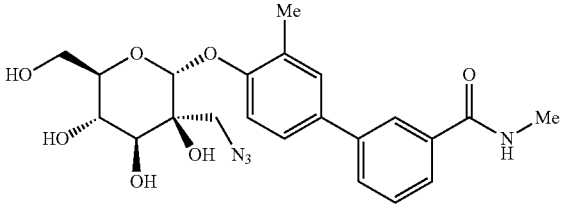 [SMILES: CNC(=O)c1cccc(-c2ccc(O[C@H]3O[C@H](CO)[C@@H](O)[C@H](O)[C@@]3(O)CN=[N+]=[N-])c(C)c2)c1] |
| 39 | 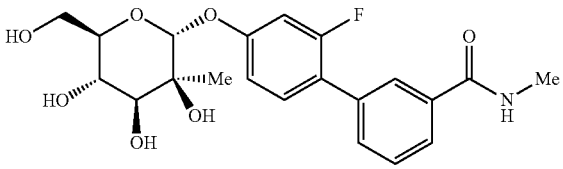 |
| 40 | 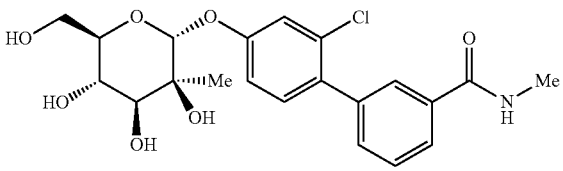 [SMILES: CNC(=O)c1cccc(-c2ccc(O[C@H]3O[C@H](CO)[C@@H](O)[C@H](O)[C@]3(C)O)cc2Cl)c1] |
| 41 | 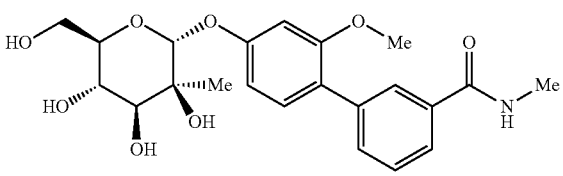 [SMILES: CNC(=O)c1cccc(-c2ccc(O[C@H]3O[C@H](CO)[C@@H](O)[C@H](O)[C@]3(C)O)cc2OC)c1] |
| 42 | 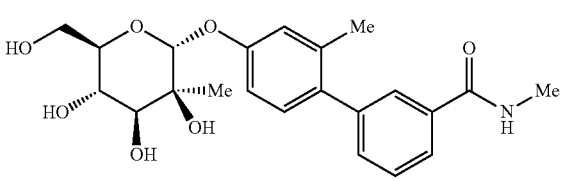 [SMILES: CNC(=O)c1cccc(-c2ccc(O[C@H]3O[C@H](CO)[C@@H](O)[C@H](O)[C@]3(C)O)cc2C)c1] |
| 43 | 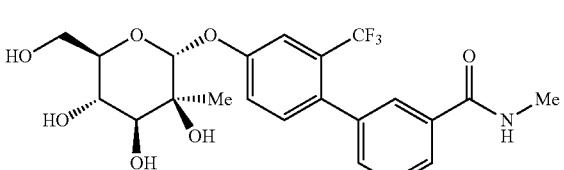 |
| 44 | 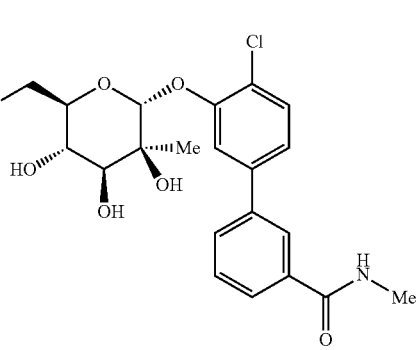 |

TABLE 5-continued

| Cmpd. | Structure |
|---|---|
| 45 | *(structure)* |
| 46 | *(structure)* |
| 47 | *(structure)* |
| 48 | *(structure)* |
| 49 | *(structure)* |
| 50 | *(structure)* |

TABLE 5-continued

| Cmpd. | Structure |
|---|---|
| 51 | 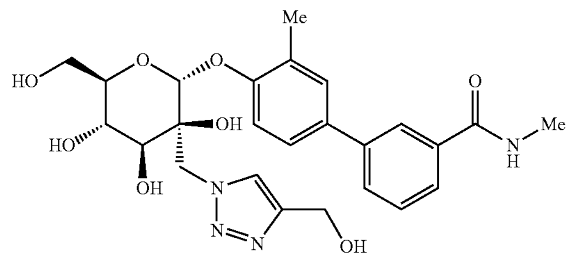 [SMILES: CNC(=O)c1cccc(-c2ccc(O[C@H]3O[C@H](CO)[C@@H](O)[C@H](O)[C@@]3(O)Cn3cc(CO)nn3)c(C)c2)c1] |
| 52 | 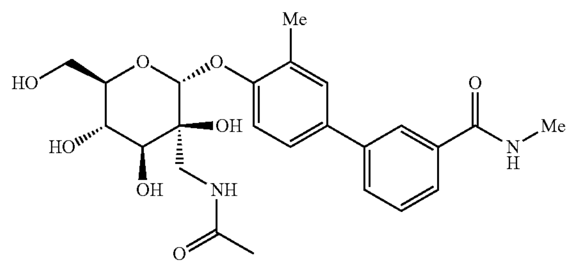 [SMILES: CNC(=O)c1cccc(-c2ccc(O[C@H]3O[C@H](CO)[C@@H](O)[C@H](O)[C@@]3(O)CNC(C)=O)c(C)c2)c1] |
| 53 | 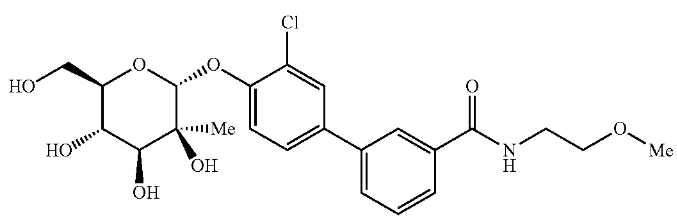 [SMILES: COCCNC(=O)c1cccc(-c2ccc(O[C@H]3O[C@H](CO)[C@@H](O)[C@H](O)[C@]3(C)O)c(Cl)c2)c1] |
| 54 | 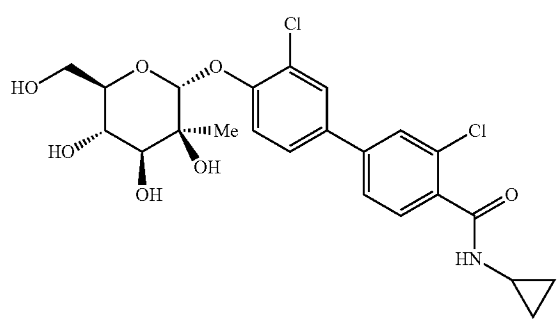 [SMILES: C[C@@]1(O)[C@@H](Oc2ccc(-c3ccc(C(=O)NC4CC4)c(Cl)c3)cc2Cl)O[C@H](CO)[C@@H](O)[C@@H]1O] |
| 55 | 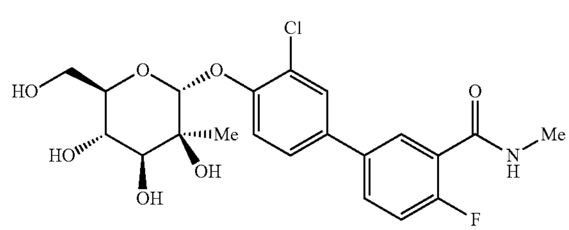 [SMILES: CNC(=O)c1cc(-c2ccc(O[C@H]3O[C@H](CO)[C@@H](O)[C@H](O)[C@]3(C)O)c(Cl)c2)ccc1F] |
| 56 | 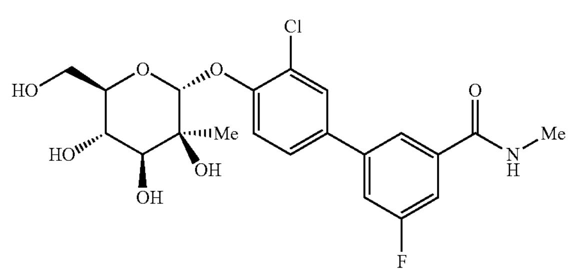 [SMILES: CNC(=O)c1cc(F)cc(-c2ccc(O[C@H]3O[C@H](CO)[C@@H](O)[C@H](O)[C@]3(C)O)c(Cl)c2)c1] |

TABLE 5-continued
| Cmpd. | Structure |
|---|---|
| 57 | 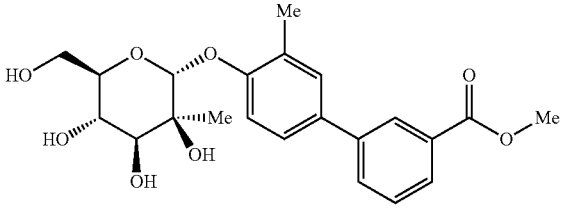 [SMILES: COC(=O)c1cccc(-c2ccc(O[C@H]3O[C@H](CO)[C@@H](O)[C@H](O)[C@]3(C)O)c(C)c2)c1] |
| 58 | 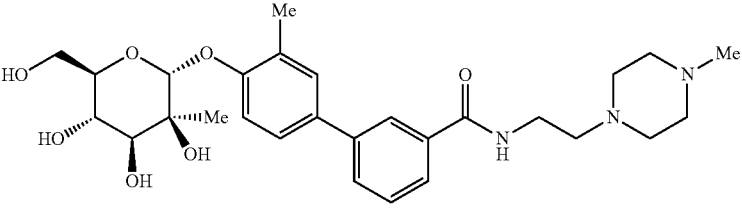 [SMILES: Cc1cc(-c2cccc(C(=O)NCCN3CCN(C)CC3)c2)ccc1O[C@H]1O[C@H](CO)[C@@H](O)[C@H](O)[C@]1(C)O] |
| 59 | 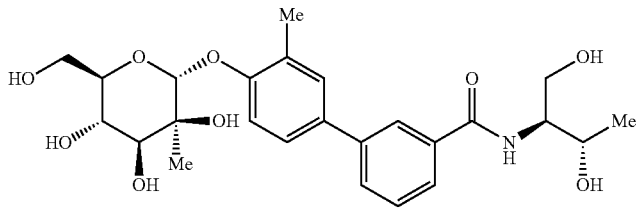 [SMILES: Cc1cc(-c2cccc(C(=O)N[C@@H](CO)[C@H](C)O)c2)ccc1O[C@H]1O[C@H](CO)[C@@H](O)[C@H](O)[C@]1(C)O] |
| 60 | 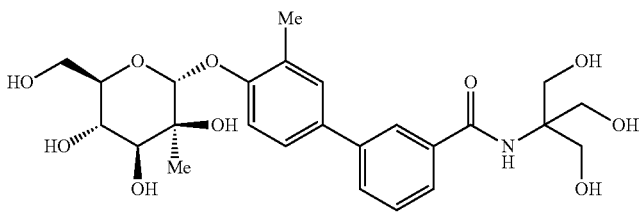 [SMILES: Cc1cc(-c2cccc(C(=O)NC(CO)(CO)CO)c2)ccc1O[C@H]1O[C@H](CO)[C@@H](O)[C@H](O)[C@]1(C)O] |
| 61 | 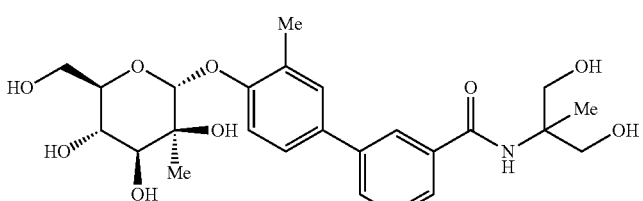 |
| 62 | 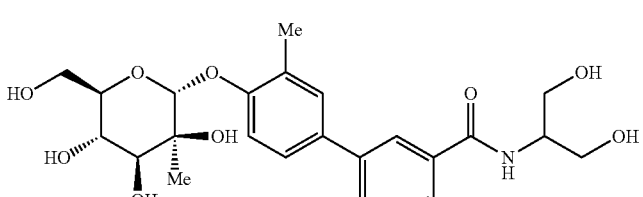 |
| 63 | 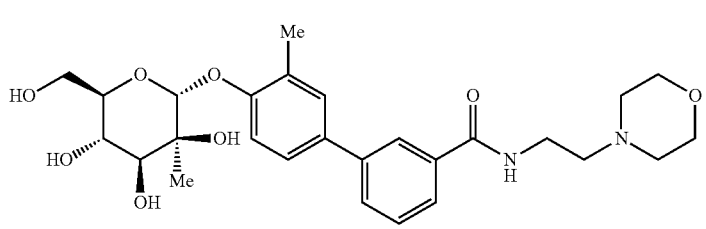 [SMILES: Cc1cc(-c2cccc(C(=O)NCCN3CCOCC3)c2)ccc1O[C@H]1O[C@H](CO)[C@@H](O)[C@H](O)[C@]1(C)O] |

TABLE 5-continued

| Cmpd. | Structure |
|---|---|
| 64 | 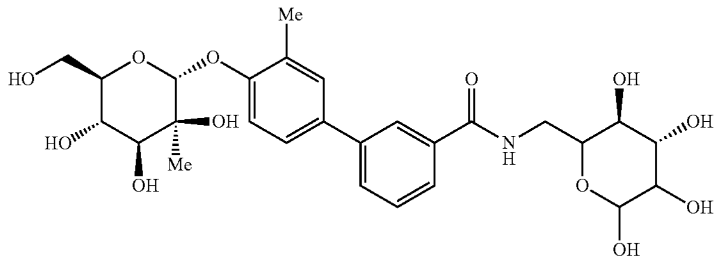 [SMILES: Cc1cc(-c2cccc(C(=O)NCC3OC(O)C(O)[C@@H](O)[C@@H]3O)c2)ccc1O[C@H]1O[C@H](CO)[C@@H](O)[C@H](O)[C@]1(C)O] |
| 65 | 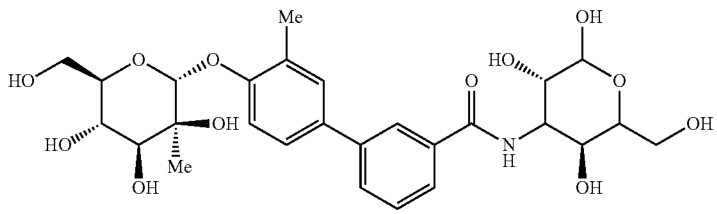 [SMILES: Cc1cc(-c2cccc(C(=O)NC3[C@H](O)C(O)OC(CO)[C@H]3O)c2)ccc1O[C@H]1O[C@H](CO)[C@@H](O)[C@H](O)[C@]1(C)O] |
| 66 | 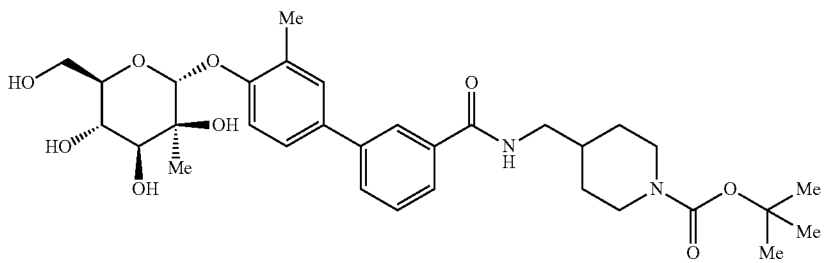 [SMILES: Cc1cc(-c2cccc(C(=O)NCC3CCN(C(=O)OC(C)(C)C)CC3)c2)ccc1O[C@H]1O[C@H](CO)[C@@H](O)[C@H](O)[C@]1(C)O] |
| 67 | 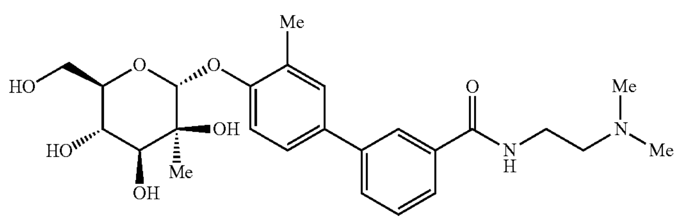 [SMILES: Cc1cc(-c2cccc(C(=O)NCCN(C)C)c2)ccc1O[C@H]1O[C@H](CO)[C@@H](O)[C@H](O)[C@]1(C)O] |
| 68 | 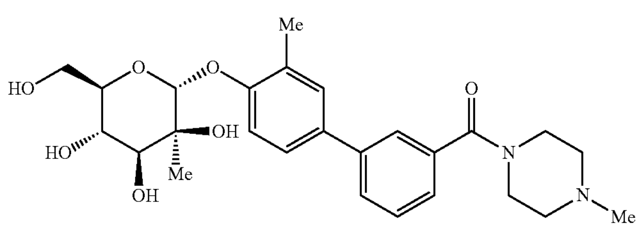 [SMILES: Cc1cc(-c2cccc(C(=O)N3CCN(C)CC3)c2)ccc1O[C@H]1O[C@H](CO)[C@@H](O)[C@H](O)[C@]1(C)O] |
| 69 | 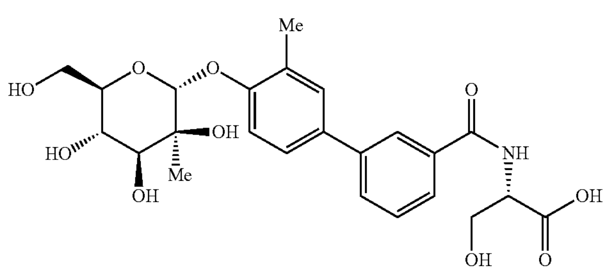 [SMILES: Cc1cc(-c2cccc(C(=O)N[C@@H](CO)C(=O)O)c2)ccc1O[C@H]1O[C@H](CO)[C@@H](O)[C@H](O)[C@]1(C)O] |

TABLE 5-continued
| Cmpd. | Structure |
|---|---|
| 70 | 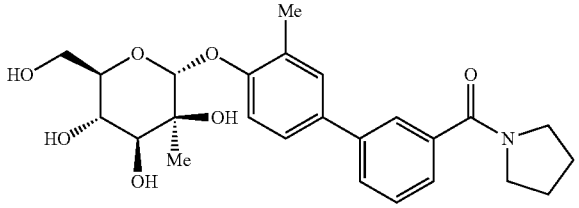 [SMILES: Cc1cc(-c2cccc(C(=O)N3CCCC3)c2)ccc1O[C@H]1O[C@H](CO)[C@@H](O)[C@H](O)[C@]1(C)O] |
| 71 | 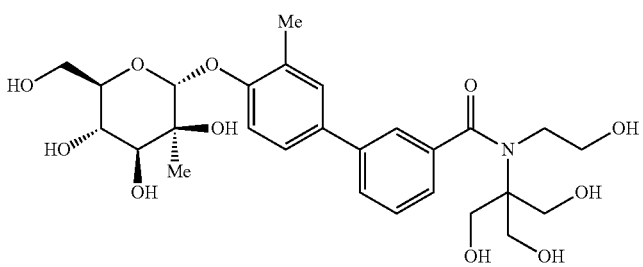 [SMILES: Cc1cc(-c2cccc(C(=O)N(CCO)C(CO)(CO)CO)c2)ccc1O[C@H]1O[C@H](CO)[C@@H](O)[C@H](O)[C@]1(C)O] |
| 72 | 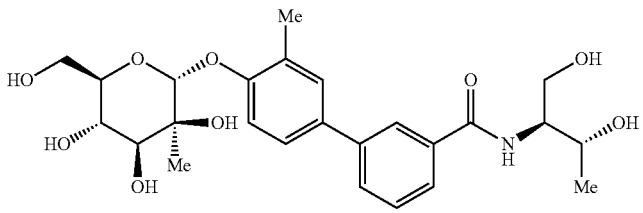 [SMILES: Cc1cc(-c2cccc(C(=O)N[C@@H](CO)[C@@H](C)O)c2)ccc1O[C@H]1O[C@H](CO)[C@@H](O)[C@H](O)[C@]1(C)O] |
| 73 | 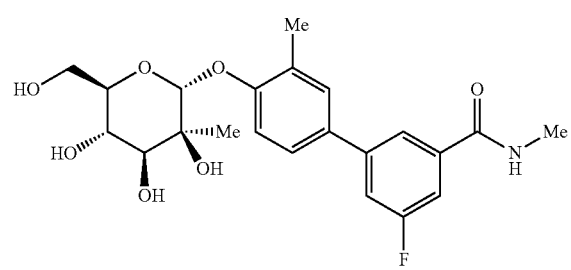 [SMILES: CNC(=O)c1cc(F)cc(-c2ccc(O[C@H]3O[C@H](CO)[C@@H](O)[C@H](O)[C@]3(C)O)c(C)c2)c1] |
| 74 | 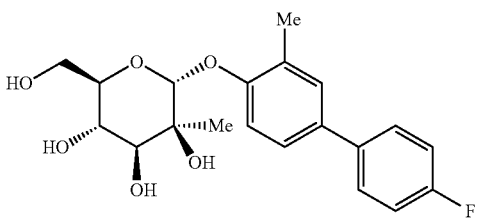 |
| 75 | 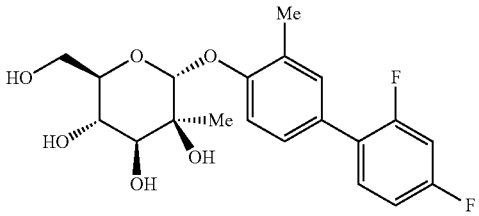 [SMILES: Cc1cc(-c2ccc(F)cc2F)ccc1O[C@H]1O[C@H](CO)[C@@H](O)[C@H](O)[C@]1(C)O] |

TABLE 5-continued

| Cmpd. | Structure |
|---|---|
| 76 | 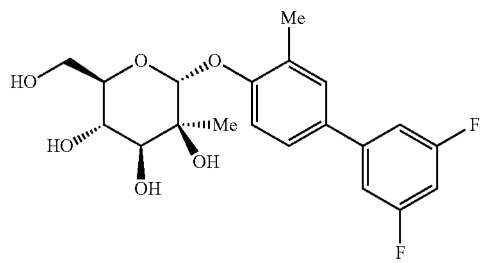 [SMILES: Cc1cc(-c2cc(F)cc(F)c2)ccc1O[C@H]1O[C@H](CO)[C@@H](O)[C@H](O)[C@]1(C)O] |
| 77 | 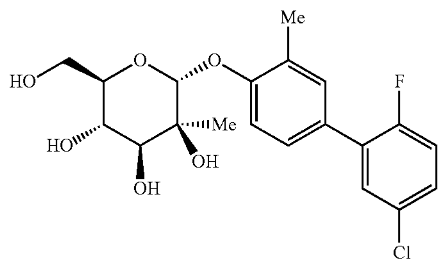 |
| 78 | 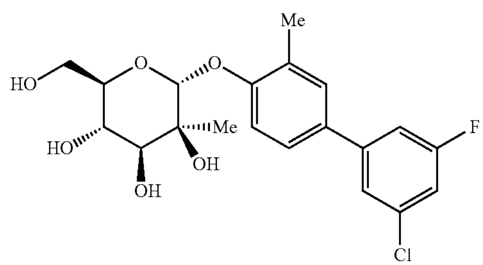 |
| 79 | 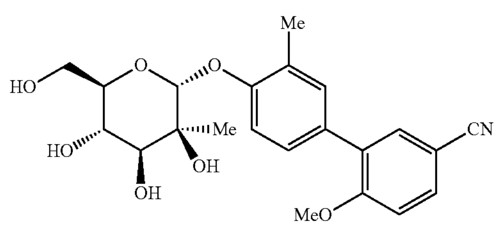 [SMILES: COc1ccc(C#N)cc1-c1ccc(O[C@H]2O[C@H](CO)[C@@H](O)[C@H](O)[C@]2(C)O)c(C)c1] |
| 80 | 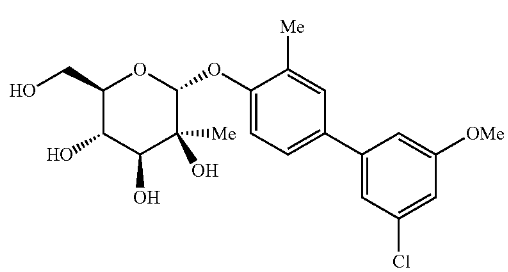 [SMILES: COc1cc(Cl)cc(-c2ccc(O[C@H]3O[C@H](CO)[C@@H](O)[C@H](O)[C@]3(C)O)c(C)c2)c1] |
| 81 | 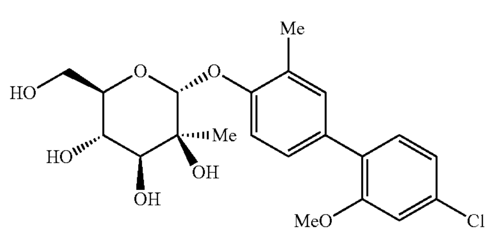 [SMILES: COc1cc(Cl)ccc1-c1ccc(O[C@H]2O[C@H](CO)[C@@H](O)[C@H](O)[C@]2(C)O)c(C)c1] |

TABLE 5-continued

| Cmpd. | Structure |
|---|---|
| 82 | 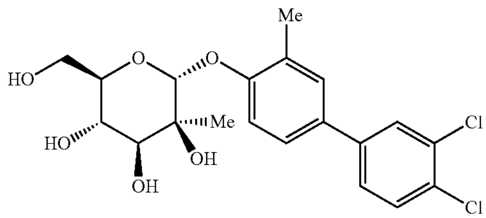 [SMILES: Cc1cc(-c2ccc(Cl)c(Cl)c2)ccc1O[C@H]1O[C@H](CO)[C@@H](O)[C@H](O)[C@]1(C)O] |
| 83 | 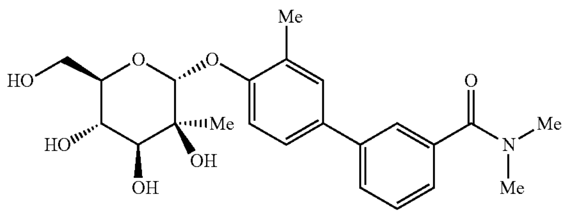 [SMILES: Cc1cc(-c2cccc(C(=O)N(C)C)c2)ccc1O[C@H]1O[C@H](CO)[C@@H](O)[C@H](O)[C@]1(C)O] |
| 84 | 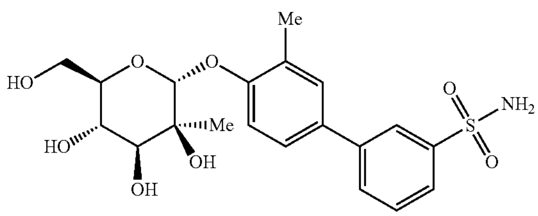 [SMILES: Cc1cc(-c2cccc(S(N)(=O)=O)c2)ccc1O[C@H]1O[C@H](CO)[C@@H](O)[C@H](O)[C@]1(C)O] |
| 85 | 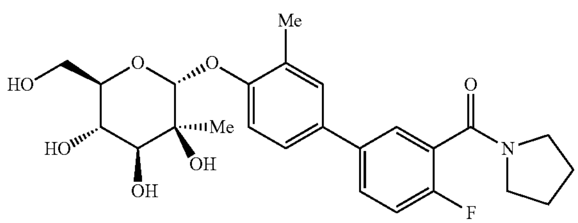 [SMILES: Cc1cc(-c2ccc(F)c(C(=O)N3CCCC3)c2)ccc1O[C@H]1O[C@H](CO)[C@@H](O)[C@H](O)[C@]1(C)O] |
| 86 | 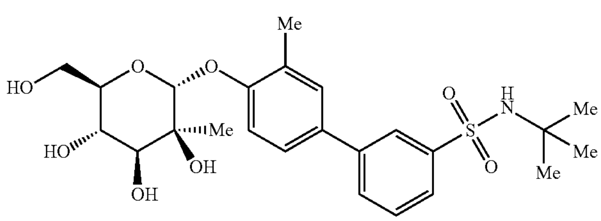 [SMILES: Cc1cc(-c2cccc(S(=O)(=O)NC(C)(C)C)c2)ccc1O[C@H]1O[C@H](CO)[C@@H](O)[C@H](O)[C@]1(C)O] |
| 87 | 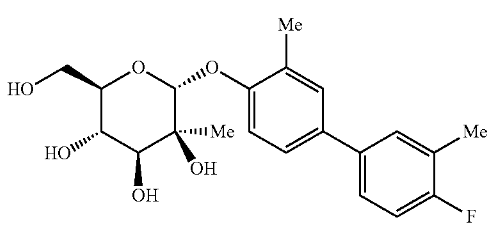 [SMILES: Cc1cc(-c2ccc(O[C@H]3O[C@H](CO)[C@@H](O)[C@H](O)[C@]3(C)O)c(C)c2)ccc1F] |
| 88 | 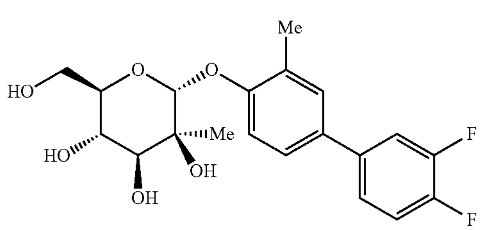 [SMILES: Cc1cc(-c2ccc(F)c(F)c2)ccc1O[C@H]1O[C@H](CO)[C@@H](O)[C@H](O)[C@]1(C)O] |

TABLE 5-continued
| Cmpd. | Structure |
|---|---|
| 89 | 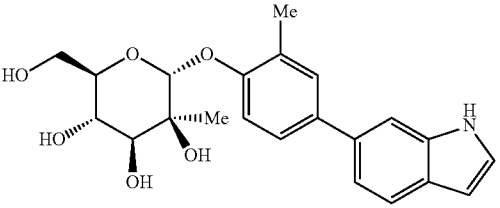 [SMILES: Cc1cc(-c2ccc3cc[nH]c3c2)ccc1O[C@H]1O[C@H](CO)[C@@H](O)[C@H](O)[C@]1(C)O] |
| 90 | 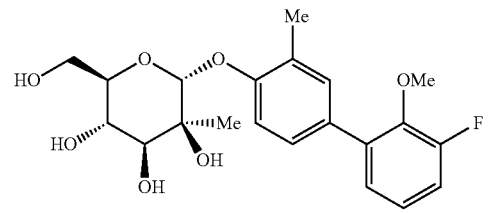 [SMILES: COc1c(F)cccc1-c1ccc(O[C@H]2O[C@H](CO)[C@@H](O)[C@H](O)[C@]2(C)O)c(C)c1] |
| 91 | 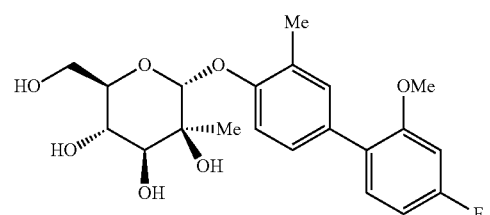 |
| 92 | 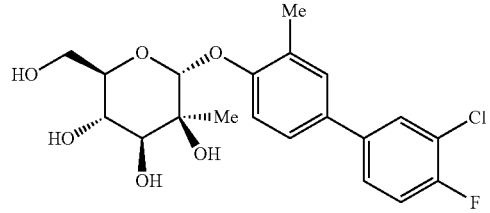 |
| 93 | 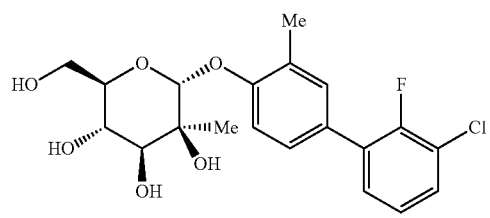 [SMILES: Cc1cc(-c2cccc(Cl)c2F)ccc1O[C@H]1O[C@H](CO)[C@@H](O)[C@H](O)[C@]1(C)O] |
| 94 | 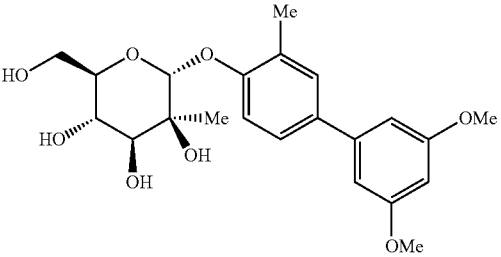 [SMILES: COc1cc(OC)cc(-c2ccc(O[C@H]3O[C@H](CO)[C@@H](O)[C@H](O)[C@]3(C)O)c(C)c2)c1] |

TABLE 5-continued
| Cmpd. | Structure |
|---|---|
| 95 | 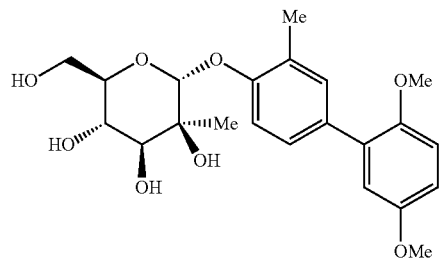 [SMILES: COc1ccc(OC)c(-c2ccc(O[C@H]3O[C@H](CO)[C@@H](O)[C@H](O)[C@]3(C)O)c(C)c2)c1] |
| 96 | 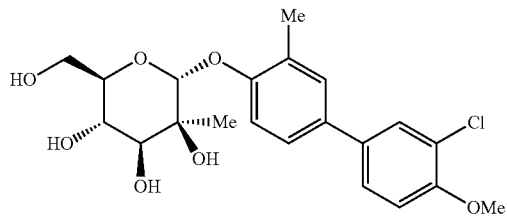 [SMILES: COc1ccc(-c2ccc(O[C@H]3O[C@H](CO)[C@@H](O)[C@H](O)[C@]3(C)O)c(C)c2)cc1Cl] |
| 97 | 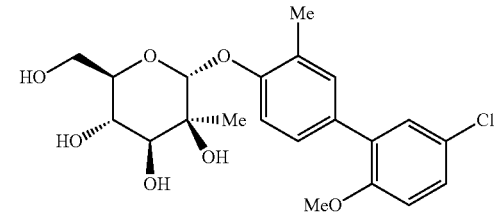 [SMILES: COc1ccc(Cl)cc1-c1ccc(O[C@H]2O[C@H](CO)[C@@H](O)[C@H](O)[C@]2(C)O)c(C)c1] |
| 98 | 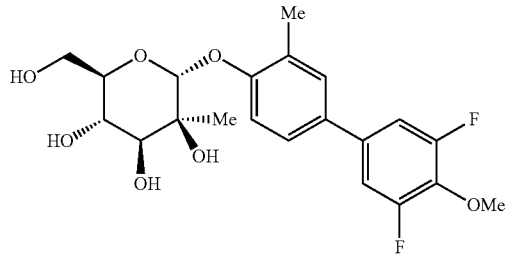 [SMILES: COc1c(F)cc(-c2ccc(O[C@H]3O[C@H](CO)[C@@H](O)[C@H](O)[C@]3(C)O)c(C)c2)cc1F] |
| 99 | 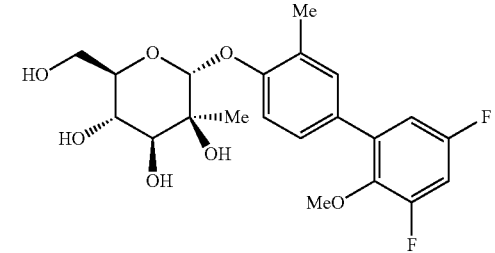 [SMILES: COc1c(F)cc(F)cc1-c1ccc(O[C@H]2O[C@H](CO)[C@@H](O)[C@H](O)[C@]2(C)O)c(C)c1] |
| 100 | 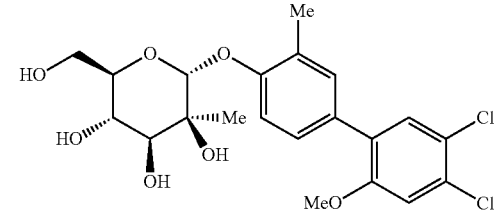 [SMILES: COc1cc(Cl)c(Cl)cc1-c1ccc(O[C@H]2O[C@H](CO)[C@@H](O)[C@H](O)[C@]2(C)O)c(C)c1] |

TABLE 5-continued

| Cmpd. | Structure |
|---|---|
| 101 | 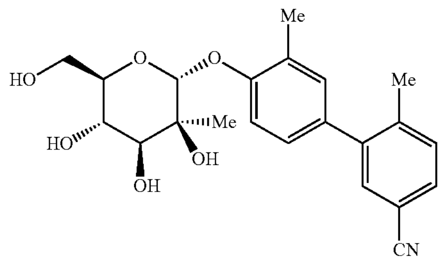 [SMILES: Cc1cc(-c2cc(C#N)ccc2C)ccc1O[C@H]1O[C@H](CO)[C@@H](O)[C@H](O)[C@]1(C)O] |
| 102 | 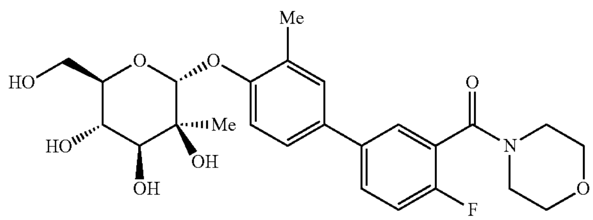 [SMILES: Cc1cc(-c2ccc(F)c(C(=O)N3CCOCC3)c2)ccc1O[C@H]1O[C@H](CO)[C@@H](O)[C@H](O)[C@]1(C)O] |
| 103 | 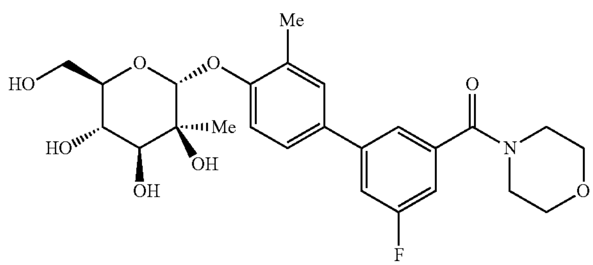 [SMILES: Cc1cc(-c2cc(F)cc(C(=O)N3CCOCC3)c2)ccc1O[C@H]1O[C@H](CO)[C@@H](O)[C@H](O)[C@]1(C)O] |
| 104 | 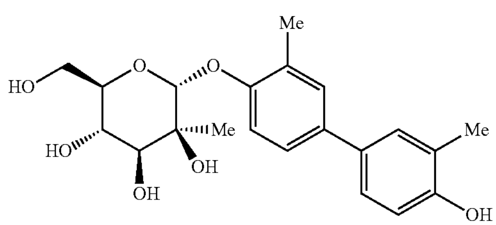 [SMILES: Cc1cc(-c2ccc(O[C@H]3O[C@H](CO)[C@@H](O)[C@H](O)[C@]3(C)O)c(C)c2)ccc1O] |
| 105 | 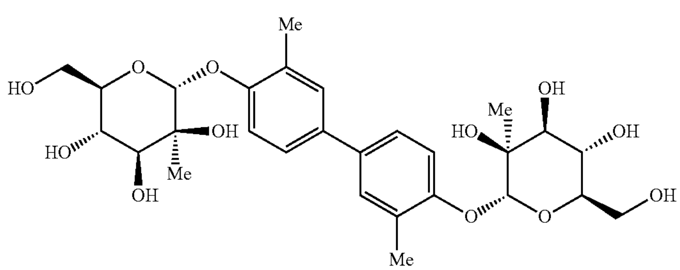 [SMILES: Cc1cc(-c2ccc(O[C@H]3O[C@H](CO)[C@@H](O)[C@H](O)[C@]3(C)O)c(C)c2)ccc1O[C@H]1O[C@H](CO)[C@@H](O)[C@H](O)[C@]1(C)O] |
| 106 | 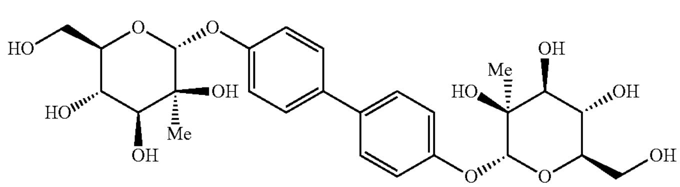 [SMILES: C[C@@]1(O)[C@@H](Oc2ccc(-c3ccc(O[C@H]4O[C@H](CO)[C@@H](O)[C@H](O)[C@]4(C)O)cc3)cc2)O[C@H](CO)[C@@H](O)[C@@H]1O] |

TABLE 5-continued

| Cmpd. | Structure |
|---|---|
| 107 | 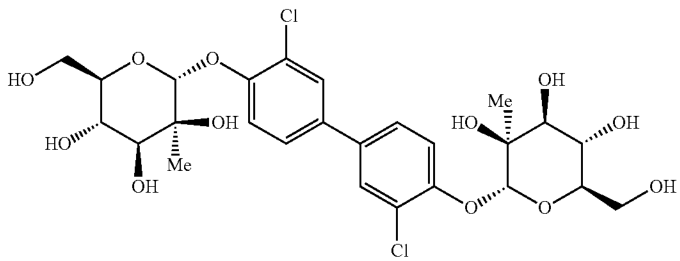 [SMILES: C[C@@]1(O)[C@@H](Oc2ccc(-c3ccc(O[C@H]4O[C@H](CO)[C@@H](O)[C@H](O)[C@]4(C)O)c(Cl)c3)cc2Cl)O[C@H](CO)[C@@H](O)[C@@H]1O] |
| 108 | 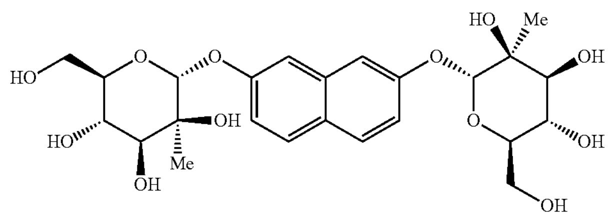 [SMILES: C[C@@]1(O)[C@@H](Oc2ccc3ccc(O[C@H]4O[C@H](CO)[C@@H](O)[C@H](O)[C@]4(C)O)cc3c2)O[C@H](CO)[C@@H](O)[C@@H]1O] |
| 109 | 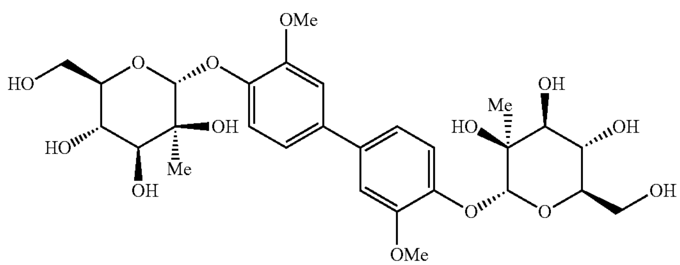 [SMILES: COc1cc(-c2ccc(O[C@H]3O[C@H](CO)[C@@H](O)[C@H](O)[C@]3(C)O)c(OC)c2)ccc1O[C@H]1O[C@H](CO)[C@@H](O)[C@H](O)[C@]1(C)O] |
| 110 | 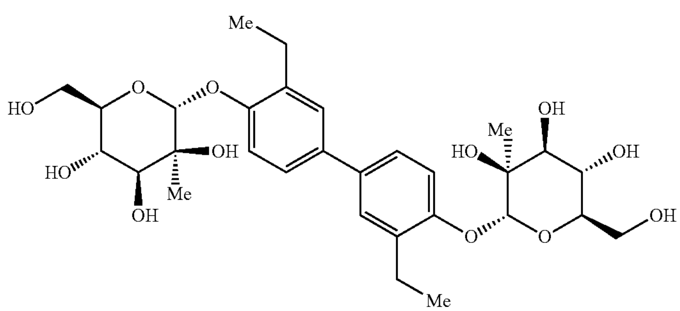 [SMILES: CCc1cc(-c2ccc(O[C@H]3O[C@H](CO)[C@@H](O)[C@H](O)[C@]3(C)O)c(CC)c2)ccc1O[C@H]1O[C@H](CO)[C@@H](O)[C@H](O)[C@]1(C)O] |
| 111 | 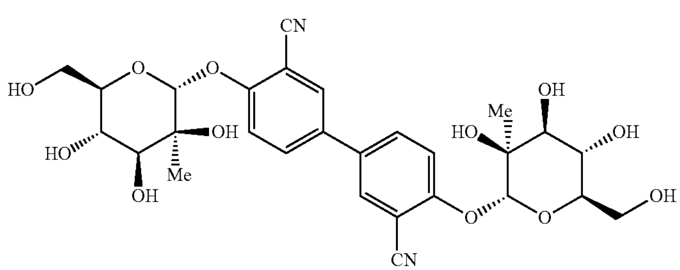 [SMILES: C[C@@]1(O)[C@@H](Oc2ccc(-c3ccc(O[C@H]4O[C@H](CO)[C@@H](O)[C@H](O)[C@]4(C)O)c(C#N)c3)cc2C#N)O[C@H](CO)[C@@H](O)[C@@H]1O] |
| 112 | 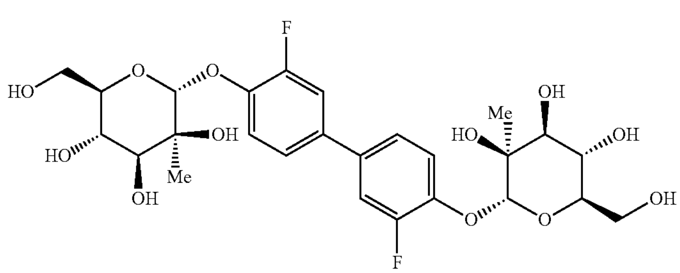 [SMILES: C[C@@]1(O)[C@@H](Oc2ccc(-c3ccc(O[C@H]4O[C@H](CO)[C@@H](O)[C@H](O)[C@]4(C)O)c(F)c3)cc2F)O[C@H](CO)[C@@H](O)[C@@H]1O] |

TABLE 5-continued

| Cmpd. | Structure |
|---|---|
| 113 | 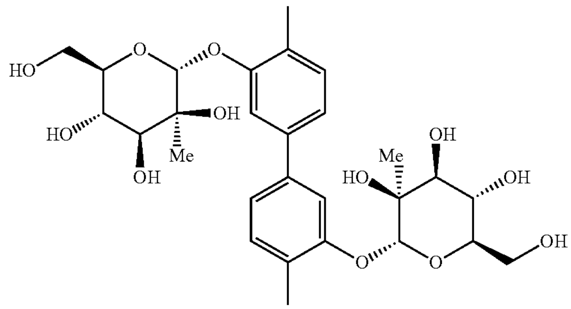 [SMILES: Cc1ccc(-c2ccc(C)c(O[C@H]3O[C@H](CO)[C@@H](O)[C@H](O)[C@]3(C)O)c2)cc1O[C@H]1O[C@H](CO)[C@@H](O)[C@H](O)[C@]1(C)O] |
| 114 | 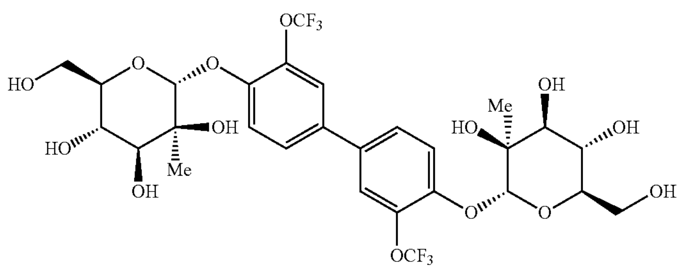 [SMILES: C[C@@]1(O)[C@@H](Oc2ccc(-c3ccc(O[C@H]4O[C@H](CO)[C@@H](O)[C@H](O)[C@]4(C)O)c(OC(F)(F)F)c3)cc2OC(F)(F)F)O[C@H](CO)[C@@H](O)[C@@H]1O] |
| 115 | 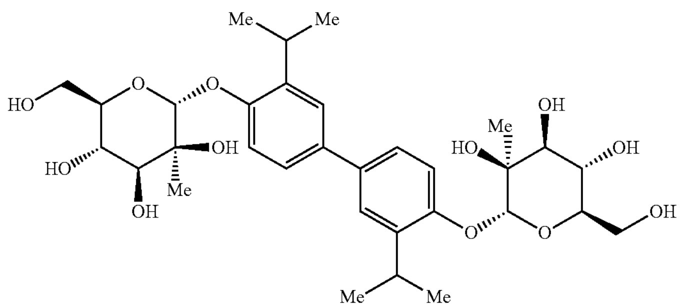 [SMILES: CC(C)c1cc(-c2ccc(O[C@H]3O[C@H](CO)[C@@H](O)[C@H](O)[C@]3(C)O)c(C(C)C)c2)ccc1O[C@H]1O[C@H](CO)[C@@H](O)[C@H](O)[C@]1(C)O] |
| 116 | 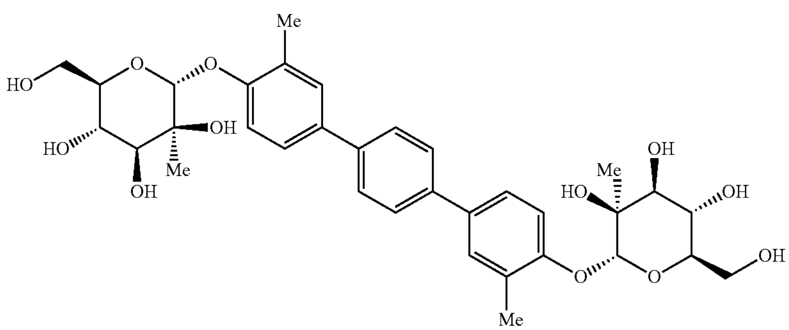 [SMILES: Cc1cc(-c2ccc(-c3ccc(O[C@H]4O[C@H](CO)[C@@H](O)[C@H](O)[C@]4(C)O)c(C)c3)cc2)ccc1O[C@H]1O[C@H](CO)[C@@H](O)[C@H](O)[C@]1(C)O] |
| 117 | 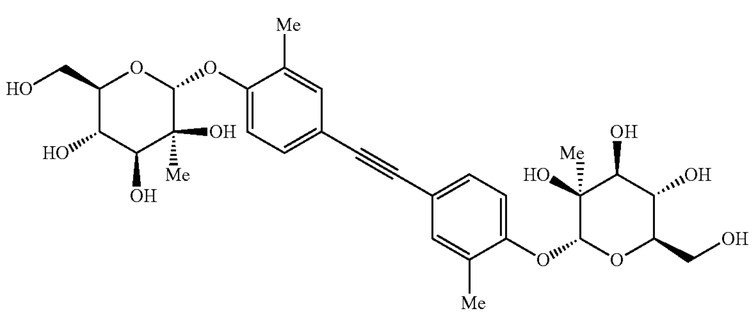 [SMILES: Cc1cc(C#Cc2ccc(O[C@H]3O[C@H](CO)[C@@H](O)[C@H](O)[C@]3(C)O)c(C)c2)ccc1O[C@H]1O[C@H](CO)[C@@H](O)[C@H](O)[C@]1(C)O] |

TABLE 5-continued

| Cmpd. | Structure |
|---|---|
| 118 | 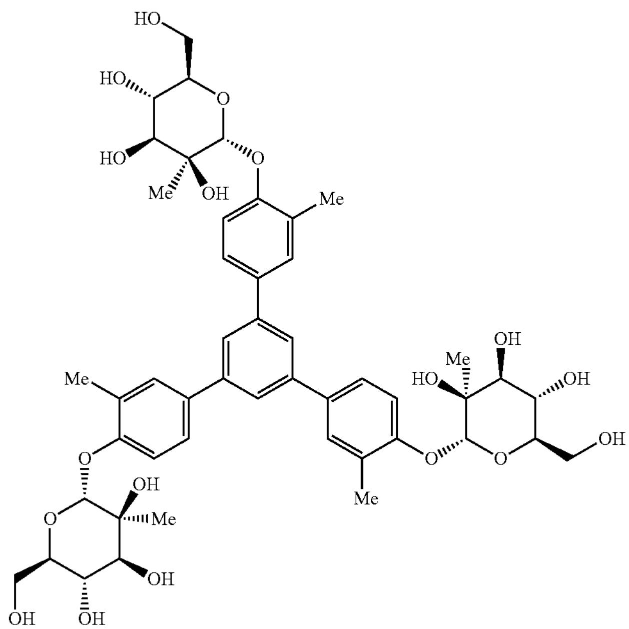 [SMILES: Cc1cc(-c2cc(-c3ccc(O[C@H]4O[C@H](CO)[C@@H](O)[C@H](O)[C@]4(C)O)c(C)c3)cc(-c3ccc(O[C@H]4O[C@H](CO)[C@@H](O)[C@H](O)[C@]4(C)O)c(C)c3)c2)ccc1O[C@H]1O[C@H](CO)[C@@H](O)[C@H](O)[C@]1(C)O] |
| 119 | 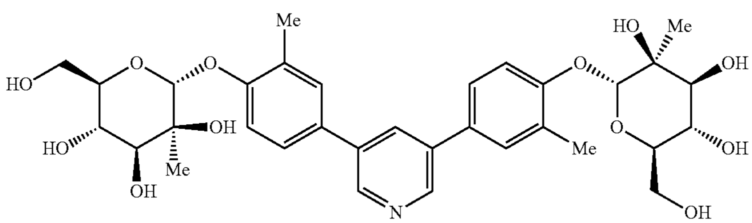 [SMILES: Cc1cc(-c2cncc(-c3ccc(O[C@H]4O[C@H](CO)[C@@H](O)[C@H](O)[C@]4(C)O)c(C)c3)c2)ccc1O[C@H]1O[C@H](CO)[C@@H](O)[C@H](O)[C@]1(C)O] |
| 120 | 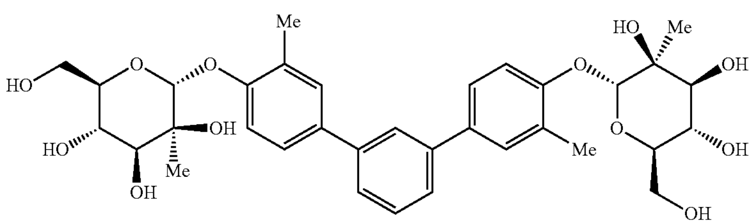 [SMILES: Cc1cc(-c2cccc(-c3ccc(O[C@H]4O[C@H](CO)[C@@H](O)[C@H](O)[C@]4(C)O)c(C)c3)c2)ccc1O[C@H]1O[C@H](CO)[C@@H](O)[C@H](O)[C@]1(C)O] |
| 121 | 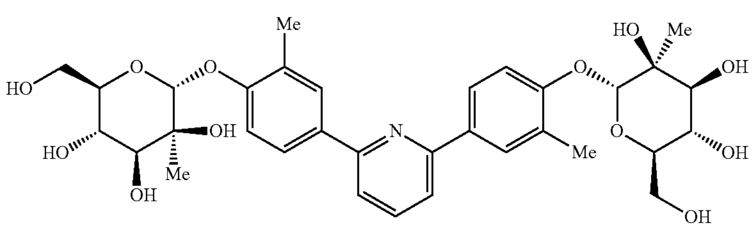 [SMILES: Cc1cc(-c2cccc(-c3ccc(O[C@H]4O[C@H](CO)[C@@H](O)[C@H](O)[C@]4(C)O)c(C)c3)n2)ccc1O[C@H]1O[C@H](CO)[C@@H](O)[C@H](O)[C@]1(C)O] |
| 122 | 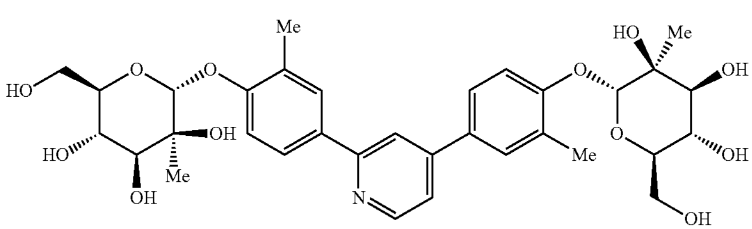 [SMILES: Cc1cc(-c2ccnc(-c3ccc(O[C@H]4O[C@H](CO)[C@@H](O)[C@H](O)[C@]4(C)O)c(C)c3)c2)ccc1O[C@H]1O[C@H](CO)[C@@H](O)[C@H](O)[C@]1(C)O] |

TABLE 5-continued

| Cmpd. | Structure |
|---|---|
| 123 | 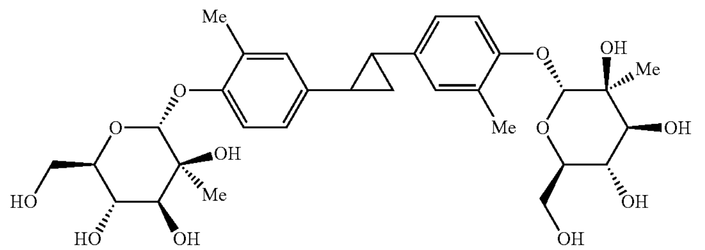 [SMILES: Cc1cc(C2CC2c2ccc(O[C@H]3O[C@H](CO)[C@@H](O)[C@H](O)[C@]3(C)O)c(C)c2)ccc1O[C@H]1O[C@H](CO)[C@@H](O)[C@H](O)[C@]1(C)O] |
| 124 | 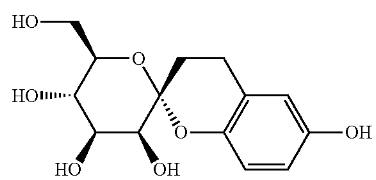 [SMILES: OC[C@H]1O[C@@]2(CCc3cc(O)ccc3O2)[C@@H](O)[C@@H](O)[C@@H]1O] |
| 125 | 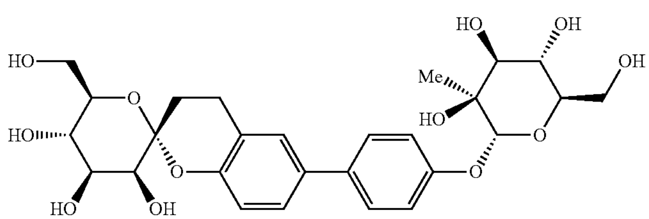 [SMILES: C[C@@]1(O)[C@@H](Oc2ccc(-c3ccc4c(c3)CC[C@]3(O4)O[C@H](CO)[C@@H](O)[C@H](O)[C@@H]3O)cc2)O[C@H](CO)[C@@H](O)[C@@H]1O] |
| 126 | 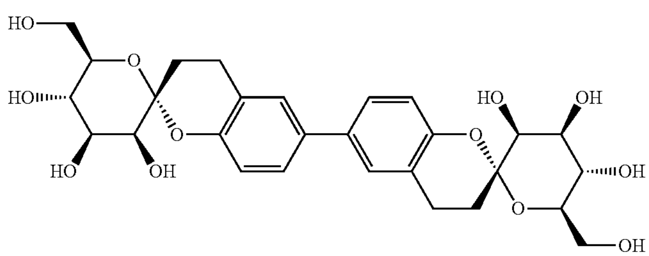 [SMILES: OC[C@H]1O[C@@]2(CCc3cc(-c4ccc5c(c4)CC[C@]4(O5)O[C@H](CO)[C@@H](O)[C@H](O)[C@@H]4O)ccc3O2)[C@@H](O)[C@@H](O)[C@@H]1O] |
| 127 | 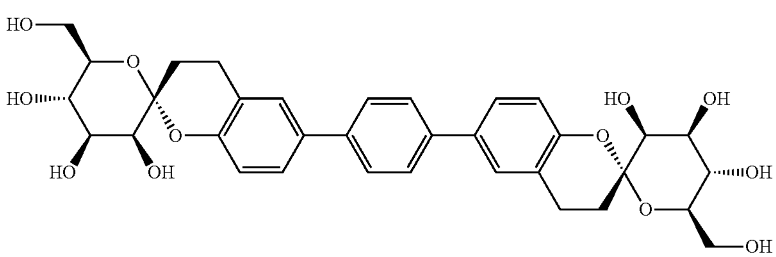 [SMILES: OC[C@H]1O[C@@]2(CCc3cc(-c4ccc(-c5ccc6c(c5)CC[C@]5(O6)O[C@H](CO)[C@@H](O)[C@H](O)[C@@H]5O)cc4)ccc3O2)[C@@H](O)[C@@H](O)[C@@H]1O] |
| 128 | 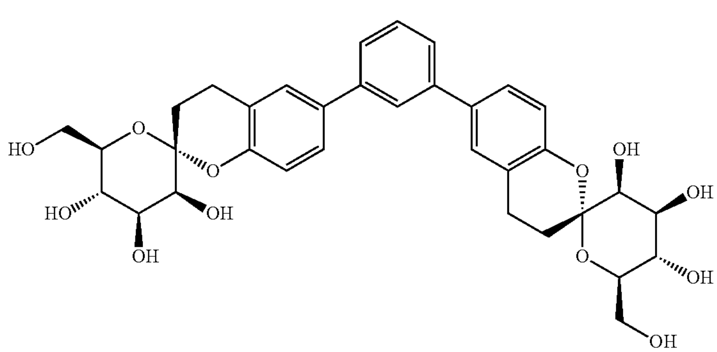 [SMILES: OC[C@H]1O[C@@]2(CCc3cc(-c4cccc(-c5ccc6c(c5)CC[C@]5(O6)O[C@H](CO)[C@@H](O)[C@H](O)[C@@H]5O)c4)ccc3O2)[C@@H](O)[C@@H](O)[C@@H]1O] |

TABLE 5-continued

| Cmpd. | Structure |
|---|---|
| 129 | 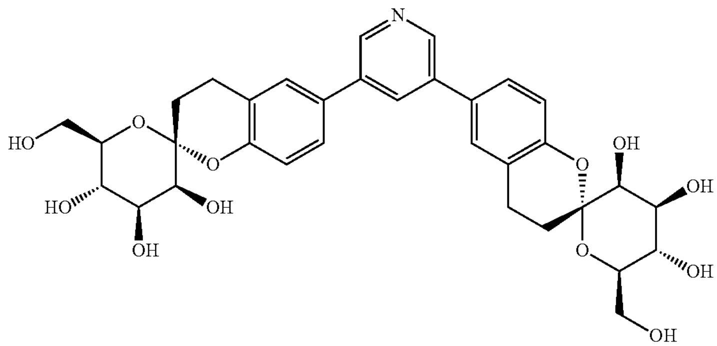 [SMILES: OC[C@H]1O[C@@]2(CCc3cc(-c4cncc(-c5ccc6c(c5)CC[C@]5(O6)O[C@H](CO)[C@@H](O)[C@H](O)[C@@H]5O)c4)ccc3O2)[C@@H](O)[C@@H](O)[C@@H]1O] |

The present invention also provides processes for making the compounds described herein. These processes are described generally in the Schemes below.

The present invention also provides a composition comprising the compound described herein, and a pharmaceutically acceptable carrier, adjuvant, or vehicle.

The present invention also provides a method of treating or preventing bacteria infection in a subject, comprising administering to the subject an effective amount of the compound or the composition described herein.

In an embodiment of the method, the bacteria infection is urinary tract infection or inflammatory bowel disease.

Another embodiment provides a method of treating or preventing a bacteria infection in a subject, comprising administering to the subject an effective amount of a compound described herein or a pharmaceutically acceptable salt thereof, or a composition comprising said compound. In some embodiments, the bacteria infection is urinary tract infection or inflammatory bowel disease. In some embodiments, the bacteria infection is ulcerative colitis. In other embodiments, the bacteria infection is Crohn's disease. In some embodiments, bacteria infection is the cause of Crohn's Disease or ulcerative colitis. In some embodiments, the bacteria infections are caused by AIEC (adherent-invasive E. coli) strains.

Another embodiment provides a method of treating or preventing inflammatory bowel disease in a subject, comprising administering to the subject an effective amount of a compound described herein or a pharmaceutically acceptable salt thereof, or a composition comprising said compound. In some embodiments, the subject is a patient. In other embodiments, the subject is a human. In some embodiments, the inflammatory bowel disease is Crohn's Disease. In other embodiments, the inflammatory bowel disease is ulcerative colitis.

Another embodiment provides a method of inhibiting FimH in bacteria from an E. coli bacterial strain isolated from patients with inflammatory bowel disease, comprising contacting the bacteria with an effective amount of a compound described herein, or a pharmaceutically acceptable salt thereof, or a composition comprising said compound. In some embodiments, the bacterial strain is LF-82.

Another embodiment provides a method of inhibiting FimH in a subject, comprising administering to the subject an effective amount of a compound described herein, or a pharmaceutically acceptable salt thereof, or a composition comprising said compound.

Another embodiment provides a method of inhibiting adhesion of E. coli in a subject, comprising administering to the subject an effective amount of a compound described herein, or a pharmaceutically acceptable salt thereof, or a composition comprising said compound. In some embodiments, the inhibition of adhesion results in the prevention of the establishment of a sub-mucosal infection.

Another embodiment provides a method of blocking the interaction between type 1 pili and CEACAM6 in a subject, comprising administering to the subject an effective amount of a compound described herein, or a pharmaceutically acceptable salt thereof, or a composition comprising said compound.

As described herein, a specified number range of atoms includes any integer therein. For example, a group having from 1-4 atoms could have 1, 2, 3, or 4 atoms. The term "stable", as used herein, refers to compounds that are not substantially altered when subjected to conditions to allow for their production, detection, recovery, storage, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

The term "aliphatic" or "aliphatic group", as used herein, means a straight-chain (i.e., unbranched), or branched, hydrocarbon chain that is completely saturated or that contains one or more units of unsaturation but is non-aromatic. Unless otherwise specified, aliphatic groups contain 1-20 aliphatic carbon atoms. In some embodiments, aliphatic groups contain 1-10 aliphatic carbon atoms. In other embodiments, aliphatic groups contain 1-8 aliphatic carbon atoms. In still other embodiments, aliphatic groups contain 1-6 aliphatic carbon atoms, and in yet other embodiments aliphatic groups contain 1-4 aliphatic carbon atoms. Aliphatic groups may be linear or branched, substituted or unsubstituted alkyl, alkenyl, or alkynyl groups. Specific examples include, but are not limited to, methyl, ethyl, isopropyl, n-propyl, sec-butyl, vinyl, n-butenyl, ethynyl, and tert-butyl.

The term "alkyl" as used herein means a saturated straight or branched chain hydrocarbon. The term "alkenyl" as used herein means a straight or branched chain hydrocarbon comprising one or more double bonds. The term "alkynyl" as used herein means a straight or branched chain hydrocarbon comprising one or more triple bonds.

The term "cycloaliphatic" (or "carbocycle" or "carbocyclyl" or "carbocyclic") refers to a non-aromatic monocyclic carbon containing ring which can be saturated or contain one or more units of unsaturation, having three to fourteen ring carbon atoms. In some embodiments, the ring has three to ten ring carbon atoms; in other embodiments, the ring has three to six carbon atoms. The term includes polycyclic fused, spiro or bridged carbocyclic ring systems. The term also includes polycyclic ring systems in which the carbocyclic ring can be fused to one or more non-aromatic carbocyclic or heterocyclic rings or one or more aromatic rings or combination thereof, wherein the radical or point of attachment is on the carbocyclic ring. Fused bicyclic ring systems comprise two rings which share two adjoining ring atoms, bridged bicyclic group comprise two rings which share three or four adjacent ring atoms, spiro bicyclic ring systems share one ring atom. Examples of cycloaliphatic groups include, but are not limited to, cycloalkyl and cycloalkenyl groups. Specific examples include, but are not limited to, cyclohexyl, cyclopropenyl, and cyclobutyl.

The term "heterocycle" (or "heterocyclyl", or "heterocyclic") as used herein means refers to a non-aromatic monocyclic ring which can be saturated or contain one or more units of unsaturation, having three to fourteen ring atoms in which one or more ring carbons is replaced by a heteroatom such as, N, S, or O. In some embodiments, the ring has three to ten ring atoms; in other embodiments, the ring has three to six ring atoms. In yet other embodiments, the ring has five to six ring atoms. The term includes polycyclic fused, spiro or bridged heterocyclic ring systems. The term also includes polycyclic ring systems in which the heterocyclic ring can be fused to one or more non-aromatic carbocyclic or heterocyclic rings or one or more aromatic rings or combination thereof, wherein the radical or point of attachment is on the heterocyclic ring.

Examples of heterocycles include, but are not limited to, piperidinyl, piperizinyl, pyrrolidinyl, pyrazolidinyl, imidazolidinyl, azepanyl, diazepanyl, triazepanyl, azocanyl, diazocanyl, triazocanyl, oxazolidinyl, isoxazolidinyl, thiazolidinyl, isothiazolidinyl, oxazocanyl, oxazepanyl, thiazepanyl, thiazocanyl, benzimidazolonyl, tetrahydrofuranyl, tetrahydropyranyl, tetrahydrothiophenyl, morpholino, including, for example, 3-morpholino, 4-morpholino, 2-thiomorpholino, 3-thiomorpholino, 4-thiomorpholino, 1-pyrrolidinyl, 2-pyrrolidinyl, 3-pyrrolidinyl, 1-tetrahydropiperazinyl, 2-tetrahydropiperazinyl, 3-tetrahydropiperazinyl, 1-piperidinyl, 2-piperidinyl, 3-piperidinyl, 1-pyrazolinyl, 3-pyrazolinyl, 4-pyrazolinyl, 5-pyrazolinyl, 1-piperidinyl, 2-piperidinyl, 3-piperidinyl, 4-piperidinyl, 2-thiazolidinyl, 3-thiazolidinyl, 4-thiazolidinyl, 1-imidazolidinyl, 2-imidazolidinyl, 4-imidazolidinyl, 5-imidazolidinyl, indolinyl, tetrahydroquinolinyl, tetrahydroisoquinolinyl, thienothienyl, thienothiazolyl, benzothiolanyl, benzodithianyl, 3-(1-alkyl)-benzimidazol-2-onyl, and 1,3-dihydro-imidazol-2-onyl.

Cyclic groups, (e.g. cycloaliphatic and heterocycles), can be linearly fused, bridged, or spirocyclic.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR$^+$ (as in N-substituted pyrrolidinyl)).

The term "unsaturated", as used herein, means that a moiety has one or more units of unsaturation. As would be known by one of skill in the art, unsaturated groups can be partially unsaturated or fully unsaturated. Examples of partially unsaturated groups include, but are not limited to, butene, cyclohexene, and tetrahydropyridine. Fully unsaturated groups can be aromatic, anti-aromatic, or non-aromatic. Examples of fully unsaturated groups include, but are not limited to, phenyl, cyclooctatetraene, pyridyl, thienyl, and 1-methylpyridin-2(1H)-one.

The term "alkoxy", or "thioalkyl", as used herein, refers to an alkyl group, as previously defined, attached to the molecule through an oxygen ("alkoxy" e.g., —O-alkyl) or sulfur ("thioalkyl" e.g., —S-alkyl) atom.

The terms "haloalkyl", "haloalkenyl", "haloaliphatic", and "haloalkoxy" mean alkyl, alkenyl or alkoxy, as the case may be, substituted with one or more halogen atoms. This term includes perfluorinated alkyl groups, such as —CF$_3$ and —CF$_2$CF$_3$.

The terms "halogen", "halo", and "hal" mean F, Cl, Br, or I.

The term "aryl" used alone or as part of a larger moiety as in "aralkyl", "aralkoxy", or "aryloxyalkyl", refers to carbocyclic aromatic ring systems. The term "aryl" may be used interchangeably with the term "aryl ring".

Carbocyclic aromatic ring groups have only carbon ring atoms (typically six to fourteen) and include monocyclic aromatic rings such as phenyl and fused polycyclic aromatic ring systems in which two or more carbocyclic aromatic rings are fused to one another. Examples include 1-naphthyl, 2-naphthyl, 1-anthracyl and 2-anthracyl. Also included within the scope of the term "carbocyclic aromatic ring", as it is used herein, is a group in which an aromatic ring is fused to one or more non-aromatic rings (carbocyclic or heterocyclic), such as in an indanyl, phthalimidyl, naphthimidyl, phenanthridinyl, or tetrahydronaphthyl, where the radical or point of attachment is on the aromatic ring.

The term "heteroaryl", "heteroaromatic", "heteroaryl ring", "heteroaryl group" and "heteroaromatic group", used alone or as part of a larger moiety as in "heteroaralkyl" or "heteroarylalkoxy", refers to heteroaromatic ring groups having five to fourteen members, including monocyclic heteroaromatic rings and polycyclic aromatic rings in which a monocyclic aromatic ring is fused to one or more other aromatic ring. Heteroaryl groups have one or more ring heteroatoms. Also included within the scope of the term "heteroaryl", as it is used herein, is a group in which an aromatic ring is fused to one or more non-aromatic rings (carbocyclic or heterocyclic), where the radical or point of attachment is on the aromatic ring. Bicyclic 6,5 heteroaromatic ring, as used herein, for example, is a six membered heteroaromatic ring fused to a second five membered ring, wherein the radical or point of attachment is on the six membered ring.

It shall be understood that a 5-10 membered heteroaryl includes both monocyclic and bicyclic rings. For example, it could include 5-6 membered monocyclic rings having 1-4 heteroatoms selected from oxygen, nitrogen, or sulfur and 8-10 membered bicyclic rings having 1-6 heteroatoms selected from oxygen, nitrogen, or sulfur.

Examples of heteroaryl groups include pyridyl, pyrazinyl, pyrimidinyl, pyridazinyl, imidazolyl, pyrrolyl, pyrazolyl, triazolyl, tetrazolyl, oxazolyl, isoxazolyl, oxadiazolyl, thiazolyl, isothiazolyl or thiadiazolyl including, for example, 2-furanyl, 3-furanyl, N-imidazolyl, 2-imidazolyl, 4-imidazolyl, 5-imidazolyl, 3-isoxazolyl, 4-isoxazolyl, 5-isoxazolyl, 2-oxadiazolyl, 5-oxadiazolyl, 2-oxazolyl, 4-oxazolyl, 5-oxazolyl, 3-pyrazolyl, 4-pyrazolyl, 1-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, 3-pyridazinyl, 2-thiazolyl, 4-thiazolyl, 5-thiazolyl, 2-triazolyl, 5-triazolyl, tetrazolyl, 2-thienyl, 3-thienyl, carbazolyl, benzimidazolyl, benzothienyl, benzofuranyl, indolyl, benzotriazolyl, benzothiazolyl, benzoxazolyl, benzimidazolyl, isoquinolinyl, indolyl, isoindolyl, acridinyl, benzisoxazolyl, isothiazolyl, 1,2,3-oxadiazolyl, 1,2,5-oxadiazolyl, 1,2,4-oxadiazolyl, 1,2,3-triazolyl, 1,2,3-thiadiazolyl, 1,3,4-thiadiazolyl, 1,2,5-thiadiazolyl, purinyl, pyrazinyl, 1,3,5-triazinyl, quinolinyl (e.g., 2-quinolinyl, 3-quinolinyl, 4-quinolinyl), and isoquinolinyl (e.g., 1-isoquinolinyl, 3-isoquinolinyl, or 4-isoquinolinyl).

The term "protecting group" and "protective group" as used herein, are interchangeable and refer to an agent used to temporarily block one or more desired functional groups in a compound with multiple reactive sites. In certain embodiments, a protecting group has one or more, or preferably all, of the following characteristics: a) is added selectively to a functional group in good yield to give a protected substrate that is b) stable to reactions occurring at one or more of the other reactive sites; and c) is selectively removable in good yield by reagents that do not attack the regenerated, deprotected functional group. As would be understood by one skilled in the art, in some cases, the reagents do not attack other reactive groups in the compound. In other cases, the reagents may also react with other reactive groups in the compound. Examples of protecting groups are detailed in Greene, T. W., Wuts, P. G in "Protective Groups in Organic Synthesis", Third Edition, John Wiley & Sons, New York: 1999 (and other editions of the book), the entire contents of which are hereby incorporated by reference. The term "nitrogen protecting group", as used herein, refers to an agent used to temporarily block one or more desired nitrogen reactive sites in a multifunctional compound. Preferred nitrogen protecting groups also possess the characteristics exemplified for a protecting group above, and certain exemplary nitrogen protecting groups are also detailed in Chapter 7 in Greene, T. W., Wuts, P. G in "Protective Groups in Organic Synthesis", Third Edition, John Wiley & Sons, New York: 1999, the entire contents of which are hereby incorporated by reference.

In some embodiments, where indicated, a methylene unit of an aliphatic chain is optionally replaced with another atom or group. Examples of such atoms or groups include, but are not limited to, —NR—, —O—, —C(O)—, —C(=N—CN)—, —C(=NR)—, —C(=NOR)—, —S—, —S(O)—, and —S(O)$_2$—. These atoms or groups can be combined to form larger groups. Examples of such larger groups include, but are not limited to, —OC(O)—, —C(O)CO—, —CO$_2$—, —C(O)NR—, —C(=N—CN), —NRC(O)—, —NRC(O)O—, —S(O)$_2$NR—, —NRSO$_2$—, —NRC(O)NR—, —OC(O)NR—, and —NRSO$_2$NR—, wherein R is for example, H or C$_{1-6}$aliphatic, or is otherwise defined herein.

It should be understood that these groups can be bonded to the methylene units of the aliphatic chain via single, double, or triple bonds. An example of an optional replacement (nitrogen atom in this case) that is bonded to the aliphatic chain via a double bond would be —CH$_2$CH=N—CH$_3$. In some cases, especially on the terminal end, an optional replacement can be bonded to the aliphatic group via a triple bond. One example of this would be CH$_2$CH$_2$CH$_2$C≡N. It should be understood that in this situation, the terminal nitrogen is not bonded to another atom.

It should also be understood that, the term "methylene unit" can also refer to branched or substituted methylene units. For example, in an isopropyl moiety [—CH(CH$_3$)$_2$], a nitrogen atom (e.g. NR) replacing the first recited "methylene unit" would result in dimethylamine [—N(CH$_3$)$_2$]. In instances such as these, one of skill in the art would understand that the nitrogen atom will not have any additional atoms bonded to it, and the "R" from "NR" would be absent in this case.

The terms "carbon units" and "methylene units" are interchangeable. It shall be understood that these terms refer to carbon units of an aliphatic group of varying bond orders, such as the four individual "methylene units" shown in the hydrocarbon below: HC≡CH—CH$_2$C=CH.

Only those replacement and combinations of groups that result in a stable structure are contemplated. Optional replacements can occur both within the chain and/or at either end of the chain; i.e. both at the point of attachment and/or also at the terminal end. Two optional replacements can also be adjacent to each other within a chain so long as it results in a chemically stable compound. The optional replacements can also completely replace all of the carbon atoms in a chain. For example, a C$_3$ aliphatic can be optionally replaced by —NR—, —C(O)—, and —NR— to form —NRC(O)NR— (a urea).

Unless otherwise indicated, if the replacement occurs at the terminal end, the replacement atom is bound to an H on the terminal end. For example, if —CH$_2$CH$_2$CH$_3$ were optionally replaced with —O—, the resulting compound could be —OCH$_2$CH$_3$, —CH$_2$OCH$_3$, or —CH$_2$CH$_2$OH. It should be understood that if the terminal atom does not contain any free valence electrons, then a hydrogen atom is not required at the terminal end (e.g., —CH$_2$CH$_2$CH=O or —CH$_2$CH$_2$C≡N).

Unless otherwise indicated, structures depicted herein are also meant to include all isomeric (e.g., enantiomeric, diastereomeric, geometric, conformational, and rotational) forms of the structure. For example, the R and S configurations for each asymmetric center, (Z) and (E) double bond isomers, and (Z) and (E) conformational isomers are included in this invention. As would be understood to one skilled in the art, a substituent can freely rotate around any rotatable bonds. For example, a substituent drawn as

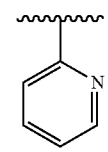

also represents

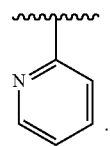

Therefore, single stereochemical isomers as well as enantiomeric, diastereomeric, geometric, conformational, and rotational mixtures of the present compounds are within the scope of the invention.

Unless otherwise indicated, all tautomeric forms of the compounds of the invention are within the scope of the invention.

In the compounds of this invention any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Also unless otherwise stated, when a position is designated specifically as "D" or "deuterium", the position is understood to have deuterium at an abundance that is at least 3340 times greater than the natural abundance of deuterium, which is 0.015% (i.e., at least 50.1% incorporation of deuterium).

"D" and "d" both refer to deuterium.

Additionally, unless otherwise indicated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}C$- or $^{14}C$-enriched carbon are within the scope of this invention. Such compounds are useful, for example, as analytical tools or probes in biological assays.

As described herein, where indicated compounds of the invention may optionally be substituted with one or more substituents, such as are illustrated generally herein, or as exemplified by particular classes, subclasses, and species of the invention. It will be appreciated that the phrase "optionally substituted" is used interchangeably with the phrase "substituted or unsubstituted." In general, the term "substituted", whether preceded by the term "optionally" or not, refers to the replacement of hydrogen radicals in a given structure with the radical of a specified substituent. Unless otherwise indicated, an optionally substituted group may have a substituent at each substitutable position of the group, and when more than one position in any given structure may be substituted with more than one substituent selected from a specified group, the substituent may be either the same or different at every position.

Only those choices and combinations of substituents that result in a stable structure are contemplated. Such choices and combinations will be apparent to those of ordinary skill in the art and may be determined without undue experimentation.

The term "ring atom" is an atom such as C, N, O or S that is in the ring of an aromatic group, cycloalkyl group or non-aromatic heterocyclic ring.

A "substitutable ring atom" in an aromatic group is a ring carbon or nitrogen atom bonded to a hydrogen atom. The hydrogen can be optionally replaced with a suitable substituent group. Thus, the term "substitutable ring atom" does not include ring nitrogen or carbon atoms which are shared when two rings are fused. In addition, "substitutable ring atom" does not include ring carbon or nitrogen atoms when the structure depicts that they are already attached to a moiety other than hydrogen.

An aryl group as defined herein may contain one or more substitutable ring atoms, which may be bonded to a suitable substituent. Examples of suitable substituents on a substitutable ring carbon atom of an aryl group include R'. R' is —Ra, —Br, —Cl, —I, —F, —ORa, —SRa, —O—CORa, —CORa, —CSRa, —CN, —NO$_2$, —NCS, —SO$_3$H, —N(RaRb), —COORa, —NRcNRcCORa, —NRcNRcCO$_2$Ra, —CHO, —CON(RaRb), —OC(O)N(RaRb), —CSN(RaRb), —NRcCORa, —NRcCOORa, —NRcCSRa, —NRcCON(RaRb), —NRcNRcC(O)N(RaRb), —NRcCSN(RaRb), —C(=NRc)-N(RaRb), —C(=S)N(RaRb), —NRd-C(=NRc)-N(RaRb), —NRcN-RaRb, —S(O)$_p$NRaRb, —NRcSO$_2$N(RaRb), —NRcS(O)$_p$Ra, —S(O)$_p$Ra, —OS(O)$_p$NRaRb or —OS(O)$_p$Ra; wherein p is 1 or 2.

Ra-Rd are each independently —H, an aliphatic group, aromatic group, non-aromatic carbocyclic or heterocyclic group or —N(RaRb), taken together, form a non-aromatic heterocyclic group. The aliphatic, aromatic and non-aromatic heterocyclic group represented by Ra-Rd and the non-aromatic heterocyclic group represented by —N(RaRb) are each optionally and independently substituted with one or more groups represented by R$^{\#}$. Preferably Ra-Rd are unsubstituted.

R$^{\#}$ is halogen, R$^+$, —OR$^+$, —SR$^+$, —NO$_2$, —CN, —N(R$^+$)$_2$, —COR$^+$, —COOR$^+$, —NHCO$_2$R$^+$, —NHC(O)R$^+$, —NHNHC(O)R$^+$, —NHC(O)N(R$^+$)$_2$, —NHNHC(O)N(R$^+$)$_2$, —NHNHCO$_2$R$^+$, —C(O)N(R$^+$)$_2$, —OC(O)R$^+$, —OC(O)N(R$^+$)$_2$, —S(O)$_2$R$^+$, —SO$_2$N(R$^+$)$_2$, —S(O)R$^+$, —NHSO$_2$N(R)$_2$, —NHSO$_2$R$^+$, —C(=S)N(R$^+$)$_2$, or —C(=NH)—N(R$^+$)$_2$.

R$^+$ is —H, a C$_1$-C$_4$ alkyl group, a monocyclic aryl group, a non-aromatic carbocyclic or heterocyclic group each optionally substituted with alkyl, haloalkyl, alkoxy, haloalkoxy, halo, —CN, —NO$_2$, amine, alkylamine or dialkylamine Preferably R+ is unsubstituted.

An aliphatic or a non-aromatic heterocyclic or carbocyclic group as used herein may contain one or more substituents. Examples of suitable substituents for an aliphatic group or a ring carbon of a non-aromatic heterocyclic group is R". R" include those substituents listed above for R' and =O, =S, =NNHR, =NN(R)$_2$, =NNHC(O)R, =NNHCO2 (alkyl), =NNHSO2 (alkyl), =NR, spiro cycloalkyl group or fused cycloalkyl group. Each R is independently selected from hydrogen, an unsubstituted alkyl group or a substituted alkyl group. Examples of substituents on the alkyl group represented by R include amino, alkylamino, dialkylamino, aminocarbonyl, halogen, alkyl, alkylaminocarbonyl, dialkylaminocarbonyl, alkylaminocarbonyloxy, dialkylaminocarbonyloxy, alkoxy, nitro, cyano, carboxy, alkoxycarbonyl, alkylcarbonyl, hydroxy, haloalkoxy, or haloalkyl.

When a heterocyclyl, heteroaryl, or heteroaralkyl group contains a nitrogen atom, it may be substituted or unsubstituted. When a nitrogen atom in the aromatic ring of a heteroaryl group has a substituent the nitrogen may be a quaternary nitrogen.

A preferred position for substitution of a non-aromatic nitrogen-containing heterocyclic group is the nitrogen ring atom. Suitable substituents on the nitrogen of a non-aromatic heterocyclic group or heteroaryl group include —R^, —N(R^)$_2$, C(O)R^, CO$_2$R^, —C(O)C(O)R^, —SO$_2$R^, SO$_2$N(R^)$_2$, C(=S)N(R^)$_2$, C(=NH)—N(R^)$_2$, and —NR^SO$_2$R^; wherein R^ is hydrogen, an aliphatic group, a substituted aliphatic group, aryl, substituted aryl, heterocyclic or carbocyclic ring or a substituted heterocyclic or carbocyclic ring. Examples of substituents on the group represented by R^ include alkyl, haloalkoxy, haloalkyl, alkoxyalkyl, sulfonyl, alkylsulfonyl, halogen, nitro, cyano, hydroxy, aryl, carbocyclic or heterocyclic ring, oxo, amino, alkylamino, dialkylamino, aminocarbonyl, alkylaminocarbonyl, dialkylaminocarbonyloxy, alkoxy, carboxy, alkoxycarbonyl, or alkylcarbonyl. Preferably R^ is not substituted.

Non-aromatic nitrogen containing heterocyclic rings that are substituted on a ring nitrogen and attached to the remainder of the molecule at a ring carbon atom are said to be N substituted. For example, an N alkyl piperidinyl group is attached to the remainder of the molecule at the two, three or four position of the piperidinyl ring and substituted at the ring nitrogen with an alkyl group. Non-aromatic nitrogen containing heterocyclic rings such as pyrazinyl that are substituted on a ring nitrogen and attached to the remainder of the molecule at a second ring nitrogen atom are said to be N' substituted-N-heterocycles. For example, an N' acyl N-pyrazinyl group is attached to the remainder of the molecule at one ring nitrogen atom and substituted at the second ring nitrogen atom with an acyl group.

As used herein an optionally substituted aralkyl can be substituted on both the alkyl and the aryl portion. Unless otherwise indicated as used herein optionally substituted aralkyl is optionally substituted on the aryl portion.

The terms "a bond" and "absent" are used interchangeably to indicate that a group is absent.

The compounds of the invention are defined herein by their chemical structures and/or chemical names. Where a compound is referred to by both a chemical structure and a chemical name, and the chemical structure and chemical name conflict, the chemical structure is determinative of the compound's identity.

The compounds of this invention can exist in free form for treatment, or where appropriate, as a pharmaceutically acceptable salt.

Pharmaceutically Acceptable Salts

As used herein, the term "pharmaceutically acceptable salt" refers to salts of a compound which are, within the scope of sound medical judgment, suitable for use in contact with the tissues of humans and lower animals without undue side effects, such as, toxicity, irritation, allergic response and the like, and are commensurate with a reasonable benefit/risk ratio.

Pharmaceutically acceptable salts are well known in the art. For example, S. M. Berge et al., describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. These salts can be prepared in situ during the final isolation and purification of the compounds. Acid addition salts can be prepared by 1) reacting the purified compound in its free-based form with a suitable organic or inorganic acid and 2) isolating the salt thus formed.

Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, glycolate, gluconate, glycolate, hemisulfate, heptanoate, hexanoate, hydrochloride, hydrobromide, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, palmoate, pectinate, persulfate, 3-phenylpropionate, phosphate, picrate, pivalate, propionate, salicylate, stearate, succinate, sulfate, tartrate, thiocyanate, p-toluenesulfonate, undecanoate, valerate salts, and the like.

Base addition salts can be prepared by 1) reacting the purified compound in its acid form with a suitable organic or inorganic base and 2) isolating the salt thus formed. Salts derived from appropriate bases include alkali metal (e.g., sodium, lithium, and potassium), alkaline earth metal (e.g., magnesium and calcium), ammonium and $N^+(C_{1-4}alkyl)_4$ salts. This invention also envisions the quaternization of any basic nitrogen-containing groups of the compounds disclosed herein. Water or oil-soluble or dispersible products may be obtained by such quaternization.

Further pharmaceutically acceptable salts include, when appropriate, nontoxic ammonium, quaternary ammonium, and amine cations formed using counterions such as halide, hydroxide, carboxylate, sulfate, phosphate, nitrate, lower-alkyl sulfonate and aryl sulfonate. Other acids and bases, while not in themselves pharmaceutically acceptable, may be employed in the preparation of salts useful as intermediates in obtaining the compounds of the invention and their pharmaceutically acceptable acid or base addition salts.

It should be understood that this invention includes mixtures/combinations of different pharmaceutically acceptable salts and also mixtures/combinations of compounds in free form and pharmaceutically acceptable salts.

In addition to the compounds of this invention, pharmaceutically acceptable derivatives or prodrugs of the compounds of this invention may also be employed in compositions to treat or prevent the herein identified disorders. As used herein and unless otherwise indicated, the term "prodrug" means a derivative of a compound that can hydrolyze, oxidize, or otherwise react under biological conditions (in vitro or in vivo) to provide a compound of this invention. Prodrugs may become active upon such reaction under biological conditions, or they may have activity in their unreacted forms. Examples of prodrugs contemplated in this invention include, but are not limited to, analogs or derivatives of compounds of the invention that comprise biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Other examples of prodrugs include derivatives of compounds of the invention that comprise —NO, —$NO_2$, —ONO, or —$ONO_2$ moieties. Prodrugs can typically be prepared using well-known methods, such as those described by BURGER'S MEDICINAL CHEMISTRY AND DRUG DISCOVERY (1995) 172-178, 949-982 (Manfred E. Wolff ed., 5th ed).

A "pharmaceutically acceptable derivative" is an adduct or derivative which, upon administration to a patient in need, is capable of providing, directly or indirectly, a compound as otherwise described herein, or a metabolite or residue thereof. Examples of pharmaceutically acceptable derivatives include, but are not limited to, esters and salts of such esters.

A "pharmaceutically acceptable derivative or prodrug" includes any pharmaceutically acceptable ester, salt of an ester or other derivative or salt thereof of a compound, of this invention which, upon administration to a recipient, is capable of providing, either directly or indirectly, a compound of this invention or an inhibitorily active metabolite or residue thereof. Particularly favoured derivatives or prodrugs are those that increase the bioavailability of the compounds of this invention when such compounds are administered to a patient (e.g., by allowing an orally administered compound to be more readily absorbed into the blood) or which enhance delivery of the parent compound to a biological compartment (e.g., the brain or lymphatic system) relative to the parent species.

Pharmaceutically acceptable prodrugs of the compounds of this invention include, without limitation, esters, amino acid esters, phosphate esters, metal salts and sulfonate esters.

As used herein, the phrase "side effects" encompasses unwanted and adverse effects of a therapy (e.g., a prophylactic or therapeutic agent). Side effects are always unwanted, but unwanted effects are not necessarily adverse. An adverse effect from a therapy (e.g., prophylactic or therapeutic agent) might be harmful or uncomfortable or risky. Side effects include, but are not limited to fever, chills, lethargy, gastrointestinal toxicities (including gastric and intestinal ulcerations and erosions), nausea, vomiting, neurotoxicities, nephrotoxicities, renal toxicities (including such conditions as papillary necrosis and chronic interstitial nephritis), hepatic toxicities (including elevated serum liver enzyme levels), myelotoxicities (including leukopenia, myelosuppression, thrombocytopenia and anemia), dry mouth, metallic taste, prolongation of gestation, weakness, somnolence, pain (including muscle pain, bone pain and headache), hair loss, asthenia, dizziness, extra-pyramidal symptoms, akathisia, cardiovascular disturbances and sexual dysfunction.

In one embodiment the present invention is a pharmaceutical composition comprising a compound of the present invention and a pharmaceutically acceptable carrier, diluent, adjuvant or vehicle. In one embodiment the present invention is a pharmaceutical composition comprising an effective amount of compound of the present invention and a pharmaceutically acceptable carrier, diluent, adjuvant or vehicle. Pharmaceutically acceptable carriers include, for example, pharmaceutical diluents, excipients or carriers suitably selected with respect to the intended form of administration, and consistent with conventional pharmaceutical practices.

A pharmaceutically acceptable carrier may contain inert ingredients which do not unduly inhibit the biological activity of the compounds. The pharmaceutically acceptable carriers should be biocompatible, e.g., non-toxic, non-inflammatory, non-immunogenic or devoid of other undesired reactions or side-effects upon the administration to a subject. Standard pharmaceutical formulation techniques can be employed.

The pharmaceutically acceptable carrier, adjuvant, or vehicle, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention.

Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The compounds of present invention or pharmaceutical salts thereof may be formulated into pharmaceutical compositions for administration to a subject as defined herein. These pharmaceutical compositions, which comprise an amount of the compounds effective to treat or prevent a bacteria infection, such as IBD, and a pharmaceutically acceptable carrier, are another embodiment of the present invention.

In one embodiment the present invention is a method of treating or preventing a bacteria infection, such as IBD, in a subject in need thereof, comprising administering to the subject an effective amount of a compound or composition of the present invention.

As used herein, the terms "subject", "patient" and "mammal" are used interchangeably. The terms "subject" and "patient" refer to an animal (e.g., a bird such as a chicken, quail or turkey, or a mammal), preferably a mammal including a non-primate (e.g., a cow, pig, horse, sheep, rabbit, guinea pig, rat, cat, dog, and mouse) and a primate (e.g., a monkey, chimpanzee and a human), and more preferably a human. In one embodiment, the subject is a non-human animal such as a farm animal (e.g., a horse, cow, pig or sheep), or a pet (e.g., a dog, cat, guinea pig or rabbit). In a preferred embodiment, the subject is a human.

As used herein, an "effective amount" refers to an amount sufficient to elicit the desired biological response. In the present invention the desired biological response is to reduce or ameliorate the severity, duration, progression, or onset of a bacteria infection, prevent the advancement of a bacteria infection, cause the regression of a bacteria infection, prevent the recurrence, development, onset or progression of a symptom associated with a bacteria infection, or enhance or improve the prophylactic or therapeutic effect(s) of another therapy. The precise amount of compound administered to a subject will depend on the mode of administration, the type and severity of the disease or condition and on the characteristics of the subject, such as general health, age, sex, body weight and tolerance to drugs. It will also depend on the degree, severity and type of bacteria infection, and the mode of administration. The skilled artisan will be able to determine appropriate dosages depending on these and other factors. When co-administered with other agents, e.g., when co-administered with a bacteria infection agent, an "effective amount" of the second agent will depend on the type of drug used. Suitable dosages are known for approved agents and can be adjusted by the skilled artisan according to the condition of the subject, the type of condition(s) being treated and the amount of a compound of the invention being used. In cases where no amount is expressly noted, an effective amount should be assumed.

As used herein, the terms "treat", "treatment" and "treating" refer to the reduction or amelioration of the progression, severity and/or duration of a bacteria infection, or the amelioration of one or more symptoms (preferably, one or more discernible symptoms) of a bacteria infection resulting from the administration of one or more therapies (e.g., one or more therapeutic agents such as a compound of the invention). In specific embodiments, the terms "treat", "treatment" and "treating" refer to the amelioration of at least one measurable physical parameter of a bacteria infection. In other embodiments the terms "treat", "treatment" and "treating" refer to the inhibition of the progression of a bacteria infection, either physically by, e.g., stabilization of a discernible symptom, physiologically by, e.g., stabilization of a physical parameter, or both. In other embodiments the terms "treat", "treatment" and "treating" refer to the reduction or stabilization of a bacteria infection.

As used herein, the terms "prevent", "prevention" and "preventing" refer to the reduction in the risk of acquiring or developing a given bacteria infection, or the reduction or inhibition of the recurrence or a bacteria infection. In one embodiment, a compound of the invention is administered as a preventative measure to a patient, preferably a human, having a genetic predisposition to any of the conditions, diseases or disorders described herein.

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in microencapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

The compositions of the present invention may be administered orally, parenterally, by inhalation spray, topically, rectally, nasally, buccally, vaginally or via an implanted reservoir. The term "parenteral" as used herein includes, but is not limited to, subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutical compositions of this invention may be orally administered in any orally acceptable dosage form including, but not limited to, capsules, tablets, aqueous suspensions or solutions. In the case of tablets for oral use, carriers commonly used include, but are not limited to, lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be administered in the form of suppositories for rectal administration. These can be prepared by mixing the agent with a suitable non-irritating excipient which is solid at room temperature but liquid at rectal temperature and therefore will melt in the rectum to release the drug. Such materials include, but are not limited to, cocoa butter, beeswax and polyethylene glycols.

The pharmaceutical compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2 octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents. The dosage regimen utilizing the compounds of present invention can be selected in accordance with a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the renal and hepatic function of the subject; and the particular compound or salt thereof employed, the duration of the treatment; drugs used in combination or coincidental with the specific compound employed, and like factors well known in the medical arts. The skilled artisan can readily determine and prescribe the effective amount of the compound of present invention required to treat, for example, to prevent, inhibit (fully or partially) or arrest the progress of the disease.

Dosages of the compounds of present invention can range from between about 0.01 to about 100 mg/kg body weight/day, about 0.01 to about 50 mg/kg body weight/day, about 0.1 to about 50 mg/kg body weight/day, or about 1 to about 25 mg/kg body weight/day. It is understood that the total amount per day can be administered in a single dose or can be administered in multiple dosings such as twice, three or four times per day.

The compounds for use in the method of the invention can be formulated in unit dosage form. The term "unit dosage form" refers to physically discrete units suitable as unitary dosage for subjects undergoing treatment, with each unit containing a predetermined quantity of active material calculated to produce the desired therapeutic effect, optionally in association with a suitable pharmaceutical carrier. The unit dosage form can be for a single daily dose or one of multiple daily doses (e.g., about 1 to 4 or more times per day). When multiple daily doses are used, the unit dosage form can be the same or different for each dose.

An effective amount can be achieved in the method or pharmaceutical composition of the invention employing a compound of present invention or a pharmaceutically acceptable salt thereof alone or in combination with an additional suitable therapeutic agent, for example, a cancer-therapeutic agent. When combination therapy is employed, an effective amount can be achieved using a first amount of a compound of present invention or a pharmaceutically acceptable salt thereof and a second amount of an additional suitable therapeutic agent.

In one embodiment, the compound of present invention and the additional therapeutic agent, are each administered in an effective amount (i.e., each in an amount which would be therapeutically effective if administered alone). In another embodiment, the compound of present invention and the additional therapeutic agent, are each administered in an amount which alone does not provide a therapeutic effect (a sub-therapeutic dose). In yet another embodiment, the compound of present invention can be administered in an effective amount, while the additional therapeutic agent is administered in a sub-therapeutic dose. In still another embodiment, the compound of present invention can be administered in a sub-therapeutic dose, while the additional therapeutic agent, for example, a suitable cancer-therapeutic agent is administered in an effective amount.

As used herein, the terms "in combination" or "coadministration" can be used interchangeably to refer to the use of more than one therapies (e.g., one or more prophylactic and/or therapeutic agents). The use of the terms does not restrict the order in which therapies (e.g., prophylactic and/or therapeutic agents) are administered to a subject. Coadministration encompasses administration of the first and second amounts of the compounds of the coadministration in an essentially simultaneous manner, such as in a single pharmaceutical composition, for example, capsule or tablet having a fixed ratio of first and second amounts, or in multiple, separate capsules or tablets for each. In addition, such coadministration also encompasses use of each compound in a sequential manner in either order.

When coadministration involves the separate administration of the first amount of a compound of present invention and a second amount of an additional therapeutic agent, the compounds are administered sufficiently close in time to have the desired therapeutic effect. For example, the period of time between each administration which can result in the desired therapeutic effect, can range from minutes to hours and can be determined taking into account the properties of each compound such as potency, solubility, bioavailability, plasma half-life and kinetic profile. For example, a compound of present invention and the second therapeutic agent can be administered in any order within about 24 hours of each other, within about 16 hours of each other, within about 8 hours of each other, within about 4 hours of each other, within about 1 hour of each other or within about 30 minutes of each other.

More, specifically, a first therapy (e.g., a prophylactic or therapeutic agent such as a compound of the invention) can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy (e.g., a prophylactic or therapeutic agent such as an anti-cancer agent) to a subject.

It is understood that the method of coadministration of a first amount of a compound of present invention and a second amount of an additional therapeutic agent can result in an enhanced or synergistic therapeutic effect, wherein the combined effect is greater than the additive effect that would result from separate administration of the first amount of the compound of present invention and the second amount of the additional therapeutic agent.

As used herein, the term "synergistic" refers to a combination of a compound of the invention and another therapy (e.g., a prophylactic or therapeutic agent), which is more effective than the additive effects of the therapies. A synergistic effect of a combination of therapies (e.g., a combination of prophylactic or therapeutic agents) permits the use of lower dosages of one or more of the therapies and/or less frequent administration of said therapies to a subject. The ability to utilize lower dosages of a therapy (e.g., a prophylactic or therapeutic agent) and/or to administer said therapy less frequently reduces the toxicity associated with the administration of said therapy to a subject without reducing the efficacy of said therapy in the prevention, management or treatment of a disorder. In addition, a synergistic effect can result in improved efficacy of agents in the prevention, management or treatment of a disorder. Finally, a synergistic effect of a combination of therapies (e.g., a combination of prophylactic or therapeutic agents) may avoid or reduce adverse or unwanted side effects associated with the use of either therapy alone.

The presence of a synergistic effect can be determined using suitable methods for assessing drug interaction. Suitable methods include, for example, the Sigmoid-Emax equation (Holford, N. H. G. and Scheiner, L. B., Clin. Pharmacokinet. 6: 429-453 (1981)), the equation of Loewe additivity (Loewe, S, and Muischnek, H., Arch. Exp. Pathol Pharmacol. 114: 313-326 (1926)) and the median-effect equation (Chou, T. C. and Talalay, P., Adv. Enzyme Regul.

22: 27-55 (1984)). Each equation referred to above can be applied with experimental data to generate a corresponding graph to aid in assessing the effects of the drug combination. The corresponding graphs associated with the equations referred to above are the concentration-effect curve, isobologram curve and combination index curve, respectively.

The activity of the compounds as inhibitors of bacteria infection may be assayed in vitro or in vivo. In vitro assays include assays that determine inhibition of the FimH activity. Alternate in vitro assays quantitate the ability of the inhibitor to bind to the FimH and may be measured either by radiolabelling the inhibitor prior to binding, isolating the inhibitor complex and determining the amount of radiolabel bound, or by running a competition experiment where new inhibitors are incubated with the FimH bound to known radioligands. Detailed conditions for assaying a compound utilized in this invention are set forth in the Examples below.

EXPERIMENTAL DETAILS

The following abbreviations are used in the examples below:
AcOH acetic acid
$Ac_2O$ acetic anhydride
aq aqueous
$BF_3.OEt_2$ diethyloxonio-trifluoro-boron
$CH_3CN$ acetonitrile
$CCl_3CN$ trichloroacetonitrile
$CDCl_3$ chloroform-D
conc concentrate
CV column volume
$Cs_2CO_3$ cesium carbonate
$Cu(OAc)_2$ diacetoxycopper
$CH_2Cl_2$ methylene chloride or dichloromethane
DMAP 4-dimethylaminopyridine
DMF dimethylformamide
DMSO dimethylsulfoxide
Eq. equivalent
EtOAc ethyl acetate
h hour
Hex hexanes
$LiOH.H_2O$ lithium hydroxide monohydrate
M molar
MeOH methanol
NaOMe sodium methoxide
Min minute
MS 4 Å molecular sieves 4 angstrom
MTBE methyl tert-butyl ether
$Na_2SO_4$ sodium sulfate
NMO N-methylmorpholine-N-oxide
$OsO_4$ osmium tetroxide
$PdCl_2$ palladium (II)chloride
$Pd(OAc)_2$ palladium (II)acetate
$PdCl_2(dppf).CH_2Cl_2$ (1,1'-Bis-(diphenylphosphino)-ferrocene)palladium (II) dichloride
$Pd(OH)_2$ dihydroxy palladium
$Pd(PPh_3)_4$ tetrakis(triphenylphosphine) palladium
Pyr pyridine
RT room temperature
Siliacat DPP-Pd Silica supported diphenylphosphine palladium
TBABr tetrabutyl ammonium bromide
TEA triethylamine
THF tetrahydrofuran
TLC thin layer chromatography
TMSOTf trimethylsilyl trifluoromethanesulfonate The compounds of this invention may be prepared in light of the specification using steps generally known to those of ordinary skill in the art. Those compounds may be analyzed by known methods, including but not limited to LC-MS (liquid chromatography mass spectrometry), HPLC (high performance liquid chromatography) and NMR (nuclear magnetic resonance). It should be understood that the specific conditions shown below are only examples, and are not meant to limit the scope of the conditions that can be used for making compounds of this invention. Instead, this invention also includes conditions that would be apparent to those skilled in that art in light of this specification for making the compounds of this invention. Unless otherwise indicated, all variables in the following schemes are as defined herein.

Mass spec. samples are analyzed on a Waters UPLC Acquity mass spectrometer operated in single MS mode with electrospray ionization. Samples are introduced into the mass spectrometer using chromatography. Mobile phase for the mass spec. analyses consisted of 0.1% formic acid and acetonitrile-water mixture. Column gradient conditions are 5%-85% acetonitrile-water over 6 minutes run time Acquity HSS T3 1.8 um 2.1 mm ID×50 mm. Flow rate is 1.0 mL/min. As used herein, the term "Rt(min)" refers to the LC-MS retention time, in minutes, associated with the compound. Unless otherwise indicated, the LC-MS method utilized to obtain the reported retention time is as detailed above.

Purification by reverse phase HPLC is carried out under standard conditions using either Phenomenex Gemini 21.2 mm ID×250 mm column (5 µm), Gemini 21.2 mm ID×75 mm column, (5 µm), 110 Å or in most cases a Waters XSELECT CSH Prep C18 (5 µm) ODB 19×100 mm column. Elution is performed using a linear gradient $CH_3CN$—$H_2O$ (with or without 0.01% TFA buffer or 0.1% HCOH) as mobile phase. Solvent system is tailored according to the polarity of the compound, Flow rate, 20 mL/min. Compounds are collected either by UV or Waters 3100 Mass Detector, ESI Positive Mode. Fractions containing the desired compound are combined, concentrated (rotary evaporator) to remove excess $CH_3CN$ and the resulting aqueous solution is lyophilized to afford the desired material in most cases as a white foam.

HPLC analytical method is performed on Phenomenex Gemini C18 3 um 110 Å 4 6 mm ID×250 mm, Phenomenex Gemini C18 3 um 110 Å 4 6 mm ID×50 mm, using different combinations of $CH_3CN$—$H_2O$ (0.01% TFA as buffer) as mobile phase, Flow rate, 1 mL/min, PDA 210 nm. Method A: Phenomenex Gemini C18 3 um 110 Å 4 6 mm ID×250 mm; (10-50% acetonitrile-water for 40 min, 0.01% TFA). Method B: Phenomenex Gemini C18 3 um 110 Å 4.6 mm ID×250 mm; (50-90% acetonitrile-water for 40 min, 0.01% TFA). Method C: Phenomenex Gemini C18 3 um 110 Å 4 6 mm ID×50 mm; (20-60% acetonitrile-water for 10 min, 0.01% TFA). Method D: Phenomenex Gemini C18 3 um 110 Å 4 6 mm ID×50 mm; (10-50% acetonitrile-water for 10 min, 0.01% TFA).

General Methods of Synthesis: Examples Described Therein are Prepared According to the Following General Methods
Method 1: Preparation of biaryl Intermediates of type III Biaryl intermediates of type III are prepared (Scheme 1) by palladium catalyzed cross-coupling between arylboronic acid or aryl-pinacol boronate of type I (commercially available of prepared from the corresponding halide) and aryl-halides of type II. Alternatively, the coupling partners are the arylboronic acid or aryl-pinacol boronate of Type IV (commercially available of prepared from the corresponding halide) and aryl-halides of type V.

Scheme 1

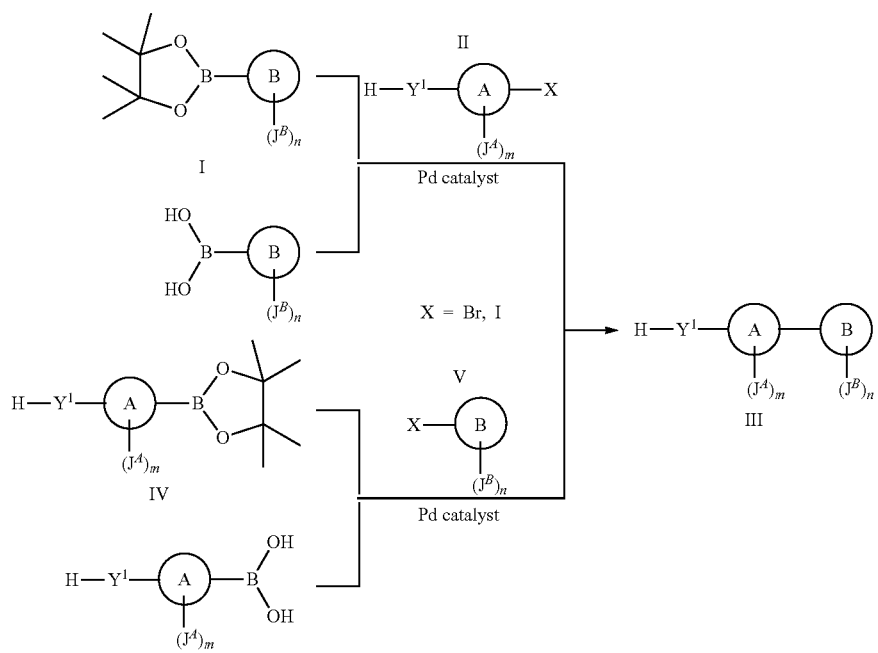

Method 2: Synthesis of Examples of Formula A and C

Compounds of Formula A and C can be prepared in a two steps synthetic sequence (Scheme 2). Glycosylation of biaryls of type III can be achieved by three distinct synthetic routes (Scheme 2). Firstly, activation of the anomeric O-acetyl derivative of type VI by Lewis acid ($BF_3OEt_2$) in presence of the biaryl of type III gives the protected (PG is Ac) mannoside of type VII. Alternatively, glycosylation of biaryls of type III can be achieved by activation of the trichloroimidate of type VIII with trimethylsilyl triflate. Lastly, activation of the anomeric fluoride of type IX with mercuric bromide in presence of biaryls type III can afford the fully protected mannosides of type VII. Finally, protective group removal (saponification for acetate and hydrogenolysis for benzyl ether) on VII will generate the desired mannosides of type X.

Scheme 2

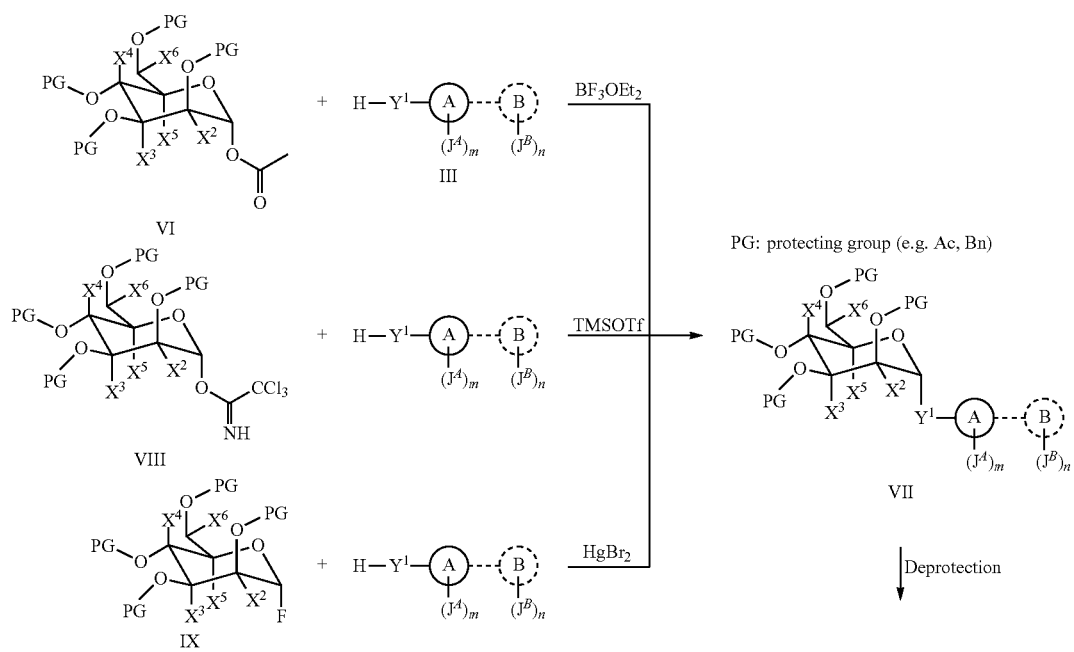

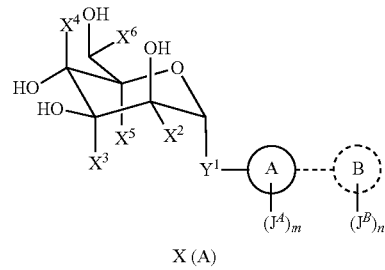

X (A)

Method 3: Synthesis of Examples of Formula A and C

Alternatively, mannosides of Formula A and C can be prepared in a three steps synthetic sequence (Scheme 3). Glycosylation of II in conditions previously described in Method 2 can generate intermediates of type XI which can be submitted to a palladium catalyzed cross coupling with I to generate fully protected mannosides of type VII. Deprotection in condition previously described generates the desired mannoside of type X.

Scheme 3

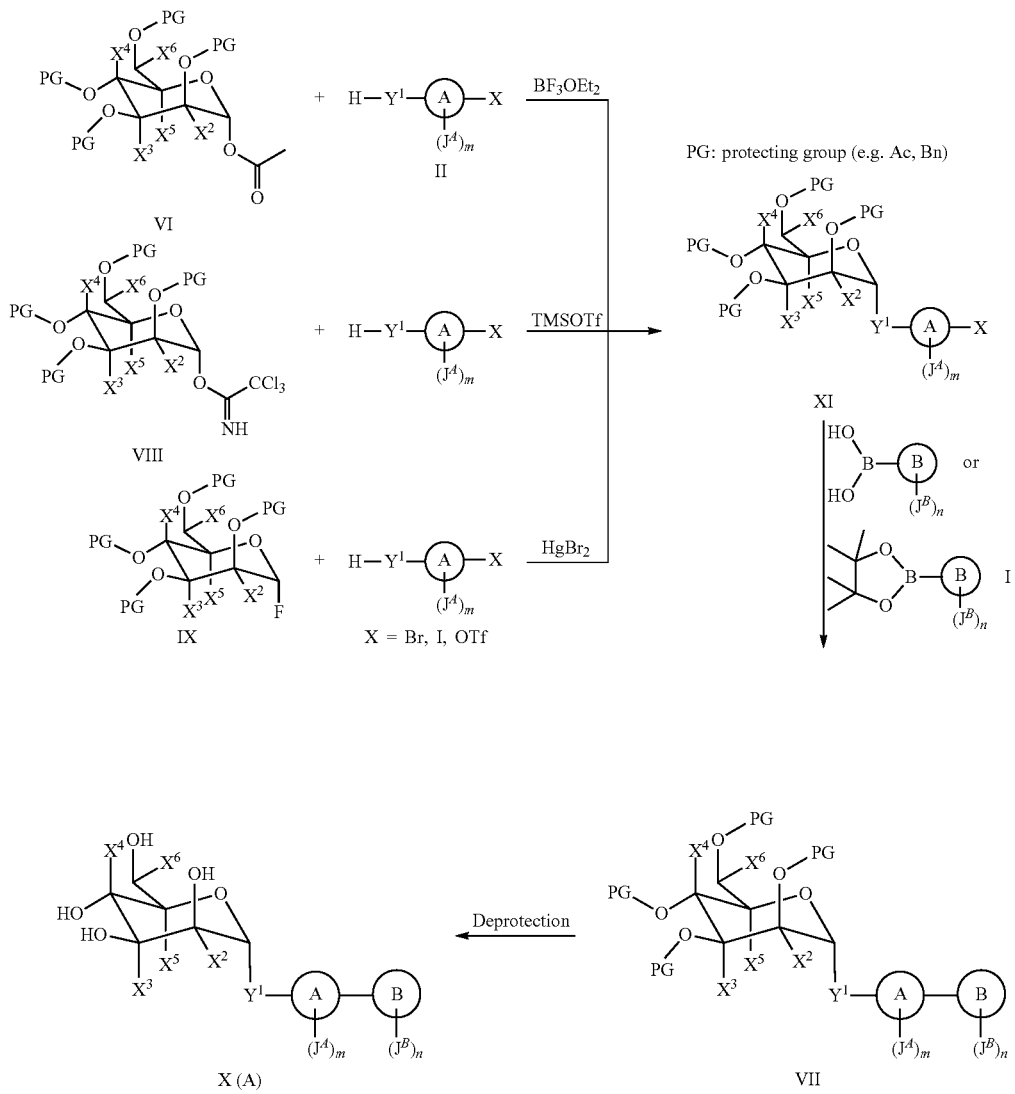

Method 4: Synthesis of Examples of Formula A and C

Alternatively, mannosides of type XI can be converted to their corresponding pinacol boronate XII followed by a palladium catalyzed cross coupling with aryl bromides of type V to generate previously described mannosides VII (Scheme 4).

Method 5: Synthesis of Examples of Formula D

Mannosides of Formula D can be prepared in a two steps sequence (Scheme 5). Lewis acid (e.g. BF$_3$OEt$_2$) promoted addition of phenols of type XIII on (E)-2-((3S,4S,5R,6R)-3,4,5-tris(benzyloxy)-6-((benzyloxy)methyl)tetrahydro-2H-pyran-2-ylidene)ethyl acetate affords the spiro-mannoside XIV (see *Tetrahedron*, 2010, 66, 5229-5234). Finally, hydrogenolysis of the benzyl protective groups generates the desired mannosides of type XV.

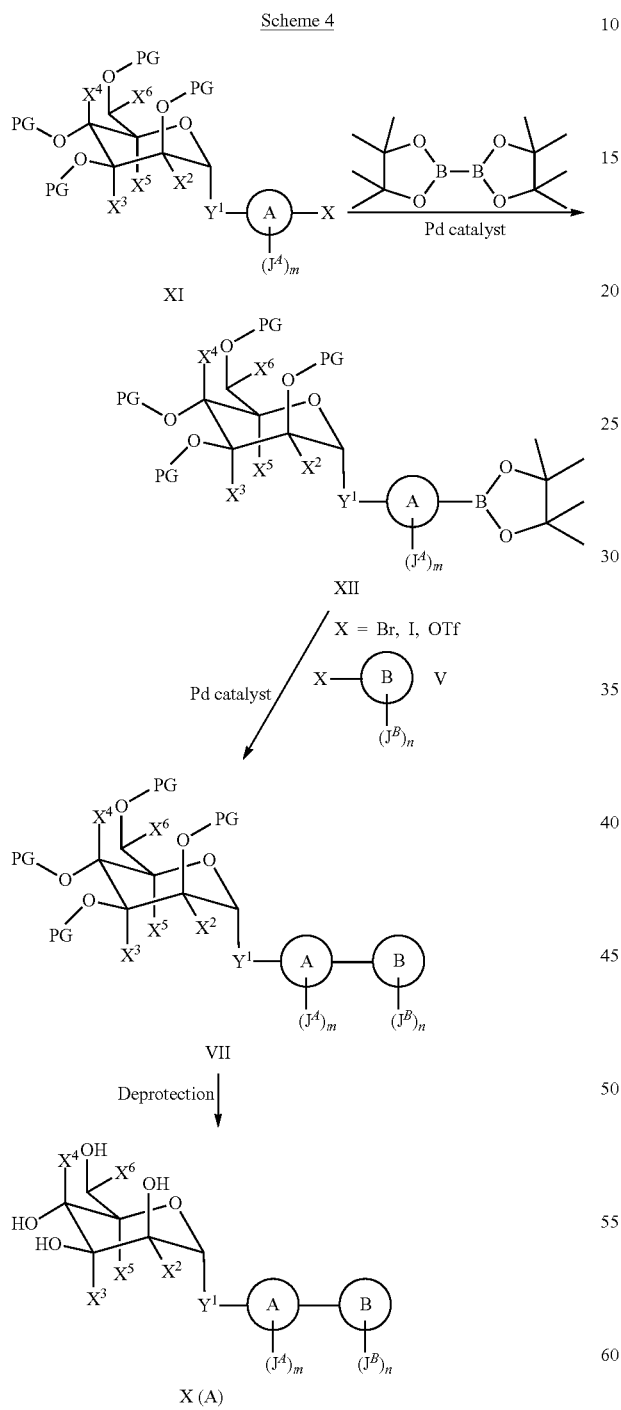

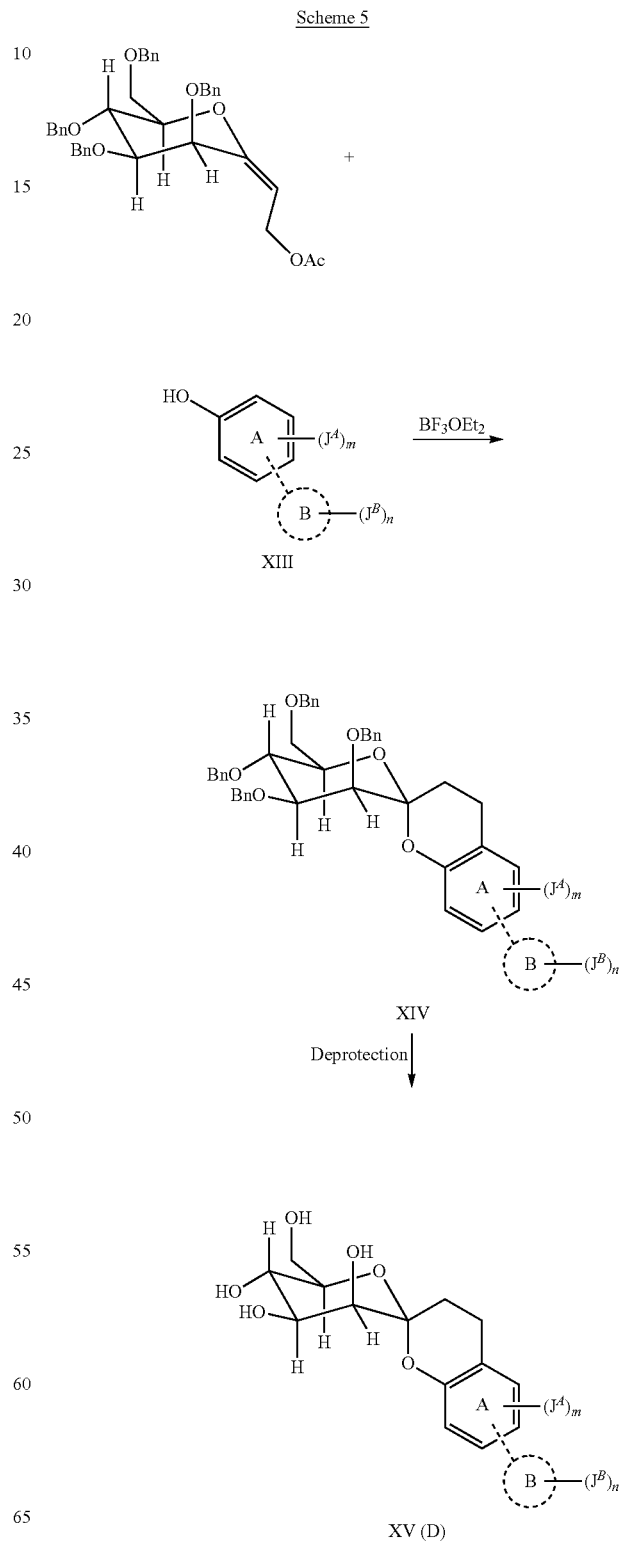

Method 6: Synthesis of Examples of Formula B

Mannosides of Formula B can be prepared in a two steps synthetic sequence (Scheme 6). Trimethylsilyl triflate promoted addition of alcohols of type XVII onto mannosides of type XVI generates the α-O-mannosides of type XVIII. Hydrogenolysis of the latter generates the desire mannosides XIX.

Method 7: Synthesis of Examples of Formula E

Bis-mannosides of Formula E can be prepared in three parallel synthetic route involving two steps each. First, palladium catalyzed coupling between the pinacole boronate XII and the halogenated aryl XX provides the fully protected bis-mannoside XXI. Removal of protective groups of XXI generates the desired bis-mannoside XXII. Alternatively, halogenated aryl XI and XX can be coupled directly under palladium catalysis (see *J. Org. Chem.* 2003, 68, 3938-3942 when X=Br and *J. Org. Chem.* 2012, 77, 2971-2977 when X=I). Finally, double glycosidation of bis-phenol of type XXIII by activation of the anomeric O-acetyl derivative of type VI by a Lewis acid (e.g. BF$_3$OEt$_2$) can also provide the desired fully protected bis-mannoside XXI.

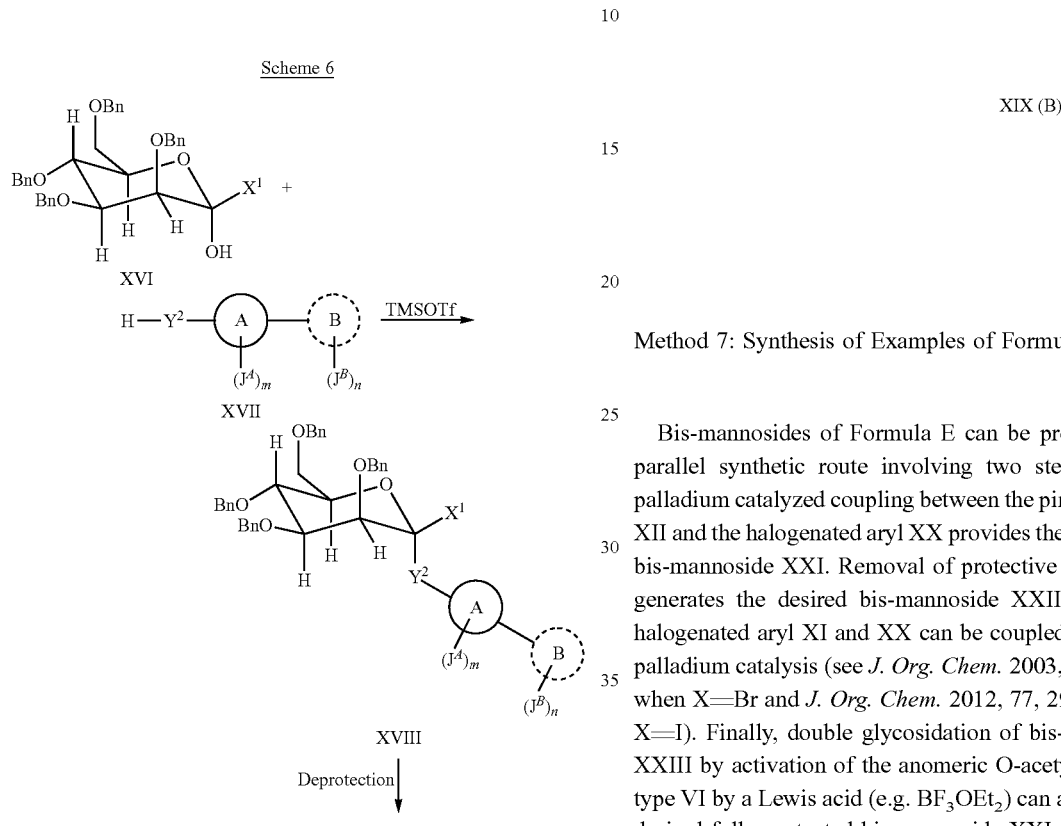

Scheme 6

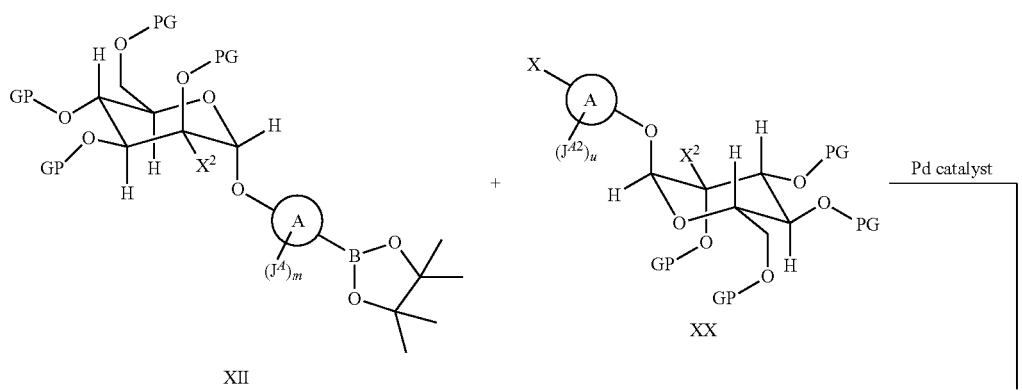

Scheme 7

-continued

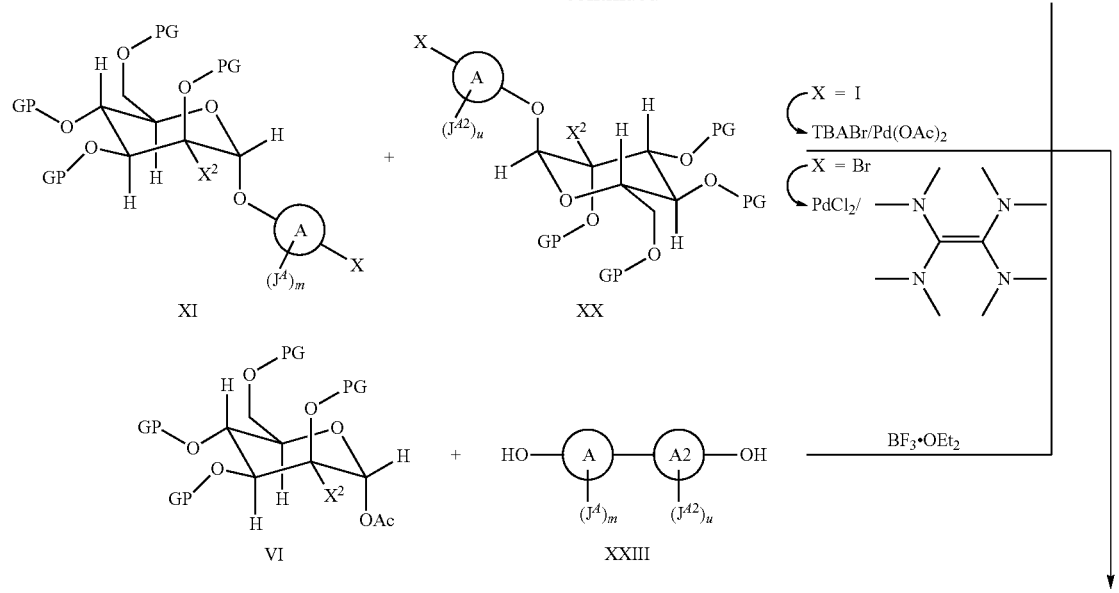

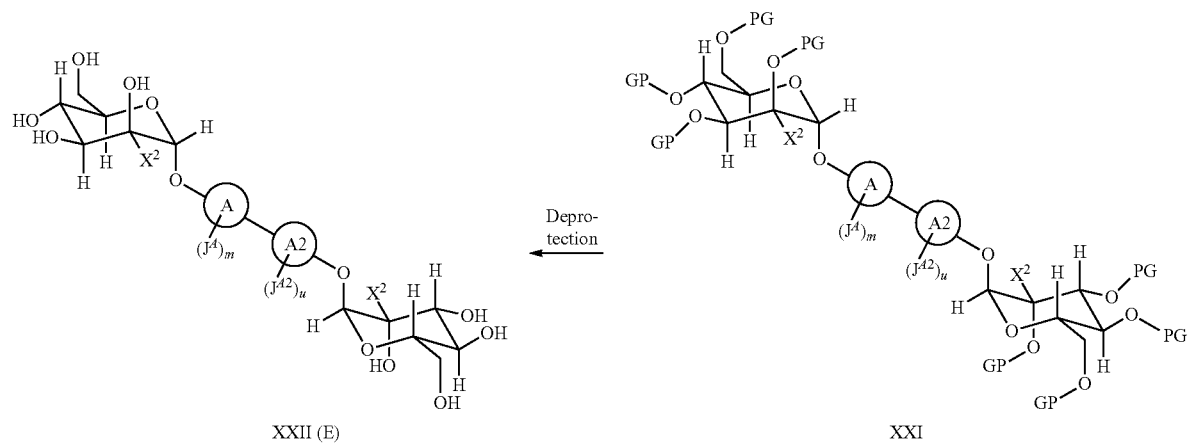

Method 8: Synthesis of Examples of Formula F

Bis-mannosides of Formula F can be prepared in two steps via a double palladium catalyzed cross coupling between the pinacol boronate XII and a bis-halogenated aryl or heteroaryl. The resulting bis-mannoside XXIV can subsequently be deprotected under standard conditions to afford the desire bis-mannoside XXV.

Scheme 8

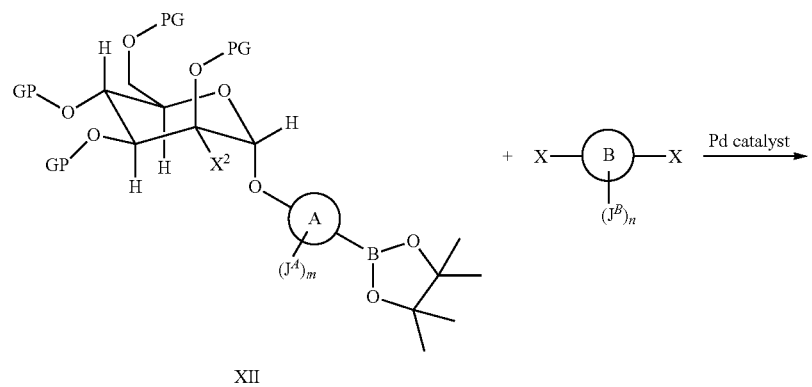

-continued
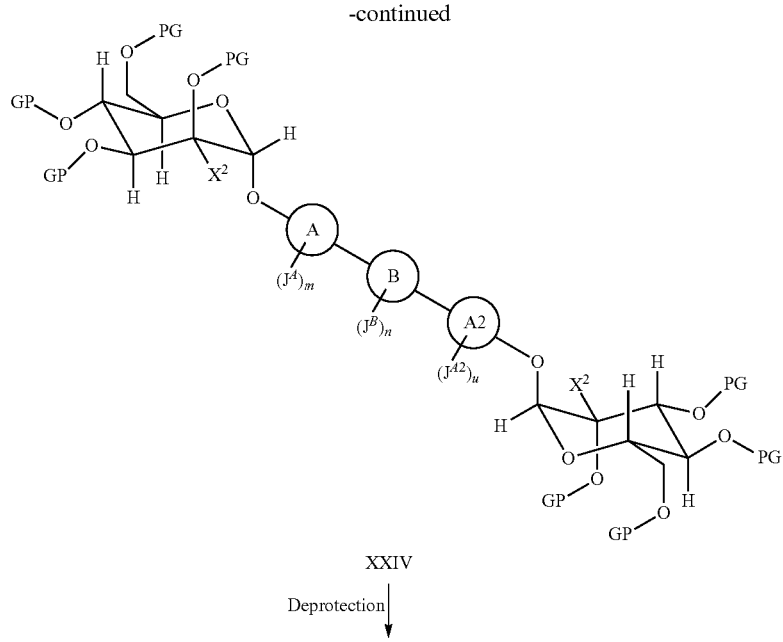
XXIV
Deprotection ↓
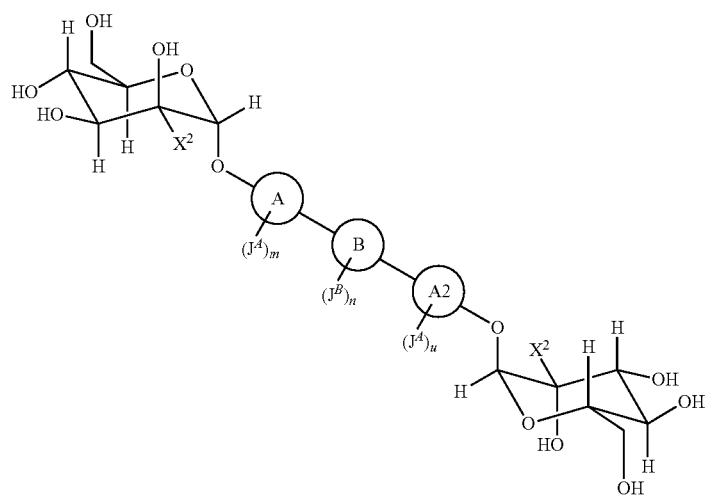
XXV (F)
X is halo and PG is a suitable hydroxyl protecting group.

Method 9: Synthesis of Examples of Formula G

Mannosides of Formula G can be prepared in one step via a double palladium/copper catalyzed Sonogashira coupling between the aryl bromide XXVI, obtained from removal of protective groups on XI, and TMS-acetylene.

Scheme 9

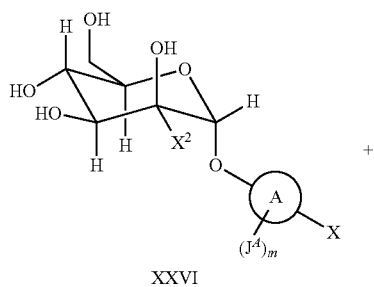

XXVI

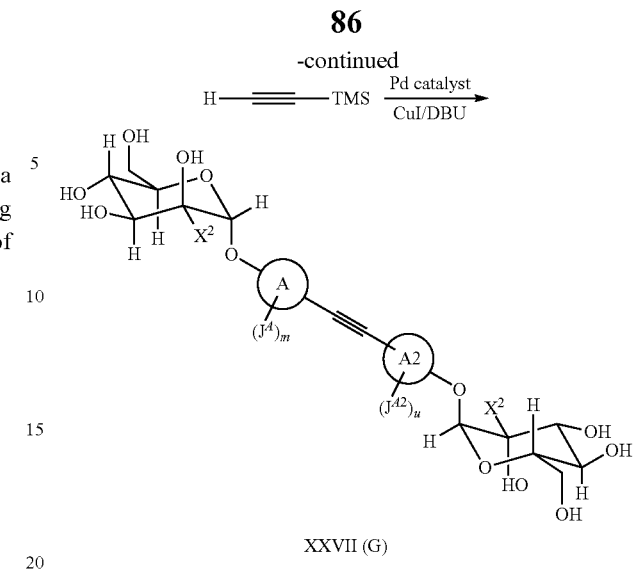

XXVII (G)

Method 10: Synthesis of Examples of Formula H

Compounds of Formula H can be prepared in two steps. Firstly, palladium catalyzed cross coupling between the aryl bromide XXIX and the pinacol boronate XXVIII can generate the desired biaryl XXX. Removal of the protective group would afford the desired bis-spiro-mannoside XXXI. Intermediates XXIX and XXVIII can be generated from coupling described in Method 5 using appropriately substituted phenols.

Scheme 10

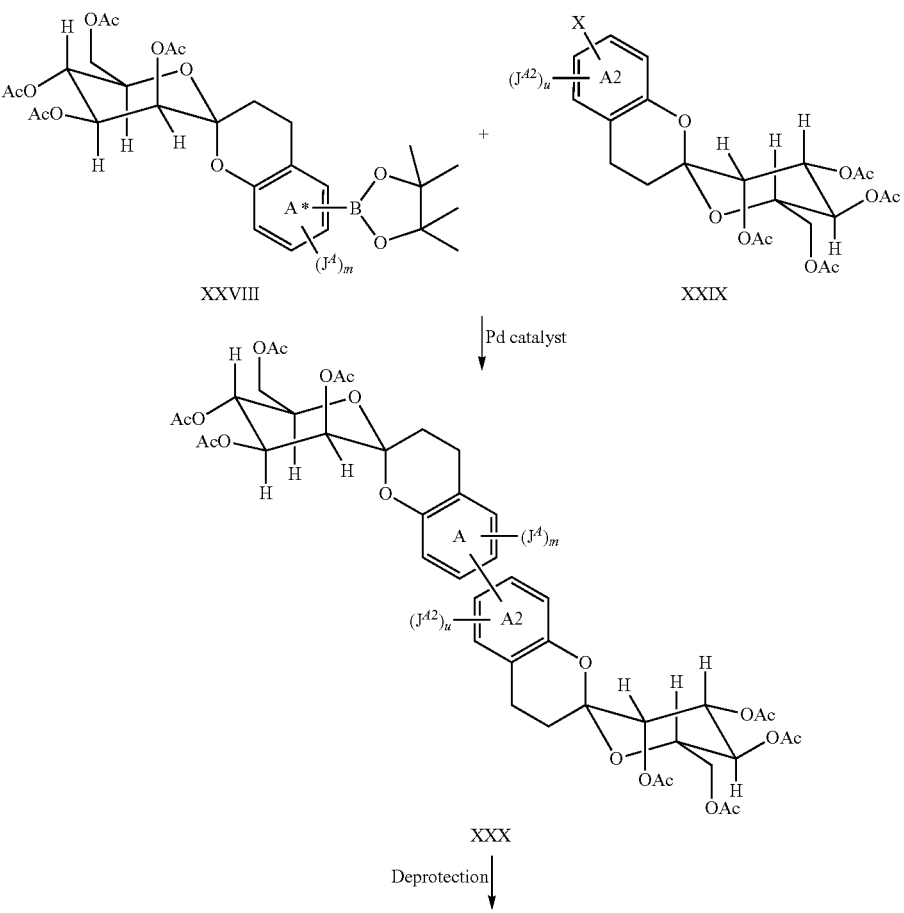

-continued
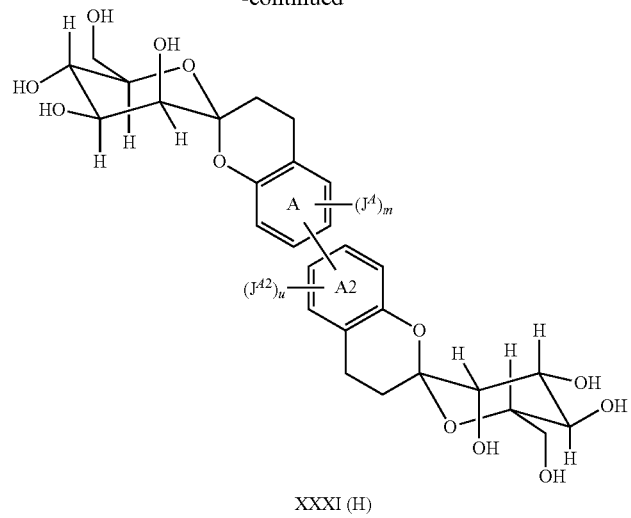
XXXI (H)
Carbohydrate INTERMEDIATEs M1 to M22 depicted in Figure 1 are used in the preparation of EXAMPLEs described therein.
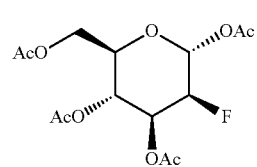 (M1)
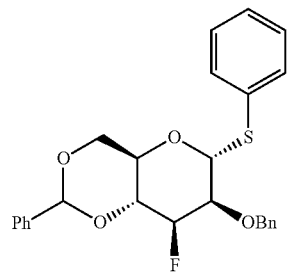 (M2)
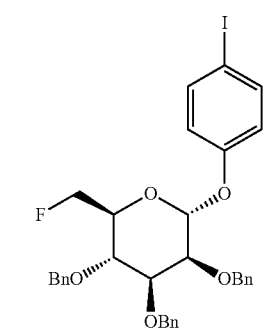 (M3)
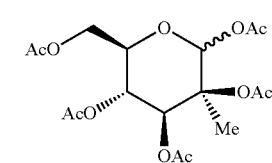 (M4)
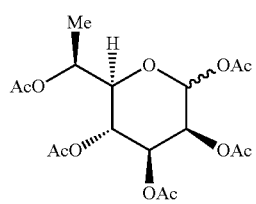 (M5)
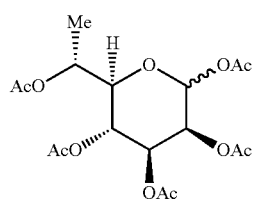 (M6)
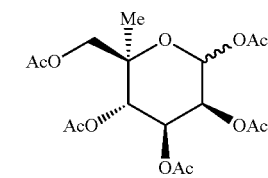 (M7)
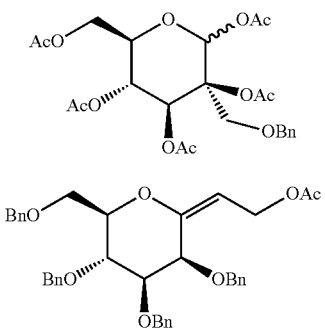 (M8)
(M9)

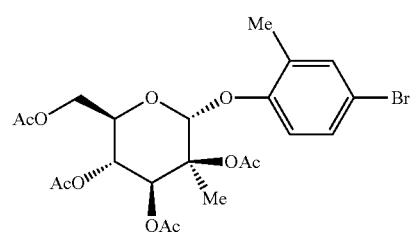 (M10)
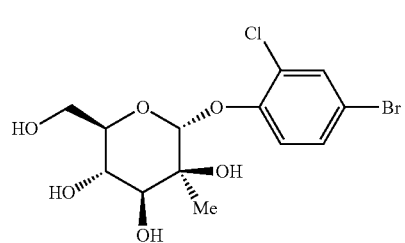 (M11)
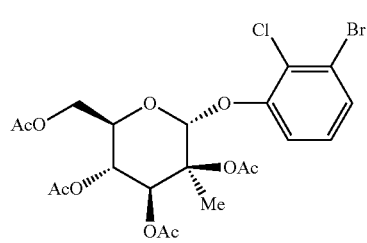 (M12)
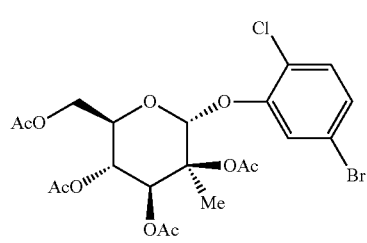 (M13)
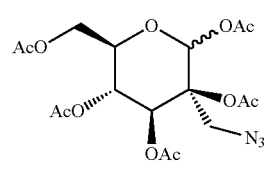 (M14)
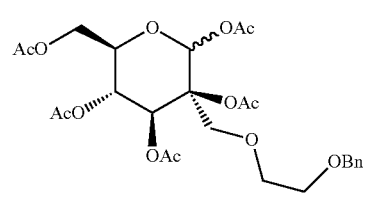 (M15)
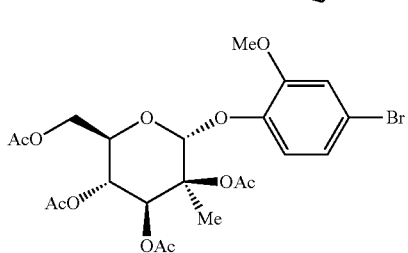 (M16)
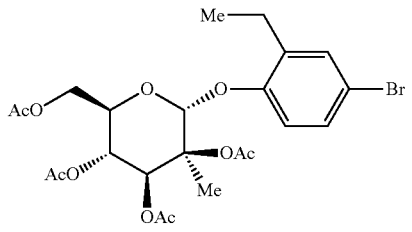 (M17)
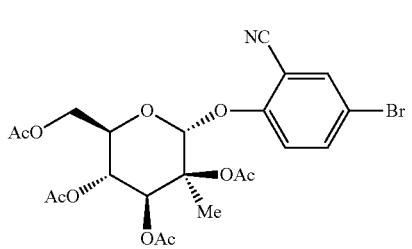 (M18)
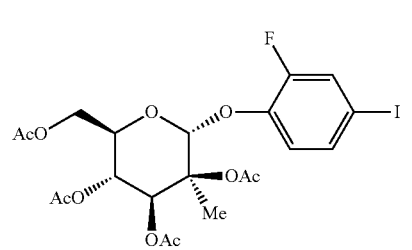 (M19)
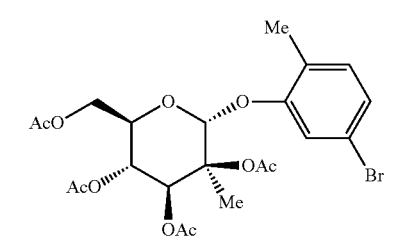 (M20)
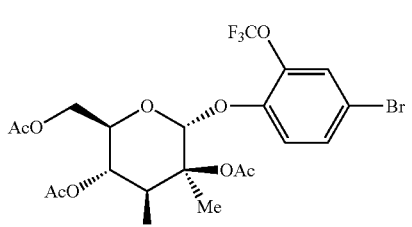 (M21)
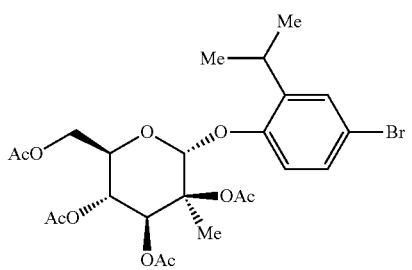 (M22)

Preparation of Intermediate M1

(2R,3S,4S,5R,6R)-6-(acetoxymethyl)-3-fluorotetrahydro-2H-pyran-2,4,5-triyl triacetate

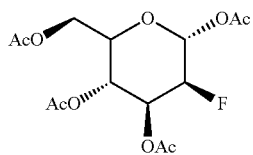

The title compound is prepared according to the procedure describe in *Angew. Chem. Int. Ed.* 2010, 49, 8724-8728

Preparation of Intermediate M2

(4aR,6R,7S,8S,8aR)-7-(benzyloxy)-8-fluoro-2-phenyl-6-(phenylthio)hexahydropyrano[3,2-d][1,3]dioxine

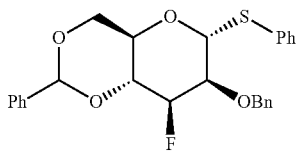

The title compound is prepared according to the procedure describe in *JOC*, 2007, 72, 1681-1690.

Preparation of Intermediate M3

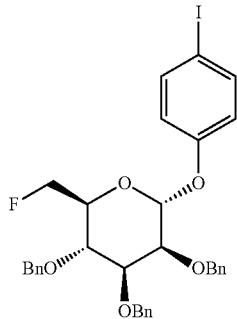 [SMILES: FC[C@H]1O[C@H](Oc2ccc(I)cc2)[C@@H](OCc2ccccc2)[C@@H](OCc2ccccc2)[C@@H]1OCc1ccccc1]

Step I: (2R,3R,4S,5S,6R)-2-(acetoxymethyl)-6-(4-iodophenoxy)tetrahydro-2H-pyran-3,4,5-triyl triacetate

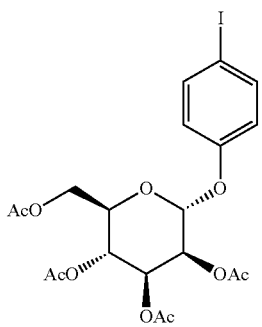 [SMILES: CC(=O)OC[C@H]1O[C@H](Oc2ccc(I)cc2)[C@@H](OC(C)=O)[C@@H](OC(C)=O)[C@@H]1OC(C)=O]

To a solution of commercially available [(2R,3R,4S,5S,6R)-3,4,5,6-tetraacetoxytetrahydropyran-2-yl]methyl acetate (3.814 g, 9.771 mmol) and 4-iodophenol (2.650 g, 12.05 mmol) in 1,2-dichloroethane (35 mL) at 0° C. was added $BF_3.OEt_2$ (1.810 mL, 14.66 mmol) dropwise. The reaction mixture is warmed to RT and stirred at 40° C. for 12 h. The reaction mixture is cooled to RT, poured in a saturated aqueous $NaHCO_3$ and diluted with $CH_2Cl_2$. The organic layer is separated and the aqueous layer is back washed with $CH_2Cl_2$. The combined organic fractions are dried over $Na_2SO_4$, filtered and concentrated. The desired compound is purified on a Silica gel column (100 g) using Hexane/EtOAc (20 to 60% EA) as the eluant on a Biotage™ system to afford the title compound (4.01 g, 75% yield).

Step II: (2R,3S,4S,5S,6R)-2-(((tert-butyldiphenylsilyl)oxy)methyl)-6-(4-iodophenoxy)tetrahydro-2H-pyran-3,4,5-triol

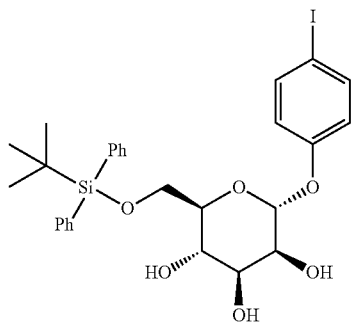 [SMILES: CC(C)(C)[Si](OC[C@H]1O[C@H](Oc2ccc(I)cc2)[C@@H](O)[C@@H](O)[C@@H]1O)(c1ccccc1)c1ccccc1]

To a solution of [(2R,3R,4S,5S,6R)-3,4,5-triacetoxy-6-(4-iodophenoxy)tetrahydropyran-2-yl]methyl acetate from Step I (4.014 g, 7.29 mmol) in MeOH (100 mL) is added NaOMe (1.58 mL of 25% w/v, 7.29 mmol). The reaction mixture is stirred overnight at RT. The reaction mixture is quenched with acetic acid (420 µL, 7.386 mmol) and concentrated. The residue is suspended in 500 mL of Tol and the mixture is concentrated in vacuo. The residue is partially dissolved in DMF (100 mL), cooled 0° C. and tert-butyl-chloro-diphenyl-silane (4.00 mL, 15.38 mmol) then 4H-imidazole (2.023 g, 29.72 mmol) are added. The reaction mixture is stirred 3 h at 0° C. then allowed to warm to RT and stirred over two days. The resulting mixture is poured in $H_2O/Et_2O$ (1/1). The organic layer is separated, washed with water (2x), brine, dried over $MgSO_4$, filtered and concentrated. The residue is purified over a large pad of silica gel eluting with 10, 20, 50 and 100% EtOAc in Hex to afford the desired material (3.725 g, 82% yield)

Step III: tert-butyldiphenyl(((2R,3R,4S,5S,6R)-3,4,5-tris(benzyloxy)-6-(4-iodophenoxy)tetrahydro-2H-pyran-2-yl)methoxy)silane

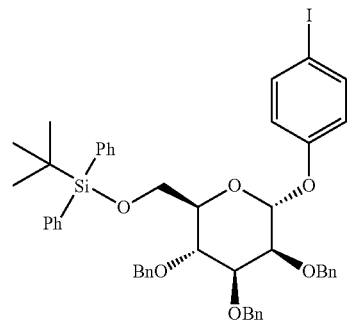 [SMILES: CC(C)(C)[Si](OC[C@H]1O[C@H](Oc2ccc(I)cc2)[C@@H](OCc2ccccc2)[C@@H](OCc2ccccc2)[C@@H]1OCc1ccccc1)(c1ccccc1)c1ccccc1]

To a solution of tert-butyldiphenyl(((2R,3R,4S,5S,6R)-3,4,5-tris(benzyloxy)-6-(4-iodophenoxy)tetrahydro-2H-pyran-2-yl)methoxy)silane from Step II (3.725 g, 6.003 mmol) and benzyl bromide (2.90 mL, 24.4 mmol) in DMF (30 mL) at 0° C. is added portion wise NaH (801 mg, 20.0 mmol). The reaction mixture was allowed to warm to RT and was stirred for 12 hrs. The reaction mixture is poured in a saturated aqueous solution on NH₄Cl and extracted with Et₂O. The organic layer was washed with water (twice), brine, dried over MgSO₄, filtered and concentrated. The resulting crude mixture is purified on a pad of silica gel using Hexane/EtOAc (0, 2, 4% EA) as the eluent to afford the title compound (4.002 g, 73% yield) as a colorless oil.

Step IV: ((2R,3R,4S,5S,6R)-3,4,5-tris(benzyloxy)-6-(4-iodophenoxy)tetrahydro-2H-pyran-2-yl)methanol

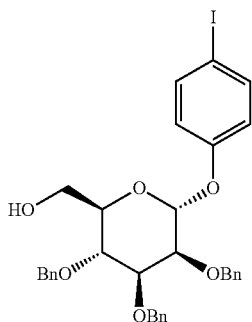 [SMILES: OC[C@H]1O[C@H](Oc2ccc(I)cc2)[C@@H](OCc2ccccc2)[C@@H](OCc2ccccc2)[C@@H]1OCc1ccccc1]

To a solution of tert-butyldiphenyl(((2R,3R,4S,5S,6R)-3,4,5-tris(benzyloxy)-6-(4-iodophenoxy)tetrahydro-2H-pyran-2-yl)methoxy)silane from Step III (4.002 g, 4.402 mmol) in THF (75 mL) is added acetic acid (100 µL, 1.76 mmol) then tetrabutylammonium fluoride (10.6 mL of 1 M, 10.6 mmol). The reaction mixture is stirred overnight at RT. The resulting mixture is concentrated in vacuo and he residue is purified on a Silica gel column (100 g) using Hexane/EtOAc (10 to 30% EA) as the eluant on a Biotage™ system to afford the title compound (2.583 g, 85% yield) as a colorless oil.

Step V: Intermediate M3

To a solution of ((2R,3R,4S,5S,6R)-3,4,5-tris(benzyloxy)-6-(4-iodophenoxy)tetrahydro-2H-pyran-2-yl)methanol from Step IV (444 mg, 0.646 mmol) in CH₂Cl₂ (5.02 mL) at 0° C. is added 2,3,4,6,7,8,9,10-octahydropyrimido[1,2-a]azepine (193 µL, 1.293 mmol) then XtalFluor-E (163 mg, 0.711 mmol). The reaction mixture is stirred at 0° C. for 2 h the poured in a saturated aqueous solution on NaHCO₃ and diluted with CH₂Cl₂. The organic layer is separated, dried over Na₂SO₄, filtered and concentrated. The resulting crude mixture is purified on a Silica gel column (25 g) using Hexane/EtOAc (0 to 20% EA) as the eluent on a Biotage™ system to afford the title compound (52 mg, 12% yield).

Preparation of Intermediate M4

(3S,4S,5R,6R)-6-(acetoxymethyl)-3-methyltetrahydro-2H-pyran-2,3,4,5-tetrayl tetraacetate

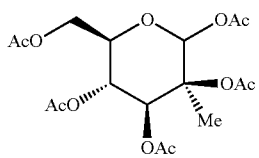 [SMILES: CC(=O)OC[C@H]1OC(OC(C)=O)[C@@](C)(OC(C)=O)[C@@H](OC(C)=O)[C@@H]1OC(C)=O]

Step I: (3aS,6R,6aS)-6-((R)-2,2-dimethyl-1,3-dioxolan-4-yl)-3a-(hydroxymethyl)-2,2-dimethyltetrahydrofuro[3,4-d][1,3]dioxol-4-ol

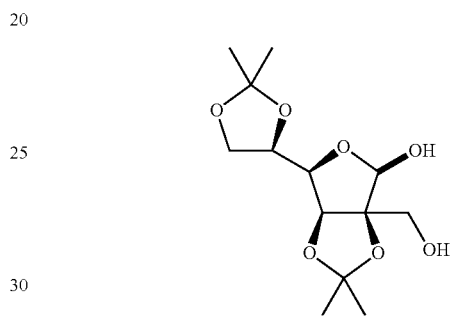

To a suspension of (3aS,4S,6R,6aS)-6-((R)-2,2-dimethyl-1,3-dioxolan-4-yl)-2,2-dimethyltetrahydrofuro[3,4-d][1,3]dioxol-4-ol (commercially available) (25.00 g, 96.1 mmol) and K₂CO₃ (19.92 g, 144.1 mmol) in MeOH (250.0 mL) is added formic acid (37% in water, 178.7 mL, 2.401 mmol). The reaction mixture is stirred 64 hrs at 95° C., cooled to 0° C., neutralized (pH 7) with aqueous H₂SO₄ (10%). The mixture is stirred 15 min at 0° C., at which point the resulting precipitate is filtered off and the mother liquor is concentrated in vacuo to provide a colorless oil. The crude oil is dissolved in CH₂Cl₂ and the organic phase is washed with water and brine. The solution is dried over Na₂SO₄, filtered, concentrated in vacuo and finally purified by flash column chromatography(220 g of silica) using 40-100% EtOAc/Hexane over 15 CV to afford the title compound (19.3 g, 66.5 mmol, 69%).

Step II: (3aS,6R,6aS)-6-((R)-2,2-dimethyl-1,3-dioxolan-4-yl)-3a-(hydroxymethyl)-2,2-dimethyldihydrofuro[3,4-d][1,3]dioxol-4(3aH)-one

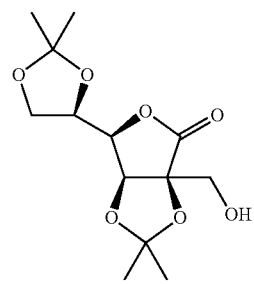 [SMILES: CC1(C)OC[C@H]([C@H]2OC(=O)[C@@]3(CO)OC(C)(C)O[C@@H]23)O1]

In a 3 neck round bottom flask of (3 L), equipped with mechanical stirring and thermocouple is added (3aS,6R,6aS)-6-((R)-2,2-dimethyl-1,3-dioxolan-4-yl)-3a-(hydroxymethyl)-2,2-dimethyltetrahydrofuro[3,4-d][1,3]dioxol-4-ol from Step I (38 g, 130.9 mmol), Cs₂CO₃ (23.58 g, 235.6 mmol) and water (1.33 L). The resulting mixture is cooled down to 3° C. using ice/water bath, then Br₂ (31.37 g, 10.11 mL, 196.3 mmol) is added over 5 min. The reaction mixture is allowed to reach RT gradually and stir 16 h. The reaction mixture is flushed with N₂ (bubbling in solution) for 30 min, treated with 300 ml of aqueous saturated Na₂S₂O₃ for 15 min and extracted with (3×200 ml) CH₂Cl₂. The combined organic phases are washed with water, dry over Na₂SO₄, filtered, concentrated and purified by flash column chromatography(220 g of silica) using 0-75% EtOAc/Hexane over 10 CV to afford the tittle compound (29.0 g, 101 mmol, 77%).

Step III: (3aS,6R,6aS)-6-((R)-2,2-dimethyl-1,3-dioxolan-4-yl)-3a-(iodomethyl)-2,2-dimethyldihydrofuro[3,4-d][1,3]dioxol-4(3aH)-one

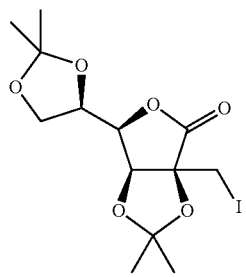 [SMILES: CC1(C)OC[C@H]([C@H]2OC(=O)[C@@]3(CI)OC(C)(C)O[C@@H]23)O1]

In a 2 L round bottom flask, equipped with mechanical stirring and a condenser is loaded (3aS,6R,6aS)-6-((R)-2,2-dimethyl-1,3-dioxolan-4-yl)-3a-(hydroxymethyl)-2,2-dimethyldihydrofuro[3,4-d][1,3]dioxol-4(3aH)-one (30.5 g, 106 mmol), imidazole (25.93 g, 380.9 mmol) and triphenylphosphane (72.15 g, 275.1 mmol), toluene (915.0 mL) followed by I₂ (69.82 g, 275.1 mmol). The reaction mixture is stirred at 85° C. for 90 min, cooled to RT and filtered. The solid is washed with 200 ml of toluene and to the combined filtrates is added 150 ml of aqueous saturated Na₂S₂O₃ and 25 ml NaCl. The resulting solution is stirred for 15 min. The organic layer is separated, washed with saturated NaHCO₃ and 25 ml of brine. The organic phase is dried over Na₂SO₄, filtered, concentrated and purified using 320 g of silica and 100% Hexane 4 CV and 0-80% over 7 CV to afford the tittle compound (39.0 g, 97.9 mmol, 92.6%) as a white solid.

Step IV: (3aS,6R,6aS)-6-((R)-2,2-dimethyl-1,3-dioxolan-4-yl)-2,2,3a-trimethyldihydrofuro[3,4-d][1,3]dioxol-4(3aH)-one

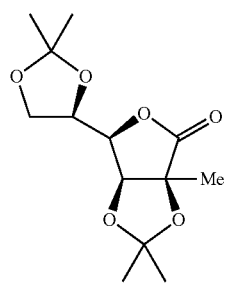 [SMILES: CC1(C)OC[C@H]([C@H]2OC(=O)[C@@]3(C)OC(C)(C)O[C@@H]23)O1]

(3aS,6R,6aS)-6-((R)-2,2-dimethyl-1,3-dioxolan-4-yl)-3a-(iodomethyl)-2,2-dimethyldihydrofuro[3,4-d][1,3]dioxol-4(3aH)-one from Step III (39 g, 97.94 mmol) is dissolve in EtOH (195 mL). To the resulting solution is added Et₃N (16.4 mL, 118 mmol) and Pd/C 10% wet (1.04 g, 9.79 mmol). The reaction mixture was stirred under H₂ atmosphere (40 psi) for 72 h. The resulting reaction mixture is filtered on celite, the latter washed with 600 ml of EtOH. The combined solutions are diluted with 1.6 L of CH₂Cl₂ and 800 ml of saturated aqueous Na₂S₂O₃ is added. This mixture is stirred for 15 min. The organic phase is separated, washed with 800 ml of saturated aqueous Na₂S₂O₃. After separation, the organic phase is dried over Na₂SO₄, filtered and concentrated. This crude materiel is recrystallized in 40 mL of EtOH and 25 mL of heptane at 83° C. Upon cooling the resulting crystalline material is collected by filtration to afford the title compound (24.3 g, 89.3 mmol, 91%) as a white solid.

Step V: (3aS,6R,6aS)-6-((R)-2,2-dimethyl-1,3-dioxolan-4-yl)-2,2,3a-trimethyltetrahydrofuro[3,4-d][1,3]dioxol-4-ol

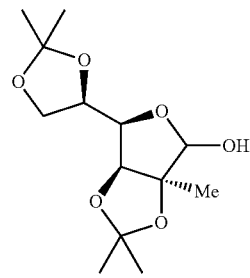

DIBAL (24.2 mL of 1.5 M, 36.4 mmol) in toluene is added dropwise over 10 min to a cold (−78° C.) solution of (3aS,6R,6aS)-6-((R)-2,2-dimethyl-1,3-dioxolan-4-yl)-2,2,3a-trimethyldihydrofuro[3,4-d][1,3]dioxol-4(3aH)-one from Step IV (9.00 g, 33.1 mmol) in CH₂Cl₂ (90 mL). The reaction mixture is stirred at −78° C. for 2 h. Upon completion, the cold reaction mixture is quenched with 4 ml of MeOH added dropwise over 2 min and then allowed to warm to RT over 30 min. 500 ml of saturated aqueous sodium tartrate is added and the resulting slurry is stirred vigorously for 1 h at room temp. The organic phase is separated, washed with water, brine, dried over Na₂SO₄, filtered and concentrated to afford the title compound (22.1 g, 80.7 mmol, 98%).

Step VI: (3S,4S,5S,6R)-6-(hydroxymethyl)-3-methyltetrahydro-2H-pyran-2,3,4,5-tetraol

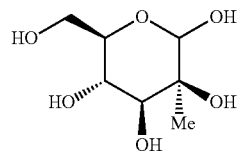

To a solution of (3aS,6R,6aS)-6-((R)-2,2-dimethyl-1,3-dioxolan-4-yl)-2,2,3a-trimethyltetrahydrofuro[3,4-d][1,3]dioxol-4-ol from Step V (9.00 g, 32.8 mmol) in H₂O (45 mL) and dioxane (45 mL) is added Dowex 50WX4 resin (4.5 g). The reaction mixture is stirred at 60° C. for 16 h, cooled to RT, filtered and concentrated to afford the tittle compound (6.25 g, 32.19 mmol, 98%).

Step VII: Intermediate M4

To a solution of (3S,4S,5S,6R)-6-(hydroxymethyl)-3-methyltetrahydro-2H-pyran-2,3,4,5-tetraol from Step VI (7.40 g, 38.11 mmol) in pyridine (148 mL) is added DMAP (931 mg, 7.62 mmol) and Ac₂O (71.9 mL, 762 mmol). The reaction mixture is stirred at 60° C. for 16 h, cooled down to RT, diluted with CH₂Cl₂ (300 mL) and water (300 mL) is added over 10 min and the final mixture stirred for 15 min. The organic phase is separated, washed twice with 250 ml of HCl 1N followed by brine, dried over Na₂SO₄, filtered, and concentrated. Purification on Biotage™ SNAP silica cartridge (220 g) using EtOAc (40% to 80% in 10 CV)/Hex as eluent afforded the title compound (11.1 g, 72%) as a one to one mixture of α and β diastereoisomers at the anomeric carbon. ¹H NMR (400 MHz, CDCl₃) a mixture of α/β (ca. 1:1) δ 6.86 (s, 1H, H$_{1\alpha}$), 5.62 (s, 1H, H$_{1\beta}$), 5.42-5.05 (m, 4H), 4.30-4.05 (m, 4H), 4.04-3.82 (m, 2H), 2.20-2.03 (m, 30H, 10 OAc), 1.62 (s, 3H, CH₃ α or β), 1.48 (s, 3H, CH₃ α or β).

Preparation of Intermediate M5

(3S,4S,5R,6R)-6-((S)-1-acetoxyethyl)tetrahydro-2H-pyran-2,3,4,5-tetrayl tetraacetate

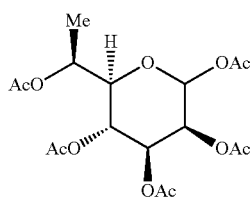 [SMILES: CC(=O)OC1O[C@H]([C@H](C)OC(C)=O)[C@@H](OC(C)=O)[C@H](OC(C)=O)[C@@H]1OC(C)=O]

Step I: (2R,3R,4S,5S,6S)-3,4,5,6-tetrabenzyloxytetrahydropyran-2-yl]methanol

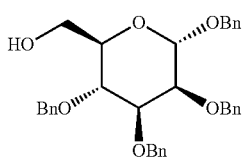 [SMILES: OC[C@H]1O[C@H](OCc2ccccc2)[C@@H](OCc2ccccc2)[C@@H](OCc2ccccc2)[C@@H]1OCc1ccccc1]

The title compound is prepared using the procedure described in: Daragics, K.; Fügedi, P. *Tet. Lett.*, 2009, 50, 2914-2916.

Step II: (1S)-1-[(2R,3S,4S,5S,6S)-3,4,5,6-tetrabenzyloxytetrahydropyran-2-yl]ethanol

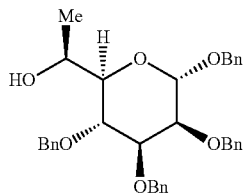 [SMILES: C[C@H](O)[C@H]1O[C@H](OCc2ccccc2)[C@@H](OCc2ccccc2)[C@@H](OCc2ccccc2)[C@@H]1OCc1ccccc1]

To a solution of (2R,3R,4S,5S,6S)-3,4,5,6-tetrabenzyloxytetrahydropyran-2-yl]methanol from Step I (856 mg, 1.58 mmol) in DMSO (4.66 mL), and Et₃N (1.103 mL, 7.915 mmol) in CH₂Cl₂ (4.7 mL) at 0° C. is added SO₃.pyridine complex (1.260 g, 7.915 mmol) in 3 portions. The reaction is stirred for 1 h. Upon completion, the reaction mixture is diluted with EtOAc, and washed successively with water, 10% aqueous potassium bisulfate, saturated aqueous NaHCO₃ and brine. The organic phase is dried over MgSO₄, filtered and concentrated in vacuo. The residue is co-evaporated twice with benzene to give crude aldehyde which is used without further purification in the next step. MeMgBr (1.90 mL of 3 M, 5.68 mmol) is added to a solution of (2S,3S,4S,5S,6S)-3,4,5,6-tetrabenzyloxytetrahydropyran-2-carbaldehyde (1.531 g, 2.842 mmol) in THF (14 mL) at 0° C. The reaction mixture is stirred for 15 min then stirred for 90 minutes at RT. Upon completion, a saturated aqueous solution of NH₄Cl is added to the mixture and the product is extracted from the aqueous phase with CH₂Cl₂ (3 times). The combined organic layers are dried over Na₂SO₄, filtered and concentrated in vacuo. The residue is purified twice by flash chromatography using first a gradient of 0-60% EtOAc: Hex, then 10-20% EtOAc: Hex for the second time, to provide the title compound (989.7 mg, 63% yield).

LC-MS: m/z=577.5 (M+Na⁺).

The ¹H NMR corresponds to the one reported in the literature in: Doores, K. J.; Fulton, Z.; Hong, V.; Patel, M. K.; Scanlan, C. N., Wormald, M. R.; Finn, M. G.; Burton, D. R.; Wilson, I. A.; Davis, B. G. *PNAS*, 2010, 107, 17107-17112.

Step III: Intermediate M5

The title compound is prepared from (1S)-1-[(2R,3S,4S,5S,6S)-3,4,5,6-tetrabenzyloxytetrahydropyran-2-yl]ethanol using the procedure described in: Doores, K. J.; Fulton, Z.; Hong, V.; Patel, M. K.; Scanlan, C. N., Wormald, M. R.; Finn, M. G.; Burton, D. R.; Wilson, I. A.; Davis, B. G. *PNAS*, 2010, 107, 17107-17112.

Preparation of Intermediate M6

(3S,4S,5R,6R)-6-((R)-1-acetoxyethyl)tetrahydro-2H-pyran-2,3,4,5-tetrayl tetraacetate

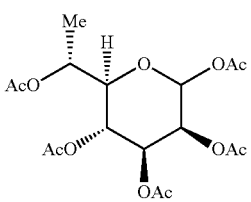

Step I: [(1R)-1-[(2R,3S,4S,5S,6S)-3,4,5,6-tetrabenzyloxytetrahydropyran-2-yl]ethyl]-4-nitrobenzoate

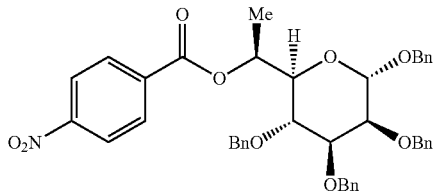 [SMILES: C[C@H](OC(=O)c1ccc([N+](=O)[O-])cc1)[C@H]1O[C@H](OCc2ccccc2)[C@@H](OCc2ccccc2)[C@@H](OCc2ccccc2)[C@@H]1OCc1ccccc1]

A solution of (1S)-1-[(2R,3S,4S,5S,6S)-3,4,5,6-tetrabenzyloxytetrahydropyran-2-yl]ethanol from INTERMEDIATE M5 Step II (990 mg, 1.78 mmol), triphenylphosphine (749 mg, 2.85 mmol), isopropyl (NE)-N-isopropoxycarbonyliminocarbamate in toluene 40% w/v (1.44 mL, 2.85 mmol) and THF (17.8 mL) is cooled to 0° C. and 4-nitrobenzoic acid (477 mg, 2.85 mmol) is added. The reaction mixture is allowed to warm up to RT over 4 hours. Upon completion, the reaction is concentrated in vacuo and the crude mixture is purified by flash chromatography using a gradient of 0-100% EtOAc: Hex to provide the title compound (1.03 g, 82% yield). $^1$H NMR (400 MHz, CDCl$_3$) δ 8.25-8.13 (m, 4H), 7.43-7.13 (m, 20H), 5.52 (qd, J=6.6, 1.9 Hz, 1H), 5.05-4.95 (m, 2H), 4.77-4.61 (m, 6H), 4.44 (d, J=11.8 Hz, 1H), 4.06-3.88 (m, 3H), 3.83 (dd, J=3.0, 2.0 Hz, 1H), 1.36 (d, J=6.6 Hz, 3H).

Step II: (1R)-1-[(2R,3S,4S,5S,6S)-3,4,5,6-tetrabenzyloxytetrahydropyran-2-yl]ethanol

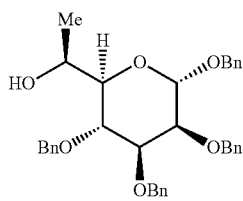

[(1R)-1-[(2R,3S,4S,5S,6S)-3,4,5,6-tetrabenzyloxytetrahydropyran-2-yl]ethyl]-4-nitrobenzoate from Step I (1.03 g, 1.46 mmol) is dissolved in EtOH (6 mL), THF (6 mL) and water (2.6 mL). NaOH (293 mg, 7.32 mmol) is added to the mixture and the resulting solution is allowed to stir at RT for 2 hours. Upon completion, the solution is concentrated in vacuo and the crude residue is partitioned between water and CH$_2$Cl$_2$ 3 times. The organic layers are combined, dried over Na$_2$SO$_4$, filtered and concentrated in vacuo. The crude residue is purified by flash chromatography using a gradient 10-40% EtOAc/Hex to provide the title compound slightly contaminated (661 mg, 81% yield). LC-MS: m/z=577.7 (M+Na$^+$)

Step III: (2S,3S,4S,5S,6R)-6-[(1R)-1-hydroxyethyl]tetrahydropyran-2,3,4,5-tetrol

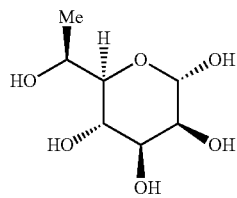 [SMILES: C[C@H](O)[C@H]1O[C@H](O)[C@@H](O)[C@@H](O)[C@@H]1O]

Nitrogen is bubbled through a solution of (1R)-1-[(2R,3S,4S,5S,6S)-3,4,5,6-tetrabenzyloxytetrahydropyran-2-yl]ethanol from Step II (661 mg, 1.192 mmol) in MeOH (12 mL). To the resulting solution is added Pd/C, wet, Degussa (126.9 mg, 0.1192 mmol). The reaction is allowed to stir at RT for 4 days under an atmosphere of hydrogen gas (1 atm). At that point, the reaction does not progress any further. The crude mixture is filtered over Celite and rinsed with MeOH and CH$_2$Cl$_2$. The filtrate is concentrate in vacuo to provide a crude mixture of several products. Palladium hydroxide (83.7 mg, 0.119 mmol) is charged in a degassed solution of the above mentioned mixture and acetic acid (68.0 μL, 1.19 mmol) in MeOH (10 mL). The reaction mixture is allowed to stir for 2 days under 1 atm of hydrogen gas. The solution is filtered over Celite and the filtrate is concentrated in vacuo to provide again a mixture of several products. Finally, palladium hydroxide (280 mg, 0.399 mmol) is charged in a degassed solution of the above mentioned mixture and acetic acid (57.0 μL, 0.996 mmol) in MeOH (7 mL). The reaction mixture is allowed to stir for 2 days under 1 atm of H$_2$. Upon completion of the reaction, the solution is filtered over Celite and rinsed with MeOH. The liquor is concentrated in vacuo and the crude product is co-evaporated 3 times with benzene to remove any remaining AcOH. The crude product is used directly in the next step. LC-MS: m/z=217.2 (M+Na$^+$)

Step IV: Intermediate M6

Crude (2S,3S,4S,5S,6R)-6-[(1R)-1-hydroxyethyl]tetrahydropyran-2,3,4,5-tetrol from Step III (193.4 mg, 0.996 mmol) is stirred in Ac$_2$O (5.0 mL, 53 mmol) and pyridine (10 mL) at RT for 18 hours. Upon completion, the reaction mixture is concentrated in vacuo and co-evaporated with benzene. The residue is purified by flash chromatography using first a gradient of 20-50% EtOAc: Hex, and then a second chromatography is performed using 20-40% EtOAc: Hex to provide de title compound (290 mg, 72% yield over 2 last steps).

LC-MS: m/z=427.3 (M+Na)$^+$.

Preparation of Intermediate M7

[(2R,3S,4S,5S)-3,4,5,6-tetraacetoxy-2-methyl-tetrahydropyran-2-yl]methyl acetate

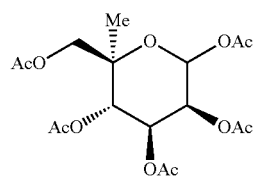 [SMILES: CC(=O)OC[C@@]1(C)OC(OC(C)=O)[C@@H](OC(C)=O)[C@@H](OC(C)=O)[C@@H]1OC(C)=O]

The title compound is prepared using the procedure described in: Doores, K. J.; Fulton, Z.; Hong, V.; Patel, M. K.; Scanlan, C. N., Wormald, M. R.; Finn, M. G.; Burton, D. R.; Wilson, I. A.; Davis, B. G. *PNAS*, 2010, 107, 17107-17112.

101

Preparation of Intermediate M8

(3S,4S,5R,6R)-6-(acetoxymethyl)-3-((benzyloxy)methyl)tetrahydro-2H-pyran-2,3,4,5-tetrayl tetraacetate

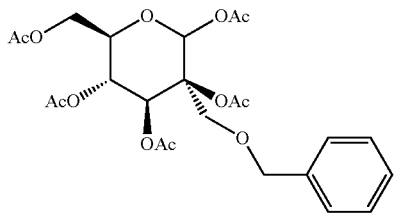 [SMILES: CC(=O)OC[C@H]1OC(OC(C)=O)[C@@](COCc2ccccc2)(OC(C)=O)[C@@H](OC(C)=O)[C@@H]1OC(C)=O]

Step I: (3aS,6R,6aS)-3a-((benzyloxy)methyl)-6-((R)-2,2-dimethyl-1,3-dioxolan-4-yl)-2,2-dimethyldihydrofuro[3,4-d][1,3]dioxol-4(3aH)-one

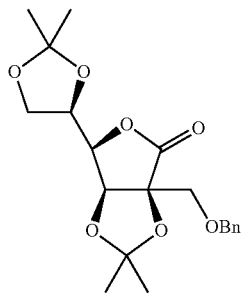 [SMILES: CC1(C)OC[C@H]([C@H]2OC(=O)[C@@]3(COCc4ccccc4)OC(C)(C)O[C@@H]23)O1]

To a cold (0° C.) solution of (3aS,6R,6aS)-6-((R)-2,2-dimethyl-1,3-dioxolan-4-yl)-3a-(hydroxymethyl)-2,2-dimethyldihydrofuro[3,4-d][1,3]dioxol-4(3aH)-one from INTERMEDIATE M4 Step II (1.500 g, 5.203 mmol) in DMF (23 mL) is added NaH (250 mg, 6.24 mmol). The reaction mixture is stirred for 15 min, then, benzyl bromide (743 μL, 6.24 mmol) is added and the final reaction mixture is stirred at RT for 2 h. The reaction mixture is partitioned between EtOAc and water. The organic layer is dried over Na$_2$SO$_4$, concentrated and purified by flash chromatography (0-50% EtOAC/Hexane) to afford the tittle compound (1200 mg, 3.171 mmol, 61%). $^1$H NMR (400 MHz, CDCl$_3$) δ 7.48-7.08 (m, 5H), 4.75 (d, J=3.2 Hz, 1H), 4.60 (d, J=12.1 Hz, 1H), 4.53 (d, J=12.0 Hz, 1H), 4.50-4.32 (m, 2H), 4.18-4.09 (m, 1H), 4.08 (dd, J=9.1, 3.9 Hz, 1H), 3.94 (d, J=9.1 Hz, 1H), 3.72 (d, J=9.1 Hz, 1H), 1.47 (s, 6H), 1.39 (s, 6H).

Step II: (3aS,6R,6aS)-3a-((benzyloxy)methyl)-6-((R)-2,2-dimethyl-1,3-dioxolan-4-yl)-2,2-dimethyltetrahydrofuro[3,4-d][1,3]dioxol-4-ol

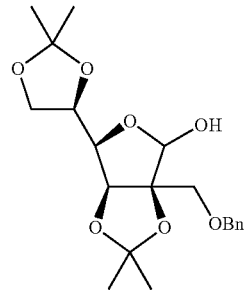

The title compound is prepared according to the procedure described in INTERMEDIATE M4 Step V but using (3aS,6R,6aS)-3a-((benzyloxy)methyl)-6-((R)-2,2-dimethyl-1,3-dioxolan-4-yl)-2,2-dimethyldihydrofuro[3,4-d][1,3]dioxol-4(3aH)-one from Step I. LC-MS: m/z=403.4 (M+Na)$^+$.

Step III: (3S,4S,5S,6R)-3-((benzyloxy)methyl)-6-(hydroxymethyl)tetrahydro-2H-pyran-2,3,4,5-tetraol

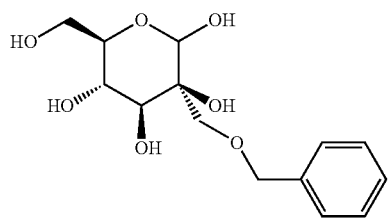 [SMILES: OC[C@H]1OC(O)[C@](O)(COCc2ccccc2)[C@@H](O)[C@@H]1O]

To a solution of (3aS,6R,6aS)-3a-((benzyloxy)methyl)-6-((R)-2,2-dimethyl-1,3-dioxolan-4-yl)-2,2-dimethyltetrahydrofuro[3,4-d][1,3]dioxol-4-ol from Step II (1000 mg, 2.63 mmol) in dioxane (17 mL) and water (8.5 mL) is added TFA (2.05 mL, 26.6 mmol). The reaction mixture is stirred at RT for 16 h. The resulting mixture is concentrated in vacuo, co-evaporated with toluene to afford the title compound (780 mg, 2.60 mmol, 98.80%) which is used in the next step without any further purification.

Step IV: Intermediate M8

To a cold (0° C.) solution of (3S,4S,5S,6R)-3-((benzyloxy)methyl)-6-(hydroxymethyl)tetrahydro-2H-pyran-2,3,4,5-tetraol from Step III (750 mg, 2.50 mmol) in pyridine (5.1 mL) is added DMAP (61 mg, 0.499 mmol) then, Ac$_2$O (2.36 mL, 24.9 mmol) was added. The reaction mixture was stirred for 16 h at RT. The reaction mixture is partitioned between EtOAc and water. The organic layer is separated, dried over Na$_2$SO$_4$, filtered and concentrated. The residue is purified on Biotage™ SNAP silica cartridge (10 g) using EtOAc (0% to 50% in 10 CV)/Hex as eluent to afford the title compound (300 mg, 24%) as a colorless oil. $^1$H NMR (400 MHz, CDCl$_3$) a mixture of α/β (ca. 1:2) δ 7.37-7.20 (m, 10H), 6.81 (s, 1H, H$_{1α}$), 6.06 (s, 1H, H$_{1β}$), 5.63 (d, J=8.1 Hz, 1H), 5.60 (d, J=8.1 Hz, 1H), 5.38 (t, J=9.9 Hz, 1H), 5.25 (t, J=9.8 Hz, 1H), 4.56-3.77 (m, 14H), 2.15-1.90 (m, 30H). LC-MS: m/z=533.8 (M+Na)$^+$.

Preparation of Intermediate M9

[(2E)-2-[(3S,4S,5R,6R)-3,4,5-tribenzyloxy-6-(benzyloxymethyl)tetrahydropyran-2-ylidene]ethyl]acetate

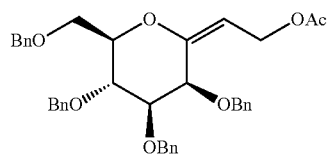 [SMILES: CC(=O)OC/C=C1/O[C@H](COCc2ccccc2)[C@@H](OCc2ccccc2)[C@H](OCc2ccccc2)[C@@H]1OCc1ccccc1]

Step I: methyl 2-(tributylphosphoranylidene)acetate

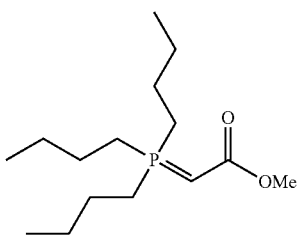 [SMILES: CCCCP(=CC(=O)OC)(CCCC)CCCC]

To a cold (0° C.) solution of tributylphosphane (5.00 mL, 20.0 mmol) in toluene (20 mL) under $N_2$ atmosphere is added methyl 2-bromoacetate (1.90 mL, 20.1 mmol). The resulting slurry is warmed to RT and stirred overnight under $N_2$ atmosphere. The resulting mixture is concentrated in vacuo, redissolved in $CH_2Cl_2$ (50 mL), washed sequentially with aqueous 1N NaOH (2×20 mL), $H_2O$ (20 mL), dried over $MgSO_4$, filtered and concentrated to provide the title compound (5.35 g, 97% yield) as a colorless oil

Step II: methyl (2E)-2-[(3S,4S,5R,6R)-3,4,5-tribenzyloxy-6-(benzyloxymethyl)tetrahydropyran-2-ylidene]acetate

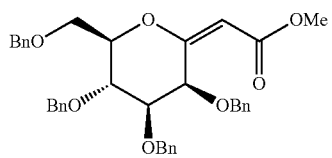 [SMILES: COC(=O)/C=C1/O[C@H](COCc2ccccc2)[C@@H](OCc2ccccc2)[C@H](OCc2ccccc2)[C@@H]1OCc1ccccc1]

To a solution of methyl 2-(tributylphosphoranylidene)acetate from Step I (2.01 g, 7.31 mmol) in toluene (9.0 mL) placed in a pressure tube is added (3S,4S,5R,6R)-3,4,5-tribenzyloxy-6-(benzyloxymethyl)tetrahydropyran-2-one (prepared according to reference *Org Lett*, 2011, 13(14), 3628-3631 (2.00 g, 3.71 mmol). The pressure tube is capped and stirred at 80° C. for 20 h. After cooling down to RT, the reaction mixture is purified by flash chromatography on a Biotage™ SNAP silica cartridge (100 g) using a gradient of EtOAc (0 to 20%) in Hex, affording the title compound (2.01 g, 91% yield) as a colorless oil.

Step III: (2E)-2-[(3S,4S,5R,6R)-3,4,5-tribenzyloxy-6-(benzyloxymethyl)tetrahydropyran-2-ylidene]ethanol

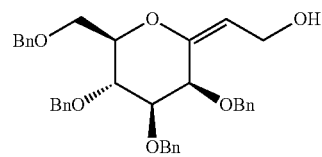 [SMILES: OC/C=C1/O[C@H](COCc2ccccc2)[C@@H](OCc2ccccc2)[C@H](OCc2ccccc2)[C@@H]1OCc1ccccc1]

To a cold (−78° C.) solution of methyl (2E)-2-[(3S,4S,5R,6R)-3,4,5-tribenzyloxy-6-(benzyloxymethyl)tetrahydropyran-2-ylidene]acetate from Step II (1.98 g, 3.30 mmol) in toluene (20 mL) under $N_2$ atmosphere is added DIBAL solution in toluene (5.60 mL of 1.5 M, 8.40 mmol) over 1 h via syringe-pump. The reaction mixture is stirred for another 2 h, then 40 mL of saturated Rochelle salt solution followed by 40 mL EtOAc is added and the mixture is stirred at RT for 3 h. The layers are separated; the aqueous layer is back extracted with EtOAc (2×40 mL). The combined organic extracts are washed with brine (40 mL), dried over $Na_2SO_4$, filtered and concentrated. The crude product is purified by flash chromatography on a Biotage™ SNAP silica cartridge (50 g) using a gradient of EtOAc (0 to 20%) in $CH_2Cl_2$, affording the title compound (1.28 g, 68% yield) as a colorless oil which solidifies to a white solid.

Step IV: Intermediate M9

To a solution of (2E)-2-[(3S,4S,5R,6R)-3,4,5-tribenzyloxy-6-(benzyloxymethyl)tetrahydropyran-2-ylidene]ethanol from Step III (1.28 g, 2.26 mmol) in $CH_2Cl_2$ (15 mL) is added pyridine (550 μL, 6.80 mmol), DMAP (28 mg, 0.23 mmol) followed by $Ac_2O$ (530 μL, 5.62 mmol). After stirring for 3 h, the reaction mixture is quenched with $H_2O$ and aqueous 1N HCl solution (10 mL each). The layers are separated, the aqueous layer is back extracted with $CH_2Cl_2$ (2×10 mL). The combined organic extracts are concentrated and co-evaporated with heptane (twice) to provide title compound (1.36 g, 99% yield) as a colorless oil. $^1H$ NMR (400 MHz, $CDCl_3$) δ 7.43-7.23 (m, 18H), 7.22-7.13 (m, 2H), 5.51 (t, J=8.2 Hz, 1H), 4.94 (d, J=10.8 Hz, 1H), 4.75-4.61 (m, 4H), 4.60-4.49 (m, 3H), 4.45-4.31 (m, 2H), 4.28-4.13 (m, 2H), 3.86-3.72 (m, 2H), 3.66-3.52 (m, 2H), 2.00 (s, 3H).

Preparation of Intermediate M10

(2R,3S,4S,5R,6R)-6-(acetoxymethyl)-2-(4-bromo-2-methylphenoxy)-3-methyltetrahydro-2H-pyran-3,4,5-triyltriacetate

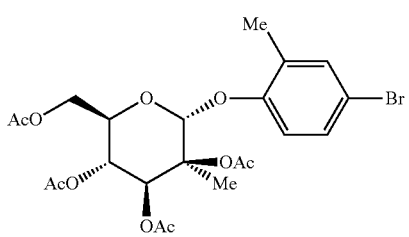

To a solution of INTERMEDIATE M4 (2.06 g, 5.094 mmol) in CH$_2$Cl$_2$ (10 mL) is added 4-bromo-2-methylphenol (1.9 g, 10.16 mmol) followed by BF$_3$.OEt$_2$ (3.87 mL, 30.5 mmol). The resulting mixture is stirred at 40° C. for 6 h, cooled to RT, poured slowly into a saturated NaHCO$_3$ aqueous solution (50 mL) while stirring vigorously. The mixture is diluted with CH$_2$Cl$_2$ (10 mL), the organic layer is separated and the aqueous layer is back extracted with CH$_2$Cl$_2$ (2×5 mL). The combined organic layers are concentrated and the residue purified on Biotage™ SNAP silica cartridge (50 g) eluting with Hex/EtOAc (0% to 50%) to afford the title compound (1.82 g, 67.2%) as a white crystalline solid. $^1$H NMR (400 MHz, CDCl$_3$) δ 7.30 (d, J=2.0 Hz, 1H), 7.28-7.22 (m, 1H), 7.04 (d, J=8.7 Hz, 1H), 6.24 (s, 1H), 5.57 (d, J=9.7 Hz, 1H), 5.39 (t, J=9.9 Hz, 1H), 4.17 (dd, J=12.2, 5.4 Hz, 1H), 4.10 (dd, J=12.2, 2.4 Hz, 1H), 4.00 (ddd, J=10.2, 5.4, 2.3 Hz, 1H), 2.26 (s, 3H), 2.15 (s, 3H), 2.14 (s, 3H), 2.04 (s, 6H), 1.63 (s, 3H).

Preparation of Intermediate M11

(2R,3S,4S,5S,6R)-2-(4-bromo-2-chlorophenoxy)-6-(hydroxymethyl)-3-methyltetrahydro-2H-pyran-3,4,5-triol

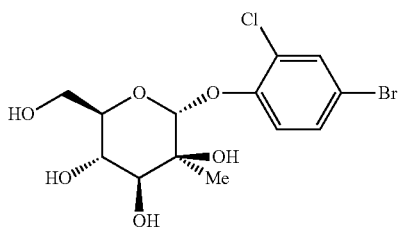 [SMILES: C[C@@]1(O)[C@@H](Oc2ccc(Br)cc2Cl)O[C@H](CO)[C@@H](O)[C@@H]1O]

Step I: (2R,3S,4S,5R,6R)-6-(acetoxymethyl)-2-(4-bromo-2-chlorophenoxy)-3-methyltetrahydro-2H-pyran-3,4,5-triyltriacetate

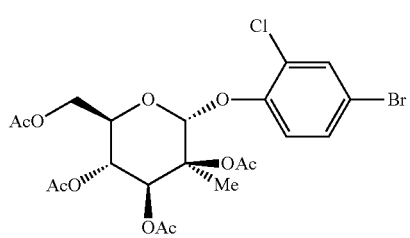 [SMILES: CC(=O)OC[C@H]1O[C@H](Oc2ccc(Br)cc2Cl)[C@@](C)(OC(C)=O)[C@@H](OC(C)=O)[C@@H]1OC(C)=O]

The title compound is prepared according to the procedure described for INTERMEDIATE M10 but using 4-bromo-2-chloro-phenol as reagent. The title compound is purified on Biotage™ SNAP silica cartridge (50 g) eluting with Hex/EtOAc (0% to 35%) and isolated as a white solid (40%).

Step II: Intermediate M11

To a solution of [(2R,3R,4S,5S,6R)-3,4,5-triacetoxy-6-(4-bromo-2-chloro-phenoxy)-5-methyl-tetrahydropyran-2-yl] methyl acetate from Step I (1.317 g, 2.387 mmol) in MeOH is added NaOMe in MeOH (4.77 mL of 0.5 M, 2.39 mmol). The reaction is stirred at RT for 18 h. The reaction is neutralized with acidic Amberlyst resin, filtered and concentrated to give the title compound (888 mg, 86.1%) as a white solid. $^1$H NMR (400 MHz, CD$_3$OD) δ 7.54 (s, 1H), 7.38 (d, J=8.9 Hz, 1H), 7.32 (d, J=8.9 Hz, 1H), 5.22 (s, 1H), 3.78-3.61 (m, 4H), 3.56 (dd, J=8.7, 4.4 Hz, 1H), 1.39 (s, 3H). LCMS (M+H)$^+$ 384.78

Preparation of Intermediate M12

(2R,3S,4S,5R,6R)-6-(acetoxymethyl)-2-(3-bromo-2-chlorophenoxy)-3-methyltetrahydro-2H-pyran-3,4,5-triyltriacetate

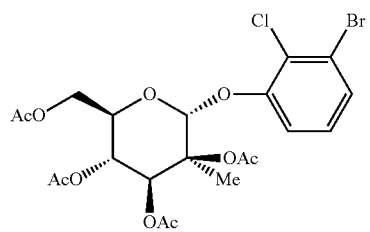 [SMILES: CC(=O)OC[C@H]1O[C@H](Oc2cccc(Br)c2Cl)[C@@](C)(OC(C)=O)[C@@H](OC(C)=O)[C@@H]1OC(C)=O]

To a mixture of INTERMEDIATE M4 (200 mg, 0.495 mmol) and 3-bromo-2-chloro-phenol (154 mg, 0.742 mmol) in dichloroethane (2.60 mL) is added BF$_3$.OEt$_2$ (190 μL, 1.50 mmol). The mixture is stirred at 60° C. overnight in a sealed tube. The resulting mixture is cooled down to RT, 2 mL of saturated aqueous NaHCO3 solution is added carefully, followed by 2 mL CH$_2$Cl$_2$. The organic layers is separated (phase separator) and the aqueous layer is back extracted with CH$_2$Cl$_2$ (2×2 mL). The combined organic extracts are concentrated and the residue purified on Biotage™ SNAP silica cartridge (10 g) eluting with is Hex/EtOAc in, (0-50%, 12CV, 50% 5CV) to afford the title compound (93 mg, 34%) as a white solid. LCMS (M+Na)$^+$ 575.18

Preparation of Intermediate M13

(2R,3S,4S,5R,6R)-6-(acetoxymethyl)-2-(5-bromo-2-chlorophenoxy)-3-methyltetrahydro-2H-pyran-3,4,5-triyltriacetate

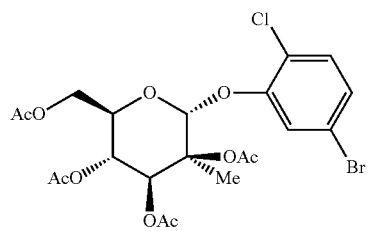 [SMILES: CC(=O)OC[C@H]1O[C@H](Oc2cc(Br)ccc2Cl)[C@@](C)(OC(C)=O)[C@@H](OC(C)=O)[C@@H]1OC(C)=O]

The title compound is prepared according to the procedure described for INTERMEDIATE M12 but using 5-bromo-2-chloro-phenol as reagent. The reaction is stirred for 48 h and the title compound is isolated as a white solid (34%). LCMS (M+Na)$^+$ 573.19

Preparation of Intermediate M14

(3S,4S,5R,6R)-6-(acetoxymethyl)-3-(azidomethyl)tetrahydro-2H-pyran-2,3,4,5-tetrayl tetraacetate

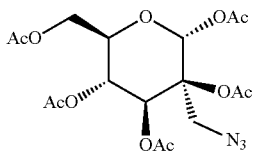

To a solution of (3S,4S,5S,6R)-3-(azidomethyl)-6-(hydroxymethyl)tetrahydropyran-2,3,4,5-tetrol (prepared according to the procedure describe in Tetrahedron: Asymmetry 18 (2007) 1502-1510) (650 mg, 2.76 mmol) in pyridine (13 mL) is added DMAP (68 mg, 0.55 mmol) and Ac$_2$O (5.2 mL, 55.3 mmol). The reaction mixture is stirred at 60° C. for 16 h, cooled down to RT, diluted with CH$_2$Cl$_2$ (13 mL) and water (13 mL) is added over 2 min and the final mixture stirred for 5 min. The organic phase is separated, washed twice with 25 ml of HCl 1N followed by brine, dried over Na$_2$SO$_4$, filtered, and concentrated. Purification on Biotage™ SNAP silica cartridge (40 g) using EtOAc (0% to 80% in 10 CV) in Hex as eluent afforded the title compound (850 mg, 69%) as a two to one mixture of α and β diastereoisomers at the anomeric carbon. $^1$H NMR (400 MHz, CDCl$_3$) a mixture of α/β (ca. 2:1) δ 6.72 (s, 1H, H$_{1\alpha}$), 5.91 (s, 1H, H$_{1\beta}$), 5.33 (d, J=9.7 Hz, 1H$_{1\alpha}$), 5.41 (d, J=9.3 Hz, 1H$_{1\beta}$), 5.38 (t, J=10.0 Hz, 1H$_{1\alpha}$), 5.38 (t, J=10.0 Hz, 1H$_{1\alpha}$), 5.24 (t, J=9.4 Hz, H$_{1\beta}$), 4.33-3.80 (m, 5H), 2.22-2.17 (m, 6H), 2.12-2.07 (m, 6H), 2.05 (s, 3H).

Preparation of Intermediate M15

(3S,4S,5R,6R)-6-(acetoxymethyl)-3-((2-(benzyloxy)ethoxy)methyl)tetrahydro-2H-pyran-2,3,4,5-tetrayl tetraacetate

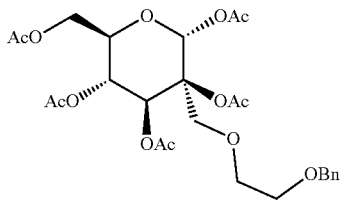

Step I: (3aS,6R,6aS)-3a-((2-(benzyloxy)ethoxy)methyl)-6-((R)-2,2-dimethyl-1,3-dioxolan-4-yl)-2,2-dimethyldihydrofuro[3,4-d][1,3]dioxol-4(3aH)-one

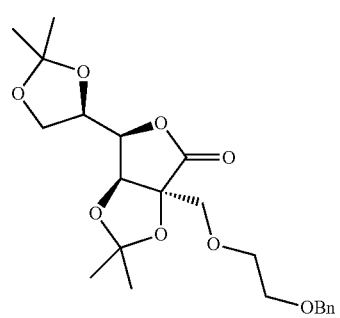 [SMILES: CC1(C)OC[C@H]([C@H]2OC(=O)[C@@]3(COCCOCc4ccccc4)OC(C)(C)O[C@@H]23)O1]

To a cold (0° C.) solution of (3aS,6R,6aS)-6-((R)-2,2-dimethyl-1,3-dioxolan-4-yl)-3a-(hydroxymethyl)-2,2-dimethyldihydrofuro[3,4-d][1,3]dioxol-4(3aH)-one from INTERMEDIATE M4 step II (800 mg, 2.78 mmol) in DMF (12.0 mL) is added sodium hydride (144 mg, 3.6 mmol). The reaction mixture is stirred for 15 min and 2-bromoethoxymethylbenzene (571 µL, 3.61 mmol) is added. The reaction mixture is stirred at 60° C. for 16 h, partitioned between EtOAc and water, the organic phase is dried over Na$_2$SO$_4$, concentrated and purified by flash chromatography on silica (0-50% EtOAC/Hexane) to afford the tittle compound (452 mg, 39%) as a colorless oil. $^1$H NMR (400 MHz, Chloroform-d) δ 7.41-7.21 (m, 5H), 4.80 (d, J=2.8 Hz, 1H), 4.53 (s, 2H), 4.46-4.36 (m, 2H), 4.13 (dd, J=9.1, 5.4 Hz, 1H), 4.09-4.01 (m, 1H), 3.99 (d, J=9.2 Hz, 1H), 3.82 (d, J=9.2 Hz, 1H), 3.77-3.64 (m, 2H), 3.58 (td, J=4.6, 1.5 Hz, 2H), 1.46 (s, 3H), 1.45 (s, 3H), 1.40 (s, 3H), 1.39 (s, 3H).

Step II: (3aS,6R,6aS)-3a-((2-(benzyloxy)ethoxy)methyl)-6-((R)-2,2-dimethyl-1,3-dioxolan-4-yl)-2,2-dimethyltetrahydrofuro[3,4-d][1,3]dioxol-4-ol

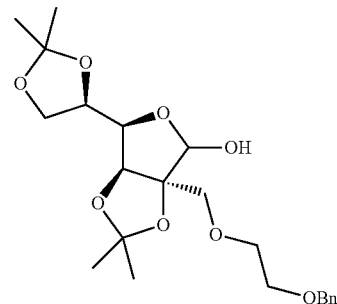

DIBAL (1.13 mL of 1.5 M, 1.7 mmol) in toluene is added dropwise to a cold (−78° C.) solution of (3aS,6R,6aS)-3a-((2-(benzyloxy)ethoxy)methyl)-6-((R)-2,2-dimethyl-1,3-dioxolan-4-yl)-2,2-dimethyldihydrofuro[3,4-d][1,3]dioxol-4(3aH)-one (650 mg, 1.5 mmol) in CH$_2$Cl$_2$ (6.5 mL). The reaction mixture is stirred at −78° C. for 2 h. Upon completion, the cold reaction mixture is quenched with 0.3 ml of MeOH added dropwise over 2 min and then is allowed to warm to RT over 30 min. 50 ml of saturated aqueous sodium tartrate is added and the resulting slurry is stirred vigorously for 1 h at room temp. The organic phase is separated, washed with water, brine, dried over Na$_2$SO$_4$, filtered and concentrated to afford the title compound (625 mg, 96%)

Step III: (3S,4S,5S,6R)-3-((2-(benzyloxy)ethoxy)methyl)-6-(hydroxymethyl)tetrahydro-2H-pyran-2,3,4,5-tetraol

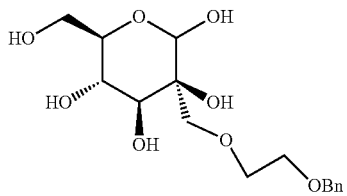 [SMILES: OC[C@H]1OC(O)[C@](O)(COCCOCc2ccccc2)[C@@H](O)[C@@H]1O]

To a solution of (3aS,6R,6aS)-3a-((2-(benzyloxy)ethoxy)methyl)-6-((R)-2,2-dimethyl-1,3-dioxolan-4-yl)-2,2-dimethyltetrahydrofuro[3,4-d][1,3]dioxol-4-ol (650 mg, 1.53 mmol) in H$_2$O (3.3 mL) and dioxane (3.3 mL) is added Dowex 50WX4 resin (300 mg). The reaction mixture is stirred at 60° C. for 16 h, cooled to RT, filtered and concentrated to afford the tittle compound (450 mg, 85%).

Step IV: Intermediate M15

To a solution of (3S,4S,5S,6R)-3-((2-(benzyloxy)ethoxy)methyl)-6-(hydroxymethyl)tetrahydro-2H-pyran-2,3,4,5-tetraol (450 mg, 1.31 mmol) in pyridine (9.0 mL) is added DMAP (32 mg, 0.26 mmol) and Ac$_2$O (2.5 mL, 26.1 mmol). The reaction mixture is stirred at 60° C. for 16 h, cooled down to RT, diluted with CH$_2$Cl$_2$ (18 mL) and water (18 mL) is added over 2 min and the final mixture stirred for 15 min. The organic phase is separated, washed twice with 10 ml of HCl 1N followed by brine, dried over Na$_2$SO$_4$, filtered, and concentrated. Purification on Biotage™ SNAP silica cartridge (80 g) using EtOAc (20% to 80% in 10 CV) in Hex as eluent afforded the title compound (450m g, 62%) as a 45/55 mixture of α and β diastereoisomers at the anomeric carbon. $^1$H NMR (400 MHz, CDCl$_3$) a mixture of α/β (ca. 45:55) δ 7.43-7.29 (m, 5H), 6.77 (s, 1H, H$_{1α}$), 6.03 (s, 1H, H$_{1β}$), 5.58 (dd, J=16.5, 9.7 Hz, 1H, H$_{1α}$), 5.38 (t, J=10.0 Hz, 1H, H$_{1β}$), 5.24 (s, 1H), 4.51 (m, 2H), 4.32-3.97 (m, 4H), 3.82 (m, 1H), 3.68-3.39 (m, 4H), 2.19-1.92 (m, 15H). INTERMEDIATE M16 to M22 are prepared according to the procedure described for INTERMEDIATE M10 using the appropriately substituted phenol.

| INTERMEDIATE | Name | $^1$H NMR |
|---|---|---|
| M16 | (2R,3S,4S,5R,6R)-6-(acetoxymethyl)-2-(4-bromo-2-methoxyphenoxy)-3-methyltetrahydro-2H-pyran-3,4,5-triyl triacetate | (400 MHz, CDCl$_3$) δ 7.00 (m, 1H), 6.98 (d, J = 1.3 Hz, 2H), 6.12 (s, 1H), 5.55 (d, J = 9.7 Hz, 1H), 5.34 (t, J = 9.9 Hz, 1H), 4.29-4.19 (m, 1H), 4.20-4.05 (m, 2H), 3.82 (s, 3H), 2.13 (s, 3H), 2.09 (s, 3H), 2.05 (s, 3H), 2.01 (s, 3H), 1.65 (s, 3H). |
| M17 | (2R,3S,4S,5R,6R)-6-(acetoxymethyl)-2-(4-bromo-2-ethylphenoxy)-3-methyltetrahydro-2H-pyran-3,4,5-triyl triacetate | (400 MHz, CDCl$_3$) δ 7.29 (dt, J = 2.5, 0.6 Hz, 1H), 7.23 (dd, J = 8.8, 2.6 Hz, 1H), 7.04 (d, J = 8.7 Hz, 1H), 6.24 (s, 1H), 5.55 (d, J = 9.7 Hz, 1H), 5.37 (t, J = 9.9 Hz, 1H), 4.15 (dd, J = 12.2, 5.3 Hz, 1H), 4.07 (dd, J = 12.3, 2.4 Hz, 1H), 4.00-3.89 (m, 1H), 2.63 (q, J = 7.5 Hz, 2H), 2.13 (s, 3H), 2.12 (s, 3H), 2.03 (s, 3H), 2.02 (s, 3H), 1.61 (s, 3H), 1.22 (t, J = 7.5 Hz, 3H). |
| M18 | (2R,3S,4S,5R,6R)-6-(acetoxymethyl)-2-(4-bromo-2-cyanophenoxy)-3-methyltetrahydro-2H-pyran-3,4,5-triyl triacetate | (400 MHz, CDCl$_3$) δ 7.72 (d, J = 2.4 Hz, 1H), 7.65 (dd, J = 9.0, 2.5 Hz, 1H), 7.24 (d, J = 9.0 Hz, 1H), 6.33 (s, 1H), 5.59 (d, J = 9.7 Hz, 1H), 5.46-5.33 (m, 1H), 4.25-4.04 (m, 3H), 2.16 (s, 3H), 2.13 (s, 3H), 2.05 (s, 3H), 2.05 (s, 3H), 1.70 (s, 3H). |
| M19 | (2R,3S,4S,5R,6R)-6-(acetoxymethyl)-2-(4-iodo-2-fluorophenoxy)-3-methyltetrahydro-2H-pyran-3,4,5-triyl triacetate | (400 MHz, CDCl$_3$) δ 7.43 (dd, J = 9.8, 2.1 Hz, 1H), 7.36 (dt, J = 8.7, 1.7 Hz, 1H), 6.97 (t, J = 8.5 Hz, 1H), 6.16 (s, 1H), 5.51 (d, J = 9.7 Hz, 1H), 5.35 (t, J = 9.6 Hz, 1H), 4.20-4.04 (m, 3H), 2.11 (s, 3H), 2.10 (s, 3H), 2.02 (s, 3H), 2.01 (s, 3H), 1.62 (s, 3H). |
| M20 | (2R,3S,4S,5R,6R)-6-(acetoxymethyl)-2-(5-bromo-2-methylphenoxy)-3-methyltetrahydro-2H-pyran-3,4,5-triyl triacetate | (400 MHz, CDCl$_3$) δ 7.34 (d, J = 1.8 Hz, 1H), 7.08 (dd, J = 8.0, 1.8 Hz, 1H), 7.01 (dd, J = 8.0, 0.5 Hz, 1H), 6.21 (s, 1H), 5.54 (d, J = 9.7 Hz, 1H), 5.33 (t, J = 9.9 Hz, 1H), 4.17 (dd, J = 12.1, 6.3 Hz, 1H), 4.12-3.96 (m, 2H), 2.20 (s, 3H), 2.13 (s, 3H), 2.12 (s, 3H), 2.06 (s, 3H), 2.02 (s, 3H), 1.61 (s, 3H). |
| M21 | (2R,3S,4S,5R,6R)-6-(acetoxymethyl)-2-(4-bromo-2-isopropylphenoxy)-3-methyltetrahydro-2H-pyran-3,4,5-triyl triacetate | (400 MHz, CDCl$_3$) δ 7.42 (dq, J = 2.4, 1.2 Hz, 1H), 7.36 (dd, J = 8.8, 2.4 Hz, 1H), 7.18 (d, J = 8.9 Hz, 1H), 6.24 (s, 1H), 5.54 (d, J = 9.7 Hz, 1H), 5.37 (t, J = 9.9 Hz, 1H), 4.19-4.04 (m, 2H), 4.03-3.95 (m, 1H), 2.13 (s, 3H), 2.11 (s, 3H), 2.03 (s, 3H), 2.02 (s, 3H), 1.60 (s, 3H). |
| M22 | (2R,3S,4S,5R,6R)-6-(acetoxymethyl)-2-(4-bromo-2-(trifluoromethoxy)phenoxy)-3-methyltetrahydro-2H-pyran-3,4,5-triyl triacetate | |

Biaryls INTERMEDIATES A1 to A12 depicted in Figure 2 are used in the preparation of EXAMPLEs described therein

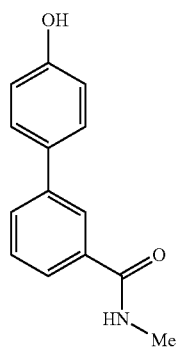 (A1)
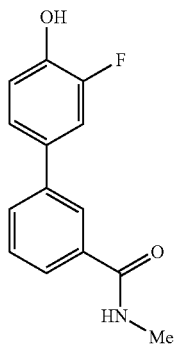 (A5)
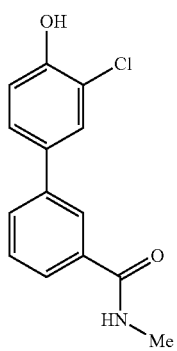 (A6)
(A2)
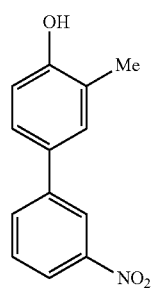 (A7)
(A3)
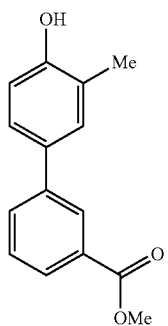 (A8)
(A4)
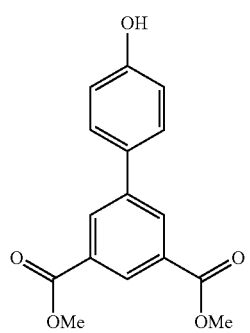 (A9)

(A10) 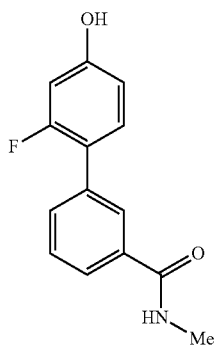

(A11) 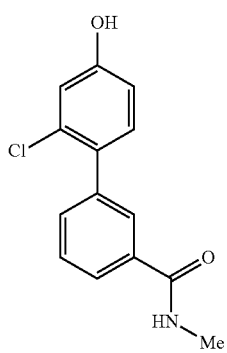

(A12) 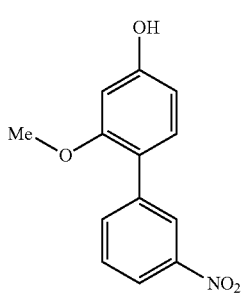

(A13) 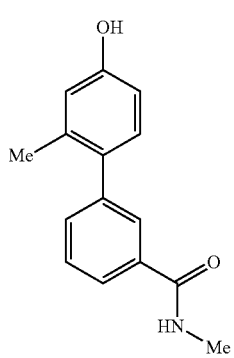

(A14) 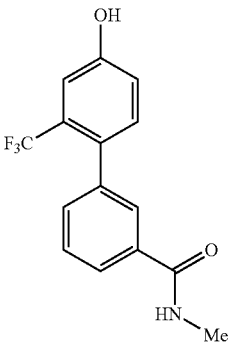

Preparation of Intermediate A1

3-(4-hydroxyphenyl)-N-methyl-benzamide

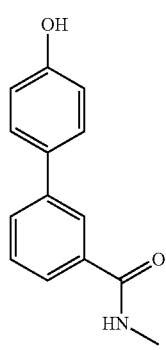 [SMILES: CNC(=O)c1cccc(-c2ccc(O)cc2)c1]

A mixture of [3-(methylcarbamoyl)phenyl]boronic acid (3.41 g, 19.1 mmol), 4-bromophenol (3.00 g, 17.3 mmol), $K_2CO_3$ (3.60 g, 26.01 mmol) and SiliaCat DPP-Pd (667 mg, 0.173 mmol) are combined in a pressure vessel. MeOH (30 mL) is added and the reaction mixture is stirred 2 h at 80° C. The reaction mixture is cooled to RT, filtered on Celite and the precipitate is washed with portions of MeOH. The combined filtrates are concentrated. The residue is partitioned between aqueous 1N HCl solution and EtOAc (50 mL each). The layers are separated and the aqueous layer is back extracted with EtOAc (2×25 mL). The combined organic extracts are washed with brine (25 mL), dried over $Na_2SO_4$, filtered and concentrated to provide crude product which is purified by flash chromatography on a Biotage™ SNAP silica cartridge (100 g) using a EtOAc (50%) in $CH_2Cl_2$ as eluent. The solids that crystallized upon concentration of the mixed fractions is collected by filtration providing a first crop of the title compound (814 mg, 21% yield) as a white solid. Concentration of the pure fractions from the chromatography affords a second crop of the title compound (1.66 g, 42% yield) as a white solid. $^1H$ NMR (400 MHz, $CDCl_3$) δ 7.96-7.87 (m, 2H), 7.68-7.58 (m, 2H), 7.50-7.39 (m, 3H), 6.97-6.85 (m, 2H), 6.37 (bs, 1H), 3.02 (d, J=4.8 Hz, 3H).

Preparation of Intermediate A2

3-(4-hydroxy-3-methyl-phenyl)-N-methyl-benzamide

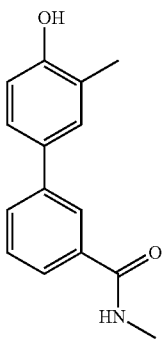 [SMILES: CNC(=O)c1cccc(-c2ccc(O)c(C)c2)c1]

The title compound is prepared following the same procedure described for INTERMEDIATE A1, using 4-bromo-2-methyl-phenol (6.67 g, 35.7 mmol) as starting material. The crude product is passed through a silica plug using EtOAc, concentrated then recrystallized using a mixture of THF (80 mL) and $CH_2Cl_2$ (25 mL), providing the title compound (2.63 g, 31% yield) as an off-white solid. Concentration of the mother liquors followed by purification by flash chromatography on a Biotage™ SNAP silica cartridge (100 g) using a gradient of EtOAc (0 to 50%) in $CH_2Cl_2$ afforded a second crop of the title compound (2.53 g, 29% yield) as an off-white solid. $^1$H NMR (400 MHz, DMSO-$D_6$) δ 9.48 (s, 1H), 8.50 (d, J=4.6 Hz, 1H), 8.00 (t, J=1.6 Hz, 1H), 7.75-7.63 (m, 2H), 7.52-7.40 (m, 2H), 7.35 (dd, J=8.3, 2.3 Hz, 1H), 6.86 (d, J=8.3 Hz, 1H), 2.79 (d, J=4.5 Hz, 3H), 2.19 (s, 3H).

General Preparation of Intermediates A3 to A14 (Table A)

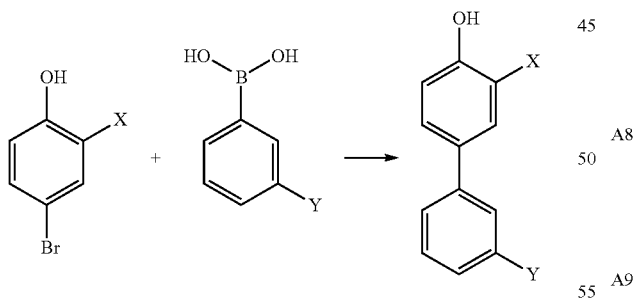

A microwave vial is charged with the appropriate substituted 4-bromophenol and phenyl boronic acid (1 eq.), $K_2CO_3$ (1.5 eq.) and SiliaCat DPP-Pd (0.1 eq.) in MeOH. The vial is capped and submitted to microwave irradiation for 15 minutes at 120° C. The reaction mixture is partitioned between aqueous 1N HCl solution and $CH_2Cl_2$. The layers are separated and the aqueous layer is back extracted twice with $CH_2Cl_2$. The combined organic extracts are dried over $Na_2SO_4$, concentrated and purified by flash chromatography on a Biotage™ SNAP silica gel cartridge using a gradient of EtOAc in $CH_2Cl_2$ to afford the title compound.

TABLE A

| INTERMEDIATE | Name | Yield | NMR |
|---|---|---|---|
| A3 | 3'-ethyl-4'-hydroxy-N-methyl-[1,1'-biphenyl]-3 carboxamide | 67% | $^1$H NMR (400 MHz, DMSO-$D_6$) δ 9.47 (s, 1H), 8.50 (d, J = 4.5 Hz, 1H), 7.99 (t, J = 1.6 Hz, 1H), 7.75-7.62 (m, 2H), 7.46 (t, J = 7.7 Hz, 1H), 7.42 (d, J = 2.2 Hz, 1H), 7.35 (dd, J = 8.3, 2.4 Hz, 1H), 6.86 (dd, J = 8.3, 2.1 Hz, 1H), 2.79 (d, J = 4.5 Hz, 3H), 2.60 (q, J = 7.5 Hz, 2H), 1.17 (t, J = 7.5 Hz, 3H). |
| A4 | 4'-hydroxy-3'-methoxy-N-methyl-[1,1'-biphenyl]-3-carboxamide | 78% | $^1$H NMR (400 MHz, DMSO-$D_6$) δ 9.16 (s, 1H), 8.51 (d, J = 4.6 Hz, 1H), 8.01 (t, J = 1.6 Hz, 1H), 7.78-7.65 (m, 2H), 7.48 (t, J = 7.7 Hz, 1H), 7.23 (d, J = 2.1 Hz, 1H), 7.13 (dd, J = 8.2, 2.1 Hz, 1H), 6.86 (d, J = 8.2 Hz, 1H), 3.86 (s, 3H), 2.80 (d, J = 4.5 Hz, 3H). |
| A5 | 3'-fluoro-4'-hydroxy-N-methyl-[1,1'-biphenyl]-3-carboxamide | 66% | $^1$H NMR (400 MHz, DMSO-$D_6$) δ 10.04 (s, 1H), 8.53 (d, J = 4.4 Hz, 1H), 8.03 (t, J = 1.6 Hz, 1H), 7.76 (d, J = 1.8 Hz, 1H), 7.74 (d, J = 1.7 Hz, 1H), 7.55 (dd, J = 12.8, 2.2 Hz, 1H), 7.49 (t, J = 7.7 Hz, 1H), 7.41-7.35 (m, 1H), 7.07-6.99 (m, 1H), 2.80 (d, J = 4.5 Hz, 3H). $^{19}$F NMR (376 MHz, dmso) δ −135.99 (dd, J = 12.8, 9.3 Hz). |
| A6 | 3'-chloro-4'-hydroxy-N-methyl-[1,1'-biphenyl]-3-carboxamide | 77% | $^1$H NMR (400 MHz, DMSO-$D_6$) δ 10.37 (s, 1H), 8.54 (d, J = 4.5 Hz, 1H), 8.03 (t, J = 1.6 Hz, 1H), 7.78-7.71 (m, 3H), 7.55-7.45 (m, 2H), 7.06 (d, J = 8.5 Hz, 1H), 2.80 (d, J = 4.5 Hz, 3H). |
| A7 | 2-methyl-4-(3-nitrophenyl) phenol | 56% | $^1$H NMR (400 MHz, CDCl$_3$) δ 8.40 (t, J = 2.0 Hz, 1H), 8.14 (ddd, J = 8.2, 2.2, 1.0 Hz, 1H), 7.86 (ddd, J = 7.8, 1.7, 1.0 Hz, 1H), 7.57 (t, J = 8.0 Hz, 1H), 7.41 (d, J = 2.0 Hz, 1H), 7.36 (dd, J = 8.2, 2.3 Hz, 1H), 6.89 (d, J = 8.2 Hz, 1H), 4.86 (s, 1H), 2.34 (s, 3H). |
| A8 | methyl 4'-hydroxy-3'-methyl-[1,1'-biphenyl]-3-carboxylate | | Prepared by esterification (MeOH/HCl) of commercially available 4'-hydroxy-3'-methyl-[1,1'-biphenyl]-3-carboxylic acid LCMS: m/z = 243.47 (M + H)$^+$ |
| A9 | dimethyl 4'-hydroxy-[1,1'-biphenyl]-3,5 dicarboxylate | 94% | $^1$H NMR (400 MHz, CDCl$_3$) δ 8.61 (t, J = 1.6 Hz, 1H), 8.41 (d, J = 1.6 Hz, 2H), 7.61-7.51 (m, 2H), 6.98-6.92 (m, 2H), 4.96 (s, 1H), 3.97 (s, 6H). |
| A10 | 2'-fluoro-4'-hydroxy-N-methyl-[1,1'-biphenyl]-3-carboxamide | 35% | $^1$H NMR (400 MHz, DMDO) δ 10.08 (s, 1H), 8.49 (d, J = 4.4 Hz, 1H), 7.91 (d, J = 1.3 Hz, 1H), 7.82-7.70 (m, 1H), 7.65-7.56 (m, 1H), 7.50 (t, J = 7.7 Hz, 1H), 7.38 (dd, J = 9.4, 8.6 Hz, 1H), 6.72 (dd, J = 8.4, 2.3 Hz, 1H), 6.68 (dd, |

TABLE A-continued

| INTER-MEDI-ATE | Name | Yield | NMR |
|---|---|---|---|
| A11 | 2'-Chloro-4'-hydroxy-N-methyl-[1,1'-biphenyl]-3-carboxamide | 77% | J = 12.8, 2.3 Hz, 1H), 2.78 (d, J = 4.5 Hz, 3H). $^1$H NMR (400 MHz, DMSO ) δ 10.04 (s, 1H), 8.48 (d, J = 4.5 Hz, 1H), 7.89-7.65 (m, 2H), 7.60-7.40 (m, 2H), 7.26 (d, J = 8.4 Hz, 1H), 6.94 (d, J = 2.4 Hz, 1H), 6.83 (dd, J = 8.4, 2.4 Hz, 1H), 2.77 (d, J = 4.5 Hz, 3H). |
| A12 | 2'-Methoxy-4'-hydroxy-N-methyl-[1,1'-biphenyl]-3-carboxamide | 59% | $^1$H NMR (400 MHz, DMSO) δ 9.61 (s, 1H), 8.42 (d, J = 4.5 Hz, 1H), 7.83 (t, J = 1.6 Hz, 1H), 7.73-7.64 (m, 1H), 7.60-7.49 (m, 1H), 7.41 (t, J = 7.7 Hz, 1H), 7.12 (d, J = 8.2 Hz, 1H), 6.51 (d, J = 2.2 Hz, 1H), 6.45 (dd, J = 8.2, 2.2 Hz, 1H), 3.70 (s, 3H), 2.77 (d, J = 4.5 Hz, 3H). |
| A13 | 2'-Methyl-4'-hydroxy-N-methyl-[1,1'-biphenyl]-3-carboxamide | 47% | $^1$H NMR (400 MHz, dmso) δ 9.40 (s, 1H), 8.45 (d, J = 4.4 Hz, 1H), 7.85-7.65 (m, 2H), 7.56-7.28 (m, 2H), 7.03 (d, J = 8.2 Hz, 1H), 6.75-6.57 (m, 2H), 2.77 (d, J = 4.5 Hz, 3H), 2.14 (s, 3H). |
| A14 | 4'-hydroxy-N-methyl-2'-(trifluoromethyl)-[1,1'-biphenyl]-3-carboxamide | 60% | $^1$H NMR (400 MHz, DMSO) δ 10.23 (s, 1H), 8.47 (d, J = 4.5 Hz, 1H), 7.86-7.81 (m, 1H), 7.73 (s, 1H), 7.48 (t, J = 7.7 Hz, 1H), 7.39 (d, J = 7.6 Hz, 1H), 7.23 (d, J = 8.4 Hz, 1H), 7.16 (d, J = 2.5 Hz, 1H), 7.08 (dd, J = 8.4, 2.4 Hz, 1H), 2.76 (d, J = 4.5 Hz, 3H). |

Preparation of Example 1

(2R,3S,4S,5S,6R)-6-(4-bromo-2-methyl-phenoxy)-5-fluoro-2-(hydroxymethyl)tetrahydropyran-3,4-diol

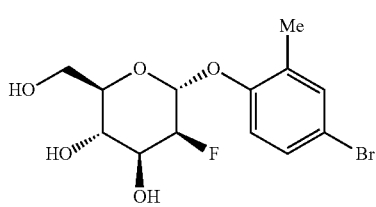 [SMILES: Cc1cc(Br)ccc1O[C@H]1O[C@H](CO)[C@@H](O)[C@H](O)[C@@H]1F]

Step I: [(2R,3R,4S,5S,6R)-3,4-diacetoxy-6-(4-bromo-2-methyl-phenoxy)-5-fluoro-tetrahydropyran-2-yl]methyl acetate

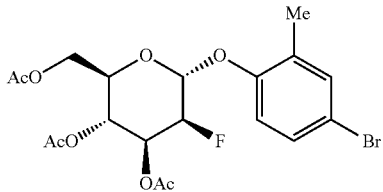 [SMILES: CC(=O)OC[C@H]1O[C@H](Oc2ccc(Br)cc2C)[C@@H](F)[C@@H](OC(C)=O)[C@@H]1OC(C)=O]

In a pressure vessel, a suspension of [(2R,3R,4S,5S)-3,4,6-triacetoxy-5-fluoro-tetrahydropyran-2-yl]methyl acetate (prepared according to the procedure described in Angew. Chem. Int. Ed. 2010, 49, 8724-8728) (199 mg, 0.568 mmol) and 4-bromo-2-methylphenol (217 mg, 1.160 mmol) in $CH_2Cl_2$ (6.0 mL) is treated with $BF_3.OEt_2$ (215 μL, 1.697 mmol) added dropwise. The reaction mixture is stirred for 5 min at RT, capped and stirred at 40° C. for 16 h. After cooling down to RT, 5 mL saturated aqueous $NaHCO_3$ is added. The layers are separated and the aqueous layer is further extracted with $CH_2Cl_2$ (2×2 mL). The combined organic extracts are concentrated and the crude product is purified by flash chromatography on a Biotage™ SNAP silica cartridge (10 g) using a gradient of EtOAc (0 to 30%) in Hex. Evaporation of the pure fractions provided the title compound as a white solid (179 mg, 66% yield). $^1$H NMR (400 MHz, CDCl$_3$) δ 7.31 (d, J=2.4 Hz, 1H), 7.29-7.24 (m, 1H), 7.02 (d, J=8.7 Hz, 1H), 5.64 (dd, J=6.4, 2.0 Hz, 1H), 5.50-5.36 (m, 2H), 4.98 (dt, J=49.5, 2.1 Hz, 1H), 4.26 (dd, J=12.4, 5.1 Hz, 1H), 4.09 (dd, J=12.4, 2.3 Hz, 1H), 4.06-3.99 (m, 1H), 2.24 (s, 3H), 2.14 (s, 3H), 2.06 (s, 3H), 2.05 (s, 3H). $^{19}$F NMR (376 MHz, CDCl$_3$) δ −204.49 (ddd, J=49.4, 29.4, 6.4 Hz). ESI-MS m/z calc. 476.05. found 499.30 (M+Na)$^+$.

Step II: Example 1

To a solution of [(2R,3R,4S,5S,6R)-3,4-diacetoxy-6-(4-bromo-2-methyl-phenoxy)-5-fluoro-tetrahydropyran-2-yl] methyl acetate from Step I (98 mg, 0.205 mmol) in MeOH (4.0 mL) is added NaOMe in MeOH (205 μL of 0.5 M, 0.103 mmol). After stirring overnight, the reaction mixture is treated with prewashed Dowex 50WX4-400 resin filtered and rinsed with MeOH (3×1 mL). Combined filtrates are concentrated to provide the title compound (70 mg, 89%) as a white solid. $^1$H NMR (400 MHz, CD$_3$OD) δ 7.31 (d, J=1.9 Hz, 1H), 7.27 (dd, J=8.6, 2.1 Hz, 1H), 7.16 (d, J=8.7 Hz, 1H), 5.70 (dd, J=6.7, 1.7 Hz, 1H), 4.91-4.72 (m, 1H), 3.96 (ddd, J=30.8, 9.7, 2.6 Hz, 1H), 3.78 (dd, J=12.1, 2.5 Hz, 1H), 3.75-3.66 (m, 2H), 3.62-3.53 (m, 1H), 2.21 (s, 3H). $^{19}$F NMR (376 MHz, CD$_3$OD) δ −206.88 (ddd, J=49.4, 30.9, 6.9 Hz). ESI-MS m/z calc. 351.17. found 373.20 (M+Na)$^+$.

119

Preparation of Example 2

(2R,3S,4S,5S,6R)-5-fluoro-2-(hydroxymethyl)-6-((3-methyl-3'-nitro-[1,1'-biphenyl]-4-yl)oxy)tetrahydro-2H-pyran-3,4-diol

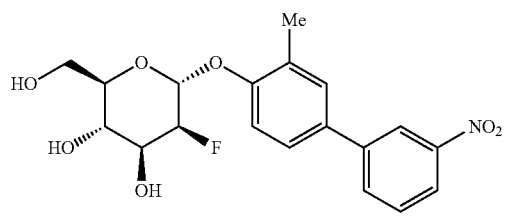 [SMILES: Cc1cc(-c2cccc([N+](=O)[O-])c2)ccc1O[C@H]1O[C@H](CO)[C@@H](O)[C@H](O)[C@@H]1F]

In a microwave vial is charged (2R,3S,4S,5S,6R)-6-(4-bromo-2-methyl-phenoxy)-5-fluoro-2-(hydroxymethyl)tetrahydropyran-3,4-diol (EXAMPLE 1) (32 mg, 0.0911 mmol), (3-nitrophenyl)boronic acid (18 mg, 0.107 mmol), $Cs_2CO_3$ (89 mg, 0.273 mmol), SiliaCat DPP-Pd (35 mg, 0.00911 mmol) and 2 mL $CH_3CN$. The vial is degassed, capped and submitted to microwave for 10 min at 100° C. The reaction mixture is diluted with MeOH and $CH_2Cl_2$ (1 mL each) and passed thru a 500 mg isolute silica cartridge, rinsed with $CH_2Cl_2$/MeOH mixture (1:1, 4×1 mL). Combined filtrates are concentrated and the crude product is purified by reverse-phase flash chromatography on a Biotage™ SNAP C18 cartridge (12 g), using a gradient of MeCN (10 to 90%) in $H_2O$. The pure fractions are combined and concentrated to provide the title compound (18 mg, 50% yield) as a pale yellow solid. $^1H$ NMR (400 MHz, $CD_3OD$) δ 8.41 (t, J=1.9 Hz, 1H), 8.17 (dd, J=8.2, 1.4 Hz, 1H), 7.99 (d, J=8.3 Hz, 1H), 7.66 (t, J=8.0 Hz, 1H), 7.57-7.47 (m, 2H), 7.37 (d, J=8.4 Hz, 1H), 5.81 (dd, J=6.7, 1.7 Hz, 1H), 4.88 (dt, J=49.4, 2.2 Hz, 1H), 4.02 (ddd, J=30.8, 9.6, 2.6 Hz, 1H), 3.86-3.77 (m, 2H), 3.73 (dd, J=12.1, 5.3 Hz, 1H), 3.63 (ddd, J=7.6, 4.9, 2.1 Hz, 1H), 2.33 (s, 3H). $^{19}F$ NMR (376 MHz, $CD_3OD$) δ −206.84 (ddd, J=49.3, 30.8, 6.7 Hz). ESI-MS m/z calc. 393.12238. found 394.34 (M+1)$^+$.

Preparation of Example 3

(2R,3S,4S,5S,6R)-6-[4-bromo-2-(trifluoromethyl)phenoxy]-5-fluoro-2-(hydroxymethyl)tetrahydropyran-3,4-diol

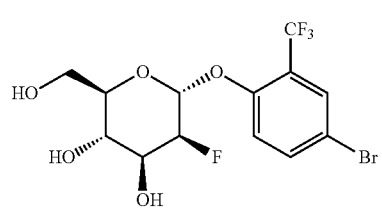 [SMILES: OC[C@H]1O[C@H](Oc2ccc(Br)cc2C(F)(F)F)[C@@H](F)[C@@H](O)[C@@H]1O]

120

Step I: [(2R,3R,4S,5S,6R)-3,4-diacetoxy-6-[4-bromo-2-(trifluoromethyl)phenoxy]-5-fluoro-tetrahydropyran-2-yl]methyl acetate

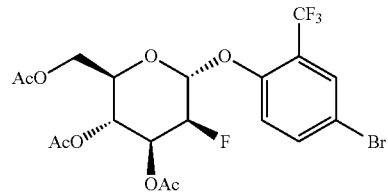 [SMILES: CC(=O)OC[C@H]1O[C@H](Oc2ccc(Br)cc2C(F)(F)F)[C@@H](F)[C@@H](OC(C)=O)[C@@H]1OC(C)=O]

The title compound is prepared from [(2R,3R,4S,5S)-3,4,6-triacetoxy-5-fluoro-tetrahydropyran-2-yl]methyl acetate (106 mg, 0.303 mmol) and 4-bromo-2-(trifluoromethyl)phenol (151 mg, 0.627 mmol) according to the procedure described in EXAMPLE 1 step I. Purification by flash chromatography on a Biotage™ SNAP silica cartridge (10 g) using a gradient of EtOAc (0 to 30%) in Hex afforded the title compound (41 mg, 26% yield) is obtained as a white foamy solid. $^1H$ NMR (400 MHz, $CDCl_3$) δ 7.75 (d, J=2.4 Hz, 1H), 7.64 (dd, J=8.9, 2.4 Hz, 1H), 7.22 (d, J=9.0 Hz, 1H), 5.72 (dd, J=6.3, 2.0 Hz, 1H), 5.50-5.34 (m, 2H), 5.00 (dt, J=49.2, 2.2 Hz, 1H), 4.27 (dd, J=12.4, 4.8 Hz, 1H), 4.09 (dd, J=12.4, 2.3 Hz, 1H), 4.03 (ddd, J=9.0, 4.7, 2.3 Hz, 1H), 2.13 (s, 3H), 2.06 (s, 6H). $^{19}F$ NMR (376 MHz, $CDCl_3$) δ −62.52 (s), −205.28 (ddd, J=49.2, 29.4, 6.3 Hz). ESI-MS m/z calc. 531.25. found 553.27 (M+Na)$^+$.

Step II: Example 3

Removal of the acetate protecting groups of [(2R,3R,4S,5S,6R)-3,4-diacetoxy-6-[4-bromo-2-(trifluoromethyl)phenoxy]-5-fluoro-tetrahydropyran-2-yl]methyl acetate from Step I (39 mg, 0.0734 mmol) using the protocol described for EXAMPLE 1 Step II provided the title compound (29 mg, 93% yield) as a white solid. $^1H$ NMR (400 MHz, $CD_3OD$) δ 7.77-7.70 (m, 2H), 7.46 (d, J=8.5 Hz, 1H), 5.86 (dd, J=6.5, 1.8 Hz, 1H), 4.80 (dt, J=49.1, 2.3 Hz, 1H), 3.93 (ddd, J=30.7, 9.6, 2.6 Hz, 1H), 3.80 (dd, J=12.1, 2.3 Hz, 1H), 3.77-3.65 (m, 2H), 3.61-3.52 (m, 1H). $^{19}F$ NMR (376 MHz, $CD_3OD$) δ −63.91 (s, 3F), −207.57 (ddd, J=49.2, 30.8, 6.7 Hz, 1F). ESI-MS m/z calc. 403.98825. found 403.37 (M+1)$^+$.

Preparation of Example 4

3-[4-[(2R,3S,4S,5S,6R)-3-fluoro-4,5-dihydroxy-6-(hydroxymethyl)tetrahydropyran-2-yl]oxy-3-(trifluoromethyl)phenyl]-N-methyl-benzamide

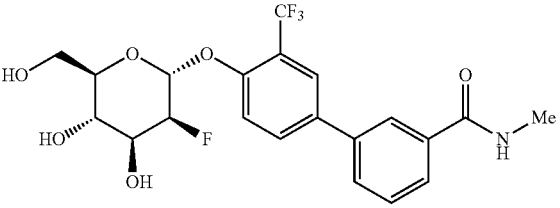 [SMILES: CNC(=O)c1cccc(-c2ccc(O[C@H]3O[C@H](CO)[C@@H](O)[C@H](O)[C@@H]3F)c(C(F)(F)F)c2)c1]

The title compound is prepared according to the procedure described for EXAMPLE 2 but using (2R,3S,4S,5S, 6R)-6-[4-bromo-2-(trifluoromethyl)phenoxy]-5-fluoro-2-(hydroxymethyl)tetrahydropyran-3,4-diol (EXAMPLE 3) (21.4 mg, 0.0501 mmol) and [3-(methylcarbamoyl)phenyl]boronic acid (13 mg, 0.07263 mmol). Purification by reverse phase HPLC and freeze-drying the combined fractions containing the desired material provided the title compound (12 mg, 51% yield) as a fluffy white solid. $^1$H NMR (400 MHz, CD$_3$OD) δ 8.06 (t, J=1.7 Hz, 1H), 7.95-7.87 (m, 2H), 7.84-7.75 (m, 2H), 7.63 (d, J=8.5 Hz, 1H), 7.56 (t, J=7.8 Hz, 1H), 5.92 (dd, J=6.5, 1.8 Hz, 1H), 4.93-4.75 (m, 1H), 3.99 (ddd, J=30.7, 9.6, 2.6 Hz, 1H), 3.82 (dd, J=12.2, 2.3 Hz, 1H), 3.78-3.69 (m, 2H), 3.67-3.58 (m, 1H), 2.95 (s, 3H). $^{19}$F NMR (376 MHz, CD$_3$OD) δ −63.47 (s, 3F), −207.47 (ddd, J=49.4, 30.7, 6.6 Hz, 1F). ESI-MS m/z calc. 459.1305. found 460.38 (M+1)$^+$.

Preparation of Example 5

(2R,3S,4S,5S,6R)-6-(4-bromo-2-methoxy-phenoxy)-5-fluoro-2-(hydroxymethyl)tetrahydropyran-3,4-diol

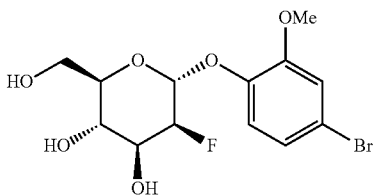 [SMILES: COc1cc(Br)ccc1O[C@H]1O[C@H](CO)[C@@H](O)[C@H](O)[C@@H]1F]

Step I: [(2R,3R,4S,5S,6R)-3,4-diacetoxy-6-(4-bromo-2-methoxy-phenoxy)-5-fluoro-tetrahydropyran-2-yl]methyl acetate

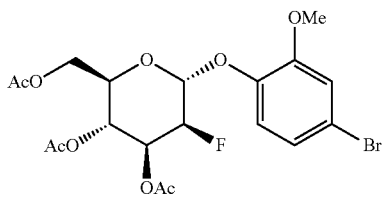 [SMILES: COc1cc(Br)ccc1O[C@H]1O[C@H](COC(C)=O)[C@@H](OC(C)=O)[C@H](OC(C)=O)[C@@H]1F]

The title compound is prepared according to the procedure described for EXAMPLE 1 Step I using [(2R,3R,4S,5S)-3,4,6-triacetoxy-5-fluoro-tetrahydropyran-2-yl]methyl acetate (102 mg, 0.291 mmol) and 4-bromo-2-methoxy-phenol (116 mg, 0.571 mmol). Purification by flash chromatography on a Biotage™ SNAP silica cartridge (10 g) using a gradient of EtOAc (0 to 40%) in Hex afforded the title compound (71 mg, 49% yield) as a colorless gum. $^1$H NMR (400 MHz, CDCl$_3$) δ 7.07-6.88 (m, 3H), 5.58 (dd, J=6.9, 1.6 Hz, 1H), 5.49 (ddd, J=28.0, 10.1, 2.4 Hz, 1H), 5.40 (t, J=9.3 Hz, 1H), 5.03 (dt, J=49.4, 2.1 Hz, 1H), 4.26 (dd, J=14.0, 4.8 Hz, 2H), 4.16-4.06 (m, 1H), 3.84 (s, 3H), 2.13 (s, 3H), 2.07 (s, 3H), 2.04 (s, 3H). $^{19}$F NMR (376 MHz, CDCl$_3$) δ −204.14 (ddd, J=49.5, 28.2, 6.9 Hz). ESI-MS m/z calc. 493.27. found 493.28 (M+1)$^+$.

Step II: Example 5

Removal of the acetate protecting groups of [(2R,3R,4S,5S,6R)-3,4-diacetoxy-6-(4-bromo-2-methoxy-phenoxy)-5-fluoro-tetrahydropyran-2-yl]methyl acetate from Step I (67 mg, 0.136 mmol) using the protocol described for EXAMPLE 1 Step II provided the title compound (50 mg, 98% yield) as a colorless solid. $^1$H NMR (400 MHz, CD$_3$OD) δ 7.18-7.09 (m, 2H), 7.03 (dd, J=8.6, 2.3 Hz, 1H), 5.56 (dd, J=7.1, 1.9 Hz, 1H), 4.94-4.72 (m, 1H), 3.96 (ddd, J=31.0, 9.3, 2.6 Hz, 1H), 3.84 (s, 3H), 3.82-3.67 (m, 4H). $^{19}$F NMR (376 MHz, CD$_3$OD) δ −206.72 (ddd, J=49.8, 30.9, 7.2 Hz). ESI-MS m/z calc. 366.01144. found 367.28 (M+1)$^+$.

Preparation of Example 6

3-[4-[(2R,3S,4S,5S,6R)-3-fluoro-4,5-dihydroxy-6-(hydroxymethyl)tetrahydropyran-2-yl]oxy-3-methyl-phenyl]-N-methyl-benzamide

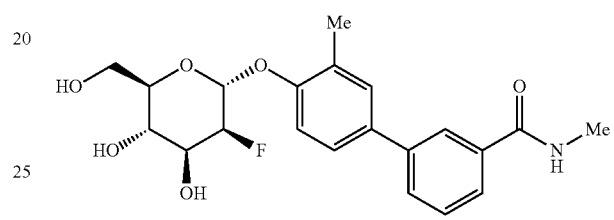

Step I: [(2R,3R,4S,5S,6R)-3,4-diacetoxy-5-fluoro-6-[2-methyl-4-[3-(methylcarbamoyl)phenyl]phenoxy]tetrahydropyran-2-yl]methyl acetate

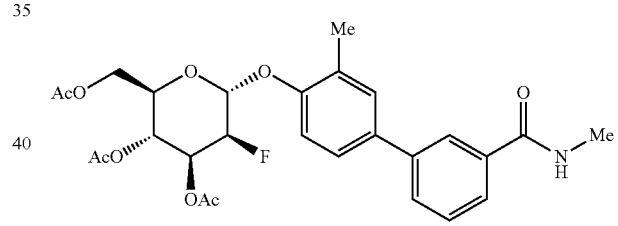

A microwave vial is charged [(2R,3R,4S,5S,6R)-3,4-diacetoxy-6-(4-bromo-2-methyl-phenoxy)-5-fluoro-tetrahydropyran-2-yl]methyl acetate from EXAMPLE 1 Step I (75 mg, 0.157 mmol), N-methyl-3-(4,4,5,5-tetramethyl-1,3,2-dioxaborolan-2-yl)benzamide (49 mg, 0.188 mmol), Cs$_2$CO$_3$ (178 mg, 0.546 mmol), SiliaCat DPP-Pd (67 mg, 0.01742 mmol) and 2 mL CH$_3$CN. The vial is degassed, capped and submitted to microwave for 10 min at 100° C. The reaction mixture is diluted with EtOAc, filtered on Celite and washed with portions of EtOAc. The combined filtrates are concentrated and the crude product is purified by flash chromatography on a Biotage™ SNAP silica cartridge (10 g) using a gradient of EtOAc (50 to 80%) in Hex to provide the title compound as a white foamy solid (55 mg, 66% yield). ESI-MS m/z calc. 531.19. found 532.62 (M+1)$^+$.

Step II: Example 6

Removal of the acetate protecting groups of [(2R,3R,4S,5S,6R)-3,4-diacetoxy-5-fluoro-6-[2-methyl-4-[3-(methylcarbamoyl)phenyl]phenoxy]tetrahydropyran-2-yl]methyl acetate from Step I (45 mg, 0.0847 mmol) using the protocol described for EXAMPLE 1 Step II provided the title compound (34 mg, 98% yield) as a white fluffy solid. $^1$H NMR (400 MHz, CD$_3$OD) δ 8.02 (t, J=1.6 Hz, 1H), 7.78-7.71 (m, 2H), 7.54-7.44 (m, 3H), 7.34 (d, J=8.5 Hz, 1H), 5.78 (dd, J=6.8, 1.9 Hz, 1H), 4.87 (dt, J=49.4, 4.9 Hz, 1H), 4.02 (ddd, J=30.9, 9.6, 2.6 Hz, 1H), 3.84-3.69 (m, 3H), 3.67-3.60 (m, 1H), 2.94 (s, 3H), 2.32 (s, 3H). $^{19}$F NMR (376 MHz, CD$_3$OD) δ −206.77 (ddd, J=49.6, 31.0, 6.8 Hz). ESI-MS m/z calc. 405.15875. found 406.52 (M+1)$^+$.

Preparation of Example 7

3-[4-[(2R,3S,4S,5S,6R)-3-fluoro-4,5-dihydroxy-6-(hydroxymethyl)tetrahydropyran-2-yl]oxyphenyl]-N-methyl-benzamide

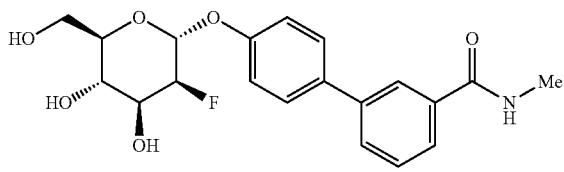 [SMILES: CNC(=O)c1cccc(-c2ccc(O[C@H]3O[C@H](CO)[C@@H](O)[C@H](O)[C@@H]3F)cc2)c1]

Step I: [(2R,3R,4S,5S,6R)-3,4-diacetoxy-5-fluoro-6-[4-[3-(methylcarbamoyl)phenyl]phenoxy]tetrahydropyran-2-yl]methyl acetate

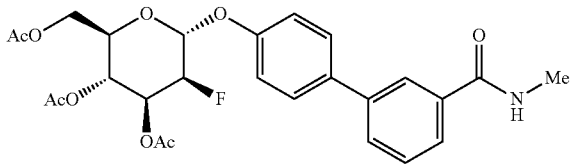 [SMILES: CNC(=O)c1cccc(-c2ccc(O[C@H]3O[C@H](COC(C)=O)[C@@H](OC(C)=O)[C@H](OC(C)=O)[C@@H]3F)cc2)c1]

In a pressure vessel, a solution of INTERMEDIATE M1 (124 mg, 0.354 mmol) and INTERMEDIATE A1(161 mg, 0.708 mmol) in CH$_2$Cl$_2$ (3.7 mL) is treated with BF$_3$.Et$_2$O (135 mL, 1.06 mmol) added dropwise, the mixture is stirred at RT for 5 min, then warmed up to 40° C. and stirred overnight then more BF$_3$.OEt$_2$ is added ((135 μL, 1.06 mmol)), and the reaction mixture is stirred at 40° C. overnight. After cooling down to RT, 3 mL saturated aqueous NaHCO$_3$ solution, and 1 mL CHCl$_3$-iPrOH mixture (4:1) are added. The layers are separated and the aqueous layer is extracted with CHCl$_3$-iPrOH mixture (4:1, 3×2 mL). The combined organic extracts are concentrated, and the resulting crude product is purified by flash chromatography on a Biotage™ SNAP silica cartridge (25 g), using a gradient of MeOH (0 to 5%) in CH$_2$Cl$_2$. Fractions containing product are concentrated and purified again on flash chromatography on a Biotage™ SNAP silica cartridge (10 g), using a gradient of EtOAc (50-100%) in Hex. The pure fractions are concentrated to dryness, affording title compound as a white foamy solid (18 mg, 10% yield). $^1$H NMR (400 MHz, CDCl$_3$) δ 7.96 (s, 1H), 7.67 (dd, J=8.1, 4.3 Hz, 2H), 7.57 (d, J=8.7 Hz, 2H), 7.48 (t, J=7.7 Hz, 1H), 7.18 (d, J=8.7 Hz, 2H), 6.21 (s, 1H), 5.75 (dd, J=6.6, 1.5 Hz, 1H), 5.59-5.34 (m, 2H), 4.99 (d, J=49.5 Hz, 1H), 4.29 (dd, J=12.6, 5.1 Hz, 1H), 4.16-4.00 (m, 2H), 3.04 (d, J=4.8 Hz, 3H), 2.15 (s, 3H), 2.06 (s, 3H), 2.04 (s, 3H).

Step II: Example 7

Removal of the acetate protecting groups of [(2R,3R,4S,5S,6R)-3,4-diacetoxy-5-fluoro-6-[4-[3-(methylcarbamoyl)phenyl]phenoxy]tetrahydropyran-2-yl]methyl acetate from Step I (18 mg, 0.034 mmol) using the protocol described for EXAMPLE 1 Step II provided the title compound (12 mg, 86% yield) as a white fluffy solid. $^1$H NMR (400 MHz, CD$_3$OD) δ 8.03 (t, J=1.7 Hz, 1H), 7.80-7.72 (m, 2H), 7.67-7.58 (m, 2H), 7.52 (t, J=7.8 Hz, 1H), 7.29-7.19 (m, 2H), 5.76 (dd, J=6.9, 1.7 Hz, 1H), 4.91-4.75 (m, 1H), 3.98 (ddd, J=30.9, 9.5, 2.6 Hz, 1H), 3.80 (dd, J=12.0, 2.4 Hz, 1H), 3.77-3.70 (m, 2H), 3.69-3.61 (m, 1H), 2.94 (s, 3H).
ESI-MS m/z calc. 391.14313. found 392.31 (M+H)$^+$.

Preparation of Example 8

3-[4-[(2R,3S,4S,5S,6R)-3-fluoro-4,5-dihydroxy-6-(hydroxymethyl)tetrahydropyran-2-yl]oxy-3-methoxy-phenyl]-N-methyl-benzamide

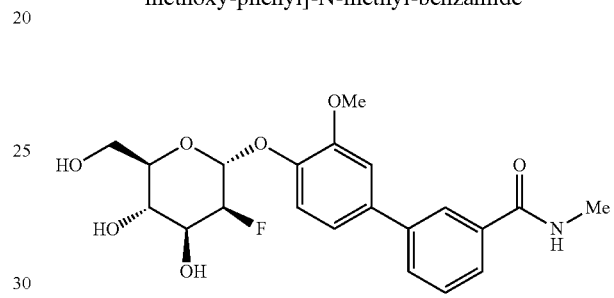

The title compound is prepared according to the procedure described for EXAMPLE 2 but using (2R,3S,4S,5S,6R)-6-(4-bromo-2-methoxy-phenoxy)-5-fluoro-2-(hydroxymethyl)tetrahydropyran-3,4-diol (EXAMPLE 5) (40 mg, 0.106 mmol) and [3-(methylcarbamoyl)phenyl]boronic acid (28 mg, 0.156 mmol). Purification by reverse phase HPLC and freeze-drying the combined fractions containing the desired material provided the title compound (18 mg, 40% yield) as a fluffy white solid. $^1$H NMR (400 MHz, CD$_3$OD) δ 8.05 (t, J=1.7 Hz, 1H), 7.82-7.70 (m, 2H), 7.52 (t, J=7.8 Hz, 1H), 7.36-7.27 (m, 2H), 7.21 (dd, J=8.3, 2.1 Hz, 1H), 5.64 (dd, J=7.1, 1.8 Hz, 1H), 4.89 (dt, J=49.6, 2.3 Hz, 1H), 4.02 (ddd, J=31.0, 9.5, 2.5 Hz, 1H), 3.94 (s, 3H), 3.88-3.70 (m, 4H), 2.95 (s, 3H). $^{19}$F NMR (376 MHz, CD$_3$OD) δ −206.65 (ddd, J=49.6, 30.8, 7.1 Hz). ESI-MS m/z calc. 421.1537. found 422.41 (M+1)$^+$.

Preparation of Example 9

Dimethyl 5-[4-[(2R,3S,4S,5S,6R)-3-fluoro-4,5-dihydroxy-6-(hydroxymethyl)tetrahydropyran-2-yl]oxyphenyl]benzene-1,3-dicarboxylate

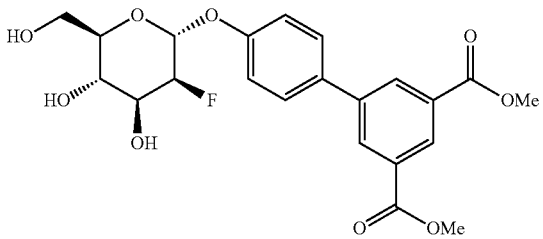 [SMILES: COC(=O)c1cc(C(=O)OC)cc(-c2ccc(O[C@H]3O[C@H](CO)[C@@H](O)[C@H](O)[C@@H]3F)cc2)c1]

Step I: dimethyl 5-[4-[(2R,3S,4S,5R,6R)-4,5-diacetoxy-6-(acetoxymethyl)-3-fluoro-tetrahydropyran-2-yl]oxyphenyl]benzene-1,3-dicarboxylate

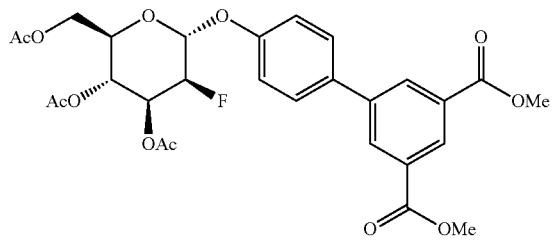 [SMILES: COC(=O)c1cc(C(=O)OC)cc(-c2ccc(O[C@H]3O[C@H](COC(C)=O)[C@@H](OC(C)=O)[C@H](OC(C)=O)[C@@H]3F)cc2)c1]

The title compound is prepared according to the procedure described for EXAMPLE 7 but using INTERMEDIATE M1 (207 mg, 0.591 mmol) and INTERMEDIATE A9 (364 mg, 1.18 mmol). After purification by flash chromatography on a Biotage™ SNAP silica cartridge (10 g) using a gradient of EtOAc (0 to 50%) in Hex, the title compound (204 mg, 60% yield) is obtained as a white solid which was used directly in the next step.

Step II: Example 9

Removal of the acetate protecting groups of dimethyl 5-[4-[(2R,3S,4S,5R,6R)-4,5-diacetoxy-6-(acetoxymethyl)-3-fluoro-tetrahydropyran-2-yl]oxyphenyl]benzene-1,3-dicarboxylate from Step I (204 mg, 0.354 mmol) using the protocol described for EXAMPLE 1 Step II and purification by reverse phase flash chromatography on Biotage™ SNAP C18 cartridge (30 g) using a gradient of MeCN (10-70%) in H$_2$O provided the title compound (64 mg, 39% yield) as a white solid. $^1$H NMR (400 MHz, CD3OD) δ 8.57 (t, J=1.6 Hz, 1H), 8.44 (d, J=1.6 Hz, 2H), 7.72-7.56 (m, 2H), 7.39-7.20 (m, 2H), 5.79 (dd, J=6.9, 1.8 Hz, 1H), 4.92-4.76 (m, 1H), 3.99 (ddd, J=30.9, 9.6, 2.7 Hz, 1H), 3.81 (dd, J=12.0, 2.4 Hz, 1H), 3.77-3.70 (m, 2H), 3.69-3.62 (m, 1H). ESI-MS m/z calc. 450.1326. found 451.24 (M+1)$^+$.

Preparation of Example 10

7-[(2R,3S,4S,5S,6R)-3-fluoro-4,5-dihydroxy-6-(hydroxymethyl)tetrahydropyran-2-yl]oxy-4-methyl-chromen-2-one

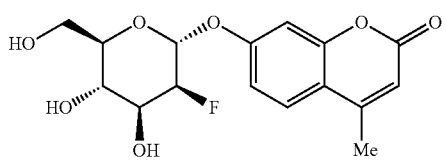 [SMILES: Cc1cc(=O)oc2cc(O[C@H]3O[C@H](CO)[C@@H](O)[C@H](O)[C@@H]3F)ccc12]

Step I: [(2R,3R,4S,5S,6R)-3,4-diacetoxy-5-fluoro-6-(4-methyl-2-oxo-chromen-7-yl)oxy-tetrahydropyran-2-yl]methyl acetate

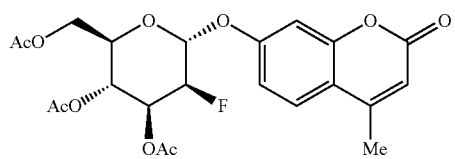 [SMILES: CC(=O)OC[C@H]1O[C@H](Oc2ccc3c(C)cc(=O)oc3c2)[C@@H](F)[C@@H](OC(C)=O)[C@@H]1OC(C)=O]

The title compound is prepared according to the procedure described for EXAMPLE 7 but using INTERMEDIATE M1 (201 mg, 0.574 mmol) and 4-methylumbelliferone (201 mg, 1.14 mmol). Purification by flash chromatography on a Biotage™ SNAP silica cartridge (10 g) using a gradient of EtOAc (0 to 20%) in CH$_2$Cl$_2$ afforded the title compound (26 mg, 10% yield) as a white foamy solid which is used directly in the next step.

Step II: Example 10

Removal of the acetate protecting groups [(2R,3R,4S,5S,6R)-3,4-diacetoxy-5-fluoro-6-(4-methyl-2-oxo-chromen-7-yl)oxy-tetrahydropyran-2-yl]methyl acetate (25 mg, 0.054 mmol) using the protocol described for EXAMPLE 1 Step II and purification by flash chromatography on a Biotage™ SNAP silica cartridge (12 g), using a gradient of MeOH (0 to 10%) in CH$_2$Cl$_2$ provided the title compound (13 mg, 68% yield) as a white solid. $^1$H NMR (400 MHz, CD$_3$OD) δ 7.73 (d, J=8.8 Hz, 1H), 7.19 (d, J=2.4 Hz, 1H), 7.15 (dd, J=8.8, 2.5 Hz, 1H), 6.22 (d, J=1.2 Hz, 1H), 5.87 (dd, J=6.9, 1.9 Hz, 1H), 4.92-4.76 (m, 1H), 3.96 (ddd, J=30.8, 9.6, 2.7 Hz, 1H), 3.84-3.65 (m, 3H), 3.62-3.52 (m, 1H), 2.46 (d, J=1.2 Hz, 3H). $^{19}$F NMR (376 MHz, CD$_3$OD) δ −207.48 (ddd, J=49.2, 30.8, 6.8 Hz). ESI-MS m/z calc. 340.09583. found 341.27 (M+1)$^+$.

Preparation of Example 11

4'-(((2R,3R,4S,5R,6R)-4-fluoro-3,5-dihydroxy-6-(hydroxymethyl)tetrahydro-2H-pyran-2-yl)oxy)-N-methyl-[1,1'-biphenyl]-3-carboxamide

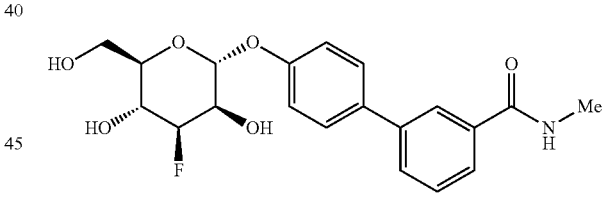

Step I: (4aR,7R,8S,8aR)-7-(benzyloxy)-8-fluoro-6-(4-iodophenoxy)-2-phenylhexahydropyrano[3,2-d][1,3]dioxine

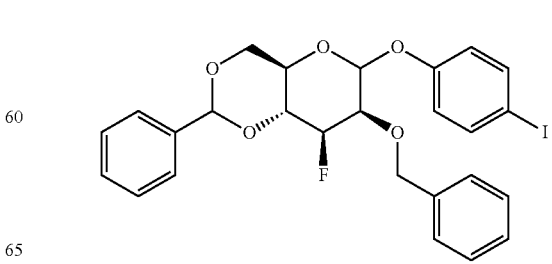

To a cold (−40° C.) solution of INTERMEDIATE M2 (140 mg, 0.3094 mmol) and 4-iodophenol (109 mg, 0.495 mmol) in CH$_2$Cl$_2$ (4.5 mL) is added 1-iodopyrrolidine-2,5-dione (111 mg, 0.495 mmol) and trifluoromethanesulfonic acid (4 µL, 0.0460 mmol). The reaction mixture is stirred 1 h at −40° C. and 16 h at RT. The resulting mixture is partitioned between saturated NaHCO$_3$ (4 ml) and CH$_2$Cl$_2$ (8 ml). The organic extract is dried (Na$_2$SO$_4$), filtered, evaporated to dryness and purified on Biotage™ SNAP silica cartridge (10 g) using EtOAc (0% to 20% in 10 CV) in Hex as eluent to afford the titled compound (100 mg, 0.178 mmol, 57%). LC-MS: m/z=563.39 (M+H)$^+$.

Step II: 4'-(((4aR,6R,7R,8S,8aR)-7-(benzyloxy)-8-fluoro-2-phenylhexahydropyrano[3,2-d][1,3]dioxin-6-yl)oxy)-N-methyl-[1,1'-biphenyl]-3-carboxamide

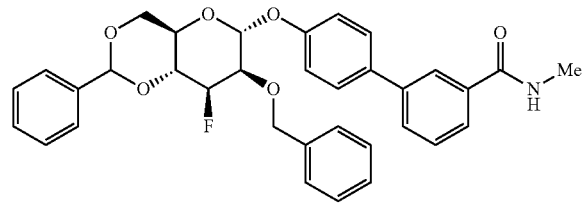

To a solution of N-methyl-3-(4,4,5,5-tetramethyl-1,3,2-dioxaborolan-2-yl)benzamide (56 mg, 0.215 mmol) and (4aR,7R,8S,8aR)-7-(benzyloxy)-8-fluoro-6-(4-iodophenoxy)-2-phenylhexahydropyrano[3,2-d][1,3]dioxine (110 mg, 0.1960 mmol) from Step I in MeOH (1.65 mL) is added Cs$_2$CO$_3$ (194 mg, 0.598 0 mmol) and SiliaCat DPP-Pd (78 mg, 0.020 mmol). The reaction mixture is stirred 10 min at 100° C. in the microwave. The resulting mixture is filtered through celite, the latter is washed with MeOH and the combined filtrate is concentrated. This material is partitioned between Water (4 ml) and EtOAc (8 ml). The organic extracts are dried over Na$_2$SO$_4$, filtered, evaporated to dryness and purified on Biotage™ SNAP silica cartridge (12 g) using EtOAc (0% to 100% in 10 CV) in Hex as eluent to afford the titled compound (45 mg, 0.079 mmol, 40%). LC-MS: m/z=570.53 (M+H)$^+$.

Step III: Example 11

A mixture of 4'-(((4aR,7R,8S,8aR)-7-(benzyloxy)-8-fluoro-2-phenylhexahydropyrano[3,2-d][1,3]dioxin-6-yl)oxy)-N-methyl-[1,1'-biphenyl]-3-carboxamide from Step II (45 mg, 0.079 mmol) and 20 wt % Pd(OH)$_2$ on carbon (32 mg, 0.0082 mmol) in dry MeOH (675 µL) is stirred for 24 hours under H$_2$ atmosphere at 80 PSI. The resulting mixture is filtered through celite, the catalyst washed with MeOH, the combined filtrates are concentrated and purified by reverse phase HPLC to afford the title compound (8.5 mg, 0.021 mmol, 27%). $^1$H NMR (400 MHz, CD$_3$OD) δ 8.01 (t, J=1.8 Hz, 1H), 7.81-7.67 (m, 2H), 7.65-7.54 (m, 2H), 7.49 (t, J=7.8 Hz, 1H), 7.33-7.16 (m, 2H), 5.57 (dd, J=4.6, 2.0 Hz, 1H), 4.77 (ddd, J=49.5, 9.3, 3.4 Hz, 1H), 4.26 (ddd, J=6.5, 3.5, 2.0 Hz, 1H), 4.03 (dt, J=12.9, 9.6 Hz, 1H), 3.84-3.66 (m, 2H), 3.61 (ddd, J=10.0, 5.0, 2.7 Hz, 1H), 2.92 (s, 3H). LC-MS: m/z=392.34 (M+H)$^+$.

Preparation of Example 12

4'-(((2R,3S,4S,5S,6S)-6-(fluoromethyl)-3,4,5-trihydroxytetrahydro-2H-pyran-2-yl)oxy)-N-methyl-[1,1'-biphenyl]-3-carboxamide

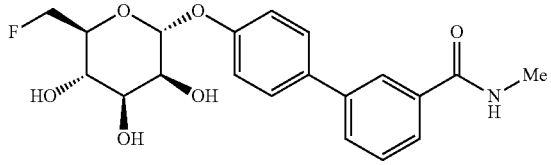 [SMILES: CNC(=O)c1cccc(-c2ccc(O[C@H]3O[C@H](CF)[C@@H](O)[C@H](O)[C@@H]3O)cc2)c1]

Step I: N-methyl-4'-(((2R,3S,4S,5S,6S)-3,4,5-tris(benzyloxy)-6-(fluoromethyl)tetrahydro-2H-pyran-2-yl)oxy)-[1,1'-biphenyl]-3-carboxamide

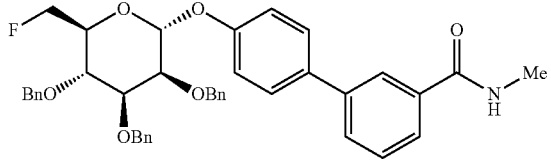 [SMILES: CNC(=O)c1cccc(-c2ccc(O[C@H]3O[C@H](CF)[C@@H](OCc4ccccc4)[C@H](OCc4ccccc4)[C@@H]3OCc3ccccc3)cc2)c1]

To a solution of INTERMEDIATE M3 (83 mg, 0.1243 mmol) and [3-(methylcarbamoyl)phenyl]boronic acid (35 mg, 0.1956 mmol) in t-butanol (4 mL) is added Na$_2$CO$_3$ (300 µL of 2 M, 0.6000 mmol) then PdCl$_2$(PPh$_3$)$_2$ (6 mg, 0.03384 mmol). The reaction mixture is degased three time (house vacuum then nitrogen) then stirred 5 hrs at 80° C. The resulting dark brown mixture is cooled to RT, diluted with 15 mL EtOAc and filtered on a pad of silica gel. The latter is washed with two portions of 15 ml of EtOAc. The combined fractions are concentrated and the residue purified on a Silica gel column (Snap 10 g) using Hexane/EtOAc (20 to 80% on 20CV) as the eluent on a Biotage™ system to afford the title compound (61 mg, 90% pure, 67% yield).

Step II: Example 12

To a solution of N-methyl-4'-((2R,3S,4S,5S,6S)-3,4,5-tris(benzyloxy)-6-(fluoromethyl)tetrahydro-2H-pyran-2-yl)oxy)-[1,1'-biphenyl]-3-carboxamide from Step I (61 mg, 0.083 mmol) in MeOH (8 mL) is added Pd(OH)$_2$ (19 mg, 0.1353 mmol). The reaction mixture is stirred overnight under 100 psi of H$_2$. The resulting mixture is filtered on a Isolut Celite 545 cartridge, the latter washed with MeOH (2×4 mL) and concentrated. The resulting mixture (29 mg) is dissolved in MeOH and purified by HPLC. Fractions (4×6 mL) containing the desired material are combined, concentrated and finally lyophilized to afford the title compound as a fluffy white solid (20 mg, 60% yield). $^1$H NMR (400 MHz, DMSO-d$_6$) δ 8.55 (d, J=4.5 Hz, 1H), 8.07 (s, 1H), 7.80-7.72 (m, 2H), 7.68 (d, J=8.8 Hz, 2H), 7.52 (t, J=7.7 Hz, 1H), 7.18 (d, J=8.8 Hz, 2H), 5.51 (d, J=1.6 Hz, 1H), 4.65-4.38 (m, 2H), 3.88 (dd, J=3.1, 1.9 Hz, 1H), 3.74 (dd, J=8.7, 3.2 Hz, 1H), 3.67-3.52 (m, 2H), 2.81 (d, J=4.5 Hz, 3H). $^{19}$F NMR (376 MHz, DMSO-d$_6$) δ −0.75 (td, J=47.9, 25.9 Hz). LC-MS: m/z=392.31 (M+H)$^+$ Preparation of Example 13

N,3'-dimethyl-4'-(((2R,3S,4S,5S,6R)-3,4,5-trihydroxy-6-(hydroxymethyl)-3-methyltetrahydro-2H-pyran-2-yl)oxy)-[1,1'-biphenyl]-3-carboxamide

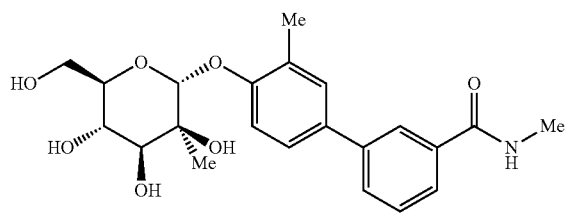 [SMILES: CNC(=O)c1cccc(-c2ccc(O[C@H]3O[C@H](CO)[C@@H](O)[C@H](O)[C@]3(C)O)c(C)c2)c1]

Step I: (2R,3S,4S,5R,6R)-6-(acetoxymethyl)-3-methyl-2-((3-methyl-3'-(methylcarbamoyl)-[1,1'-biphenyl]-4-yl)oxy)tetrahydro-2H-pyran-3,4,5-triyl-triacetate

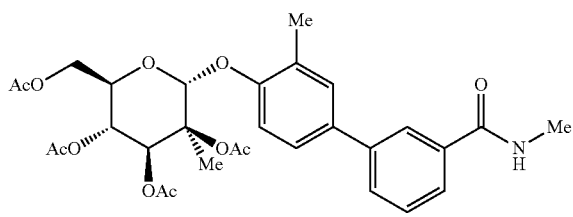 [SMILES: CNC(=O)c1cccc(-c2ccc(O[C@H]3O[C@H](COC(C)=O)[C@@H](OC(C)=O)[C@H](OC(C)=O)[C@]3(C)OC(C)=O)c(C)c2)c1]

To a suspension of INTERMEDIATE M4 (10.80 g, 26.71 mmol) and INTERMEDIATE A2 (10.31 g, 42.74 mmol) in 1,2-dichloroethane (162.0 mL) at 0° C. is added BF$_3$.Et$_2$O (10.15 mL, 80.13 mmol) dropwise. The resulting mixture is stirred at 40° C. for 48 h, cooled down to 3° C. and quenched with 30 ml of saturated aqueous NaHCO$_3$ while stirring. The resulting suspension is filtered and the organic phase is separated, dried over Na$_2$SO$_4$, filtered, and concentrated. Purification on 220 g of silica with 40-100% EtOAc/Hexane over 15 CV on a Biotage™ system to afford the title compound (7.8 g, 12.70 mmol, 48%) as a white solid. $^1$H NMR (400 MHz, CD$_3$OD) δ 8.02 (t, J=1.8 Hz, 1H), 7.74 (ddt, J=7.8, 4.7, 1.3 Hz, 2H), 7.58-7.34 (m, 3H), 7.21 (d, J=8.5 Hz, 1H), 6.33 (s, 1H), 5.63 (d, J=9.7 Hz, 1H), 5.40 (t, J=9.9 Hz, 1H), 4.20 (dd, J=12.3, 5.0 Hz, 1H), 4.14-3.94 (m, 2H), 2.93 (s, 3H), 2.36 (s, 3H), 2.13 (s, 3H), 2.12 (s, 3H), 2.02 (s, 3H), 1.98 (s, 3H), 1.64 (s, 3H).

Step II: Example 13

To a stirred solution of [(2R,3R,4S,5S,6R)-3,4,5-triacetoxy-5-methyl-6-[2-methyl-4-[3-(methylcarbamoyl)phenyl]phenoxy]tetrahydropyran-2-yl]methyl acetate from Step I (3.70 g, 6.32 mmol) in dry MeOH (93 mL) at RT is added NaOMe (704 µL of 25% w/w, 3.16 mmol). The resulting mixture is stirred 2 h, followed by addition of Ambilite IR-120 resin until the reaction mixture pH reaches 4. The resulting mixture is filtered, and concentrated to dryness to afford the tittle compound (2.600 g, 6.141 mmol, 97%) as a white solid. $^1$H NMR (400 MHz, CD$_3$OD) δ 8.00 (t, J=1.8 Hz, 1H), 7.72 (ddt, J=8.0, 5.2, 1.2 Hz, 2H), 7.52-7.38 (m, 3H), 7.31 (d, J=8.5 Hz, 1H), 5.27 (s, 1H), 3.82-3.62 (m, 4H), 3.58 (m, 1H), 2.92 (s, 3H), 2.31 (s, 3H), 1.40 (s, 3H). LC-MS: m/z=418.2 (M+H)$^+$.

Preparation of Example 14

N-methyl-3-[4-[(2R,3S,4S,5S,6R)-3,4,5-trihydroxy-6-(hydroxymethyl)-3-methyl-tetrahydropyran-2-yl]oxyphenyl]benzamide

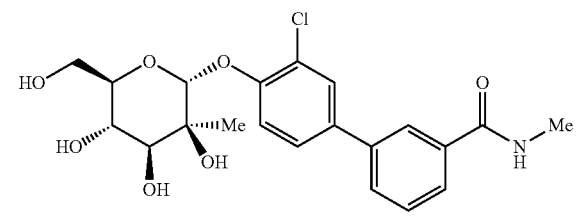

The title compound is prepared according to the procedure described in EXAMPLE 13 but using INTERMEDIATE A1 in Step I. In Step II, the reaction is quenched by treating the reaction mixture through a prewashed 1 g SCX-2 cartridge, washing with portions of MeOH. The combined filtrates are concentrated and purified by reverse phase HPLC to afford the desired compound (41% yield over two steps). $^1$H NMR (400 MHz, CD$_3$OD) δ 8.03 (t, J=1.7 Hz, 1H), 7.80-7.69 (m, 2H), 7.67-7.57 (m, 2H), 7.51 (t, J=7.8 Hz, 1H), 7.28-7.15 (m, 2H), 5.24 (s, 1H), 3.78-3.62 (m, 6H), 2.94 (s, 3H), 1.39 (s, 3H). ESI-MS m/z calc. 403.43. found 404.14 (M+1)$^+$.

Preparation of Example 15

3-[3-chloro-4-[(2R,3S,4S,5S,6R)-3,4,5-trihydroxy-6-(hydroxymethyl)-3-methyl-tetrahydropyran-2-yl]oxy-phenyl]-N-methyl-benzamide The title compound is prepared according to the procedure described in EXAMPLE 13 but using INTERMEDIATE A6 in Step I. In Step II, the reaction is quenched by treating the reaction mixture through a prewashed 1 g SCX-2 cartridge, washing with portions of MeOH. The combined filtrates are concentrated and purified by reverse phase HPLC to afford the desired compound (6.5% yield over two steps). $^1$H NMR (400 MHz, CD$_3$OD) δ 8.04 (t, J=1.7 Hz, 1H), 7.83-7.70 (m, 3H), 7.59 (dd, J=8.6, 2.3 Hz, 1H), 7.54 (d, J=7.8 Hz, 1H), 7.50 (d, J=8.7 Hz, 1H), 5.32 (s, 1H), 3.85-3.59 (m, 5H), 2.95 (s, 3H), 1.45 (s, 3H). ESI-MS m/z calc. 437.87. found 438.09 (M+1)$^+$.

Preparation of Example 16

3-[3-fluoro-4-[(2R,3S,4S,5S,6R)-3,4,5-trihydroxy-6-(hydroxymethyl)-3-methyl-tetrahydropyran-2-yl]oxy-phenyl]-N-methyl-benzamide

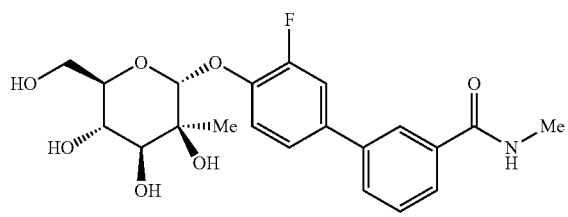 [SMILES: CNC(=O)c1cccc(-c2ccc(O[C@H]3O[C@H](CO)[C@@H](O)[C@H](O)[C@]3(C)O)c(Cl)c2)c1]

The title compound is prepared according to the procedure described in EXAMPLE 13 but using INTERMEDIATE A5 in Step I. In Step II, the reaction is quenched by treating the reaction mixture through a prewashed 1 g SCX-2 cartridge, washing with portions of MeOH. The combined filtrates are concentrated and purified by reverse phase HPLC to afford the desired compound (27% yield over two steps). $^1$H NMR (400 MHz, CD$_3$OD) δ 8.04 (t, J=1.7 Hz, 1H), 7.82-7.73 (m, 2H), 7.57-7.40 (m, 4H), 5.23 (s, 1H), 3.86-3.64 (m, 5H), 2.95 (s, 3H), 1.43 (s, 3H). $^{19}$F NMR (376 MHz, CD$_3$OD) δ −134.69 (dd, J=12.1, 7.7 Hz). ESI-MS m/z calc. 421.42. found 422.37 (M+1)$^+$.

Preparation of Example 17

3-[3-methoxy-4-[(2R,3S,4S,5S,6R)-3,4,5-trihydroxy-6-(hydroxymethyl)-3-methyl-tetrahydropyran-2-yl]oxy-phenyl]-N-methyl-benzamide

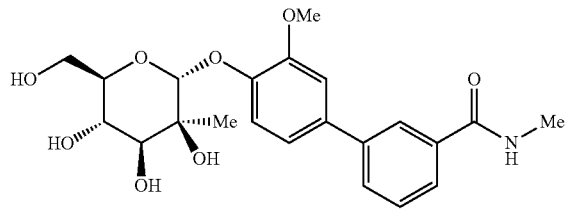 [SMILES: CNC(=O)c1cccc(-c2ccc(O[C@H]3O[C@H](CO)[C@@H](O)[C@H](O)[C@]3(C)O)c(OC)c2)c1]

The title compound is prepared according to the procedure described in EXAMPLE 13 but using INTERMEDIATE A4 in Step I. In Step II, the reaction is quenched by treating the reaction mixture through a prewashed 1 g SCX-2 cartridge, washing with portions of MeOH. The combined filtrates are concentrated and purified by reverse phase HPLC to afford the desired compound (21% yield over two steps). $^1$H NMR (400 MHz, CD$_3$OD) δ 8.05 (t, J=1.7 Hz, 1H), 7.81-7.71 (m, 2H), 7.52 (t, J=7.8 Hz, 1H), 7.34-7.25 (m, 2H), 7.20 (dd, J=8.3, 2.2 Hz, 1H), 5.17 (s, 1H), 3.92 (s, 3H), 3.89-3.82 (m, 1H), 3.81-3.66 (m, 4H), 2.95 (s, 3H), 1.45 (s, 3H). ESI-MS m/z calc. 433.45. found 434.17 (M+1)$^+$.

Preparation of Example 18

(2R,3S,4S,5S,6R)-6-(hydroxymethyl)-3-methyl-2-[2-methyl-4-(3-nitrophenyl)phenoxy]tetrahydropyran-3,4,5-triol

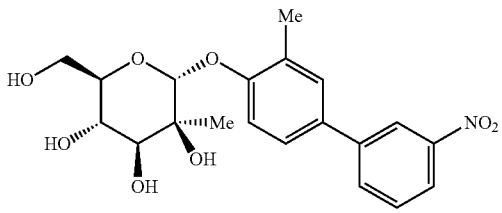 [SMILES: Cc1cc(-c2cccc([N+](=O)[O-])c2)ccc1O[C@H]1O[C@H](CO)[C@@H](O)[C@H](O)[C@]1(C)O]

The title compound is prepared according to the procedure described in EXAMPLE 13 but using INTERMEDIATE A7 in Step I. In Step II, the reaction is quenched by treating the reaction mixture through a prewashed 1 g SCX-2 cartridge, washing with portions of MeOH. The combined filtrates are concentrated and purified by reverse phase HPLC to afford the desired compound (46% yield over two steps). $^1$H NMR (400 MHz, CD$_3$OD) δ 8.42 (t, J=2.0 Hz, 1H), 8.16 (ddd, J=8.2, 2.2, 0.8 Hz, 1H), 8.00 (ddd, J=7.8, 1.6, 0.9 Hz, 1H), 7.66 (t, J=8.0 Hz, 1H), 7.55-7.44 (m, 2H), 7.37 (d, J=8.4 Hz, 1H), 5.31 (s, 1H), 3.81-3.67 (m, 4H), 3.64-3.52 (m, 1H), 2.34 (s, 3H), 1.42 (s, 3H). ESI-MS m/z calc. 405.40. found 428.18 (M+Na)$^+$.

Preparation of Example 19

(2R,3S,4S,5S,6R)-2-(2-chloro-4-(5-nitroindolin-1-yl)phenoxy)-6-(hydroxymethyl)-3-methyltetrahydro-2H-pyran-3,4,5-triol

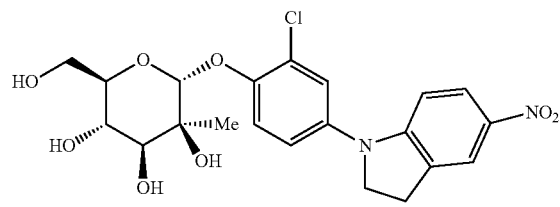 [SMILES: C[C@@]1(O)[C@@H](Oc2ccc(N3CCc4cc([N+](=O)[O-])ccc43)cc2Cl)O[C@H](CO)[C@@H](O)[C@@H]1O]

Step II: (2R,3S,4S,5R,6R)-6-(acetoxymethyl)-2-(2-chloro-4-(5-nitroindolin-1-yl)phenoxy)-3-methyltetrahydro-2H-pyran-3,4,5-triyltriacetate

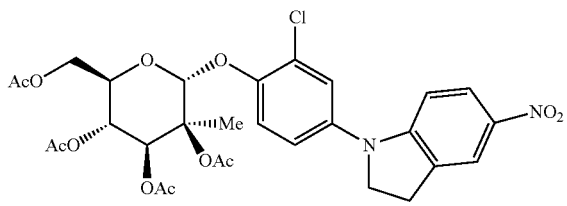 [SMILES: CC(=O)OC[C@H]1O[C@H](Oc2ccc(N3CCc4cc([N+](=O)[O-])ccc43)cc2Cl)[C@@](C)(OC(C)=O)[C@@H](OC(C)=O)[C@@H]1OC(C)=O]

A microwave vial is charged with (2R,3S,4S,5R,6R)-6-(acetoxymethyl)-2-(4-bromo-2-chlorophenoxy)-3-methyl-tetrahydro-2H-pyran-3,4,5-triyltriacetate from INTERME- DIATE M11 Step I (60 mg, 0.109 mmol), 5-nitroindoline (26.8 mg, 0.163 mmol), Cs₂CO₃ (110 mg, 0.337 mmol), X-Phos (5.2 mg, 0.011 mmol), Pd₂(dba)₃ (1.5 mg, 0.0016 mmol) and toluene (880 μL). The mixture is then heated to 100° C. for 15 minutes in the microwave, filtered on Celite, concentrated to dryness and the residue purified by flash column chromatography on silica gel (10 to 80% EtOAc in Hex) to give the title compound (32 mg, 47% yield).

Step II: Example 19

The title compound is prepared according to the procedure described in EXAMPLE 13 in Step II. The reaction is quenched by treating the reaction mixture through a prewashed 1 g SCX-2 cartridge, washing with portions of MeOH. The combined filtrates are concentrated and purified by reverse phase HPLC to afford the desired compound.
¹H NMR (400 MHz, CD₃OD) δ 8.00 (m, 2H), 7.45 (d, J=8.9 Hz, 1H), 7.38 (d, J=2.7 Hz, 1H), 7.26 (dd, J=8.9, 2.7 Hz, 1H), 6.84 (d, J=8.8 Hz, 1H), 5.22 (s, 1H), 4.09 (t, J=9.0 Hz, 2H), 3.72 (m, 5H), 3.21 (t, J=9.0 Hz, 2H), 1.43 (s, 3H). LCMS m/z (M+H)⁺=467.23

Preparation of Example 20

3-[3-ethyl-4-[(2R,3S,4S,5S,6R)-3,4,5-trihydroxy-6-(hydroxymethyl)-3-methyl-tetrahydropyran-2-yl]oxy-phenyl]-N-methyl-benzamide

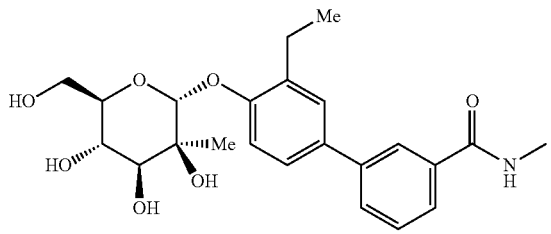 [SMILES: CCc1cc(-c2cccc(C(=O)NC)c2)ccc1O[C@H]1O[C@H](CO)[C@@H](O)[C@H](O)[C@]1(C)O]

The title compound is prepared according to the procedure described in EXAMPLE 13 but using INTERMEDIATE A3 in Step I. In Step II, the reaction is quenched by treating the reaction mixture through a prewashed 1 g SCX-2 cartridge, washing with portions of MeOH. The combined filtrates are concentrated and purified by reverse phase HPLC to afford the desired compound (37% yield over two steps). ¹H NMR (400 MHz, CD₃OD) δ 8.03 (t, J=1.7 Hz, 1H), 7.80-7.64 (m, 2H), 7.54-7.42 (m, 3H), 7.35 (d, J=8.4 Hz, 1H), 5.31 (s, 1H), 3.80-3.68 (m, 4H), 3.66-3.52 (m, 1H), 2.95 (s, 3H), 2.83-2.67 (m, 2H), 1.42 (s, 3H), 1.27 (t, J=7.5 Hz, 3H). ESI-MS m/z calc. 431.1944. found 432.24 (M+1)⁺.

Preparation of Example 21

3-[3-methyl-4-[(2R,3S,4S,5S,6R)-3,4,5-trihydroxy-6-(hydroxymethyl)-3-methyl-tetrahydropyran-2-yl]oxyphenyl]benzoic acid

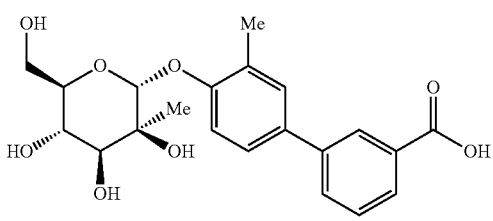 [SMILES: Cc1cc(-c2cccc(C(=O)O)c2)ccc1O[C@H]1O[C@H](CO)[C@@H](O)[C@H](O)[C@]1(C)O]

Step I: Methyl 3-[3-methyl-4-[(2R,3S,4S,5R,6R)-3,4,5-triacetoxy-6-(acetoxymethyl)-3-methyltetrahydropyran-2-yl]oxy-phenyl]benzoate

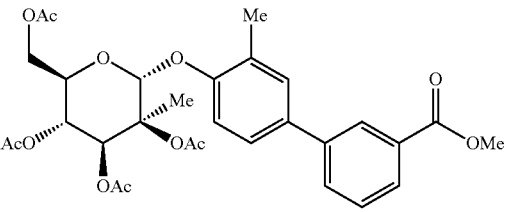 [SMILES: COC(=O)c1cccc(-c2ccc(O[C@H]3O[C@H](COC(C)=O)[C@@H](OC(C)=O)[C@H](OC(C)=O)[C@]3(C)OC(C)=O)c(C)c2)c1]

The title compound is prepared according to the procedure described in EXAMPLE 13 but using INTERMEDIATE A8 in Step I. Purification on Biotage™ SNAP silica cartridge afforded the title compound (21% yield) as a colorless oil. ¹H NMR (400 MHz, CDCl₃) δ 8.23 (s, 1H), 7.99 (d, J=7.6 Hz, 1H), 7.74 (d, J=7.6 Hz, 1H), 7.53-7.38 (m, 3H), 7.28 (d, J=6.3 Hz, 1H), 5.51-5.35 (m, 3H), 4.31 (dd, J=12.5, 5.2 Hz, 1H), 4.14-4.06 (m, 2H), 3.96 (s, 3H), 2.38 (s, 3H), 2.26 (s, 3H), 2.16 (s, 3H), 2.05 (d, J=2.3 Hz, 6H), 1.39 (s, 3H). LC-MS: m/z=609.31 (M+Na)⁺.

Step II: 3'-methyl-4'-(((2R,3S,4S,5R,6R)-3,4,5-triacetoxy-6-(acetoxymethyl)-3-methyltetrahydro-2H-pyran-2-yl)oxy)-[1,1'-biphenyl]-3-carboxylic acid To a solution of methyl 3-[3-methyl-4-[(2R,3S,4S,5R,6R)-3,4,5-triacetoxy-6-(acetoxymethyl)-3-methyl-tetrahydropyran-2-yl]oxy-phenyl]benzoate from Step I (237 mg, 0.404 mmol) in MeOH (4 mL) was added aqueous NaOH 2M (807 μL of 2 M, 1.61 mmol) and the reaction was stirred for 3 h. The reaction mixture is quenched with aqueous HCl 4M (101 μL of 4 M, 0.404 mmol) until pH reaches 2 and the resulting mixture was lyophilized overnight. The residue is dissolved in pyridine and to the solution is added Ac₂O (305 μL, 3.23 mmol) and DMAP (2.5 mg, 0.020 mmol). The reaction is stirred at RT for 18 h, poured in HCl 1N, diluted with EtOAc and stirred 15 min. The organic phase is separated, washed with water, brine, dried over Na₂SO₄, filtered, concentrated in vacuo. The residue is purified on Biotage™ SNAP silica cartridge (10 g) to give title compound (168 mg, 73% yield) as a colorless oil.
¹H NMR (400 MHz, CDCl₃) δ 8.28 (t, J=1.6 Hz, 1H), 8.08-8.03 (m, 1H), 7.82-7.76 (m, 1H), 7.53 (t, J=7.8 Hz, 1H), 7.48-7.40 (m, 2H), 7.27 (s, 1H), 5.52-5.35 (m, 3H), 4.31 (dd, J=12.7, 5.4 Hz, 1H), 4.13-4.06 (m, 2H), 2.37 (s, 3H), 2.16 (s, 3H), 2.13 (s, 3H), 2.05 (d, J=1.0 Hz, 6H), 1.38 (s, 3H). LC-MS: m/z=595.62 (M+Na)⁺.

Step III: Example 21

To a solution of 3'-methyl-4'-(((2R,3S,4S,5R,6R)-3,4,5-triacetoxy-6-(acetoxymethyl)-3-methyltetrahydro-2H-pyran-2-yl)oxy)-[1,1'-biphenyl]-3-carboxylic acid from Step II (20 mg, 0.035 mmol) in MeOH (300 μL) was added NaOMe in MeOH (35 μL of 0.5 M, 0.018 mmol) until pH=9 is reached. The reaction is stirred at RT for 18 h. The reaction is neutralized with acidic Amberlyst resin, filtered and concentrated to give title compound (12 mg, 75%) as a white solid. ¹H NMR (400 MHz, CD₃OD) δ 8.19 (s, 1H), 7.93 (d, J=7.7 Hz, 1H), 7.78 (d, J=7.7 Hz, 1H), 7.49 (t, J=7.7 Hz, 1H), 7.42 (d, J=9.3 Hz, 2H), 7.31 (d, J=8.3 Hz, 1H), 5.27 (s, 1H), 3.78-3.67 (m, 4H), 3.64-3.55 (m, 1H), 2.31 (s, 3H), 1.40 (s, 3H). LC-MS: m/z=405.18 (M+H)⁺.

Preparation of Example 22

N-[2-[2-(2-aminoethoxy)ethoxy]ethyl]-3-[3-methyl-4-[(2R,3S,4S,5S,6R)-3,4,5-trihydroxy-6-(hydroxymethyl)-3-methyl-tetrahydropyran-2-yl]oxy-phenyl]benzamide

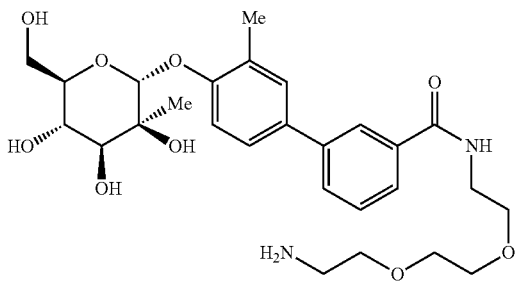 [SMILES: Cc1cc(-c2cccc(C(=O)NCCOCCOCCN)c2)ccc1O[C@H]1O[C@H](CO)[C@@H](O)[C@H](O)[C@]1(C)O]

Step I: tert-butyl N-[2-[2-[2-[[3-[3-methyl-4-[(2R,3S,4S,5S,6R)-3,4,5-trihydroxy-6-(hydroxymethyl)-3-methyl-tetrahydropyran-2-yl]oxy-phenyl]benzoyl]amino]ethoxy]ethoxy]ethyl]carbamate

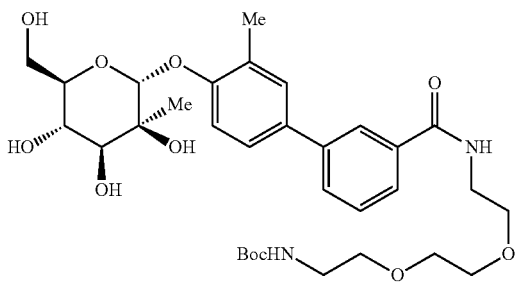 [SMILES: Cc1cc(-c2cccc(C(=O)NCCOCCOCCNC(=O)OC(C)(C)C)c2)ccc1O[C@H]1O[C@H](CO)[C@@H](O)[C@H](O)[C@]1(C)O]

To a solution of 3'-methyl-4'-(((2R,3S,4S,5R,6R)-3,4,5-triacetoxy-6-(acetoxymethyl)-3-methyltetrahydro-2H-pyran-2-yl)oxy)-[1,1'-biphenyl]-3-carboxylic acid from EXAMPLE 21 Step II (148 mg, 0.259 mmol) in DMF (5.2 mL) is added tert-butyl N-[2-[2-(2-aminoethoxy)ethoxy]ethyl]carbamate (70.6 mg, 0.284 mmol). The solution is cooled at 0° C., HATU (118 mg, 0.310 mmol) and DIPEA (59 µL, 0.34 mmol) are added. The resulting mixture is warmed to RT and stirred for 3 h. The reaction is diluted with EtOAc and washed 3 times with saturated aqueous NH$_4$Cl. The combined aqueous phases are extracted 5 times with EtOAc. The combined organic phases are dried over MgSO$_4$ and concentrated in vacuo. The residue is purified on Biotage™ SNAP silica cartridge (10 g). The combined fractions containing the desired product are combined, concentrated and dissolved in MeOH (5 mL). To this was added NaOMe in MeOH (517 µL of 0.5 M, 0.259 mmol) until pH=9 is reached. The resulting mixture is stirred overnight. The reaction was neutralized with Amberlyst acidic resin and concentrated to give title compound (81 mg, 45%) as a white solid. $^1$H NMR (400 MHz, CD$_3$OD) δ 8.02 (s, 1H), 7.73 (ddd, J=7.8, 3.3, 1.5 Hz, 2H), 7.51-7.42 (m, 3H), 7.30 (d, J=8.5 Hz, 1H), 5.27 (s, 1H), 3.75-3.56 (m, 11H), 3.48 (t, J=5.6 Hz, 2H), 3.31-3.27 (m, 4H), 3.17 (t, J=5.6 Hz, 2H), 2.30 (s, 3H), 1.39 (2s, 12H). LC-MS: m/z=635.43 (M+H)$^+$ Step II: Example 22

To tert-butyl N-[2-[2-[2-[[3-[3-methyl-4-[(2R,3S,4S,5S,6R)-3,4,5-trihydroxy-6-(hydroxymethyl)-3-methyl-tetrahydropyran-2-yl]oxy-phenyl]benzoyl]amino]ethoxy]ethoxy]ethyl]carbamate from Step I (70.6 mg, 0.102 mmol) is added TFA in CH$_2$Cl$_2$ 1:1 (7 mL) and the mixture is stirred for 5 min. The reaction is concentrated in vacuo to give title compound as a TFA salt (65 mg, 91%) as a white solid. $^1$H NMR (400 MHz, CD$_3$OD) δ 8.02 (s, 1H), 7.77-7.70 (m, 2H), 7.48 (dd, J=18.4, 10.9 Hz, 3H), 7.31 (d, J=8.0 Hz, 1H), 5.27 (s, 1H), 3.78-3.63 (m, 12H), 3.61 (d, J=5.6 Hz, 4H), 3.04 (s, 2H), 2.31 (s, 3H), 1.40 (s, 3H). LC-MS: m/z=535.75 (M+H)$^+$ Preparation of Example 23

4'-(((2R,3S,4S,5S,6R)-3-((benzyloxy)methyl)-3,4,5-trihydroxy-6-(hydroxymethyl)tetrahydro-2H-pyran-2-yl)oxy)-N,3'-dimethyl-[1,1'-biphenyl]-3-carboxamide

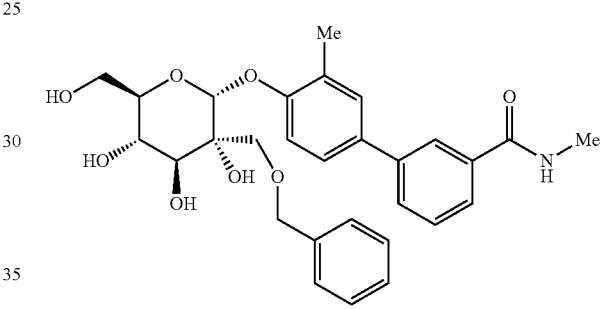

The title compound is prepared according to the procedure described in EXAMPLE 13 but using INTERMEDIATE M8 in Step I. $^1$H NMR (400 MHz, CD$_3$OD) δ 8.03 (t, J=1.8 Hz, 1H), 7.73 (ddt, J=9.3, 7.9, 1.3 Hz, 2H), 7.55-7.37 (m, 3H), 7.35-7.22 (m, 1H), 7.20-7.04 (m, 5H), 5.64 (s, 1H), 4.61 (d, J=12.2 Hz, 1H), 4.36 (d, J=12.1 Hz, 1H), 3.88-3.67 (m, 5H), 3.67-3.40 (m, 2H), 2.93 (s, 3H), 2.13 (s, 3H). LC-MS: m/z=524.3 (M+H)$^+$ Preparation of Example 24

N,3'-dimethyl-4'-(((2R,3S,4S,5S,6R)-3,4,5-trihydroxy-3,6-bis(hydroxymethyl)tetrahydro-2H-pyran-2-yl)oxy)-[1,1'-biphenyl]-3-carboxamide

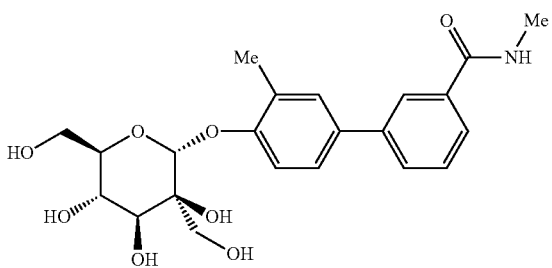 [SMILES: CNC(=O)c1cccc(-c2ccc(O[C@H]3O[C@H](CO)[C@@H](O)[C@H](O)[C@@]3(O)CO)c(C)c2)c1]

137

Step I: (2R,3S,4S,5R,6R)-6-(acetoxymethyl)-3-(hydroxymethyl)-2-((3-methyl-3'-(methylcarbamoyl)-[1,1'-biphenyl]-4-yl)oxy)tetrahydro-2H-pyran-3,4,5-triyl triacetate

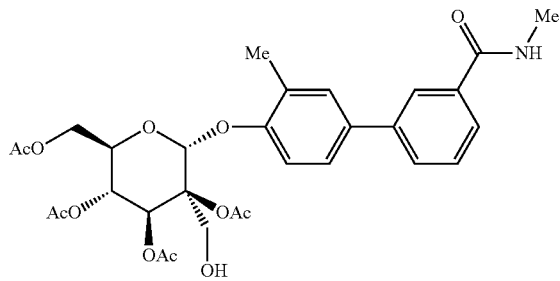 [SMILES: CNC(=O)c1cccc(-c2ccc(O[C@H]3O[C@H](COC(C)=O)[C@@H](OC(C)=O)[C@H](OC(C)=O)[C@]3(CO)OC(C)=O)c(C)c2)c1]

To a solution of [(2R,3R,4S,5S,6R)-3,4,5-triacetoxy-5-(benzyloxymethyl)-6-[2-methyl-4-[3-(methylcarbamoyl)phenyl]phenoxy]tetrahydropyran-2-yl]methyl acetate from EXAMPLE 23 Step I (100 mg, 0.145 mmol) in EtOH (3.3 mL) and AcOH (33 μL, 0.5784 mmol) is added Pd(OH)$_2$ 20% (41 mg, 0.058 mmol). The reaction mixture is stirred under 1 atm of H$_2$ for 16 h. The resulting mixture is filtered over celite, the latter is rinsed with MeOH and the combined MeOH fractions are concentrated in vacuo. The residue is purified on Biotage™ SNAP silica cartridge (10 g) using EtOAc (0-75%, 10CV) in Hex as eluent to afford the title compound (65 mg, 75%) as a solid. LC-MS: m/z=602.6 (M+H)$^+$.

Step II: Example 24

To a stirred solution of (2R,3S,4S,5R,6R)-6-(acetoxymethyl)-3-(hydroxymethyl)-2-((3-methyl-3'-(methylcarbamoyl)-[1,1'-biphenyl]-4-yl)oxy)tetrahydro-2H-pyran-3,4,5-triyl triacetate from Step I (20 mg, 0.033 mmol) in dry MeOH (1.2 mL) at RT is added NaOMe (66 μL of 0.5 M, 0.039 mmol). The resulting mixture is stirred 16 hour, neutralized with Dowex 50 WX4-400 ion-exchange resin (H+). The mixture is was filtered, concentrated in vacuo and purified by reverse phase HPLC to afford the title compound (6.0 mg, 41%) as a white solid. $^1$H NMR (400 MHz, CD$_3$OD) δ 8.00 (t, J=1.8 Hz, 1H), 7.71 (ddt, J=7.7, 4.9, 1.2 Hz, 2H), 7.55-7.40 (m, 3H), 7.33 (d, J=8.5 Hz, 1H), 5.56 (s, 1H), 3.95 (d, J=11.5 Hz, 1H), 3.87 (d, J=11.4 Hz, 1H), 3.82-3.65 (m, 4H), 3.58 (dt, J=6.8, 3.3 Hz, 1H), 2.92 (s, 3H), 2.28 (s, 3H).

Preparation of Example 25

N-methyl-3-[3-methyl-4-[(2R,3S,4S,5R,6R)-3,4,5-trihydroxy-6-(hydroxymethyl)-4-methyl-tetrahydro-pyran-2-yl]oxy-phenyl]benzamide

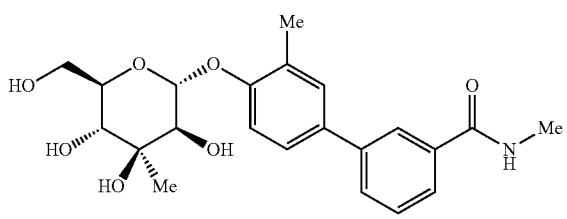 [SMILES: CNC(=O)c1cccc(-c2ccc(O[C@H]3O[C@H](CO)[C@@H](O)[C@](C)(O)[C@@H]3O)c(C)c2)c1]

138

Step 1: (2R,4aR,6S,7S,8R,8aR)-6-(benzyloxy)-8-((tert-butyldimethylsilyl)oxy)-2-phenylhexahydropyrano[3,2-d][1,3]dioxin-7-ol

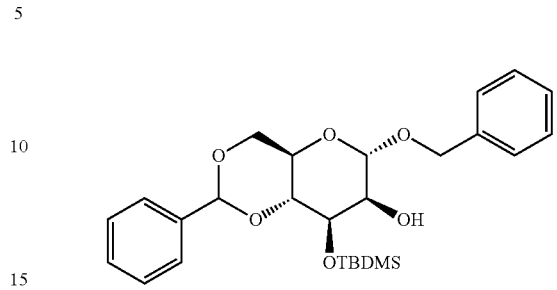

To a solution of commercially available (4aR,6S,7S,8R,8aS)-6-benzyloxy-2-phenyl-4,4a,6,7,8,8a-hexahydropyrano[5,6-d][1,3]dioxine-7,8-diol (8.00 g, 22.3 mmol) and 4H-imidazole (2.181 g, 32.03 mmol) in DMF (72 mL) is added tert-butyl-chloro-dimethyl-silane (4.189 g, 5.17 mL, 27.79 mmol). The reaction mixture is stirred for 120 minutes, and then partitioned between EtOAc and water. The organic extracts are dried over Na$_2$SO$_4$, filtered, evaporated to dryness and purified on silica gel using 0-20% EtOAc: Hex as eluent to afford the title compound (9.83 g, 88% yield). $^1$H NMR (400 MHz, DMSO-D6) δ 7.54-7.26 (m, 10H), 5.68 (s, 1H), 5.10 (dd, J=11.8, 4.6 Hz, 1H), 4.83 (d, J=1.3 Hz, 1H), 4.74 (d, J=12.2 Hz, 1H), 4.55 (d, J=12.2 Hz, 1H), 4.16 (dt, J=12.2, 6.1 Hz, 1H), 4.03-3.92 (m, 2H), 3.87-3.76 (m, 1H), 3.75-3.57 (m, 1H), 0.87 (s, 9H), 0.07 (s, 3H), 0.02 (s, 3H).

Step 2: (4aR,6S,7S,8R,8aR)-6-(benzyloxy)-8-((tert-butyldimethylsilyl)oxy)-2-phenylhexahydro-pyrano[3,2-d][1,3]dioxin-7-ol

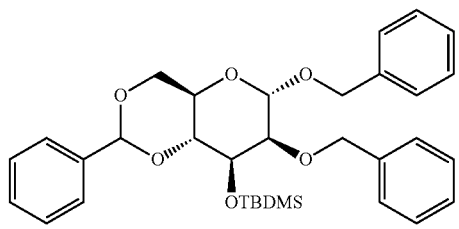

To a solution of (2R,4aR,6S,7S,8R,8aR)-6-(benzyloxy)-8-((tert-butyldimethylsilyl)oxy)-2-phenylhexahydropyrano[3,2-d][1,3]dioxin-7-ol from Step I (600 mg, 1.269 mmol) in DMF (6.0 mL) at 0° C. is added NaH (55 mg, 1.40 mmol). The reaction mixture is stirred for 15 minutes, then BnBr (181 μL, 1.52 mmol) is added. The reaction mixture is stirred 2 h at RT. Upon completion, the reaction mixture is partitioned between water and EtOAc. The organic extracts are dried over Na$_2$SO$_4$, filtered, and evaporated to dryness. The crude product is purified on silica gel using 0-10% EtOAc: Hex as eluent to afford the title compound (530 mg, 71% yield). $^1$H NMR (400 MHz, DMSO-d6) δ 7.55-7.22 (m, 15H), 5.75 (s, 1H), 5.03 (d, J=1.1 Hz, 1H), 4.73 (m, 3H), 4.56 (d, J=12.1 Hz, 1H), 4.21-3.88 (m, 3H), 3.82-3.52 (m, 3H), 0.82 (s, 9H), 0.05 (s, 3H), 0.01 (s, 3H).

Step III: (4aR,6S,7S,8S,8aS)-6,7-bis(benzyloxy)-2-phenylhexahydropyrano[3,2-d][1,3]dioxin-8-ol

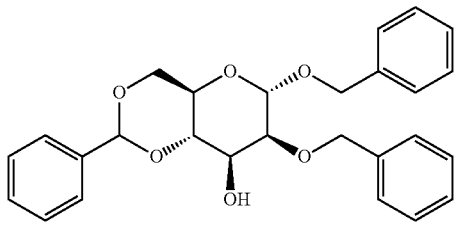

To a solution of (4aR,6S,7S,8R,8aR)-6-(benzyloxy)-8-((tert-butyldimethylsilyl)oxy)-2-phenylhexahydropyrano[3,2-d][1,3]dioxin-7-ol from Step II (7.80 g, 13.86 mmol) in THF (78 mL), in a closed reaction vessel, is added AcOH (1.18 mL, 20.8 mmol) and tetrabutylammonium fluoride (41.6 mL of 1 M, 41.6 mmol). The reaction mixture is stirred at 60° C. for 1 h and cooled down to RT. The reaction mixture is then partitioned between water and EtOAc, and the aqueous phase is extracted with EtOAc 3 times. The combined organic extracts are dried over Na$_2$SO$_4$, filtered and evaporated to dryness. The crude product is purified on silica gel using 0-25% EtOAc: Hex as eluent to afford the title compound (4.90 g, 79%). $^1$H NMR (400 MHz, DMSO-D6) δ 7.47-7.11 (m, 15H), 5.69-5.53 (m, 1H), 5.30-5.16 (m, 1H), 4.97 (t, J=9.3 Hz, 1H), 4.77-4.56 (m, 3H), 4.54-4.36 (m, 1H), 4.17-4.05 (m, 1H), 3.94-3.78 (m, 2H), 3.78-3.47 (m, 3H).

Step IV: (4aR,6S,7R,8aR)-6,7-dibenzyloxy-2-phenyl-4a,6,7,8a-tetrahydro-4H-pyrano[3,2-d][1,3]dioxin-8-one

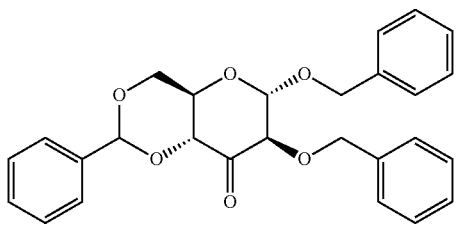

To a solution of (4aR,6S,7S,8S,8aS)-6,7-bis(benzyloxy)-2-phenylhexahydropyrano[3,2-d][1,3]dioxin-8-ol from Step III (500 mg, 1.115 mmol) in CH$_2$Cl$_2$ (5.0 mL) is added a solution of Dess-Martin periodinane (709 mg, 1.672 mmol) in CH$_2$Cl$_2$ (5.0 mL) drop wise over 5 minutes. The mixture is stirred for 3 hours. The reaction mixture is partitioned between aqueous saturated solution of NaHCO$_3$ and CH$_2$Cl$_2$. The aqueous phase is extracted 3 times using CH$_2$Cl$_2$ The combined organic extracts are dried over Na$_2$SO$_4$, filtered and evaporated to dryness. The crude product is purified on silica gel using 0-25% EtOAc: Hex as eluent to afford the title compound (320 mg, 64% yield). $^1$H NMR (400 MHz, DMSO-D6) δ 7.44-7.21 (m, 15H), 5.79 (s, 1H), 5.32 (d, J=1.2 Hz, 1H), 5.00 (d, J=9.5 Hz, 1H), 4.70 (d, J=11.7 Hz, 1H), 4.59-4.46 (m, 3H), 4.25 (dd, J=9.6, 4.4 Hz, 1H), 4.05-3.83 (m, 3H).

Step V: (4aR,6S,7S,8aS)-6,7-dibenzyloxy-8-methylene-2-phenyl-4a,6,7,8a-tetrahydro-4H-pyrano[3,2-d][1,3]dioxine

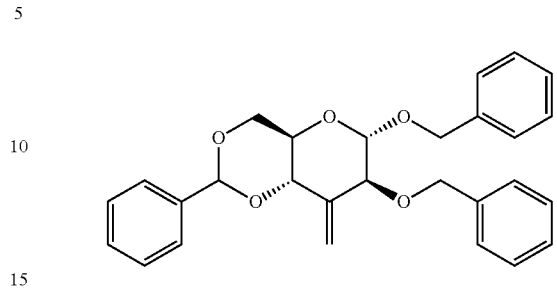

To a solution of methyl(triphenyl)phosphonium bromide (2.080 g, 5.823 mmol) in THF (22.40 mL) at 0° C. is added potassium tert-butoxide (5.38 mL of 1 M, 5.38 mmol). The mixture is stirred at 0° C. for 30 minutes. To this mixture is added via syringe a solution of (4aR,6S,7R,8aR)-6,7-dibenzyloxy-2-phenyl-4a,6,7,8a-tetrahydro-4H-pyrano[3,2-d][1,3]dioxin-8-one from Step IV (2 g, 4.479 mmol) in THF (22.40 mL). The resulting mixture is allowed to warm up to RT and stir overnight. Upon completion, a saturated solution of aqueous NH$_4$Cl is added and the reaction mixture is extracted with EtOAc 3 times. The combined organic extracts are dried over Na$_2$SO$_4$, filtered and concentrated in vacuo. The crude product is purified by flash chromatography using a gradient of 5-20% EtOAc: Hex to afford the title compound (1.31 g, 66% yield). $^1$H NMR (400 MHz, CDCl$_3$) δ 7.62-7.50 (m, 2H), 7.46-7.23 (m, 13H), 5.68 (s, 1H), 5.46 (dt, J=2.0, 1.2 Hz, 1H), 5.18 (d, J=1.9 Hz, 1H), 4.96 (d, J=1.2 Hz, 1H), 4.74 (d, J=12.0 Hz, 1H), 4.67 (d, J=12.1 Hz, 1H), 4.59-4.49 (m, 1H), 4.41 (dd, J=15.1, 10.3 Hz, 2H), 4.22 (dd, J=5.6, 2.6 Hz, 1H), 3.98 (s, 1H), 3.95-3.83 (m, 2H). LCMS: m/z=467.4 (M+Na)$^+$.

Step VI: (4aR,6S,7S,8S,8aR)-6,7-dibenzyloxy-2-phenyl-spiro[4a,6,7,8a-tetrahydro-4H-pyrano[3,2-d][1,3]dioxine-8,2'-oxirane]

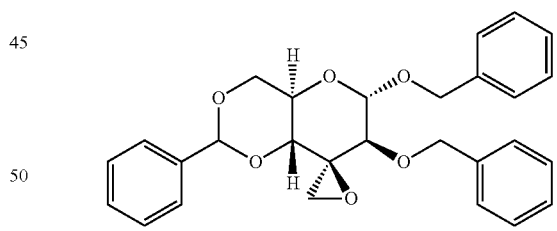

(4aR,6S,7S,8aS)-6,7-dibenzyloxy-8-methylene-2-phenyl-4a,6,7,8a-tetrahydro-4H-pyrano[3,2-d][1,3]dioxine from Step V (1.23 g, 2.767 mmol) is dissolved in CH$_2$Cl$_2$ (28 mL) and m-CPBA (1.116 g, 4.981 mmol) is added. The mixture is stirred at RT for 3 hours. Another load of m-CPBA (1.116 g, 4.981 mmol) is added and the resulting solution is stirred for 3 days. Then m-CPBA (272 mg) is added again and the solution is stirred overnight. Upon completion, the mixture is filtered over Celite and a saturated solution of NaHCO$_3$ is added. The resulting mixture is extracted 3 times with CH$_2$Cl$_2$. The combined organic extracts are dried over Na$_2$SO$_4$, filtered and concentrated in vacuo. The crude residue obtained is purified by flash chromatography using a gradient of 5-20% EtOAc: Hex.

The desired fractions are combined and the concentrated in vacuo. Then a second purification is performed using 5-15% EtOAc: Hex to afford the title compound (396 mg, 31% yield). $^1$H NMR (400 MHz, CDCl$_3$) δ 7.58-7.19 (m, 15H), 5.60 (s, 1H), 5.01-4.88 (m, 2H), 4.75 (d, J=12.1 Hz, 1H), 4.68 (d, J=12.1 Hz, 1H), 4.52 (d, J=12.0 Hz, 1H), 4.44 (d, J=9.4 Hz, 1H), 4.27 (dd, J=10.0, 4.5 Hz, 1H), 4.04 (td, J=9.8, 4.5 Hz, 1H), 3.97-3.86 (m, 1H), 3.40-3.34 (m, 1H), 3.21 (d, J=5.1 Hz, 1H), 2.74 (d, J=5.1 Hz, 1H). LCMS: m/z=483.1 (M+Na)$^+$.

Step VII: (4aR,6S,7S,8S,8aR)-6,7-dibenzyloxy-8-(iodomethyl)-2-phenyl-4a,6,7,8a-tetrahydro-4H-pyrano[3,2-d][1,3]dioxin-8-ol

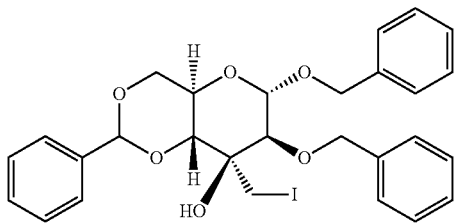 [SMILES: O[C@]1(CI)[C@H](OCc2ccccc2)[C@@H](OCc2ccccc2)O[C@@H]2COC(c3ccccc3)O[C@H]21]

I$_2$ (393 mg, 1.55 mmol) is added to a solution of PPh$_3$ (404 mg, 1.55 mmol) in CH$_2$CL$_2$ (5.9 mL) and the mixture is stirred at RT for 5 minutes, at which point a solution of (4aR,6S,7S,8S,8aR)-6,7-dibenzyloxy-2-phenyl-spiro[4a,6,7,8a-tetrahydro-4H-pyrano[3,2-d][1,3]dioxine-8,2'-oxirane] from Step VI (396 mg, 0.8599 mmol) in CH$_2$Cl$_2$ (4.887 mL) is added. The resulting solution is stirred for 5 hours. Upon completion, the reaction is quenched with a 10% aqueous solution of NaHSO$_3$ and the mixture is vigorously stirred for 5 minutes. The resulting mixture is diluted with ether and the layers are separated. The organic phase is washed successively with water and brine, dried over Na$_2$SO$_4$, filtered and concentrated in vacuo. The crude product is purified by flash chromatography using 0-20% EtOAc: Hex as eluent to afford the title compound (204 mg, 40% yield). $^1$H NMR (400 MHz, CDCl$_3$) δ 7.53-7.28 (m, 15H), 5.54 (s, 1H), 4.94 (d, J=1.4 Hz, 1H), 4.75 (d, J=12.3 Hz, 1H), 4.72-4.62 (m, 2H), 4.54 (d, J=12.3 Hz, 1H), 4.27-4.17 (m, 1H), 4.05-3.90 (m, 3H), 3.88-3.68 (m, 3H), 3.07 (d, J=2.3 Hz, 1H).

Step VIII: (4aR,6S,7S,8S,8aR)-6,7-dibenzyloxy-8-methyl-2-phenyl-4a,6,7,8a-tetrahydro-4H-pyrano[3,2-d][1,3]dioxin-8-ol

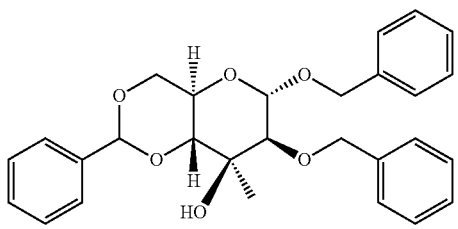 [SMILES: C[C@@]1(O)[C@H](OCc2ccccc2)[C@@H](OCc2ccccc2)O[C@@H]2COC(c3ccccc3)O[C@H]21]

To a solution of (4aR,6S,7S,8S,8aR)-6,7-dibenzyloxy-8-(iodomethyl)-2-phenyl-4a,6,7,8a-tetrahydro-4H-pyrano[3,2-d][1,3]dioxin-8-ol from Step VII (204 mg, 0.3467 mmol) in toluene (6.932 mL) is added tributyltin hydride (15 mg, 140 μL, 0.520 mmol) and AIBN (3.4 mg, 0.021 mmol). The resulting solution is stirred at 90° C. for 12 hours. Upon completion, the reaction mixture is concentrated in vacuo. The residue is purified by flash chromatography using 0-30% EtOAc: Hex to afford the title compound (121 mg, 75% yield). $^1$H NMR (400 MHz, CDCl$_3$) δ 7.54-7.45 (m, 2H), 7.43-7.28 (m, 13H), 5.56 (s, 1H), 5.02-4.95 (m, 1H), 4.80-4.55 (m, 3H), 4.49 (d, J=12.1 Hz, 1H), 4.28-4.17 (m, 1H), 3.90-3.71 (m, 3H), 3.53-3.44 (m, 1H), 2.93 (s, 1H), 1.51 (s, 3H). LCMS: m/z=463.4 (M+H)$^+$ Step IX: [(2R,3R,4S,5S)-3,4,5,6-tetraacetoxy-4-methyl-tetrahydropyran-2-yl]methyl acetate

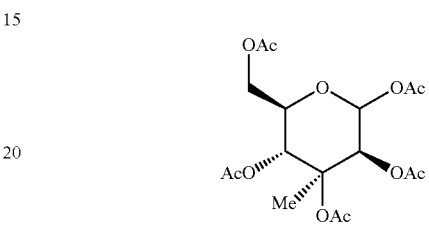

(4aR,6S,7S,8S,8aR)-6,7-dibenzyloxy-8-methyl-2-phenyl-4a,6,7,8a-tetrahydro-4H-pyrano[3,2-d][1,3]dioxin-8-ol from Step VIII (151 mg, 0.3265 mmol) is dissolved in MeOH (3.265 mL) and the mixture is degassed with nitrogen. Pd/C, wet, Degussa (139 mg, 0.131 mmol) is added to the mixture, which is then stirred at RT under 1 atm of H$_2$ for 6 days. The reaction mixture is filtered over Celite and rinsed with MeOH and CH$_2$Cl$_2$. The solution is concentrated in vacuo.

The mixture of crude products (mixture of the fully deprotected and mono-benzylated compounds) is then stirred in pyridine (5 mL) with acetic anhydride (2.5 mL, 26.50 mmol) at RT for 18 hours. (7.9 mg, 0.065 mmol) DMAP is added and the reaction mixture is stirred 2 hours, then pyridine (1 mL), and acetic anhydride (0.5 mL, 5.30 mmol) and (7.9 mg, 0.065 mmol) DMAP are added and the reaction is stirred overnight. Upon completion, the reaction mixture is concentrated in vacuo and co-evaporated with benzene 3 times. The crude product is purified by flash chromatography using a gradient of 0-50% EtOAc: Hex. A second purification is necessary, this time using 10-30% EtOAc: Hex.

The product obtained is dissolved in MeOH (1.658 mL) and the mixture is degassed with nitrogen for several minutes, at which point Pd/C, wet, Degussa (52.93 mg, 0.04974 mmol) is added and the mixture is stirred over weekend under 1 atm of H$_2$. The mixture is filtered over Celite and rinsed with MeOH and CH$_2$Cl$_2$. The filtrate is concentrated in vacuo and the product is dissolved in pyridine (5 mL) and Ac$_2$O (2.5 mL, 26.50 mmol) is added. The mixture is stirred at RT for 12 hours. Upon completion, the reaction mixture is concentrated in vacuo and co-evaporated with benzene. The crude product is purified by flash chromatography using 0-50% EtOAc: Hex as gradient to afford the title compound (37 mg, 13% overall yield). LCMS: m/z=427.3 (M+Na)$^+$.

Step X: [(2R,3R,4S,5S,6R)-3,4,5-triacetoxy-4-methyl-6-[2-methyl-4-[3-(methylcarbamoyl)phenyl]phenoxy]tetrahydropyran-2-yl]methyl acetate Step I: [(2R,3S,4S,5S,6S)-3,4,5-triacetoxy-2-methyl-6-[2-methyl-4-[3-(methylcarbamoyl)phenyl]phenoxy]tetrahydropyran-2-yl]methyl acetate

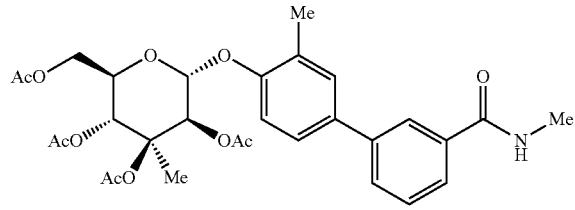 [SMILES: CNC(=O)c1cccc(-c2ccc(O[C@H]3O[C@H](COC(C)=O)[C@@H](OC(C)=O)[C@](C)(OC(C)=O)[C@@H]3OC(C)=O)c(C)c2)c1]

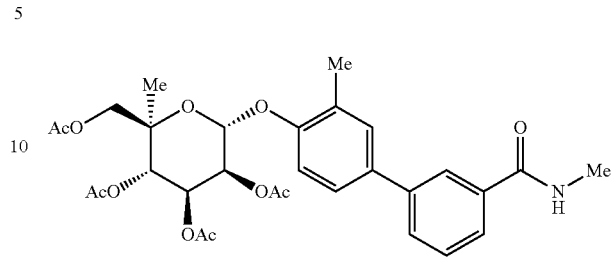

To a solution of [(2R,3R,4S,5S)-3,4,5,6-tetraacetoxy-4-methyl-tetrahydropyran-2-yl]methyl acetate from Step IX (37.0 mg, 0.0915 mmol) and INTERMEDIATE A2 (44.2 mg, 0.1830 mmol) in 1,2-dichloroethane (523.2 µL) at 0° C. in a microwave vial is added BF$_3$.OEt$_2$ (34.8 µL, 0.275 mmol) dropwise. The mixture is allowed to warm up to RT and then is warmed up to 40° C. and stirred overnight. Upon completion, the reaction mixture is cooled to RT and the reaction mixture is purified directly by flash chromatography using a gradient of 40-90% EtOAc: Hex to afford the title compound (27 mg, 50% yield). LCMS: m/z=586.4 (M+H)$^+$ Step XI: Example 25

To a stirred solution of [(2R,3R,4S,5S,6R)-3,4,5-triacetoxy-4-methyl-6-[2-methyl-4-[3-(methylcarbamoyl)phenyl]phenoxy]tetrahydropyran-2-yl]methyl acetate from Step X (27 mg, 0.0461 mmol) in dry methanol (461 µL) at RT is added a solution of NaOMe 25% w/v in MeOH (9.964 µL, 0.04611 mmol). The resulting mixture is stirred 2 hours. LCMS indicated that the reaction is completed. Upon completion the mixture is loaded onto a SPE, SXC cartridge (1 g). The column is rinsed with MeOH for the equivalent of 4 CV. The filtrate is concentrated in vacuo to provide the crude desired product. Finally, the product is submitted for reverse phase purification to afford the title compound (19 mg, 66% yield). $^1$H NMR (400 MHz, CD$_3$OD) δ 8.02 (d, J=1.9 Hz, 1H), 7.74 (ddd, J=8.0, 5.0, 1.6 Hz, 2H), 7.54-7.42 (m, 3H), 7.31 (d, J=8.4 Hz, 1H), 5.55 (d, J=1.8 Hz, 1H), 3.86-3.63 (m, 5H), 2.94 (s, 3H), 2.32 (s, 4H), 1.50 (s, 3H). LCMS: m/z=418.31 (M+H)$^+$ Preparation of Example 26

N-methyl-3-[3-methyl-4-[(2S,3S,4S,5S,6R)-3,4,5-trihydroxy-6-(hydroxymethyl)-6-methyl-tetrahydropyran-2-yl]oxy-phenyl]benzamide

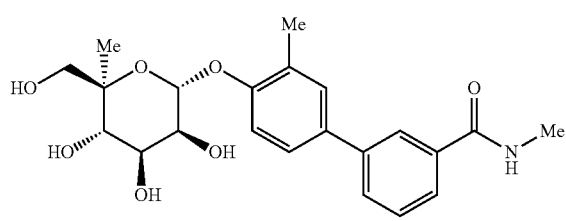 [SMILES: CNC(=O)c1cccc(-c2ccc(O[C@H]3O[C@](C)(CO)[C@@H](O)[C@H](O)[C@@H]3O)c(C)c2)c1]

To a solution of INTERMEDIATE M7 (123 mg, 0.304 mmol) and INTERMEDIATE A2 (147 mg, 0.608 mmol) in 1,2-dichloroethane (1.73 mL) at 0° C. is added BF$_3$.OEt$_2$ (116 µL, 0.913 mmol) dropwise. The mixture is allowed to warm up to RT and then is heated up to 40° C. and stirred overnight. Upon completion, the reaction mixture is cooled down to RT and loaded directly on a flash chromatography column. The purification is performed using a gradient of 20-80% EtOAc: Hex. The mixed fractions are collected and purified again by flash chromatography using a gradient of 30-70% EtOAc: Hex. The pure product collected from the first and second purifications are combined to provide the desired title compound (150 mg, 84% yield). $^1$H NMR (400 MHz, CD$_3$OD) δ 8.02 (t, J=1.8 Hz, 1H), 7.77-7.68 (m, 2H), 7.55-7.40 (m, 3H), 7.19 (d, J=8.5 Hz, 1H), 5.71 (d, J=2.8 Hz, 1H), 5.70 (s, 1H), 5.68-5.66 (m, 1H), 5.51 (dd, J=2.8, 2.1 Hz, 1H), 4.05-3.94 (m, 2H), 2.94 (s, 3H), 2.32 (s, 3H), 2.20 (s, 3H), 2.11 (s, 3H), 2.08 (s, 3H), 2.04 (s, 3H), 1.31 (s, 3H). LC-MS: m/z=586.7 (M+H)$^+$ Step II: Example 26

To a stirred solution of [(2R,3S,4S,5S,6S)-3,4,5-triacetoxy-2-methyl-6-[2-methyl-4-[3-(methylcarbamoyl)phenyl]phenoxy]tetrahydropyran-2-yl]methyl acetate (150 mg, 0.2561 mmol) in dry methanol (2.561 mL) at RT is added a solution of sodium methoxide in methanol 25% w/v (55.34 µL, 0.2561 mmol). The resulting mixture is stirred 2 hours. Upon completion, the mixture is diluted with minimum MeOH and loaded onto a SPE, SXC cartridge (1 g). The column is rinsed with MeOH for the equivalent of 4 CV. The filtrate is concentrated in vacuo to provide the title compound (89 mg, 71% yield). $^1$H NMR (400 MHz, CD$_3$OD) δ 8.00 (t, J=1.8 Hz, 1H), 7.76-7.67 (m, 2H), 7.52-7.41 (m, 3H), 7.27 (d, J=8.4 Hz, 1H), 5.58 (d, J=1.8 Hz, 1H), 4.16 (dd, J=10.1, 3.2 Hz, 1H), 4.12-4.02 (m, 2H), 3.52 (d, J=11.5 Hz, 1H), 3.43 (d, J=11.6 Hz, 1H), 2.92 (s, 3H), 2.27 (s, 3H), 1.09 (s, 3H). LC-MS: m/z=418.3 (M+H)$^+$

145

Preparation of Example 27

N-methyl-3-[3-methyl-4-[(2R,3S,4S,5S,6R)-3,4,5-trihydroxy-6-[(1S)-1-hydroxyethyl]tetrahydropyran-2-yl]oxy-phenyl]benzamide

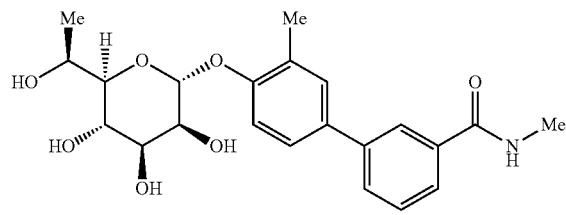 [SMILES: CNC(=O)c1cccc(-c2ccc(O[C@H]3O[C@H]([C@H](C)O)[C@@H](O)[C@H](O)[C@@H]3O)c(C)c2)c1]

Step 1: [(2R,3R,4S,5S,6R)-3,5-diacetoxy-2-[(1S)-1-acetoxyethyl]-6-[2-methyl-4-[3-(methylcarbamoyl)phenyl]phenoxy]tetrahydropyran-4-yl]acetate

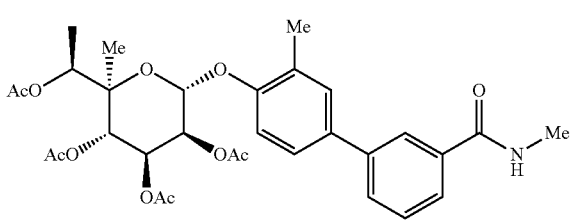 [SMILES: CNC(=O)c1cccc(-c2ccc(O[C@H]3O[C@](C)([C@H](C)OC(C)=O)[C@@H](OC(C)=O)[C@H](OC(C)=O)[C@@H]3OC(C)=O)c(C)c2)c1]

To a solution of INTERMEDIATE M5 (96.0 mg, 0.237 mmol) and INTERMEDIATE A2 (115 mg, 0.475 mmol) in 1,2-dichloroethane (1.4 mL) at 0° C. is added $BF_3.OEt_2$ (90.3 µL, 0.712 mmol) drop wise. The mixture is allowed to warm up to RT and then is heated up to 40° C. The resulting solution is stirred overnight. Upon completion, the reaction mixture is cooled to RT and loaded directly on a flash chromatography column. The purification is performed using a gradient of 30-100% EtOAc: Hex. A second flash chromatography is performed, this time using a 30-70% EtOAc: Hex to afford the title compound (66 mg, 47% yield). LC-MS: m/z=586.6 $(M+H)^+$

Step II: Example 27

To a stirred solution of [(2R,3R,4S,5S,6R)-3,5-diacetoxy-2-[(1S)-1-acetoxyethyl]-6-[2-methyl-4-[3-(methylcarbamoyl)phenyl]phenoxy]tetrahydropyran-4-yl]acetate from Step I (66 mg, 0.113 mmol) in dry methanol (1.2 mL) at RT is added a solution of NaOMe in MeOH 25% w/v (24.35 µL, 0.1127 mmol). The resulting mixture is stirred 1 hour. Upon completion the mixture is concentrated and loaded onto a SPE, SXC cartridge (1 g). The column is rinsed with MeOH for the equivalent of 4 CV. The filtrate is concentrated in vacuo to provide the product which is lyophilized in a mixture of MeOH and water (41 mg, 82% yield). $^1$H NMR (400 MHz, $CD_3OD$) δ 8.52 (s, 1H), 8.01 (t, J=1.8 Hz, 1H), 7.72 (ddt, J=7.9, 5.0, 1.3 Hz, 2H), 7.47 (td, J=8.5, 8.1, 6.1 Hz, 3H), 7.24 (d, J=8.5 Hz, 1H), 5.61 (d, J=1.8 Hz, 1H), 4.12-4.01 (m, 2H), 4.00-3.82 (m, 2H), 2.98-2.86 (m, 3H), 2.29 (s, 3H), 1.08 (d, J=6.6 Hz, 3H). LC-MS: m/z=418.5 $(M+H)^+$

146

Preparation of Example 28

(2R,3S,4S,5S,6R)-2-[2-chloro-4-(5-nitroindolin-1-yl)phenoxy]-6-[(1S)-1-hydroxyethyl]tetrahydropyran-3,4,5-triol

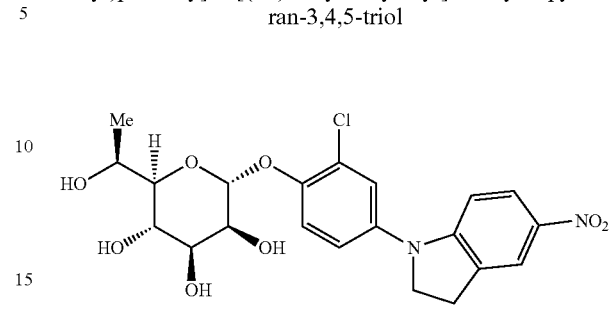

Step I: [(2R,3R,4S,5S,6R)-3,5-diacetoxy-2-[(1S)-1-acetoxyethyl]-6-(4-bromo-2-chloro-phenoxy)tetrahydropyran-4-yl]acetate

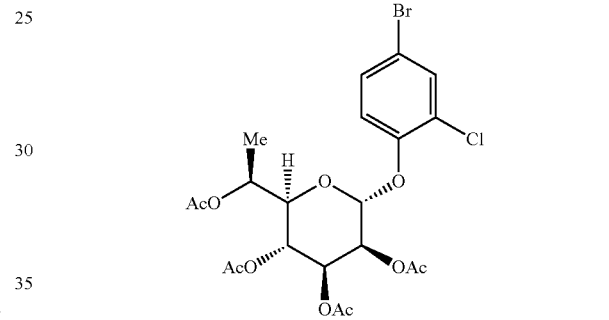

To a solution of INTERMEDIATE M5 (100 mg, 0.250 mmol) and 4-bromo-2-chloro-phenol (101 mg, 0.490 mmol) in $CH_2Cl_2$ (1.5 mL) at 0° C. is added $BF_3.OEt_2$ (97 µL, 0.76 mmol) dropwise. The mixture is allowed to warm up to RT and then is heated up to 40° C. The resulting solution is stirred overnight. Upon completion, the reaction mixture is cooled to RT and loaded directly on a flash chromatography column. The purification is performed using a gradient of 0-40% EtOAc/Hex to afford the title product (95 mg, 0.17 mmol, 69.60%). LC-MS: m/z=575.43 $(M+Na)^+$

Step II

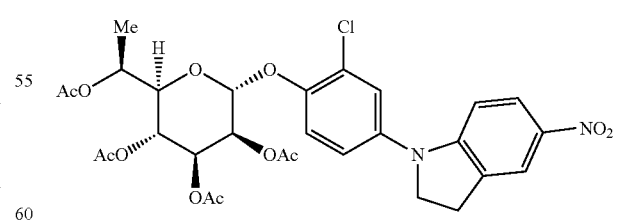

A microwave vial is charged with [(2R,3R,4S,5S,6R)-3,5-diacetoxy-2-[(1S)-1-acetoxyethyl]-6-(4-bromo-2-chloro-phenoxy)tetrahydropyran-4-yl]acetate from Step I (82.0 mg, 0.150 mmol), 5-nitroindoline (12.0 mg, 0.072 mmol), $Cs_2CO_3$ (48.0 mg, 0.15 mmol), X-Phos (2.0 mg, 0.0042 mmol) and $Pd_2(DBA)_3$ (0.55 mg, 0.00060 mmol). Toluene (1.2 mL) is added, and the vial is degassed (house-vacuum then N2), capped and submitted to microwave for 15 min at 100° C. The reaction mixture is diluted with EtOAc passed on a 500 mg silica cartridge and eluted with EtOAc. The residual mixture is concentrated under reduced pressure and is used as is for the next step without further purification.

Step III: Example 28

To a stirred solution of [(2R,3R,4S,5S,6R)-3,5-diacetoxy-2-[(1S)-1-acetoxyethyl]-6-[2-chloro-4-(5-nitroindolin-1-yl)phenoxy]tetrahydropyran-4-yl]acetate from Step II (0.15 mmol) in dry MeOH (2 mL) at RT is added NaOMe (150 µL of 0.5 M, 0.0740 mmol). The resulting mixture is stirred for 4 hour at RT. Upon completion the mixture is concentrated and loaded onto a cation-exchange resin (SXC, cartridge, 1 g). The column is rinsed with methanol for the equivalent of 4 CV. The mixture is purified using reverse phase HPLC. The combined fractions containing the desired material are lyophilized to afford the title compound (47 mg, 82% yield). $^1$H NMR (400 MHz, CD$_3$OD) δ 8.53 (s, 1H), 8.11-7.94 (m, 1H), 7.49-7.18 (m, 3H), 6.84 (d, J=8.7 Hz, 1H), 5.60 (s, 1H), 4.18-4.01 (m, 2H), 3.92 (dd, J=20.5, 11.3 Hz, 2H), 3.41-3.33 (m, 1H), 3.25-3.16 (m, 1H), 1.07 (d, J=6.6 Hz, 3H). LC-MS: m/z=467.35 (M+H)$^+$ Preparation of Example 29

N-methyl-3-[3-methyl-4-[(2R,3S,4S,5S,6R)-3,4,5-trihydroxy-6-[(1R)-1-hydroxyethyl]tetrahydropyran-2-yl]oxy-phenyl]benzamide

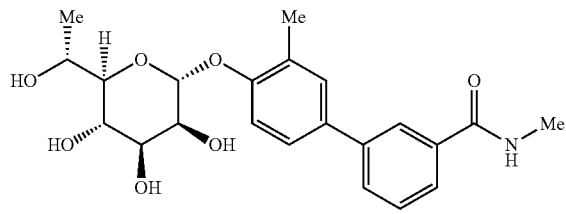 [SMILES: CNC(=O)c1cccc(-c2ccc(O[C@H]3O[C@H]([C@@H](C)O)[C@@H](O)[C@H](O)[C@@H]3O)c(C)c2)c1]

Step I: (2R,3R,4S,5S,6R)-3,5-diacetoxy-2-[(1R)-1-acetoxyethyl]-6-[2-methyl-4-[3-(methylcarbamoyl)phenyl]phenoxy]tetrahydropyran-4-yl]acetate

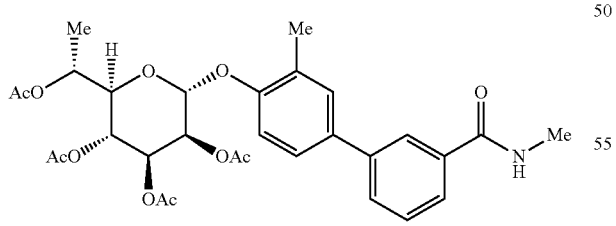

To a solution of INTERMEDIATE M6 (145 mg, 0.359 mmol) and INTERMEDIATE A2 (173 mg, 0.717 mmol) in 1,2-dichloroethane (2.050 mL) at 0° C. in a microwave vial is added BF$_3$.OEt$_2$ 136 µL, 1.08 mmol) dropwise. The mixture is allowed to warm up to RT, and then stirred overnight at 40° C. and. Upon completion, the reaction mixture is cooled down to RT and loaded directly onto a flash chromatography column. The purification is performed using a gradient of 30-100% EtOAc: Hex. The mixed fractions are collected and purified again by flash chromatography using a gradient of 50-85% EtOAc: Hex. The pure product collected from the first and second purifications are combined to provide the desired compound (210 mg, 67% yield). LC-MS: m/z=586.7 (M+H)$^+$ Step II: Example 29

To a stirred solution of [(2R,3R,4S,5S,6R)-3,5-diacetoxy-2-[(1R)-1-acetoxyethyl]-6-[2-methyl-4-[3-(methylcarbamoyl)phenyl]phenoxy]tetrahydropyran-4-yl]acetate from Step I (141 mg, 0.241 mmol) in dry MeOH (2.5 mL) at RT is added a solution of NaOMe in MeOH 25% w/v (52 µL, 0.24 mmol). The resulting mixture is stirred 1 hour at RT. Upon completion, the mixture is concentrated and the crude product is loaded in minimum methanol onto a SPE, SXC cartridge (1 g). The column is rinsed with MeOH for the equivalent of 4 CV. The filtrate is concentrated in vacuo to provide the crude product which is submitted for reverse phase HPLC. The pure fractions are combined and lyophilized directly to provide the title compound (38.9 mg, 36% yield). $^1$H NMR (400 MHz, CD$_3$OD) δ 8.00 (t, J=1.8 Hz, 1H), 7.72 (ddt, J=7.9, 5.1, 1.3 Hz, 2H), 7.51-7.42 (m, 3H), 7.28 (d, J=8.5 Hz, 1H), 5.52 (d, J=1.8 Hz, 1H), 4.05 (dd, J=3.4, 1.8 Hz, 1H), 4.00 (qd, J=6.5, 4.6 Hz, 1H), 3.94 (dd, J=9.3, 3.4 Hz, 1H), 3.76 (t, J=9.6 Hz, 1H), 3.49 (dd, J=9.8, 4.5 Hz, 1H), 2.92 (s, 3H), 2.30 (s, 3H), 1.18 (d, J=6.4 Hz, 3H). LC-MS: m/z=418.2 (M+H)$^+$ Preparation of Example 30

N-methyl-3-[3-methyl-4-[(2R,3S,4S,5S,6R)-3,4,5-trihydroxy-6-[(1S)-1-hydroxy-2-methyl-propyl]tetrahydropyran-2-yl]oxy-phenyl]benzamide

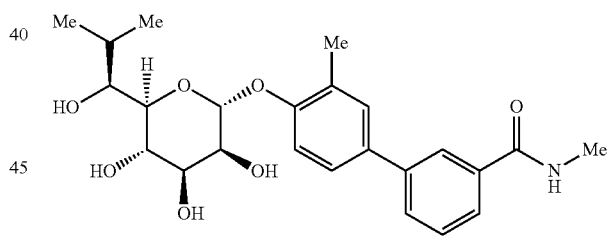

Step I: (1S)-2-methyl-1-[(2R,3S,4S,5S,6S)-3,4,5,6-tetrabenzyloxytetrahydropyran-2-yl]propan-1-ol

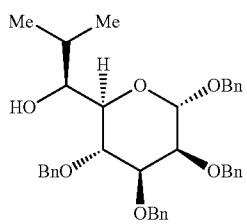 [SMILES: CC(C)[C@H](O)[C@H]1O[C@H](OCc2ccccc2)[C@@H](OCc2ccccc2)[C@@H](OCc2ccccc2)[C@@H]1OCc1ccccc1]

To a solution of (2R,3R,4S,5S,6S)-3,4,5,6-tetrabenzyloxytetrahydropyran-2-yl]methanol (Daragics, K.; Fügedi, P. Tet. Lett., 2009, 50, 2914-2916) (1.500 g, 2.774 mmol), DMSO (8.159 mL), and NEt₃ (1.93 mL, 13.9 mmol) in CH₂Cl₂ (8.2 mL) at 0° C. is added SO3.pyridine complex (2.208 g, 13.87 mmol) in 3 portions. The reaction is stirred for 1 hour. Upon completion, the reaction mixture is diluted with EtOAc, and washed with water, 10% aqueous potassium bisulfate, saturated aqueous NaHCO₃ and brine. The organic layer is dried over MgSO₄ and concentrated in vacuo. The residue is co-evaporated twice with benzene to give crude aldehyde which is used without further purification.

Bromo-isopropyl-magnesium (957 µL of 2.9 M, 2.77 mmol) is added to a solution of (2S,3S,4S,5S,6S)-3,4,5,6-tetrabenzyloxytetrahydropyran-2-carbaldehyde (747 mg, 1.39 mmol) in THF (7.0 mL) at 0° C. The solution is stirred for 15 min and the ice bath is removed and the mixture is stirred over 15 min at RT. Upon completion, the mixture is quenched with a saturated aqueous NH₄Cl. The aqueous layer is back extracted 3 times with EtOAc. The combined organic layers are dried over Na₂SO₄, filtered and concentrated in vacuo. The crude product is purified by flash chromatography using a gradient of 0-50% EtOAc: Hex to afford the title compound (407 mg, 50% yield over 2 steps). ¹H NMR (400 MHz, CD₃Cl) δ 7.26 (s, 20H), 5.00-4.87 (m, 2H), 4.79-4.59 (m, 6H), 4.42 (d, J=12.0 Hz, 1H), 4.26-4.14 (m, 1H), 3.97 (dd, J=9.5, 3.1 Hz, 1H), 3.89-3.75 (m, 2H), 3.43 (dd, J=10.7, 8.8 Hz, 1H), 1.98 (d, J=10.8 Hz, 1H), 1.92 (dt, J=8.9, 6.7 Hz, 1H), 1.07 (d, J=6.7 Hz, 3H), 0.91 (d, J=6.7 Hz, 3H). LC-MS: m/z=605.0 (M+Na)⁺.

Step II: (3S,4S,5S,6R)-6-[(1S)-1-hydroxy-2-methyl-propyl]tetrahydropyran-2,3,4,5-tetrol

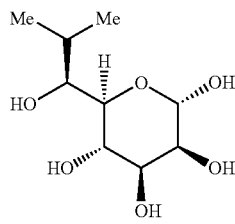

(1S)-2-methyl-1-[(2R,3S,4S,5S,6S)-3,4,5,6-tetrabenzyloxytetrahydropyran-2-yl]propan-1-ol from step I (407 mg, 0.698 mmol) is dissolved in MeOH (7.2 mL) and the mixture is degassed with nitrogen. Pd/C, wet, Degussa (446 mg, 0.419 mmol) is added to the mixture, which is then stirred at RT under 1 atm of H₂ overnight. The next day, the H₂ is refilled and AcOH (159 µL, 2.794 mmol) is added. The reaction is stirred over the weekend. The reaction mixture is filtered over Celite, rinsed with MeOH and CH₂Cl₂ and the filtrate is concentrated in vacuo. The residue is dissolved in EtOH (6.983 mL) and AcOH (159 µL, 2.79 mmol) and the mixture is degassed with nitrogen. Pd(OH)₂ (294 mg, 0.419 mmol) is added to the mixture, which is then stirred at RT for 2 days under 1 atm of H₂. The reaction mixture is filtered over Celite, rinsed with MeOH and CH₂Cl₂. The filtrate is concentrated in vacuo to afford the title compound which is used as such in the next step. LC-MS: m/z=245.2 (M+Na)⁺.

Step III: [(3S,4S,5R,6R)-2,3,5-triacetoxy-6-[(1S)-1-acetoxy-2-methyl-propyl]tetrahydropyran-4-yl]acetate

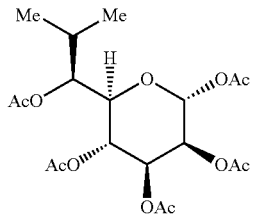 [SMILES: CC(=O)O[C@H]1O[C@H]([C@@H](OC(C)=O)C(C)C)[C@@H](OC(C)=O)[C@H](OC(C)=O)[C@@H]1OC(C)=O]

(3S,4S,5S,6R)-6-[(1S)-1-hydroxy-2-methyl-propyl]tetrahydropyran-2,3,4,5-tetrol from Step II (155 mg, 0.698 mmol) is dissolved in pyridine (10 mL) and Ac₂O (5.0 mL, 53 mmol) is added. The mixture is stirred at RT for 12 hours. The reaction mixture is concentrated in vacuo and co-evaporated with benzene 3 times. Purification of the crude product is performed by flash chromatography using a gradient of 0-50% EtOAc: Hex to afford the title compound (35.7 mg, 11% yield). LC-MS: m/z=455.3 (M+Na)⁺.

Step IV: [(2R,3R,4S,5S,6R)-3,5-diacetoxy-2-[(1S)-1-acetoxy-2-methyl-propyl]-6-[2-methyl-4-[3-(methylcarbamoyl)phenyl]phenoxy]tetrahydropyran-4-yl] acetate

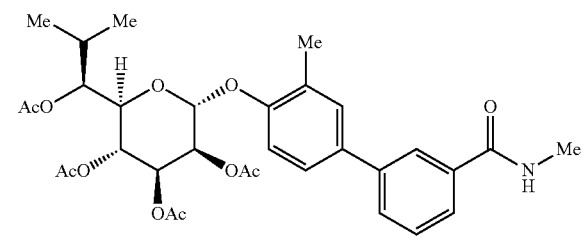 [SMILES: CNC(=O)c1cccc(-c2ccc(O[C@H]3O[C@H]([C@@H](OC(C)=O)C(C)C)[C@@H](OC(C)=O)[C@H](OC(C)=O)[C@@H]3OC(C)=O)c(C)c2)c1]

To a solution of [(3S,4S,5R,6R)-2,3,5-triacetoxy-6-[(1S)-1-acetoxy-2-methyl-propyl]tetrahydropyran-4-yl]acetate from Step III (35.7 mg, 0.0826 mmol) and INTERMEDIATE A2 (39.8 mg, 0.165 mmol) in 1,2-dichloroethane (505 µL) at 0° C. is added BF₃.OEt₂ (31.4 µL, 0.248 mmol) dropwise. The mixture is allowed to warm up to RT and then is warmed up to 40° C. and stirred overnight. Upon completion, the reaction mixture is cooled down to RT and purified directly by flash chromatography using a gradient of 40-100% EtOAc: Hex to afford the title compound (29.3 mg, 58% yield). LC-MS: m/z=614.4 (M+H)⁺

Step V: Example 30

To a stirred solution of [(2R,3R,4S,5S,6R)-3,5-diacetoxy-2-[(1S)-1-acetoxy-2-methyl-propyl]-6-[2-methyl-4-[3-(methylcarbamoyl)phenyl]phenoxy]tetrahydropyran-4-yl] acetate from Step IV (29.3 mg, 0.04775 mmol) in dry MeOH (500.2 µL) at RT is added a solution of NaOMe in MeOH 25% w/v (10.3 µL, 0.0478 mmol). The resulting mixture is stirred 2 hours at RT. Upon completion the mixture is diluted in minimum MeOH and loaded onto a SPE, SXC cartridge (1 g). The column is rinsed with MeOH for the equivalent of 4 CV. The filtrate is concentrated in vacuo to provide the crude product which is purified by reverse phase HPLC to afford the title compound (10.8 mg, 51% yield). ¹H NMR (400 MHz, CD₃OD) δ 8.00 (t, J=1.8 Hz, 1H), 7.72 (ddt, J=7.1, 4.0, 1.2 Hz, 2H), 7.56-7.37 (m, 3H), 7.20 (d, J=8.5 Hz, 1H), 5.66 (d, J=1.8 Hz, 1H), 4.10-4.01 (m, 1H), 3.96 (dd, J=5.4, 2.1 Hz, 2H), 3.58 (dt, J=7.3, 1.4 Hz, 1H), 3.38-3.30 (m, 1H), 2.92 (s, 3H), 2.29 (s, 3H), 1.84-1.64 (m, 1H), 0.92 (d, J=6.7 Hz, 3H), 0.38 (d, J=6.7 Hz, 3H). LC-MS: m/z=446.0 (M+H)⁺.

Preparation of Example 31

N-methyl-3-[3-methyl-4-[(2R,3S,4S,5S,6R)-3,4,5-trihydroxy-6-[(1S)-1-hydroxypropyl]tetrahydropyran-2-yl]oxy-phenyl]benzamide

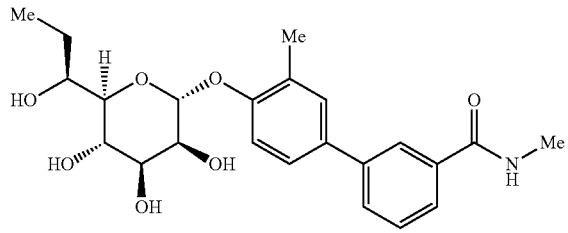 [SMILES: CC[C@H](O)[C@H]1O[C@H](Oc2ccc(-c3cccc(C(=O)NC)c3)cc2C)[C@@H](O)[C@@H](O)[C@@H]1O]

Step I: (S)-1-((2R,3S,4S,5S,6S)-3,4,5,6-tetrakis(benzyloxy)tetrahydro-2H-pyran-2-yl)propan-1-ol

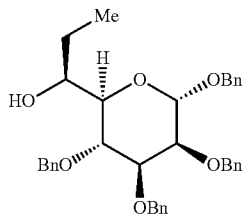 [SMILES: CC[C@H](O)[C@H]1O[C@H](OCc2ccccc2)[C@@H](OCc2ccccc2)[C@@H](OCc2ccccc2)[C@@H]1OCc1ccccc1]

To a solution of (2R,3R,4S,5S,6S)-3,4,5,6-tetrabenzyloxytetrahydropyran-2-yl]methanol (Daragics, K.; Fügedi, P. Tet. Lett., 2009, 50, 2914-2916) (1.500 g, 2.774 mmol), DMSO (8.159 mL), and NEt₃ (1.93 mL, 13.9 mmol) in CH₂Cl₂ (8.15 mL) at 0° C. is added SO3.pyridine complex (2.208 g, 13.87 mmol) in 3 portions. The reaction is stirred for 1 hour. Upon completion, the reaction mixture is diluted with EtOAc, and washed with water, 10% aqueous potassium bisulfate, saturated aqueous NaHCO₃ and brine. The organic is dried over MgSO₄ and concentrated in vacuo. The residue is co-evaporated twice with benzene to give crude aldehyde which is used without further purification. EtMgBr (924.7 µL, of 3M in Et2O, 2.774 mmol) is added to a solution of (2S,3S,4S,5S,6S)-3,4,5,6-tetrabenzyloxytetrahydropyran-2-carbaldehyde (747 mg, 1.39 mmol) in THF (6.9 mL) at 0° C. The reaction mixture is allowed to stir for 15 minutes at that temperature and then the ice bath is removed. The mixture is allowed to stir at RT for another 15 minutes. Upon completion, the mixture is quenched with saturated aqueous NH₄Cl. The aqueous layer is back extracted 3 times with EtOAc. The combined organic layers are dried over Na₂SO₄, filtered and concentrated in vacuo. The crude product is purified by flash chromatography using a gradient of 0-50% EtOAc: Hex to provide the title compound. (633 mg, 80% yield over 2 steps). LC-MS: m/z=591.5 (M+Na)⁺.

Step II: (3S,4S,5S,6R)-6-[(1S)-1-hydroxypropyl]tetrahydropyran-2,3,4,5-tetrol

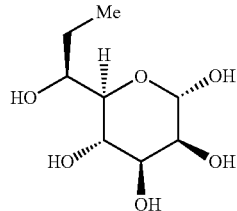 [SMILES: CC[C@H](O)[C@H]1O[C@H](O)[C@@H](O)[C@@H](O)[C@@H]1O]

(1S)-1-[(2R,3S,4S,5S,6S)-3,4,5,6-tetrabenzyloxytetrahydropyran-2-yl]propan-1-ol (633 mg, 1.113 mmol) is dissolved in MeOH (11.13 mL) and the mixture is degassed with nitrogen. Pd on C, 10% w/w, wet, Degussa (710.7 mg, 0.6678 mmol) is then added to the mixture. The reaction mixture is allowed to stir at RT under 1 atm of H2. After 1 day, the H₂ is refilled, AcOH (253 µL, 4.45 mmol) is added and the reaction is stirred over the weekend. The mixture is filtered over Celite, rinsed with MeOH and CH₂Cl₂ and the filtrate is concentrated in vacuo. This crude mixture is the dissolved in EtOH (11 mL) and AcOH (253 µL, 4.45 mmol) and the mixture is degassed with nitrogen. Palladium hydroxide 10% w/w (313 mg, 0.445 mmol) is added to the mixture. The solution is then stirred at RT under 1 atm of H₂ for 2 days. At that point, the reaction mixture is filtered over Celite, rinsed with MeOH and CH₂Cl₂ and the filtrate is concentrated in vacuo. The crude product is used as such in the next step. LC-MS: m/z=231.2 (M+Na)⁺.

Step III: [(3S,4S,5R,6R)-2,3,5-triacetoxy-6-[(1S)-1-acetoxypropyl]tetrahydropyran-4-yl]acetate

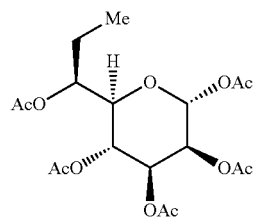 [SMILES: CC[C@H](OC(C)=O)[C@H]1O[C@H](OC(C)=O)[C@@H](OC(C)=O)[C@@H](OC(C)=O)[C@@H]1OC(C)=O]

(3S,4S,5S,6R)-6-[(1S)-1-hydroxypropyl]tetrahydropyran-2,3,4,5-tetrol from Step II (231 mg, 1.11 mmol) is dissolved in pyridine (10 mL) and Ac₂O (5.0 mL, 53.0 mmol) is added. The mixture is stirred at RT for 12 hours. The reaction mixture is then concentrated in vacuo and co-evaporated with benzene. Purification using flash chromatography is performed using a gradient of 0-50% EtOAc: Hex. The title compound is obtained and is used as such in the next step. LC-MS: m/z=441.2 (M+Na)⁺.

Step IV: [(2R,3R,4S,5S,6R)-3,5-diacetoxy-2-[(1S)-1-acetoxypropyl]-6-[2-methyl-4-[3-(methylcarbamoyl)phenyl]phenoxy]tetrahydropyran-4-yl]acetate

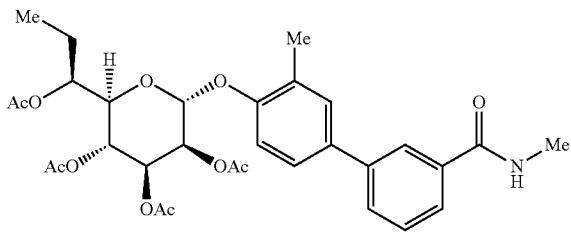 [SMILES: CC[C@H](OC(C)=O)[C@H]1O[C@H](Oc2ccc(-c3cccc(C(=O)NC)c3)cc2C)[C@@H](OC(C)=O)[C@@H](OC(C)=O)[C@@H]1OC(C)=O]

To a solution of [(3S,4S,5R,6R)-2,3,5-triacetoxy-6-[(1S)-1-acetoxypropyl]tetrahydropyran-4-yl]acetate from Step III (51.4 mg, 0.123 mmol) and INTERMEDIATE A2 (59.31 mg, 0.246 mmol) in 1,2-dichloroethane (730 µL) at 0° C. is added $BF_3.OEt_2$ (46.7 µL, 0.369 mmol) dropwise. The mixture is allowed to warm up to RT and is then heated up to 40° C. and stirred overnight. Upon completion, the reaction mixture is cooled down to RT and purified directly by flash chromatography using a gradient of 40-100% EtOAc: Hex. The title compound is obtained and can be used as such in the next step.

LC-MS: m/z=622.4 $(M+Na)^+$.

Step V: Example 31

To a stirred solution of [(2R,3R,4S,5S,6R)-3,5-diacetoxy-2-[(1S)-1-acetoxypropyl]-6-[2-methyl-4-[3-(methylcarbamoyl)phenyl]phenoxy]tetrahydropyran-4-yl]acetate from Step IV (47.7 mg, 0.07955 mmol) in dry MeOH (814 µL) at RT is added a solution of NaOMe in MeOH 25% w/v (17.19 µL, 0.07955 mmol). The resulting mixture is stirred for 2 hours. Upon completion, the reaction mixture is diluted in minimum MeOH and loaded onto a SPE, SXC cartridge (1 g). The column is rinsed with MeOH for the equivalent of 4 CV. The filtrate is concentrated in vacuo to provide the crude product which is purified by reverse phase HPLC to provide the title compound (15.5 mg, 3% yield over 4 steps). $^1H$ NMR (400 MHz, $CD_3OD$) δ 8.02 (t, J=1.8 Hz, 1H), 7.81-7.68 (m, 2H), 7.56-7.41 (m, 3H), 7.23 (d, J=8.5 Hz, 1H), 5.65 (d, J=1.8 Hz, 1H), 4.09-4.03 (m, 1H), 3.97 (dd, J=5.4, 1.8 Hz, 2H), 3.77-3.69 (m, 1H), 3.44-3.38 (m, 1H), 2.94 (s, 3H), 2.31 (s, 3H), 1.56 (dt, J=13.5, 7.5 Hz, 1H), 1.35 (tq, J=14.5, 7.3 Hz, 1H), 0.66 (t, J=7.4 Hz, 3H).

LC-MS: m/z=432.1 $(M+H)^+$.

Preparation of Example 32

(2R,3'S,4'S,5'S,6'R)-6'-(hydroxymethyl)-6-methoxy-spiro[chromane-2,2'-tetrahydropyran]-3',4',5'-triol

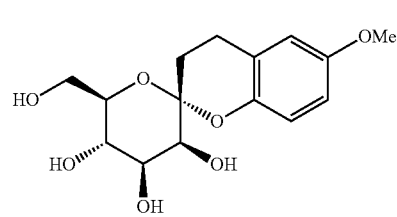 [SMILES: COc1ccc2c(c1)CC[C@]1(O2)O[C@H](CO)[C@@H](O)[C@H](O)[C@@H]1O]

Step I: (2R,3'S,4'S,5'R,6'R)-3',4',5'-tribenzyloxy-6'-(benzyloxymethyl)-6-methoxy-spiro[chromane-2,2'-tetrahydropyran]

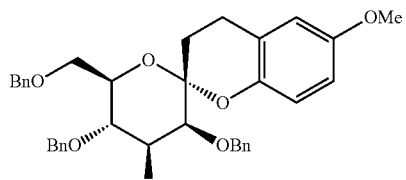

To a cold (0° C.) solution of INTERMEDIATE M9 (87 mg, 0.143 mmol) and 4-methoxyphenol (53.0 mg, 0.430 mmol) in $CH_2Cl_2$ (2 mL) is added $BF_3.OEt_2$ (18.0 µL, 0.142 mmol). After stirring for 30 min at 0° C., the reaction mixture is diluted with $H_2O$ and $CH_2Cl_2$ (3 mL each). The layers are separated and the aqueous layer is back extracted with $CH_2Cl_2$ (1 mL). The combined organic extracts are concentrated and purified by flash chromatography on a Biotage™ SNAP silica cartridge (10 g) using a gradient of EtOAc (0 to 20%) in Hex, affording the title compound (43 mg, 45% yield) as a white foamy solid.

Step II: Example 32

$Pd(OH)_2$ (16.5 mg, 0.0024 mmol) is charged in a pressure vessel flushed with $N_2$. MeOH is added (1 mL), followed by a solution of (2R,3'S,4'S,5'R,6'R)-3',4',5'-tribenzyloxy-6'-(benzyloxymethyl)-6-methoxy-spiro[chromane-2,2'-tetrahydropyran] from Step I (43 mg, 0.064 mmol) in MeOH (2 mL) and EtOAc (2 mL). AcOH (15.0 µL, 0.264 mmol) is added, the pressure vessel is purged with $H_2$ (3×), and then stirred overnight under 45 psi $H_2$. The reaction mixture is filtered on Celite, and the catalyst is rinsed with portions of MeOH. The combined filtrates are concentrated and co-evaporated with benzene to provide crude product, which is purified by flash chromatography on a Biotage™ SNAP silica cartridge (10 g) using a gradient of MeOH (0 to 20%) in $CH_2Cl_2$ affording the title compound (12 mg, 57% yield) as a white solid. $^1H$ NMR (400 MHz, $CD_3OD$) δ 6.74-6.60 (m, 3H), 4.06 (dd, J=9.5, 3.4 Hz, 1H), 3.79-3.60 (m, 7H), 3.52 (ddd, J=9.9, 4.5, 2.7 Hz, 1H), 3.00 (ddd, J=16.6, 12.9, 6.2 Hz, 1H), 2.63 (ddd, J=16.4, 5.8, 2.2 Hz, 1H), 2.35 (ddd, J=13.6, 6.2, 2.4 Hz, 1H), 1.71 (td, J=13.2, 6.0 Hz, 1H). ESI-MS m/z calc. 312.32. found 335.29 $(M+Na)^+$.

Preparation of Example 33

N-methyl-3-[(2R,3'S,4'S,5'S,6'R)-3',4',5'-trihydroxy-6'-(hydroxymethyl)spiro[chromane-2,2'-tetrahydropyran]-6-yl]benzamide

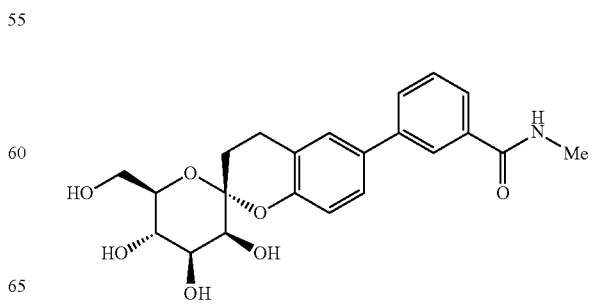

Step I: N-methyl-3-[(2R,3'S,4'S,5'R,6'R)-3',4',5'-tribenzyloxy-6'-(benzyloxymethyl)spiro[chromane-2,2'-tetrahydropyran]-6-yl]benzamide

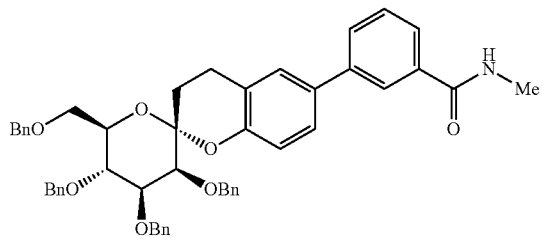 [SMILES: CNC(=O)c1cccc(-c2ccc3c(c2)CC[C@]2(O3)O[C@H](COCc3ccccc3)[C@@H](OCc3ccccc3)[C@H](OCc3ccccc3)[C@@H]2OCc2ccccc2)c1]

The title compound is prepared according to the procedure described in EXAMPLE 32 using INTERMEDIATE M9 (116 mg, 0.19 mmol) and INTERMEDIATE A1(138 mg, 0.610 mmol) in THF (2.7 mL). After 1 h at 0° C., another equivalent of $BF_3.OEt_2$ is added and stirring is pursued for 1.5 h at 0° C. and 2.5 h at RT. Purification by flash chromatography on a Biotage™ SNAP silica cartridge (10 g) using a gradient of EtOAc (0 to 20%) in $CH_2Cl_2$ provided the title (18 mg, 12% yield) as a colorless gum.

Step II: Example 33

Using N-methyl-3-[(2R,3'S,4'S,5'R,6'R)-3',4',5'-tribenzyloxy-6'-(benzyloxymethyl)spiro[chromane-2,2'-tetrahydropyran]-6-yl]benzamide from Step I (23 mg, 0.030 mmol). Purification of the crude product by preparative thin layer chromatography on silica gel (10×20 cm, 1 mm thickness) using 20% MeOH in $CH_2Cl_2$ as eluent. Final material is dissolved in $H_2O$/MeCN mixture (20% MeCN), filtrated and lyophilized to afford the title compound (8.9 mg, 69% yield) as a white fluffy solid. $^1$H NMR (400 MHz, $CD_3OD$) δ 8.01 (t, J=1.7 Hz, 1H), 7.78-7.67 (m, 2H), 7.49 (t, J=7.8 Hz, 1H), 7.45-7.35 (m, 2H), 6.96-6.83 (m, 1H), 4.11 (dd, J=9.5, 3.4 Hz, 1H), 3.81 (d, J=3.4 Hz, 1H), 3.74 (t, J=9.7 Hz, 1H), 3.70-3.66 (m, 1H), 3.58 (ddd, J=9.9, 4.2, 3.1 Hz, 1H), 3.18-3.05 (m, 1H), 2.76 (ddd, J=15.8, 5.6, 2.2 Hz, 1H), 2.43 (ddd, J=13.5, 6.0, 2.4 Hz, 1H), 1.79 (td, J=13.3, 5.9 Hz, 1H). ESI-MS m/z calc. 415.44. found 416.39 (M+1)$^+$.

Preparation of Example 34

(2R,3'S,4'S,5'S,6'R)-6'-(hydroxymethyl)-6-(3-nitrophenyl)spiro[chromane-2,2'-tetrahydropyran]-3',4',5'-triol

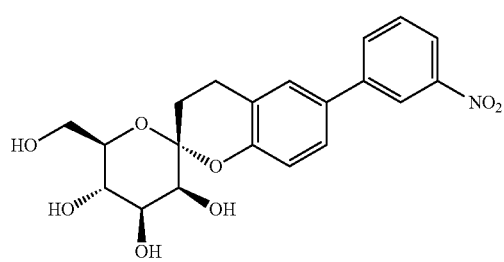 [SMILES: O=[N+]([O-])c1cccc(-c2ccc3c(c2)CC[C@]2(O3)O[C@H](CO)[C@@H](O)[C@H](O)[C@@H]2O)c1]

Step I: (2R,3'S,4'S,5'R,6'R)-3',4',5'-tribenzyloxy-6'-(benzyloxymethyl)-6-(3-nitrophenyl)spiro[chromane-2,2'-tetrahydropyran]

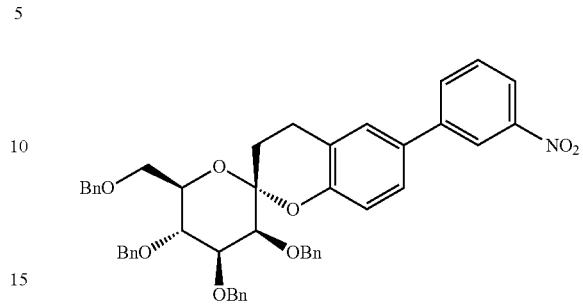

The title compound is prepared according to the procedure described in EXAMPLE 32 using INTERMEDIATE M9 (307 mg, 0.50 mmol) and 4-(3-nitrophenyl)phenol (326 mg, 1.52 mmol) as starting materials and 45 minutes reaction time. Purification by flash chromatography on a Biotage™ SNAP silica cartridge (25 g) using a gradient of EtOAc (0 to 30%) in Hex then a second purification on a Biotage™ SNAP silica cartridge (10 g) using a gradient of EtOAc (0 to 10%) in $CH_2Cl_2$ provided the title compound (87 mg, 23% yield) as an off-white foamy solid.

Step II: Example 34

To a cold (−78° C.) stirred solution (2R,3'S,4'S,5'R,6'R)-3',4',5'-tribenzyloxy-6'-(benzyloxymethyl)-6-(3-nitrophenyl)spiro[chromane-2,2'-tetrahydropyran] from Step I (85 mg, 0.11 mmol) and 1,2,3,4,5-pentamethylbenzene (166 mg, 1.12 mmol) in $CH_2Cl_2$ (6.8 mL) is added a solution of $BCl_3$ in $CH_2Cl_2$ (1.10 mL of 1.0 M, 1.11 mmol). After stirring for 2 h at −78° C., the reaction mixture is quenched with MeOH (6.8 mL), warmed to RT, concentrated and purified on a Biotage™ SNAP silica cartridge (10 g) using a gradient of MeOH (0 to 20%) in $CH_2Cl_2$ to afford the title compound (32 mg, 69% yield) as a pale yellow solid. $^1$H NMR (400 MHz, $CD_3OD$+DMSO-$D_6$) δ 8.42 (t, J=2.0 Hz, 1H), 8.17 (ddd, J=8.2, 2.2, 0.9 Hz, 1H), 8.01 (ddd, J=7.8, 1.6, 1.0 Hz, 1H), 7.67 (t, J=8.0 Hz, 1H), 7.53-7.40 (m, 2H), 6.96 (d, J=9.1 Hz, 1H), 4.10 (dd, J=9.5, 3.4 Hz, 1H), 3.81 (d, J=3.4 Hz, 1H), 3.77-3.66 (m, 3H), 3.57 (dt, J=9.9, 3.7 Hz, 1H), 3.20-3.05 (m, 1H), 2.79 (ddd, J=16.3, 5.7, 2.3 Hz, 1H), 2.44 (ddd, J=13.7, 6.2, 2.6 Hz, 1H), 1.80 (td, J=13.1, 5.8 Hz, 1H). ESI-MS m/z calc. 403.1267. found 404.23 (M+H)$^+$.

Preparation of Example 35

N-methyl-4-(2-(((2S,3S,4S,5S,6R)-3,4,5-trihydroxy-6-(hydroxymethyl)-2-methyltetrahydro-2H-pyran-2-yl)oxy)ethyl)benzamide

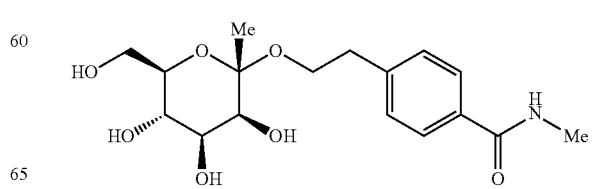

Step I: N-methyl-4-(2-(((2S,3S,4S,5R,6R)-3,4,5-tris(benzyloxy)-6-((benzyloxy)methyl)-2-methyltetrahydro-2H-pyran-2-yl)oxy)ethyl)benzamide

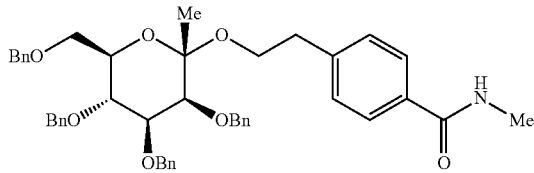 [SMILES: CNC(=O)c1ccc(CCO[C@@]2(C)O[C@H](COCc3ccccc3)[C@@H](OCc3ccccc3)[C@H](OCc3ccccc3)[C@@H]2OCc2ccccc2)cc1]

To a stirred solution of (2S,3S,4S,5R,6R)-3,4,5-tris(benzyloxy)-6-((benzyloxy)methyl)-2-methyltetrahydro-2H-pyran-2-ol (prepared according to the procedure described in *Tetrahedron* 2001, 57, 4297-4309) (309 mg, 0.558 mmol) and 4-(2-hydroxyethyl)-N-methyl-benzamide (100 mg, 0.558 mmol) in CH₂Cl₂ (4.6 mL) is added trimethylsilyl trifluoromethanesulfonate (20.0 µL, 0.112 mmol). The reaction mixture is stirred at RT for 16 h. The resulting mixture is quenched with NEt₃ (39.0 µL, 0.279 mmol), stirred for 20 min, concentrated and purified on Biotage™ SNAP silica cartridge (10 g) eluting with EtOAc (0% to 100%, in 10 CV) in Hex to afford the title compound (190 mg, 0.2521 mmol, 45%) as a gum. LC-MS: m/z=716.66 (M+H)⁺.

Step II: Example 35

To a stirred solution of N-methyl-4-(2-(((2S,3S,4S,5R,6R)-3,4,5-tris(benzyloxy)-6-((benzyloxy)methyl)-2-methyltetrahydro-2H-pyran-2-yl)oxy)ethyl)benzamide from Step I (190 mg, 0.265 mmol) in MeOH (1.9 mL) and EtOAC (1.9 mL) is added Pd/C 20% wet (40.0 mg, 0.376 mmol). The reaction mixture is stirred 16 h under an atmosphere of H₂ (1 atm). The catalyst is filtered off and washed with MeOH/CH₂Cl₂. The combined filtrates are concentrated and purified by flash chromatography (0-20% MeOH/CH2Cl2) to afford the title compound (60 mg, 60% yield). ¹H NMR (400 MHz, CD₃OD) δ 7.70 (d, J=8.2 Hz, 2H), 7.31 (d, J=8.2 Hz, 2H), 3.77 (dd, J=9.5, 3.4 Hz, 1H), 3.75-3.66 (m, 3H), 3.57 (dd, J=11.7, 5.9 Hz, 1H), 3.53 (d, J=3.4 Hz, 1H), 3.46 (t, J=9.7 Hz, 1H), 3.08 (ddd, J=10.0, 6.0, 2.4 Hz, 1H), 2.92-2.83 (m, 5H), 1.32 (s, 3H). LC-MS: m/z=356.0 (M+H)⁺.

Preparation of Example 36

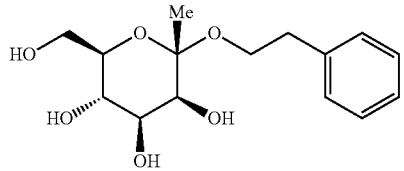

The title compound is prepared according to the procedure described for EXAMPLE 35 but using 2-phenylethanol in Step I. ¹H NMR (400 MHz, CD₃OD) δ 7.32-7.07 (m, 5H), 3.87-3.54 (m, 5H), 3.54 (d, J=3.3 Hz, 1H), 3.47 (d, J=9.7 Hz, 1H), 3.19 (dddd, J=9.8, 6.0, 2.4, 0.9 Hz, 1H), 2.82 (t, J=6.9 Hz, 2H), 1.32 (s, 3H). LC-MS: m/z=299.3 (M+H)⁺.

Preparation of Example 37

(2S,3S,4S,5S,6R)-2-(benzyloxy)-6-(hydroxymethyl)-3-methyltetrahydro-2H-pyran-3,4,5-triol

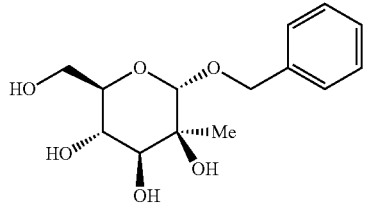 [SMILES: C[C@@]1(O)[C@@H](OCc2ccccc2)O[C@H](CO)[C@@H](O)[C@@H]1O]

Step I: (3S,4S,5R,6R)-6-(acetoxymethyl)-2-hydroxy-3-methyltetrahydro-2H-pyran-3,4,5-triyl triacetate

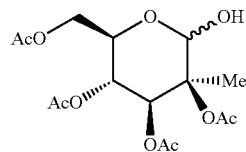 [SMILES: CC(=O)OC[C@H]1OC(O)[C@@](C)(OC(C)=O)[C@@H](OC(C)=O)[C@@H]1OC(C)=O]

To a cold (0° C.) solution of INTERMEDIATE M4 (505 mg, 1.25 mmol) in THF (7 mL) is added a solution of NH₃ in MeOH (3.60 mL of 7 M, 25.2 mmol). The resulting mixture is stirred for 2 h at 0° C., concentrated and purified by flash chromatography on a Biotage™ SNAP silica cartridge (25 g) using a gradient of EtOAc (0 to 60%) in Hex to afford the title compound (273 mg, 60% yield) as a white foamy solid. ¹H NMR (400 MHz, CDCl₃) δ 5.98 (d, J=4.5 Hz, 1H), 5.44 (d, J=9.7 Hz, 1H), 5.33 (d, J=9.8 Hz, 1H), 4.23 (dt, J=9.9, 3.7 Hz, 1H), 4.15 (d, J=3.7 Hz, 2H), 3.12 (d, J=4.5 Hz, 1H), 2.10 (s, 6H), 2.09 (s, 3H), 2.04 (s, 3H), 1.54 (s, 3H).

Step II: (2R,3S,4S,5R,6R)-6-(acetoxymethyl)-3-methyl-2-(2,2,2-trichloro-1-iminoethoxy)tetrahydro-2H-pyran-3,4,5-triyltriacetate

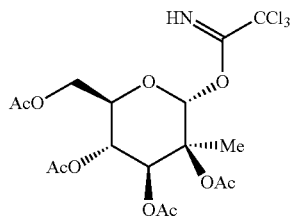

To a cold (0° C.) solution of (3S,4S,5R,6R)-6-(acetoxymethyl)-2-hydroxy-3-methyltetrahydro-2H-pyran-3,4,5-triyl-triacetate from step I (273 mg, 0.754 mmol) in CH₂Cl₂ (11 mL) is added 2,2,2-trichloroacetonitrile (765 µL, 7.54 mmol) followed by DBU (12.0 µL, 0.0754 mmol) dropwise. The reaction mixture is stirred for 1 h at 0° C. then 2 h at RT. The resulting mixture is concentrated and purified on a Biotage™ SNAP silica cartridge (25 g) using a gradient of EtOAc (0 to 50%) in Hex to provide the title compound (278 mg, 73% yield) as a colorless gum. ¹H NMR (400 MHz, CDCl₃) δ 8.82 (s, 1H), 7.04 (s, 1H), 5.43 (d, J=3.7 Hz, 1H), 4.27-4.04 (m, 4H), 2.14 (s, 3H), 2.12 (s, 3H), 2.06 (s, 3H), 2.05 (s, 3H), 1.59 (s, 3H).

Step III: (2S,3S,4S,5R,6R)-6-(acetoxymethyl)-2-(benzyloxy)-3-methyltetrahydro-2H-pyran-3,4,5-triyltriacetate

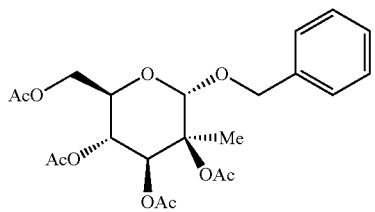 [SMILES: CC(=O)OC[C@H]1O[C@H](OCc2ccccc2)[C@@](C)(OC(C)=O)[C@@H](OC(C)=O)[C@@H]1OC(C)=O]

To a cold (−20° C.) stirred solution of (2R,3S,4S,5R,6R)-6-(acetoxymethyl)-3-methyl-2-(2,2,2-trichloro-1-iminoethoxy)tetrahydro-2H-pyran-3,4,5-triyltriacetate from Step II (111 mg, 0.219 mmol) in CH₂Cl₂ (2.0 mL) are added powdered molecular sieve 4 Å (110 mg) and phenylmethanol (23.7 mg, 0.219 mmol) under N₂ atmosphere and the mixture is stirred for 10 min. TMSOTf (9.0 µL, 0.23 eq.) is then added and the resulting mixture is stirred for 30 min. The reaction mixture is quenched with saturated aqueous NaHCO₃, the organic phase is washed with brine, dried over MgSO₄, filtered and concentrated in vacuo. The residue is purified on Biotage™ SNAP silica cartridge (10 g) using EtOAc (10% to 50%) in Hex as eluent to give title compound (45.0 mg, 50%) as a colorless oil Step IV: Example 37

To a cold (0° C.) solution of (2S,3S,4S,5R,6R)-6-(acetoxymethyl)-2-(benzyloxy)-3-methyltetrahydro-2H-pyran-3,4,5-triyltriacetate from Step II (45.0 mg, 0.110 mmol) in MeOH (1 mL) is added, NaOMe (110 mL, 0.5 M, 0.055 mmol). The reaction mixture is warmed to RT and stirred overnight. The reaction mixture is quenched with DOWEX 50WX4-400 resin until pH reaches 4-5, filtered, and concentrated. The residue is purified by Biotage™ SNAP C18 cartridge (10 g) eluting with CH₃CN (20-30%) in water to afford the title compound (25 mg, 76% yield) as a white solid. ¹H NMR (400 MHz, CD₃OD) δ 7.39-7.22 (m, 5H), 4.72 (d, J=11.9 Hz, 1H), 4.52 (s, 1H), 4.48 (d, J=11.9 Hz, 1H), 3.81 (dd, J=11.7, 2.2 Hz, 1H), 3.72 (dd, J=11.7, 5.4 Hz, 1H), 3.65-3.59 (m, 1H), 3.56 (t, J=9.2 Hz, 1H), 3.48 (d, J=8.7 Hz, 1H), 1.22 (s, 3H).

Preparation of Example 38

3-[4-[(2R,3S,4S,5S,6R)-3-(azidomethyl)-3,4,5-trihydroxy-6-(hydroxymethyl)tetrahydropyran-2-yl]oxy-3-methyl-phenyl]-N-methyl-benzamide

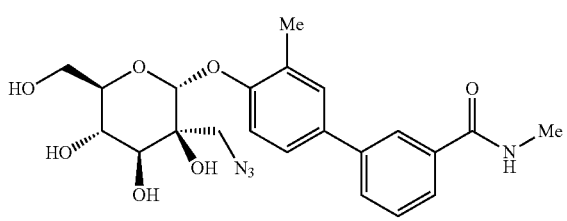

Step I: (2R,3S,4S,5R,6R)-6-(acetoxymethyl)-3-(azidomethyl)-2-((3-methyl-3'-(methylcarbamoyl)-[1,1'-biphenyl]-4-yl)oxy)tetrahydro-2H-pyran-3,4,5-triyl triacetate

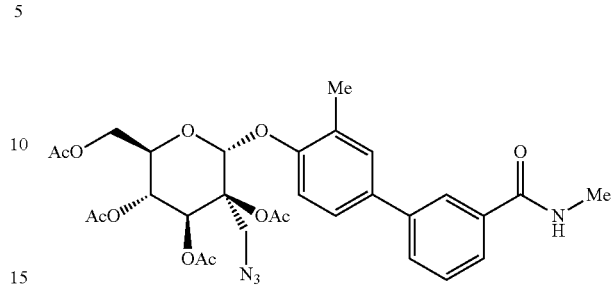

To a suspension of INTERMEDIATE M14 (850 mg, 1.90 mmol) and INTERMEDIATE A2 (737 mg, 3.10 mmol) in 1,2-dichloroethane (13.0 mL) at 0° C. is added BF₃.Et₂O (725 uL, 5.70 mmol) dropwise. The resulting mixture is stirred at 40° C. for 16 h, cooled down to 3° C. and quenched with 2 ml of saturated aqueous NaHCO₃ while stirring. The resulting suspension is filtered and the organic phase is separated, dried over Na₂SO₄, filtered, and concentrated. Purification on Isco CombiFlash® silica gel cartridge (40 g) eluting with EtOAc (40-100%) in Hex (15 CV) afforded the title compound (192 mg, 16%) as a white solid. LC-MS: m/z=627.5 (M+H)⁺.

Step II: Example 38

To a stirred solution of (2R,3S,4S,5R,6R)-6-(acetoxymethyl)-3-(azidomethyl)-2-((3-methyl-3'-(methylcarbamoyl)-[1,1'-biphenyl]-4-yl)oxy)tetrahydro-2H-pyran-3,4,5-triyl triacetate from Step I (200 mg, 0.32 mmol) in dry MeOH (5.0 mL) at RT is added a solution of NaOMe in MeOH (36 µL of 0.50 M, 0.16 mmol). The resulting mixture is stirred for 2 h, neutralized by the addition of Ambilite IR-120 resin until the reaction mixture pH reached 4. The resulting mixture is filtered, concentrated and purified on Isco CombiFlash® silica gel cartridge (12 g) eluting with MeOH (0-10%) in CH₂Cl₂/(15 CV) to afford the title compound (105 mg, 68%) as a white solid. ¹H NMR (400 MHz, CD₃OD) δ 8.01 (t, J=1.8 Hz, 1H), 7.72 (ddt, J=7.7, 6.0, 1.3 Hz, 2H), 7.53-7.40 (m, 3H), 7.34 (d, J=8.4 Hz, 1H), 5.52 (s, 1H), 3.83 (d, J=12.8 Hz, 1H), 3.78-3.70 (m, 4H), 3.62-3.65 (m, 1H), 3.51 (d, J=12.8 Hz, 1H), 2.92 (s, 3H), 2.30 (s, 3H). LC-MS: m/z=459.3 (M+H)⁺.

Preparation of Example 39 to 43

EXAMPLES 39 to 43 are prepared according to the following general procedure using INTERMEDIATEs M4 and A10 to A14 respectively. Vials are charged with the appropriate phenols (1.2 eq. A9-A14). A solution of INTERMEDIATE M4 (100 mg, 0.247 mmol) in 1,2-dichloroethane (1.5 mL) is added followed by (100 µL, 0.789) is added to each vial. The vial is capped and the final mixture is stirred at 60° C. overnight. The resulting crude mixture is cooled down to RT, quenched by careful addition of 2 mL saturated aqueous NaHCO₃ solution and diluted with CH₂Cl₂ (2 mL). The organic layer is separated and the aqueous layer is back extracted with CH₂Cl₂ (2×2 mL). The combined organic extracts are concentrated. The resulting crude residue is dissolved in MeOH (2 mL) and treated with NaOMe in MeOH (500 µL, of 0.5 M). The mixture is stirred for 2 h at RT, passed through a prewashed 1 g SCX-2 cartridge. The latter is washed MeOH (3×1 mL) and the combined fractions are concentrated. The residue is finally purified by reverse phase HPLC to afford the title compounds.

| EXAMPLE # | Name | ¹H-NMR | LCMS m/z (M + H)⁺ |
|---|---|---|---|
| 39 | 3-[2-fluoro-4-[(2R,3S,4S,5S,6R)-3,4,5-trihydroxy-6-(hydroxymethyl)-3-methyl-tetrahydropyran-2-yl]oxy-phenyl]-N-methyl-benzamide | (400 MHz, CD₃OD) δ 7.95 (d, J = 1.3 Hz, 1H), 7.83-7.72 (m, 1H), 7.68 (dd, J = 7.8, 1.2 Hz, 1H), 7.58-7.41 (m, 2H), 7.10-6.95 (m, 2H), 5.25 (s, 1H), 3.88-3.56 (m, 5H), 2.94 (s, 3H), 1.38 (s, 3H). | 422.62 |
| 40 | 3-[2-chloro-4-[(2R,3S,4S,5S,6R)-3,4,5-trihydroxy-6-(hydroxymethyl)-3-methyl-tetrahydropyran-2-yl]oxy-phenyl]-N-methyl-benzamide | (400 MHz, CD₃OD) δ 7.84 (t, J = 1.5 Hz, 1H), 7.83-7.77 (m, 1H), 7.58 (dt, J = 7.7, 1.4 Hz, 1H), 7.52 (t, J = 7.6 Hz, 1H), 7.34 (d, J = 8.5 Hz, 1H), 7.31 (d, J = 2.5 Hz, 1H), 7.18 (dd, J = 8.5, 2.5 Hz, 1H), 5.25 (s, 1H), 3.85 – 3.57 (m, 5H), 2.93 (s, 3H), 1.38 (s, 3H). | 438.02 |
| 41 | 3-[2-methoxy-4-[(2R,3S,4S,5S,6R)-3,4,5-trihydroxy-6-(hydroxymethyl)-3-methyl-tetrahydropyran-2-yl]oxy-phenyl]-N-methyl-benzamide | (400 MHz, CD₃OD) δ 7.90 (t, J = 1.6 Hz, 1H), 7.77-7.67 (m, 1H), 7.66-7.58 (m, 1H), 7.44 (t, J = 7.7 Hz, 1H), 7.26 (d, J = 8.4 Hz, 1H), 6.86 (d, J = 2.2 Hz, 1H), 6.82 (dd, J = 8.4, 2.3 Hz, 1H), 5.23 (s, 1H), 3.80 (s, 3H), 3.79-3.66 (m, 5H), 2.93 (s, 3H), 1.40 (s, 3H). | 434.62 |
| 42 | N-methyl-3-[2-methyl-4-[(2R,3S,4S,5S,6R)-3,4,5-trihydroxy-6-(hydroxymethyl)-3-methyl-tetrahydropyran-2-yl]oxy-phenyl]benzamide | (400 MHz, CD₃OD) δ 7.77 (dt, J = 7.5, 1.5 Hz, 1H), 7.75-7.70 (m, 1H), 7.50 (t, J = 7.5 Hz, 1H), 7.46 (dt, J = 7.6, 1.5 Hz, 1H), 7.16 (d, J = 8.3 Hz, 1H), 7.06 (d, J = 2.4 Hz, 1H), 7.02 (dd, J = 8.3, 2.5 Hz, 1H), 5.21 (s, 1H), 3.82-3.61 (m, 5H), 2.93 (s, 3H), 2.23 (s, 3H), 1.38 (s, 3H). | 418.59 |
| 43 | N-methyl-3-[2-(trifluoromethyl)-4-[(2R,3S,4S,5S,6R)-3,4,5-trihydroxy-6-(hydroxymethyl)-3-methyl-tetrahydropyran-2-yl]oxy-phenyl]benzamide | (400 MHz, CD₃OD) δ 7.84 (dt, J = 7.5, 1.6 Hz, 1H), 7.76 (s, 1H), 7.56-7.41 (m, 4H), 7.34 (d, J = 8.5 Hz, 1H), 5.31 (s, 1H), 3.82-3.57 (m, 5H), 2.92 (s, 3H), 1.40 (s, 3H). | 472.67 |
| 44 | 3-[4-chloro-3-[(2R,3S,4S,5S,6R)-3,4,5-trihydroxy-6-(hydroxymethyl)-3-methyl-tetrahydropyran-2-yl]oxy-phenyl]-N-methyl-benzamide | (400 MHz, CD₃OD) δ 8.07 (t, J = 1.7 Hz, 1H), 7.86-7.77 (m, 2H), 7.72 (d, J = 2.0 Hz, 1H), 7.54 (t, J = 7.8 Hz, 1H), 7.48 (d, J = 8.3 Hz, 1H), 7.33 (dd, J = 8.3, 2.0 Hz, 1H), 5.36 (s, 1H), 3.91-3.60 (m, 5H), 2.95 (s, 3H), 1.47 (s, 3H). | 439.28 |
| 45 | 4-[4-chloro-3-[(2R,3S,4S,5S,6R)-3,4,5-trihydroxy-6-(hydroxymethyl)-3-methyl-tetrahydropyran-2-yl]oxy-phenyl]-N-methyl-benzamide | (400 MHz, CD₃OD) δ 7.89 (d, J = 8.4 Hz, 2H), 7.74 (d, J = 8.4 Hz, 2H), 7.71 (d, J = 2.0 Hz, 1H), 7.48 (d, J = 8.3 Hz, 1H), 7.32 (dd, J = 8.3, 2.0 Hz, 1H), 5.34 (s, 1H), 3.91-3.60 (m, 5H), 2.94 (s, 3H), 1.47 (s, 3H). | 439.28 |
| 46 | 3-[2-chloro-3-[(2R,3S,4S,5S,6R)-3,4,5-trihydroxy-6-(hydroxymethyl)-3-methyl-tetrahydropyran-2-yl]oxy-phenyl]-N-methyl-benzamide | (400 MHz, CD₃OD) δ 7.88-7.80 (m, 2H), 7.61-7.49 (m, 2H), 7.44 (dd, J = 8.4, 1.4 Hz, 1H), 7.34 (t, J = 8.0 Hz, 1H), 7.05 (dd, J = 7.6, 1.4 Hz, 1H), 5.32 (s, 1H), 3.86-3.61 (m, 5H), 2.93 (s, 3H), 1.44 (s, 3H). | 438.58 |
| 47 | 4-[2-chloro-3-[(2R,3S,4S,5S,6R)-3,4,5-trihydroxy-6-(hydroxymethyl)-3-methyl-tetrahydropyran-2-yl]oxy-phenyl]-N-methyl-benzamide | (400 MHz, CD₃OD) δ 7.93-7.81 (m, 2H), 7.55-7.48 (m, 2H), 7.44 (dd, J = 8.4, 1.4 Hz, 1H), 7.37-7.28 (m, 1H), 7.03 (dd, J = 7.6, 1.4 Hz, 1H), 5.32 (s, 1H), 3.86-3.60 (m, 5H), 2.95 (s, 3H), 1.44 (s, 3H). | 438.54 |

Preparation of Example 44 to 47

EXAMPLES 44 and 45 are prepared using INTERMEDIATE M13, EXAMPLES 46 and 47 using INTERMEDIATE M12 according to the following general procedure. Microwave vials are loaded with the appropriate phenyl boronic acid (1.5 eq.), Cs₂CO₃ (3.0 eq.), and SiliaCat DPP-Pd (0.1 eq.). INTERMEDIATE M12 or M13 (45 mg, 1.0 eq.) are dissolved in MeCN (2 mL) and added to each vial. The vials are capped and microwaved, 15 min at 100° C. The resulting mixture is diluted with CH₂Cl₂:EtOAc (1:1) and passed through a 500 mg bondelut silica gel cartridge, eluting with CH₂Cl₂-EtOAc (1:1) (ca 5 mL total). The resulting fractions are combined and concentrated. The residue is dissolved in MeOH (1 mL) and NaOMe in MeOH is added and the final mixture is stirred for 2 h at RT. The resulting mixture is passed through a prewashed 1 g SCX-2 cartridge, washed with MeOH (3×1 mL). The combined filtrates are concentrated and the residue is purified by reverse phase HPLC to afford to desired material.

Preparation of Example 48

3-[4-[(2R,3S,4S,5S,6R)-3-(aminomethyl)-3,4,5-trihydroxy-6-(hydroxymethyl)tetrahydropyran-2-yl]oxy-3-methyl-phenyl]-N-methyl-benzamide

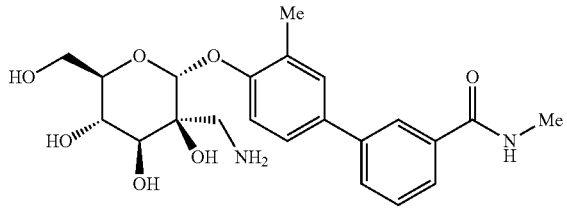

To a stirred solution of EXAMPLE 38 (35 mg, 0.076 mmol) in EtOH (700 μL) and water (700 μL) is added 10% Pd/C (4 mg, 0.033 mmol). The resulting mixture is stirred for 16 hours under an H₂ atmosphere, filtered on celite, concentrated and purified on Isco CombiFlash® C18 cartridge (12 g) eluting with CH₃CN (5 to 50%) in water to afford the title compound (8 mg, 23%) as a white solid. ¹H NMR (400 MHz, CD₃OD) δ 8.00 (t, J=1.7 Hz, 1H), 7.72 (ddt, J=7.2, 4.1, 1.2 Hz, 2H), 7.43-7.51 (m, 3H), 7.34 (d, J=8.5 Hz, 1H), 5.47 (s, 1H), 3.86 (d, J=9.1 Hz, 1H), 3.80-3.69 (m, 3H), 3.59-3.49 (m, 1H), 3.22 (d, J=13.5 Hz, 1H), 2.98 d, (J=13.5 Hz, 1H), 2.92 (s, 3H), 2.32 (s, 3H). LC-MS: m/z=433.15 (M+H)⁺.

Preparation of Example 49

3-[4-[(2R,3S,4S,5S,6R)-3-(2-benzyloxyethoxymethyl)-3,4,5-trihydroxy-6-(hydroxymethyl)tetrahydropyran-2-yl]oxy-3-methyl-phenyl]-N-methyl-benzamide

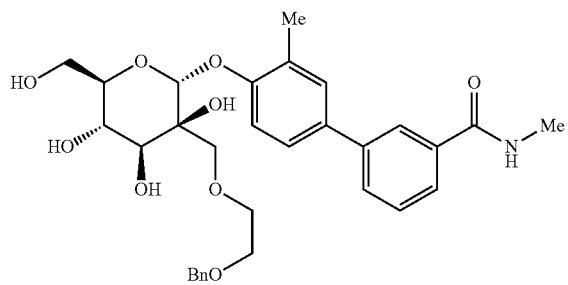 [SMILES: CNC(=O)c1cccc(-c2ccc(O[C@H]3O[C@H](CO)[C@@H](O)[C@H](O)[C@@]3(O)COCCOCc3ccccc3)c(C)c2)c1]

Step I: (2R,3S,4S,5R,6R)-6-(acetoxymethyl)-3-((2-(benzyloxy)ethoxy)methyl)-2-((3-methyl-3'-(methylcarbamoyl)-[1,1'-biphenyl]-4-yl)oxy)tetrahydro-2H-pyran-3,4,5-triyltriacetate

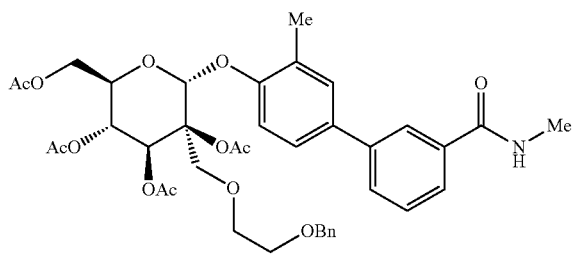 [SMILES: CNC(=O)c1cccc(-c2ccc(O[C@H]3O[C@H](COC(C)=O)[C@@H](OC(C)=O)[C@H](OC(C)=O)[C@]3(COCCOCc3ccccc3)OC(C)=O)c(C)c2)c1]

To a mixture of INTERMEDIATE M15 (450 mg, 0.820 mmol) and INTERMEDIATE A2 (392 mg, 1.62 mmol) in dichloroethane (6.3 mL) is added $BF_3 \cdot OEt_2$ (309 μL, 2.43 mmol). The mixture is stirred at 40° C. overnight. The resulting mixture is cooled down to RT; quenched by addition of 2 mL of saturated aqueous $NaHCO_3$. The resulting suspension is filtered and the organic phase is separated, dried over $Na_2SO_4$, filtered, and concentrated. The residue is purified on Isco CombiFlash® silica gel cartridge (40 g) eluting with EtOAc (0-100%) in Hex (15 CV) to afford the title compound (165 mg, 28%) as a white solid. LC-MS: m/z=758.2 $(M+Na)^+$.

Step II: Example 49

To a stirred solution of (2R,3S,4S,5R,6R)-6-(acetoxymethyl)-3-((2-(benzyloxy)ethoxy)methyl)-2-((3-methyl-3'-(methylcarbamoyl)-[1,1'-biphenyl]-4-yl)oxy)tetrahydro-2H-pyran-3,4,5-triyl triacetate from Step I (20 mg, 0.027 mmol) in dry MeOH (1.0 mL) at RT is added a solution of MeONa in MeOH (3 μL of 25% w/w, 0.014 mmol). The resulting mixture is stirred for 2 hours, neutralized by the addition of Ambilite IR-120 resin until the reaction mixture pH reached 4. The resulting mixture is filtered and concentrated to afford the tittle compound (14 mg, 86%) as a white solid. $^1$H NMR (400 MHz, $CD_3OD$) δ 7.98 (t, J=1.8 Hz, 1H), 7.73-7.64 (m, 2H), 7.52-7.40 (m, 2H), 7.38 (dd, J=8.6, 2.4 Hz, 1H), 7.31 (d, J=8.6 Hz, 1H), 7.25-7.05 (m, 5H), 5.57 (s, 1H), 4.37 (s, 2H), 3.91 (d, J=9.9 Hz, 1H), 3.84 (d, J=9.9 Hz, 1H), 3.80-3.65 (m, 5H), 3.64-3.49 (m, 4H), 2.93 (s, 3H), 2.31 (s, 3H). LC-MS: m/z=658.11 $(M+1)^+$.

Preparation of Example 50

N-methyl-3-[3-methyl-4-[(2R,3S,4S,5S,6R)-3,4,5-trihydroxy-3-(2-hydroxyethoxymethyl)-6-(hydroxymethyl)tetrahydropyran-2-yl]oxy-phenyl]benzamide

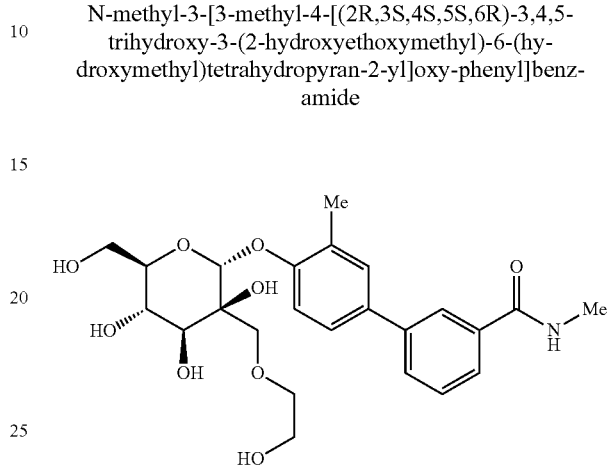

Step I: (2R,3S,4S,5R,6R)-6-(acetoxymethyl)-3-((2-hydroxyethoxy)methyl)-2-((3-methyl-3'-(methylcarbamoyl)-[1,1'-biphenyl]-4-yl)oxy)tetrahydro-2H-pyran-3,4,5-triyltriacetate

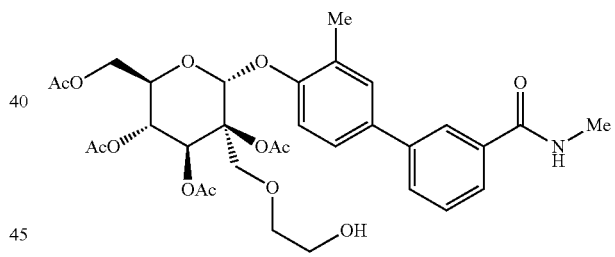

To a stirred solution of (2R,3S,4S,5R,6R)-6-(acetoxymethyl)-3-((2-(benzyloxy)ethoxy)methyl)-2-((3-methyl-3'-(methylcarbamoyl)-[1,1'-biphenyl]-4-yl)oxy)tetrahydro-2H-pyran-3,4,5-triyl triacetate from EXAMPLE 49 Step I (150 mg, 0.200 mmol) in dry EtOH (3.8 mL) and AcOH (47 μL, 0.82 mmol) is added $Pd(OH)_2$ (20% wet, 57 mg, 0.082 mmol). The resulting mixture is stirred for 16 hours under an $H_2$ atmosphere, filtered on celite and concentrated to afford the tittle compound (125 mg, 95%) as a white solid. $^1$H NMR (400 MHz, $CDCl_3$) δ 7.96 (t, J=1.8 Hz, 1H), 7.66 (dd, J=7.9, 1.8 Hz, 2H), 7.54-7.42 (m, 2H), 7.42-7.33 (m, 1H), 7.23 (d, J=8.5 Hz, 1H), 6.21 (s, 1H), 5.86 (d, J=9.7 Hz, 1H), 5.43 (t, J=10.0 Hz, 1H), 4.29-4.16 (m, 2H), 4.16-4.04 (m, 2H), 3.99 (d, J=10.0 Hz, 1H), 3.71 (m, 1H), 3.65-3.55 (m, 1H), 3.56-3.39 (m, 2H), 3.05 (d, J=4.8 Hz, 3H), 2.36 (s, 3H), 2.21 (s, 3H), 2.12 (s, 3H), 2.06 (s, 3H), 2.04 (s, 3H).

Step II: Example 50

To a stirred solution of (2R,3S,4S,5R,6R)-6-(acetoxymethyl)-3-((2-hydroxyethoxy)-methyl)-2-((3-methyl-3'-(methylcarbamoyl)-[1,1'-biphenyl]-4-yl)oxy)tetrahydro-2H-pyran-3,4,5-triyl triacetate from Step I (30 mg, 0.046 mmol) in dry MeOH (1.5 mL) at RT is added a solution of NaOMe in MeOH (5 µL of 25% w/w, 0.023 mmol). The resulting mixture is stirred for 2 hours, neutralized by the addition of Ambilite IR-120 resin until the reaction mixture pH reached 4. The resulting mixture is filtered and concentrated to afford the tittle compound (19 mg, 82%) as a white solid. $^1$H NMR (400 MHz, CD$_3$OD) δ 7.92 (t, J=1.8 Hz, 1H), 7.64 (ddt, J=8.1, 5.3, 1.3 Hz, 2H), 7.45-7.30 (m, 4H), 7.25 (d, J=8.4 Hz, 1H), 5.48 (s, 1H), 3.85-3.73 (m, 2H), 3.73-3.58 (m, 4H), 3.58-3.33 (m, 5H), 2.84 (s, 3H), 2.24 (s, 3H). LC-MS: m/z=478.3 (M+H)$^+$.

Preparation of Example 51

N-methyl-3-[3-methyl-4-[(2R,3S,4S,5S,6R)-3,4,5-trihydroxy-6-(hydroxymethyl)-3-[[4-(hydroxymethyl)triazol-1-yl]methyl]tetrahydropyran-2-yl]oxy-phenyl]benzamide

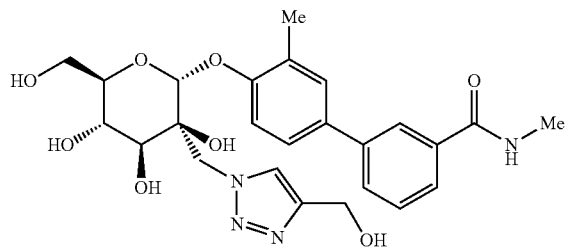 [SMILES: CNC(=O)c1cccc(-c2ccc(O[C@H]3O[C@H](CO)[C@@H](O)[C@H](O)[C@@]3(O)Cn3cc(CO)nn3)c(C)c2)c1]

To a stirred solution of EXAMPLE 38 (25 mg, 0.054 mmol), sodium ascorbate (29 mg, 0.16 mmol), prop-2-yn-1-ol (174 µL, 0.055 mmol) in NMP (235 µL) is added CuOAc (1.0 mg, 0.010 mmol). The resulting mixture is stirred for 48 hours at room temperature, filtered and purified by reverse phase HPLC to afford the title compound (15 mg, 54%) as a white solid.
LC-MS: m/z=515.16 (M+1).

Preparation of Example 52

3-[4-[(2R,3S,4S,5S,6R)-3-(acetamidomethyl)-3,4,5-trihydroxy-6-(hydroxymethyl)tetrahydropyran-2-yl]oxy-3-methyl-phenyl]-N-methyl-benzamide

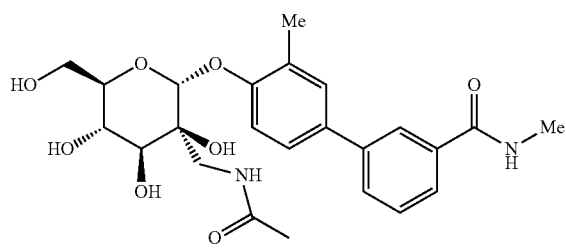 [SMILES: CNC(=O)c1cccc(-c2ccc(O[C@H]3O[C@H](CO)[C@@H](O)[C@H](O)[C@@]3(O)CNC(C)=O)c(C)c2)c1]

To a stirred solution of EXAMPLE 48 (70 mg, 0.16 mmol) in THF (1.6 mL) is added NaOAc (1.6 mL of 50% w/v, 9.8 mmol) and acetyl chloride (10.0 µL, 0.16 mmol). The resulting mixture is stirred for 16 hours at RT, filtered, concentrated and purified using reverse phase HPLC to afford the tittle compound (8 mg, 10%). LC-MS: m/z=475.76 (M+1).

Preparation of Example 53

3-[3-chloro-4-[(2R,3S,4S,5S,6R)-3,4,5-trihydroxy-6-(hydroxymethyl)-3-methyl-tetrahydropyran-2-yl]oxy-phenyl]-N-(2-methoxyethyl)benzamide

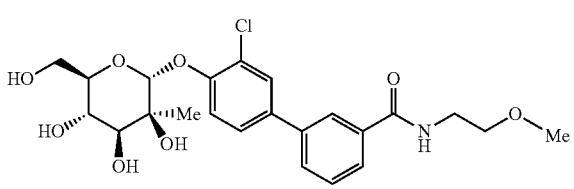 [SMILES: COCCNC(=O)c1cccc(-c2ccc(O[C@H]3O[C@H](CO)[C@@H](O)[C@H](O)[C@]3(C)O)c(Cl)c2)c1]

To a degased (N$_2$) mixture of INTERMEDIATE M11 (40 mg, 0.09261 mmol), t-Bu$_3$PH$^+$.BF$_4^-$ (5.0 mg, 0.017 mmol) and Pd$_2$(dba)$_3$ (17.0 mg, 0.0186 mmol) in THF (300 µL)/water (300 µL) is added a solution of [3-(2-methoxyethylcarbamoyl)phenyl]boronic acid (21.0 mg, 0.0942 mmol) in NMP (200 µL). K$_3$PO$_4$ (39 mg, 0.1837 mmol) is then added and the reaction mixture is stirred at 75° C. for 18 hours. The resulting mixture is filtered, and the filtrate is purified by reverse phase HPLC to afford the title compounds (8.5 mg, 18%) as a white solid. $^1$H NMR (400 MHz, CD$_3$OD) δ 8.03 (d, J=1.5 Hz, 1H), 7.81-7.69 (m, 3H), 7.54 (ddd, J=25.0, 12.9, 5.4 Hz, 3H), 5.30 (s, 1H), 3.80-3.61 (m, 6H), 3.57 (s, 4H), 3.38 (s, 3H), 1.44 (s, 3H). LC-MS: m/z=482.25 (M+H)$^+$.

Preparation of Example 54

2-chloro-4-[3-chloro-4-[(2R,3S,4S,5S,6R)-3,4,5-trihydroxy-6-(hydroxymethyl)-3-methyl-tetrahydropyran-2-yl]oxy-phenyl]-N-cyclopropyl-benzamide

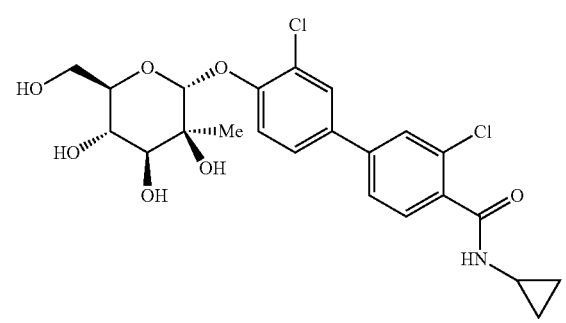 [SMILES: C[C@@]1(O)[C@@H](Oc2ccc(-c3ccc(C(=O)NC4CC4)c(Cl)c3)cc2Cl)O[C@H](CO)[C@@H](O)[C@@H]1O]

To a mixture of INTERMEDIATE M11 (40.0 mg, 0.104 mmol), Pd(OAc)$_2$ (5.0 mg, 0.022 mmol) and [3-(2-dicyclohexylphosphanylphenyl)-2,4-dimethoxy-phenyl]sulfonyloxysodium (23.0 mg, 0.0449 mmol) in 500 uL of MeTHF is added [3-chloro-4-(cyclopropylcarbamoyl)phenyl]boronic acid (200 µL of 0.5 M, 0.100 mmol) and K$_2$CO$_3$ aq. (100 µL of 4.5 M, 0.450 mmol). The reaction mixture is stirred at 65° C. for 18 hours. The resulting mixture is filtered, and the filtrate is purified by reverse phase HPLC to afford the title compounds (3.0 mg, 5%) as a white solid. $^1$H NMR (400 MHz, CD$_3$OD) δ 7.62-7.57 (m, 2H), 7.47 (dd, J=15.7, 5.1 Hz, 2H), 7.39 (t, J=8.3 Hz, 2H), 5.22 (s, 1H), 3.70-3.57 (m, 3H), 3.57-3.50 (m, 2H), 2.78 (ddd, J=11.1, 7.5, 4.0 Hz, 1H), 1.34 (s, 3H), 0.77-0.68 (m, 2H), 0.58-0.50 (m, 2H). LC-MS: m/z=499.15 (M+H)$^+$.

Preparation of Example 55

5-[3-chloro-4-[(2R,3S,4S,5S,6R)-3,4,5-trihydroxy-6-(hydroxymethyl)-3-methyl-tetrahydropyran-2-yl]oxy-phenyl]-2-fluoro-N-methyl-benzamide

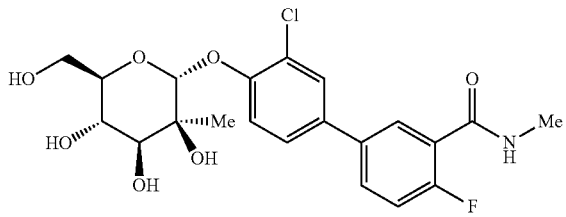 [SMILES: CNC(=O)c1cc(-c2ccc(O[C@H]3O[C@H](CO)[C@@H](O)[C@H](O)[C@]3(C)O)c(Cl)c2)ccc1F]

EXAMPLE 55 is prepared according to the procedure described for EXAMPLE 54 using 4-fluoro-3-(methylcarbamoyl)phenyl]boronic acid as starting material. The reaction mixture is stirred 2 h at 80° C. The title compound is purified by reverse phase HPLC and isolated as a white solid (2.4 mg, 6%). LC-MS: m/z=456.22 (M+H)$^+$.

Preparation of Example 56

3-[3-chloro-4-[(2R,3S,4S,5S,6R)-3,4,5-trihydroxy-6-(hydroxymethyl)-3-methyl-tetrahydropyran-2-yl]oxy-phenyl]-5-fluoro-N-methyl-benzamide

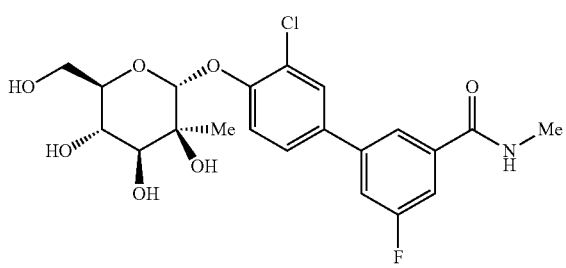

EXAMPLE 56 is prepared according to the procedure described for EXAMPLE 54 using 3-fluoro-3-(methylcarbamoyl)phenyl]boronic acid as starting material. The reaction mixture is stirred 2 h at 80° C. The title compound is purified by reverse phase HPLC and isolated as a white solid (0.96 mg, 2%). LC-MS: m/z=455.11 (M+H)$^+$.

Preparation of Example 57

Methyl 3-[3-methyl-4-[(2R,3S,4S,5S,6R)-3,4,5-trihydroxy-6-(hydroxymethyl)-3-methyl-tetrahydropyran-2-yl]oxy-phenyl]benzoate

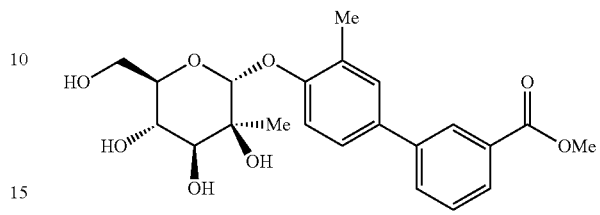

To a suspension of Methyl 3-[3-methyl-4-[(2R,3S,4S,5R,6R)-3,4,5-triacetoxy-6-(acetoxymethyl)-3-methyltetrahydropyran-2-yl]oxy-phenyl]benzoate from EXAMPLE 21, Step I (1.62 g, 2.762 mmol) in MeOH (6 mL) is added NaOMe in MeOH (5.94 mL of 0.5 M, 2.97 mmol). The reaction mixture is stirred at RT. After 30 min a white precipitate formed and an additional amount of MeOH (6 mL) is added. The mixture is stirred for 2 h, quenched with DOWEX acid resin until pH 4, stirred for 5 min. The resin is filtered off, washed with MeOH (30 mL). The combined filtrates are concentrated to afford the title compound (1.12 g, 67%) as a white solid. $^1$H NMR (400 MHz, CD$_3$OD) δ 8.18 (t, J=1.6 Hz, 1H), 7.96-7.88 (m, 1H), 7.83-7.74 (m, 1H), 7.50 (t, J=7.8 Hz, 1H), 7.46-7.39 (m, 2H), 7.31 (d, J=8.3 Hz, 1H), 5.27 (s, 1H), 3.92 (s, 4H), 3.77-3.65 (m, 3H), 3.63-3.53 (m, 1H), 2.31 (s, 2H), 1.40 (s, 3H).

Preparation of Example 58

N-[2-(4-methylpiperazin-1-yl)ethyl]-3-[3-methyl-4-[(2R,3S,4S,5S,6R)-3,4,5-trihydroxy-6-(hydroxymethyl)-3-methyl-tetrahydropyran-2-yl]oxy-phenyl]benzamide

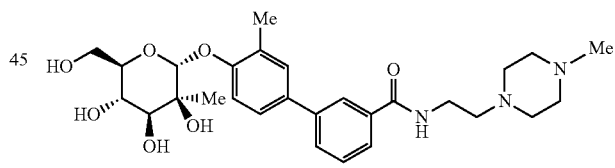

EXAMPLE 58 is prepared according to the procedure described for EXAMPLE 22 Step I using EXAMPLE 21 and 2-(4-methylpiperazin-1-yl)ethan-1-amine as starting material. The reaction mixture is stirred 2 h at RT. The resulting crude mixture is purified directly by reverse phase HPLC to afford the title compound as a white solid (67% yield). $^1$H NMR (400 MHz, CD$_3$OD) δ 8.02 (brs, 1H), 7.73 (brd, J=7.7 Hz, 2H), 7.51-7.42 (m, 3H), 7.31 (d, J=8.5 Hz, 1H), 5.27 (s, 1H), 3.77-3.67 (m, 4H), 3.62-3.51 (m, 3H), 2.71-2.39 (m, 10H), 2.31 (s, 3H), 2.28 (s, 3H), 1.40 (s, 3H). LC-MS: m/z=530.52 (M+H)$^+$.

Preparation of Examples 59 to 72

EXAMPLEs 59 to 72 are prepared according to the procedure described for EXAMPLE 58 using the appropriate commercially available amine.

| EXAMPLE # | Name | ¹H-NMR | LCMS m/z (M + H)⁺ |
|---|---|---|---|
| 59 | N-[(1S,2S)-2-hydroxy-1-(hydroxymethyl)propyl]-3-[3-methyl-4-[(2R,3S,4S,5S,6R)-3,4,5-trihydroxy-6-(hydroxymethyl)-3-methyl-tetrahydropyran-2-yl]oxy-phenyl]benzamide | (400 MHz, CD₃OD) δ 8.06 (brs, J = 1.6 Hz, 1H), 7.80-7.71 (m, 2H), 7.53-7.43 (m, 3H), 7.31 (d, J = 8.5 Hz, 1H), 5.27 (s, 1H), 4.15-4.04 (m, 2H), 3.81-3.65 (m, 6H), 3.63-3.54 (m, 1H), 2.31 (s, 3H), 1.40 (s, 3H), 1.21 (d, J = 6.3 Hz, 3H). | 492.43 |
| 60 | N-[2-hydroxy-1,1-bis(hydroxymethyl)ethyl]-3-[3-methyl-4-[(2R,3S,4S,5S,6R)-3,4,5-trihydroxy-6-(hydroxymethyl)-3-methyl-tetrahydropyran-2-yl]oxy-phenyl]benzamide | (400 MHz, CD₃OD) δ 8.00 (t, J = 1.7 Hz, 1H), 7.72 (td, J = 8.5, 1.7 Hz, 2H), 7.52-7.41 (m, 3H), 7.30 (d, J = 8.5 Hz, 1H), 5.27 (s, 1H), 3.87 (s, 6H), 3.76-3.67 (m, 4H), 3.63-3.53 (m, 1H), 2.31 (s, 3H). | 508.44 |
| 61 | N-[2-hydroxy-1-(hydroxymethyl)-1-methyl-ethyl]-3-[3-methyl-4-[(2R,3S,4S,5S,6R)-3,4,5-trihydroxy-6-(hydroxymethyl)-3-methyl-tetrahydropyran-2-yl]oxy-phenyl]benzamide | (400 MHz, CD₃OD) δ 7.97 (s, 1H), 7.76-7.65 (m, 2H), 7.53-7.41 (m, 3H), 7.30 (d, J = 8.4 Hz, 1H), 5.27 (s, 1H), 3.88-3.66 (m, 8H), 3.65-3.53 (m, 1H), 2.31 (s, 3H), 1.40 (s, 3H), 1.38 (s, 3H). [1] | 492.43 |
| 62 | N-[2-hydroxy-1-(hydroxymethyl)ethyl]-3-[3-methyl-4-[(2R,3S,4S,5S,6R)-3,4,5-trihydroxy-6-(hydroxymethyl)-3-methyl-tetrahydropyran-2-yl]oxy-phenyl]benzamide | (400 MHz, CD₃OD) δ 8.06 (t, J = 1.7 Hz, 1H), 7.79-7.68 (m, 2H), 7.52-7.43 (m, 3H), 7.30 (d, J = 8.5 Hz, 1H), 5.27 (s, 1H), 4.24-4.12 (m, 1H), 3.80-3.67 (m, 8H), 3.63-3.53 (m, 1H), 2.31 (s, 3H), 1.40 (s, 3H). | 478.42 |
| 63 | 3-[3-methyl-4-[(2R,3S,4S,5S,6R)-3,4,5-trihydroxy-6-(hydroxymethyl)-3-methyl-tetrahydropyran-2-yl]oxy-phenyl]-N-(2-morpholinoethyl)benzamide | (400 MHz, CD₃OD) δ 8.02 (t, J = 1.7 Hz, 1H), 7.73 (dd, J = 7.8, 1.5 Hz, 2H), 7.53-7.42 (m, 3H), 7.31 (d, J = 8.5 Hz, 1H), 5.27 (s, 1H), 3.76-3.66 (m, 8H), 3.62-3.53 (m, 3H), 2.62 (t, J = 6.7 Hz, 2H), 2.58-2.50 (m, 4H), 2.31 (s, 3H), 1.40 (s, 3H). | 517.5 |
| 64 | 3-[3-methyl-4-[(2R,3S,4S,5S,6R)-3,4,5-trihydroxy-6-(hydroxymethyl)-3-methyl-tetrahydropyran-2-yl]oxy-phenyl]-N-[[(2R,3S,4S,5R)-3,4,5,6-tetrahydroxytetrahydropyran-2-yl]methyl]benzamide | (400 MHz, CD₃OD) δ 8.05-8.00 (m, 1H), 7.77-7.69 (m, 2H), 7.51-7.42 (m, 3H), 7.31 (d, J = 8.5 Hz, 1H), 5.27 (s, 1H), 4.48 (d, J = 7.8 Hz, 1H), 3.99-3.33 (m, 9H), 3.22-3.08 (m, 2H), 2.31 (s, 3H), 1.40 (s, 3H). | 566.47 |
| 65 | 3-[3-methyl-4-[(2R,3S,4S,5S,6R)-3,4,5-trihydroxy-6-(hydroxymethyl)-3-methyl-tetrahydropyran-2-yl]oxy-phenyl]-N-[(3R,4S,5S,6R)-2,3,5-trihydroxy-6-(hydroxymethyl)tetrahydropyran-4-yl]benzamide | (400 MHz, CD₃OD) δ 8.13-8.08 (m, 1H), 7.79 (d, J= 7.7 Hz, 1H), 7.76-7.69 (m, 1H), 7.53-7.43 (m, 3H), 7.30 (d, J = 8.5 Hz, 1H), 5.27 (s, 1H), 4.60 (d, J = 7.7 Hz, 1H), 4.06 (t, J = 10.1 Hz, 1H), 3.94-3.33 (m, 10H), 2.31 (s, 3H), 1.40 (s, 3H). | 566.43 |
| 66 | tert-butyl 4-[[[3-[3-methyl-4-[(2R,3S,4S,5S,6R)-3,4,5-trihydroxy-6-(hydroxymethyl)-3-methyl-tetrahydropyran-2-yl]oxy-phenyl]benzoyl]amino]methyl]piperidine-1-carboxylate | (400 MHz, CD₃OD) δ 8.00 (brs, 1H), 7.72 (d, J = 7.8 Hz, 2H), 7.51-7.42 (m, 3H), 7.31 (d, J = 8.5 Hz, 1H), 5.27 (s, 1H), 4.12-4.02 (m, 2H), 3.75-3.68 (m, 4H), 3.63-3.54 (m, 1H), 2.84-2.66 (m, 2H), 2.31 (s, 3H), 1.89-1.69 (m, 3H), 1.43 (s, 9H), 1.40 (s, 3H), 1.23-1.06 (m, 2H). | |
| 67 | N-[2-(dimethylamino)ethyl]-3-[3-methyl-4-[(2R,3S,4S,5S,6R)-3,4,5-trihydroxy-6-(hydroxymethyl)-3-methyl-tetrahydropyran-2-yl]oxy-phenyl]benzamide | (400 MHz, CD₃OD) δ 8.46 (s, 1H), 8.07 (t, J = 1.7 Hz, 1H), 7.79-7.72 (m, 2H), 7.53-7.41 (m, 3H), 7.31 (d, J= 8.5 Hz, 1H), 5.27 (s, 1H), 3.76-3.66 (m, 6H), 3.62-3.54 (m, 1H), 3.19-3.12 (m, 2H), 2.79 (s, 6H), 2.31 (s, 3H), 1.40 (s, 3H). | 475.52 |
| 68 | (4-methylpiperazin-1-yl)-[3-[3-methyl-4-[(2R,3S,4S,5S,6R)-3,4,5-trihydroxy-6-(hydroxymethyl)-3-methyl-tetrahydropyran-2-yl]oxy-phenyl]phenyl]methanone | (400 MHz, CD₃OD) δ 8.29 (brs, 1H), 7.70-7.66 (m, 1H), 7.60 (t, J = 1.6 Hz, 1H), 7.49 (t, J = 7.7 Hz, 1H), 7.44-7.38 (m, 2H), 7.35-7.26 (m, 2H), 5.26 (s, 1H), 3.94-3.44 (m, 9H), 2.74-2.48 (m, 4H), 2.41 (s, 3H), 2.30 (s, 3H), 1.40 (s, 3H). | 487.48 |
| 69 | (2S)-3-hydroxy-2-[[3-[3-methyl-4-[(2R,3S,4S,5S,6R)-3,4,5-trihydroxy-6-(hydroxymethyl)-3-methyl-tetrahydropyran-2-yl]oxy-phenyl]benzoyl]amino]propanoic acid | (400 MHz, CD₃OD) δ 8.09 (s, 1H), 7.83-7.72 (m, 2H), 7.55-7.43 (m, 3H), 7.31 (d, J = 8.4 Hz, 1H), 5.27 (s, 1H), 4.73 (t, J = 4.4 Hz, 1H), 4.06-3.93 (m, 2H), 3.79-3.67 (m, 4H), 3.62-3.54 (m, 1H), 2.31 (s, 3H), 1.40 (s, 3H). | 492.31 |
| 70 | [3-[3-methyl-4-[(2R,3S,4S,5S,6R)-3,4,5-trihydroxy-6-(hydroxymethyl)-3-methyl-tetrahydropyran-2-yl]oxy-phenyl]phenyl]-pyrrolidin-1-yl-methanone | N/A | 458.34 |
| 71 | N-[2-hydroxy-1,1-bis(hydroxymethyl)ethyl]-N-(2-hydroxyethyl)-3-[3-methyl-4-[(2R,3S,4S,5S,6R)-3,4,5-trihydroxy-6-(hydroxymethyl)-3-methyl-tetrahydropyran-2-yl]oxy-phenyl]benzamide | (400 MHz, CD₃OD) δ 8.27 (d, J = 18.5 Hz, 1H), 8.02 (t, J = 8.7 Hz, 1H), 7.85 (d, J = 7.5 Hz, 1H), 7.53 (q, J = 7.4 Hz, 1H), 7.44 (d, J = 9.2 Hz, 2H), 7.32 (d, J = 8.3 Hz, 1H), 5.27 (s, 1H), 4.59 (dd, J = 15.5, 8.3 Hz, 3H), 3.86-3.78 (m, 4H), 3.73 (dd, J = 11.7, 7.3 Hz, 6H), 3.63-3.55 | 552.42 |

| EXAMPLE # | Name | ¹H-NMR | LCMS m/z (M + H)⁺ |
|---|---|---|---|
| 72 | N-[(1S,2R)-2-hydroxy-1-(hydroxymethyl)propyl]-3-[3-methyl-4-[(2R,3S,4S,5S,6R)-3,4,5-trihydroxy-6-(hydroxymethyl)-3-methyl-tetrahydropyran-2-yl]oxy-phenyl]benzamide | (m, 2H), 2.31 (s, 3H), 1.40 (s, 3H). N/A | 492.54 |

Preparation of Example 73

3-fluoro-N-methyl-5-[3-methyl-4-[(2R,3S,4S,5S,6R)-3,4,5-trihydroxy-6-(hydroxymethyl)-3-methyl-tetrahydropyran-2-yl]oxy-phenyl]benzamide

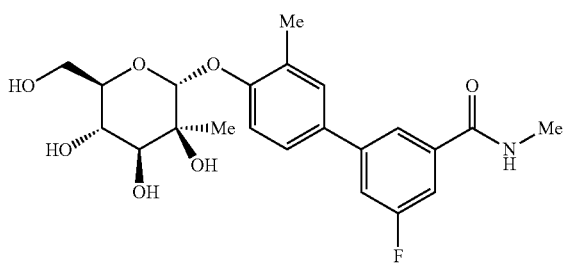

To a mixture of INTERMEDIATE M10 (30.0 mg, 0.0565 mmol), Pd(OAc)₂ (4.0 mg, 0.018 mmol) and [3-(2-dicyclohexylphosphanylphenyl)-2,4-dimethoxy-phenyl]sulfonyloxysodium (14.0 mg, 0.0273 mmol) is added a degased NMP solution of [3-fluoro-5-(methylcarbamoyl)phenyl]boronic acid (200 µL of 0.50 M, 0.100 mmol) followed by a degased aqueous solution of K₂CO₃ (100 µL of 2.5 M, 0.250 mmol). The final mixture is stirred at 65° C. for 18 h. To the resulting reaction mixture is cooled to RT and NaOMe (50 µL of 25% w/v, 0.231 mmol in MeOH) is added. The resulting mixture is stirred 4 h at RT and finally neutralized with AcOH (50 µL). The resulting mixture is filtered (CHROMSPEC Syringe Filters 4 mm PTFE, 0.45 µm), the volatile are concentrated and the residual NMP solution is purified by reverse phase HPLC to afford the title compound as a white solid. LC-MS: m/z=436.28 (M+H)⁺.

Preparation of Examples 74 to 104

EXAMPLEs 74 to 104 are prepared according to the procedure described for compound 73 using the appropriate boronic acid.

| EXAMPLE # | Name | LCMS m/z (M + H)⁺ |
|---|---|---|
| 74 | (2R,3S,4S,5S,6R)-2-[4-(4-fluorophenyl)-2-methyl-phenoxy]-6-(hydroxymethyl)-3-methyl-tetrahydropyran-3,4,5-triol | 378.35 |
| 75 | (2R,3S,4S,5S,6R)-2-[4-(2,4-difluorophenyl)-2-methyl-phenoxy]-6-(hydroxymethyl)-3-methyl-tetrahydropyran-3,4,5-triol | 397.11 |
| 76 | (2R,3S,4S,5S,6R)-2-[4-(3,5-difluorophenyl)-2-methyl-phenoxy]-6-(hydroxymethyl)-3-methyl-tetrahydropyran-3,4,5-triol | 397.04 |
| 77 | (2R,3S,4S,5S,6R)-2-[4-(5-chloro-2-fluoro-phenyl)-2-methyl-phenoxy]-6-(hydroxymethyl)-3-methyl-tetrahydropyran-3,4,5-triol | 413.1 |
| 78 | (2R,3S,4S,5S,6R)-2-[4-(3-chloro-5-fluoro-phenyl)-2-methyl-phenoxy]-6-(hydroxymethyl)-3-methyl-tetrahydropyran-3,4,5-triol | 413.45 |
| 79 | 4-methoxy-3-[3-methyl-4-[(2R,3S,4S,5S,6R)-3,4,5-trihydroxy-6-(hydroxymethyl)-3-methyl-tetrahydropyran-2-yl]oxy-phenyl]benzonitrile | 416.31 |
| 80 | (2R,3S,4S,5S,6R)-2-[4-(3-chloro-5-methoxy-phenyl)-2-methyl-phenoxy]-6-(hydroxymethyl)-3-methyl-tetrahydropyran-3,4,5-triol | 425.22 |
| 81 | (2R,3S,4S,5S,6R)-2-[4-(4-chloro-2-methoxy-phenyl)-2-methyl-phenoxy]-6-(hydroxymethyl)-3-methyl-tetrahydropyran-3,4,5-triol | 425.19 |
| 82 | (2R,3S,4S,5S,6R)-2-[4-(3,4-dichlorophenyl)-2--methyl-phenoxy]-6-(hydroxymethyl)-3-methyl-tetrahydro-3,4,5-triol | 429.29 |
| 83 | N,N-dimethyl-3-[3-methyl-4-[(2R,3S,4S,5S,6R)-3,4,5-trihydroxy-6-(hydroxymethyl)-3-methyl-tetrahydropyran-2-yl]oxy-phenyl]benzamide | 432.34 |
| 84 | 3-[3-methyl-4-[(2R,3S,4S,5S,6R)-3,4,5-trihydroxy-6-(hydroxymethyl)-3-methyl-tetrahydropyran-2-yl]oxy-phenyl]benzenesulfonamide | 440.27 |
| 85 | [2-fluoro-5-[3-methyl-4-[(2R,3S,4S,5S,6R)-3,4,5-trihydroxy-6-(hydroxymethyl)-3-methyl-tetrahydropyran-2-yl]oxy-phenyl]phenyl]-pyrrolidin-1-yl-methanone | 476.34 |
| 86 | N-tert-butyl-3-[3-methyl-4-[(2R,3S,4S,5S,6R)-3,4,5-trihydroxy-6-(hydroxymethyl)-3-methyl-tetrahydropyran-2-yl]oxy-phenyl]benzenesulfonamide | 496.29 |
| 87 | (2R,3S,4S,5S,6R)-2-[4-(4-fluoro-3-methyl-phenyl)-2-methyl-phenoxy]-6-(hydroxymethyl)-3-methyl-tetrahydropyran-3,4,5-triol | 393.01 |
| 88 | (2R,3S,4S,5S,6R)-2-[4-(3,4-difluorophenyl)-2-methyl-phenoxy]-6-(hydroxymethyl)-3-methyl-tetrahydropyran-3,4,5-triol | 397.2 |
| 89 | (2R,3S,4S,5S,6R)-6-(hydroxymethyl)-2-[4-(1H-indol-6-yl)-2-methyl-phenoxy]-3-methyl-tetrahydropyran-3,4,5-triol | 400.29 |
| 90 | (2R,3S,4S,5S,6R)-2-[4-(3-fluoro-2-methoxy-phenyl)-2-methyl-phenoxy]-6-(hydroxymethyl)-3-methyl-tetrahydropyran-3,4,5-triol | 410.07 |
| 91 | (2R,3S,4S,5S,6R)-2-[4-(4-fluoro-2-methoxy-phenyl)-2-methyl-phenoxy]-6-(hydroxymethyl)-3-methyl-tetrahydropyran-3,4,5-triol | 410.2 |
| 92 | (2R,3S,4S,5S,6R)-2-[4-(3-chloro-4-fluoro-phenyl)-2-methyl-phenoxy]-6-(hydroxymethyl)-3-methyl-tetrahydropyran-3,4,5-triol | 414.4 |
| 93 | (2R,3S,4S,5S,6R)-2-[4-(3-chloro-2-fluoro-phenyl)-2-methyl-phenoxy]-6-(hydroxymethyl)-3-methyl-tetrahydropyran-3,4,5-triol | 413.32 |
| 94 | (2R,3S,4S,5S,6R)-2-[4-(3,5-dimethoxyphenyl)-2-methyl-phenoxy]-6-(hydroxymethyl)-3-methyl-tetrahydropyran-3,4,5-triol | 421.32 |
| 95 | (2R,3S,4S,5S,6R)-2-[4-(2,5-dimethoxyphenyl)-2-methyl-phenoxy]-6-(hydroxymethyl)-3-methyl-tetrahydropyran-3,4,5-triol | 421.32 |
| 96 | (2R,3S,4S,5S,6R)-2-[4-(3-chloro-4-methoxy-phenyl)-2-methyl-phenoxy]-6-(hydroxymethyl)-3-methyl-tetrahydropyran-3,4,5-triol | 425.02 |
| 97 | (2R,3S,4S,5S,6R)-2-[4-(5-chloro-2-methoxy-phenyl)-2-methyl-phenoxy]-6-(hydroxymethyl)-3-methyl-tetrahydropyran-3,4,5-triol | 425.28 |
| 98 | (2R,3S,4S,5S,6R)-2-[4-(3,5-difluoro-4-methoxy-phenyl)-2-methyl-phenoxy]-6-(hydroxymethyl)-3-methyl-tetrahydropyran-3,4,5-triol | 427.04 |

-continued

| EXAMPLE # | Name | LCMS m/z (M + H)+ |
|---|---|---|
| 99 | (2R,3S,4S,5S,6R)-2-[4-(3,5-difluoro-2-methoxy-phenyl)-2-methyl-phenoxy]-6-(hydroxymethyl)-3-methyl-tetrahydropyran-3,4,5-triol | 427.23 |
| 100 | (2R,3S,4S,5S,6R)-2-[4-(4,5-dichloro-2-methoxy-phenyl)-2-methyl-phenoxy]-6-(hydroxymethyl)-3-methyl-tetrahydropyran-3,4,5-triol | 460.19 |
| 101 | 4-methyl-3-[3-methyl-4-[(2R,3S,4S,5S,6R)-3,4,5-trihydroxy-6-(hydroxymethyl)-3-methyl-tetrahydro-pyran-2-yl]oxy-phenyl]benzonitrile | 400.00 |
| 102 | [2-fluoro-5-[3-methyl-4-[(2R,3S,4S,5S,6R)-3,4,5-trihydroxy-6-(hydroxymethyl)-3-methyl-tetrahydro-pyran-2-yl]oxy-phenyl]phenyl]-morpholino-methanone | 492.33 |
| 103 | [3-fluoro-5-[3-methyl-4-[(2R,3S,4S,5S,6R)-3,4,5-trihydroxy-6-(hydroxymethyl)-3-methyl-tetrahydro-pyran-2-yl]oxy-phenyl]phenyl]-morpholino-methanone | 492.33 |
| 104 | (2R,3S,4S,5S,6R)-6-(hydroxymethyl)-2-[4-(4-hydroxy-3-methyl-phenyl)-2-methyl-phenoxy]-3-methyl-tetrahydropyran-3,4,5-triol | 391.4 |

Preparation of Example 105 (Route A)

(2R,3S,4S,5S,6R)-6-(hydroxymethyl)-3-methyl-2-[2-methyl-4-[3-methyl-4-[(2R,3S,4S,5S,6R)-3,4,5-trihydroxy-6-(hydroxymethyl)-3-methyl-tetrahydropyran-2-yl]oxy-phenyl]phenoxy]tetrahydropyran-3,4,5-triol

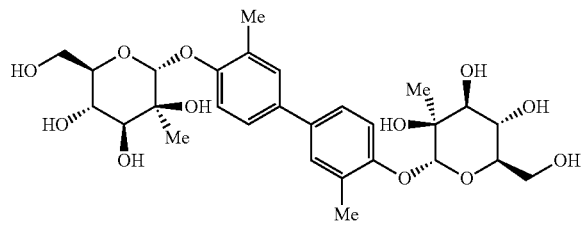 [SMILES: Cc1cc(-c2ccc(O[C@H]3O[C@H](CO)[C@@H](O)[C@H](O)[C@]3(C)O)c(C)c2)ccc1O[C@H]1O[C@H](CO)[C@@H](O)[C@H](O)[C@]1(C)O]

Step I: (2R,3S,4S,5R,6R)-6-(acetoxymethyl)-3-methyl-2-(2-methyl-4-(4,4,5,5-tetramethyl-1,3,2-dioxaborolan-2-yl)phenoxy)tetrahydro-2H-pyran-3,4,5-triyltriacetate

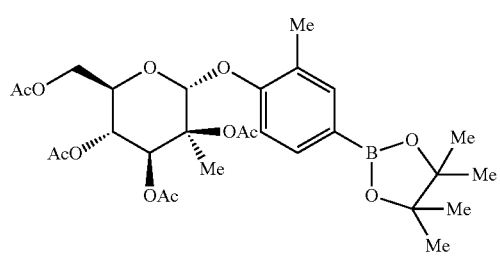 [SMILES: CC(=O)OC[C@H]1O[C@H](Oc2ccc(B3OC(C)(C)C(C)(C)O3)cc2C)[C@@](C)(OC(C)=O)[C@@H](OC(C)=O)[C@@H]1OC(C)=O]

To a degased (N₂) solution of INTERMEDIATE M10 (11.00 g, 20.70 mmol), KOAc (1.06 g, 41.1 mmol) and Bis(pinacolato)diboron (7.885 g, 31.1 mmol) in DMF (110 mL) is added PdCl₂(dppf)-DCM (845 mg, 1.04 mmol). The reaction mixture is degased (3×) and stirred at 80° C. for 16 h. The reaction is cooled to RT, quenched with EtOAc and aqueous saturated NH₄Cl and filtered on celite. The organic phase is separated, dried over Na₂SO₄, filtered, concentrated and purified on Isco CombiFlash® silica gel cartridge (220 g) eluting with EtOAc (0-60%) in Hex (13 CV) to afford the title compound (10.6 g, 89%) as a white solid. ¹H NMR (400 MHz, CDCl₃) δ 7.64-7.54 (m, 2H), 7.13 (d, J=8.1 Hz, 1H), 6.31 (s, 1H), 5.59 (d, J=9.7 Hz, 1H), 5.38 (t, J=9.9 Hz, 1H), 4.17 (dd, J=12.2, 5.2 Hz, 1H), 4.07-3.93 (m, 2H), 2.27 (s, 3H), 2.13 (s, 3H), 2.12 (s, 3H), 2.02 (s, 6H), 1.61 (s, 3H), 1.32 (s, 12H).

Step II: [(2R,3R,4S,5S,6R)-3,4,5-triacetoxy-6-[2-methyl-4-[3-methyl-4-[(2R,3S,4S,5R,6R)-3,4,5-triacetoxy-6-(acetoxymethyl)-3-methyl-tetrahydropyran-2-yl]oxy-phenyl]phenoxy]-5-methyl-tetrahydropyran-2-yl]methyl acetate

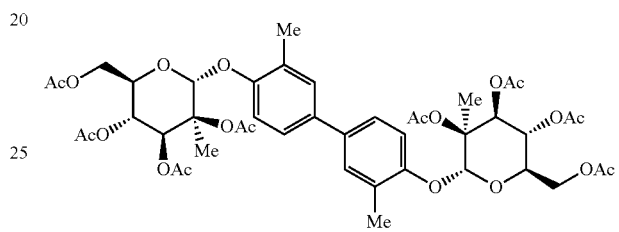

To a degased mixture of INTERMEDIATE M10 (10.0 g, 18.8 mmol), (2R,3S,4S,5R,6R)-6-(acetoxymethyl)-3-methyl-2-(2-methyl-4-(4,4,5,5-tetramethyl-1,3,2-dioxaborolan-2-yl)phenoxy)tetrahydro-2H-pyran-3,4,5-triyltriacetate from Step I (10.9 g, 18.8 mmol) and K₂CO₃ (13.03 g, 94.3 mmol) in 2-MeTHF (217 mL) is added water (43.4 mL), Pd(OAc)₂ (623 mg, 2.78 mmol) and [3-(2-dicyclohexylphosphanylphenyl)-2,4-dimethoxy-phenyl]sulfonyloxy-sodium (2.89 g, 5.64 mmol). The reaction mixture is degased (3 times) and heated at 65° C. for 80 min. The reaction mixture is cooled down with an ice bath, the aqueous phase is separated, extracted with 200 ml EtOAc. The combined organic phase is washed with 300 ml of aqueous saturated NH₄Cl, brine, dried over Na₂SO₄, filtered on celite and concentrated. The residue is purified on Isco CombiFlash® silica gel cartridge (330 g) eluting with Acetone (0-35%) in Hex (22 CV) to afford the title compound (14.7 g, 86%) as a white solid. ¹H NMR (400 MHz, CDCl₃) δ 7.33 (dd, J=2.4, 0.9 Hz, 2H), 7.28 (ddd, J=8.5, 2.4, 0.7 Hz, 2H), 7.19 (d, J=8.5 Hz, 2H), 6.29 (s, 2H), 5.60 (d, J=9.7 Hz, 2H), 5.40 (t, J=9.8 Hz, 2H), 4.18 (dd, J=12.2, 5.2 Hz, 2H), 4.14-4.00 (m, 4H), 2.33 (s, 6H), 2.14 (s, 6H), 2.13 (s, 6H), 2.03 (s, 6H), 2.02 (s, 6H), 1.64 (s, 6H).

Step III: Example 105

To a suspension of [(2R,3R,4S,5S,6R)-3,4,5-triacetoxy-6-[2-methyl-4-[3-methyl-4-[(2R,3S,4S,5R,6R)-3,4,5-triacetoxy-6-(acetoxymethyl)-3-methyl-tetrahydropyran-2-yl]oxy-phenyl]phenoxy]-5-methyl-tetrahydropyran-2-yl]methyl acetate (16.0 g, 17.7 mmol) in MeOH (910 mL) is added NaOMe (1.97 mL of 25% w/w, 8.86 mmol). The reaction mixture is stirred 90 min and neutralized by passing through 133 g of Dowex 50W4 H+ resin and 250 ml of methanol is used to wash the column after neutralization. The filtrate is concentrated until a white solid precipitated and the suspension is stirred for 45 min at 0° C., filtered and washed with 10 ml of cold MeOH. The solid is dried at 40°

C. under vacuum for 16 h to afford the title compound (8.50 g, 85%). $^1$H NMR (400 MHz, CD$_3$OD) δ 7.38-7.30 (m, 4H), 7.26 (d, J=8.4 Hz, 2H), 5.25 (s, 2H), 3.79-3.69 (m, 8H), 3.66-3.55 (m, 2H), 2.30 (s, 6H), 1.41 (s, 6H). LC-MS: m/z=567.59 (M+H)$^+$.

Alternative Preparation of Example 105 (Route B)

Step I: (2R,3S,4S,5R,6R)-6-(acetoxymethyl)-2-(4-iodo-2-methylphenoxy)-3-methyltetrahydro-2H-pyran-3,4,5-triyltriacetate

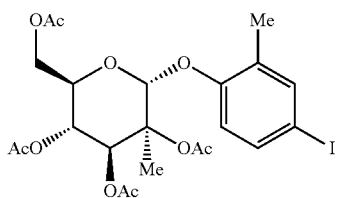 [SMILES: CC(=O)OC[C@H]1O[C@H](Oc2ccc(I)cc2C)[C@@](C)(OC(C)=O)[C@@H](OC(C)=O)[C@@H]1OC(C)=O]

To a solution of INTERMEDIATES M4 (5.00 g, 12.4 mmol) in CH$_2$Cl$_2$ (25 mL) is added 4-iodo-2-methyl-phenol (5.79 g, 24.7 mmol) and BF$_3$.OEt$_2$ (9.5 mL, 74.9 mmol). The reaction mixture is stirred at 40° C. for 90 min, cooled down to RT and poured slowly into a saturated aqueous NaHCO$_3$ (100 mL) while stirring vigorously. The organic layer is separated and the aqueous layer is back extracted with CH$_2$Cl$_2$ (2×25 mL). The combined organic layers are concentrated and purified on Biotage™ SNAP silica cartridge (100 g) eluting with EtOAc (0-50%) in Hex (14CV) to afford the title compound (3.56 g, 50%) as a light yellow solid. $^1$H NMR (400 MHz, CDCl$_3$) δ 7.47 (dd, J=2.2, 0.9 Hz, 1H), 7.41 (ddd, J=8.6, 2.3, 0.7 Hz, 1H), 6.91 (d, J=8.6 Hz, 1H), 6.22 (s, 1H), 5.54 (d, J=9.7 Hz, 1H), 5.37 (t, J=9.9 Hz, 1H), 4.20-4.02 (m, 2H), 4.00-3.94 (m, 1H), 2.22 (d, J=0.7 Hz, 3H), 2.13 (s, 3H), 2.12 (s, 3H), 2.02 (s, 6H), 1.60 (s, 3H).

Step II: [(2R,3R,4S,5S,6R)-3,4,5-triacetoxy-5-methyl-6-[2-methyl-4-[3-methyl-4-[(2R,3S,4S,5R,6R)-3,4,5-triacetoxy-6-(acetoxymethyl)-3-methyl-tetrahydropyran-2-yl]oxy-phenyl]phenoxy] tetrahydropyran-2-yl]methyl acetate

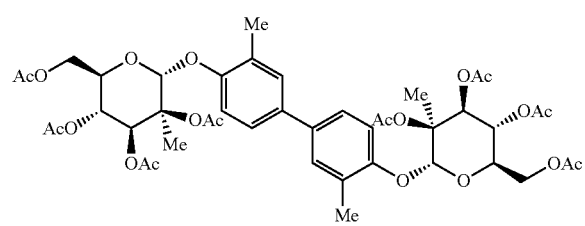 [SMILES: CC(=O)OC[C@H]1O[C@H](Oc2ccc(-c3ccc(O[C@H]4O[C@H](COC(C)=O)[C@@H](OC(C)=O)[C@H](OC(C)=O)[C@]4(C)OC(C)=O)c(C)c3)cc2C)[C@@](C)(OC(C)=O)[C@@H](OC(C)=O)[C@@H]1OC(C)=O]

To a mixture of (2R,3S,4S,5R,6R)-6-(acetoxymethyl)-2-(4-iodo-2-methylphenoxy)-3-methyltetrahydro-2H-pyran-3,4,5-triyltriacetate from Step I (1.00 g, 1.73 mmol), TBABr (557 mg, 1.73 mmol) and Pd(OAc)$_2$ (19 mg, 0.086 mmol) in DMF (15 mL) is added triethylamine (602 μL, 4.32 mmol). The reaction mixture is stirred at 110° C. for 15 h, cooled down to RT and diluted with EtOAc (50 mL). The organic layer is washed with water (2×25 mL), brine, dried over Na$_2$SO$_4$, filtered and concentrated. The residue is purified on Biotage™ SNAP silica cartridge (100 g) eluting with EtOAc (10-60%) in Hex gradient (13CV) to afford the title compound (303 mg, 39%) as a yellow solid.

Step III: Example 105

Removal of the acetate protective group to afford EXAMPLE 105 is performed as previously described in Route A Step III.

Alternative Preparation of Example 105 (Route C)

Step I: [(2R,3R,4S,5S,6R)-3,4,5-triacetoxy-5-methyl-6-[2-methyl-4-[3-methyl-4-[(2R,3S,4S,5R, 6R)-3,4,5-triacetoxy-6-(acetoxymethyl)-3-methyl-tetrahydropyran-2-yl]oxy-phenyl]phenoxy] tetrahydropyran-2-yl]methyl acetate

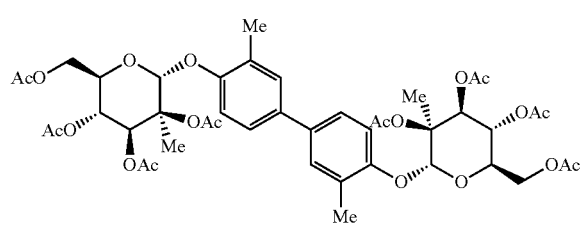 [SMILES: CC(=O)OC[C@H]1O[C@H](Oc2ccc(-c3ccc(O[C@H]4O[C@H](COC(C)=O)[C@@H](OC(C)=O)[C@H](OC(C)=O)[C@]4(C)OC(C)=O)c(C)c3)cc2C)[C@@](C)(OC(C)=O)[C@@H](OC(C)=O)[C@@H]1OC(C)=O]

To a solution of INTERMEDIATE M10 (50.0 mg, 0.0940 mmol) in DMF (1.25 mL) is added PdCl$_2$.(CH$_3$CN)$_2$ (1.8 mg, 0.0047 mmol) and N1,N1,N1',N1',N2,N2,N2',N2'-octamethylethene-1,1,2,2-tetramine (44 mL, 0.19 mmol). The reaction mixture is heated at 50° C. for 16 h, cooled to RT, diluted with water and extracted with EtOAc (3×15 mL). The combined organic layers are dried over Na$_2$SO$_4$, filtered, concentrated and purified on Biotage™ SNAP silica cartridge (10 g) eluting with EtOAc (10% to 75%) in Hex to afford the title compound (12 mg, 28%).

Step II: Example 105

Removal of the acetate protective group to afford EXAMPLE 105 is performed as previously described in Route A Step III.

Alternative Preparation of Example 105 (Route D)

Step I: [(2R,3R,4S,5S,6R)-3,4,5-triacetoxy-5-methyl-6-[2-methyl-4-[3-methyl-4-[(2R,3S,4S,5R, 6R)-3,4,5-triacetoxy-6-(acetoxymethyl)-3-methyl-tetrahydropyran-2-yl]oxy-phenyl]phenoxy] tetrahydropyran-2-yl]methyl acetate

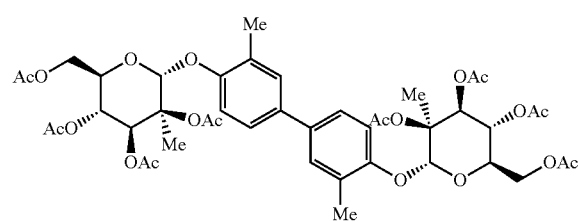 [SMILES: CC(=O)OC[C@H]1O[C@H](Oc2ccc(-c3ccc(O[C@H]4O[C@H](COC(C)=O)[C@@H](OC(C)=O)[C@H](OC(C)=O)[C@]4(C)OC(C)=O)c(C)c3)cc2C)[C@@](C)(OC(C)=O)[C@@H](OC(C)=O)[C@@H]1OC(C)=O]

To a solution of INTERMEDIATES M4 (100 mg, 0.25 mmol) in CH$_2$Cl$_2$ (500 μL) is added 4-(4-hydroxy-3-methylphenyl)-2-methyl-phenol (26 mg, 0.12 mmol) and BF₃.OEt₂ (188 μL, 1.48 mmol). The reaction mixture is heated at 40° C. for 4.5 h, cooled to RT and poured slowly into saturated aqueous NaHCO₃ (2 mL) while stirring vigorously. The organic phase is separated and the he aqueous phase is back extracted with CH₂Cl₂. The combined organic layers are dried over Na₂SO₄, filtered, concentrated and purified on Biotage™ SNAP silica cartridge (12 g) eluting with EtOAc (20% to 55%) in Hex to afford title compound (25 mg, 22%).

Step II: Example 105

Removal of the acetate protective group to afford EXAMPLE 105 is performed as previously described in Route A Step III.

Preparation of Example 106

(2R,3S,4S,5S,6R)-6-(hydroxymethyl)-3-methyl-2-[4-[4-[(2R,3S,4S,5S,6R)-3,4,5-trihydroxy-6-(hydroxymethyl)-3-methyl-tetrahydropyran-2-yl]oxy-phenyl]phenoxy]tetrahydropyran-3,4,5-triol

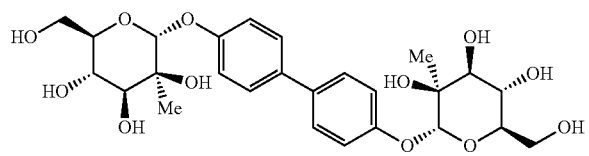 [SMILES: C[C@@]1(O)[C@@H](Oc2ccc(-c3ccc(O[C@H]4O[C@H](CO)[C@@H](O)[C@H](O)[C@]4(C)O)cc3)cc2)O[C@H](CO)[C@@H](O)[C@@H]1O]

EXAMPLE 106 is prepared in two steps according to the procedure described for EXAMPLE 105 Route D but using [1,1'-biphenyl]-4,4'-diol as reagent. In the first step (glycosidation), the reaction mixture is stirred 3 days at 40° C. In the second step (deprotection), the reaction mixture is stirred overnight and the resulting mixture is purified Biotage™ SNAP C18 cartridge (12 g) eluting using CH₃CN (10% to 25%) in water as eluent to afford the title compound. ¹H NMR (400 MHz, CD₃OD) δ 7.52-7.46 (m, 2H), 7.18-7.11 (m, 2H), 5.18 (s, 1H), 3.78-3.59 (m, 5H), 1.36 (s, 3H).

Preparation of Example 107

(2R,3S,4S,5S,6R)-2-[2-chloro-4-[3-chloro-4-[(2R,3S,4S,5S,6R)-3,4,5-trihydroxy-6-(hydroxymethyl)-3-methyl-tetrahydropyran-2-yl]oxy-phenyl]phenoxy]-6-(hydroxymethyl)-3-methyl-tetrahydropyran-3,4,5-triol

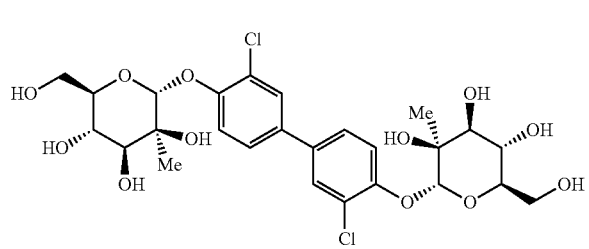 [SMILES: C[C@@]1(O)[C@@H](Oc2ccc(-c3ccc(O[C@H]4O[C@H](CO)[C@@H](O)[C@H](O)[C@]4(C)O)c(Cl)c3)cc2Cl)O[C@H](CO)[C@@H](O)[C@@H]1O]

EXAMPLE 107 is prepared in two steps according to the procedure described for EXAMPLE 105 Route C but using INTERMEDIATE M11. ¹H NMR (400 MHz, CD₃OD) δ 7.60 (m, 2H), 7.51-7.34 (m, 4H), 5.27 (s, 2H), 3.81-3.53 (m, 10H), 1.42 (s, 6H). LC-MS: m/z=608.43 (M+H)⁺.

Preparation of Example 108

(2R,3S,4S,5S,6R)-6-(hydroxymethyl)-3-methyl-2-[[7-[(2R,3S,4S,5S,6R)-3,4,5-trihydroxy-6-(hydroxymethyl)-3-methyl-tetrahydropyran-2-yl]oxy-2-naphthyl]oxy]tetrahydropyran-3,4,5-triol

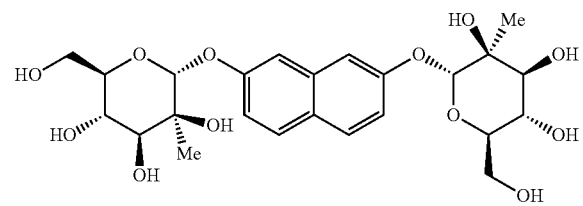 [SMILES: C[C@@]1(O)[C@@H](Oc2ccc3ccc(O[C@H]4O[C@H](CO)[C@@H](O)[C@H](O)[C@]4(C)O)cc3c2)O[C@H](CO)[C@@H](O)[C@@H]1O]

EXAMPLE 108 is prepared in two steps according to the procedure described for EXAMPLE 105 Route D but using naphthalene-2,7-diol as reagent. In the first step (glycosidation), the reaction mixture is stirred overnight at 40° C. In the second step the title compound is purified by reverse phase HPLC. 1H NMR (400 MHz, CD₃OD) δ 7.70 (d, J=8.9 Hz, 1H), 7.54 (dd, J=49.6, 2.9 Hz, 1H), 7.25-6.95 (m, 1H), 5.29 (s, 1H), 3.83-3.54 (m, 5H), 1.37 (d, J=10.4 Hz, 3H).

Preparation of Examples 109 to 115

EXAMPLEs 109 to 115 are prepared according to the procedure described for EXAMPLE 105 Route C but using the INTERMEDIATEs M16 to M22 respectively in the first step. All EXAMPLEs are purified by reverse phase HPLC following final deprotection (NaOMe/MeOH).

| EXAMPLE | Name | ¹H-NMR | LCMS m/z (M + H)⁺ |
|---|---|---|---|
| 109 | (2R,3S,4S,5S,6R)-6-(hydroxymethyl)-2-[2-methoxy-4-[3-methoxy-4-[(2R,3S,4S,5S,6R)-3,4,5-trihydroxy-6-(hydroxymethyl)-3-methyl-tetrahydropyran-2-yl]oxy-phenyl]phenoxy]-3-methyl-tetrahydropyran-3,4,5-triol | (400 MHz, CD₃OD) δ 7.23 (d, J = 8.4 Hz, 2H), 7.16 (d, J = 2.1 Hz, 2H), 7.09 (dd, J = 8.3, 2.1 Hz, 2H), 5.12 (s, 2H), 3.88 (s, 6H), 3.84 (dt, J = 7.3, 2.6 Hz, 2H), 3.80-3.64 (m, 8H), 1.42 (s, 6H). | 599.6 |
| 110 | (2R,3S,4S,5S,6R)-2-[2-ethyl-4-[3-ethyl-4-[(2R,3S,4S,5S,6R)-3,4,5-trihydroxy-6-(hydroxymethyl)-3-methyl-tetrahydropyran-2-yl]oxy-phenyl]phenoxy]-6-(hydroxymethyl)-3-methyl-tetrahydropyran-3,4,5-triol | (400 MHz, CD₃OD) δ 7.35-7.30 (m, 4H), 7.29-7.24 (m, 2H), 5.25 (s, 2H), 3.77-3.66 (m, 8H), 3.62-3.51 (m, 2H), 2.70 (qd, J = 7.3, 2.2 Hz, 4H), 1.39 (s, 6H), 1.23 (t, J = 7.5 Hz, 6H). | 595.2 |
| 111 | 5-[3-cyano-4-[(2R,3S,4S,5S,6R)-3,4,5-trihydroxy-6-(hydroxymethyl)-3-methyl-tetrahydropyran-2-yl]oxy-phenyl]-2-[(2R,3S,4S,5S,6R)-3,4,5-trihydroxy-6-(hydroxymethyl)-3-methyl-tetrahydropyran-2-yl]oxy-benzonitrile | (400 MHz, CD₃OD) δ 7.92 (d, J = 2.3 Hz, 2H), 7.86 (dd, J = 8.9, 2.4 Hz, 2H), 7.57 (d, J = 8.9 Hz, 2H), 5.37 (s, 2H), 3.81-3.64 (m, 8H), 3.59 (ddd, J = 8.9, 5.5, 2.4 Hz, 2H), 1.44 (s, 6H). | 589.6 |

| EXAMPLE | Name | ¹H-NMR | LCMS m/z (M + H)⁺ |
|---|---|---|---|
| 112 | (2R,3S,4S,5S,6R)-2-[2-fluoro-4-[3-fluoro-4-[(2R,3S,4S,5S,6R)-3,4,5-trihydroxy-6-(hydroxymethyl)-3-methyl-tetrahydropyran-2-yl]oxy-phenyl]phenoxy]-6-(hydroxymethyl)-3-methyl-tetrahydropyran-3,4,5-triol | (400 MHz, CD₃OD) δ 7.48-7.25 (m, 6H), 5.18 (s, 2H), 3.83-3.63 (m, 10H), 1.40 (s, 6H). | 575.42 |
| 113 | (2R,3S,4S,5S,6R)-6-(hydroxymethyl)-3-methyl-2-[2-methyl-5-[4-methyl-3-[(2R,3S,4S,5S,6R)-3,4,5-trihydroxy-6-(hydroxymethyl)-3-methyl-tetrahydropyran-2-yl]oxy-phenyl]phenoxy]tetrahydropyran-3,4,5-triol | (400 MHz, CD₃OD) δ 7.43 (s, 2H), 7.22-7.09 (m, 4H), 5.27 (s, 2H), 3.84-3.59 (m, 10H), 2.25 (s, 6H), 1.40 (s, 6H). | 567.55 |
| 114 | (2R,3S,4S,5S,6R)-6-(hydroxymethyl)-3-methyl-2-[2-(trifluoromethoxy)-4-[3-(trifluoromethoxy)-4-[(2R,3S,4S,5S,6R)-3,4,5-trihydroxy-6-(hydroxymethyl)-3-methyl-tetrahydropyran-2-yl]oxy-phenyl]phenoxy]tetrahydropyran-3,4,5-triol | (400 MHz, CD₃OD) δ 7.55-7.52 (m, 4H), 7.48-7.46 (m, 2H), 5.26 (s, 2H), 3.81-3.64 (m, 8H), 3.61 (m, 2H), 1.38 (s, 6H). | |
| 115 | (2R,3S,4S,5S,6R)-6-(hydroxymethyl)-2-[2-isopropyl-4-[3-isopropyl-4-[(2R,3S,4S,5S,6R)-3,4,5-trihydroxy-6-(hydroxymethyl)-3-methyl-tetrahydropyran-2-yl]oxy-phenyl]phenoxy]-3-methyl-tetrahydropyran-3,4,5-triol | (400 MHz, CD₃OD) δ 7.36 (d, J = 1.9 Hz, 2H), 7.33-7.26 (m, 4H), 5.27 (s, 2H), 3.80-3.63 (m, 8H), 3.61-3.52 (m, 2H), 3.43-3.31 (m, 2H), 1.40 (s, 6H), 1.27 (dd, J = 6.9, 4.6 Hz, 12H). | 623.6 |

Preparation of Example 116

(2R,3S,4S,5S,6R)-6-(hydroxymethyl)-3-methyl-2-[2-methyl-4-[4-[3-methyl-4-[(2R,3S,4S,5S,6R)-3,4,5-trihydroxy-6-(hydroxymethyl)-3-methyl-tetrahydropyran-2-yl]oxy-phenyl]phenyl]phenoxy]tetrahydropyran-3,4,5-triol

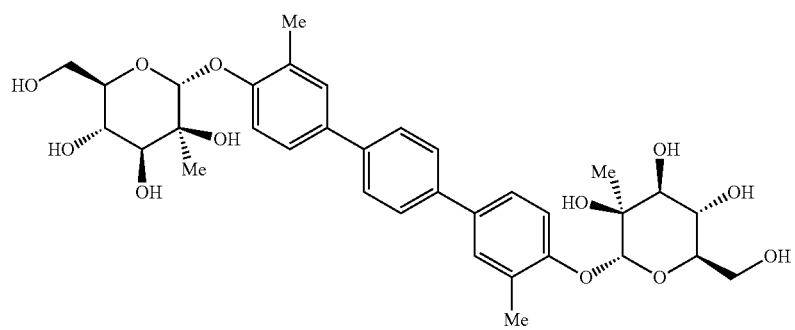 [SMILES: Cc1cc(-c2ccc(-c3ccc(O[C@H]4O[C@H](CO)[C@@H](O)[C@H](O)[C@]4(C)O)c(C)c3)cc2)ccc1O[C@H]1O[C@H](CO)[C@@H](O)[C@H](O)[C@]1(C)O]

To a degased mixture of 4,4,5,5-tetramethyl-2-[4-(4,4,5,5-tetramethyl-1,3,2-dioxaborolan-2-yl)phenyl]-1,3,2-dioxaborolane (30.0 mg, 0.0909 mmol), INTERMEDIATE M10 (96.6 mg, 0.182 mmol) and 3-(2-dicyclohexylphosphanyl-phenyl)-2,4-dimethoxy-benzenesulfonic acid (Sodium Ion (1)) (18.67 mg, 0.0364 mmol) in 2-Me THF (600.0 μL) and Water (120.0 μL) is added sequentially K₂CO₃ (62.8 mg, 0.455 mmol) and Pd(OAc)₂ (4.1 mg, 0.018 mmol). The resulting mixture is stirred at 60° C. for 16 h, cooled to RT, diluted with water and extracted with EtOAc (3×8 mL). The combined organic extracts are passed through a phase separator and concentrated to afford a crude mixture which was dissolved in MeOH (400 mL). To the resulting solution is added NaOMe in MeOH (400 μL of 0.5 M, 0.200 mmol) and the mixture is stirred for 18 h. The reaction is quenched with DOWEX 50WX4 hydrogen form resin until pH 4-5, diluted with methanol (25 mL), filtered and concentrated. The residue is dissolved in ~0.75 mL of DMSO and the solution is purified on a Biotage™ SNAP C18 (30 g) eluting with CH₃CN (10% to 63%, 11 CV) in water to afford the title compound (10.8 mg, 18%) as a white solid. ¹H NMR (400 MHz, CD₃OD) δ 7.59 (s, 4H), 7.46-7.39 (m, 4H), 7.29 (d, J=8.4 Hz, 2H), 5.26 (s, 2H), 3.78-3.69 (m, 8H), 3.65-3.55 (m, 2H), 2.30 (s, 6H), 1.40 (s, 6H).

Preparation of Example 117

(2R,3S,4S,5S,6R)-6-(hydroxymethyl)-3-methyl-2-[2-methyl-4-[2-[3-methyl-4-[(2R,3S,4S,5S,6R)-3,4,5-trihydroxy-6-(hydroxymethyl)-3-methyl-tetrahydropyran-2-yl]oxy-phenyl]ethynyl]phenoxy]tetrahydropyran-3,4,5-triol

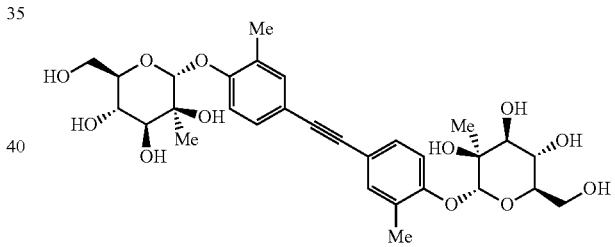

Step I: (2R,3S,4S,5S,6R)-2-(4-bromo-2-methylphenoxy)-6-(hydroxymethyl)-3-methyltetrahydro-2H-pyran-3,4,5-triol

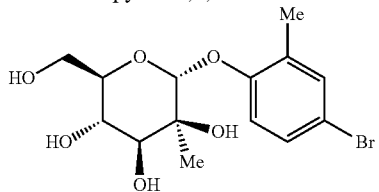

To a solution of INTERMEDIATE M10 (320 mg, 0.602 mmol) in MeOH (4.8 mL) is added NaOMe (600 μL of 0.5 M, 0.300 mmol). The mixture is stirred at RT for 3 h, filtered through a prewashed 1 g SCX-2 cartridge. The latter is wash three times with MeOH. The combined MeOH fractions are concentrated to dryness to afford the title compound (215 mg, 92%). $^1$H NMR (400 MHz, CD$_3$OD) δ 7.29 (d, J=2.0 Hz, 1H), 7.25 (dd, J=8.7, 2.4 Hz, 1H), 7.16 (d, J=8.8 Hz, 1H), 5.20 (s, 1H), 3.79-3.64 (m, 4H), 3.62-3.45 (m, 1H), 2.23 (s, 3H), 1.38 (s, 3H). LCMS m/z (M+Na)$^+$=387.53

Step II: Example 117

A mixture of (2R,3S,4S,5S,6R)-2-(4-bromo-2-methylphenoxy)-6-(hydroxymethyl)-3-methyl-tetrahydropyran-3,4,5-triol from Step I (108 mg, 0.297 mmol), PdCl$_2$(PPh$_3$)$_2$ (12.5 mg, 0.0178 mmol) and copper iodide (5.6 mg, 0.030 mmol) in CH$_3$CN (1.5 mL) is placed in a microwave vial (10 mL). DBU (267 μL, 1.78 mmol) and Water (10 μL, 0.55 mmol) are added and the mixture is degased before TMS-acetylene (21 μL, 0.15 mmol) is added. The tube is sealed and stirred vigorously at 80° C. for 20 h. The mixture is cooled to RT, concentrated and the residue is dissolved in DMSO (0.5 mL). The resulting solution is purified on Biotage™ SNAP C18 (30 g) eluting with CH$_3$CN (0% to 50%, 15 CV) in water. The fractions containing the desired material are combined and concentrated. The residue is further purified by reverse phase HPLC to afford the title compound (12.4 mg, 14%) as a white solid. $^1$H NMR (400 MHz, CD$_3$OD) δ 7.28-7.24 (m, 4H), 7.20 (d, J=9.2 Hz, 2H), 5.24 (s, 2H), 3.76-3.64 (m, 8H), 3.59-3.49 (m, 2H), 2.22 (s, 6H), 1.37 (s, 6H). LCMS m/z (M+H)$^+$=591.47

Preparation of Example 118
(2R,3S,4S,5S,6R)-2-[4-[3,5-bis[3-methyl-4-[(2R,3S,4S,5S,6R)-3,4,5-trihydroxy-6-(hydroxymethyl)-3-methyl-tetrahydropyran-2-yl]oxy-phenyl]phenyl]-2-methyl-phenoxy]-6-(hydroxymethyl)-3-methyl-tetrahydropyran-3,4,5-triol

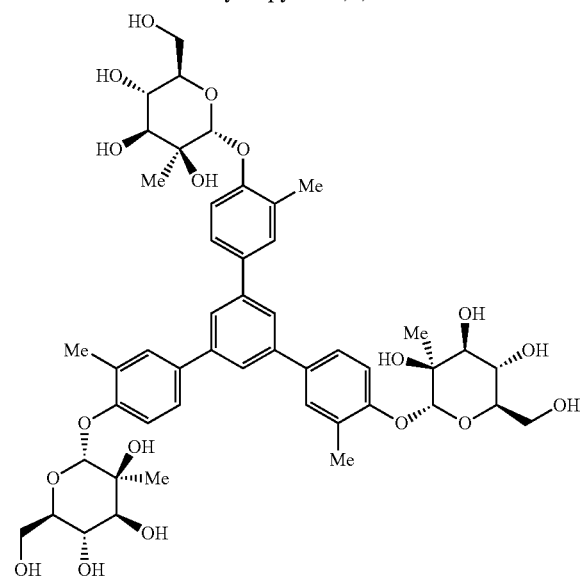

Step I: (2R,3S,4S,5R,6R)-6-(acetoxymethyl)-3-methyl-2-(2-methyl-4-(4,4,5,5-tetramethyl-1,3,2-dioxaborolan-2-yl)phenoxy)tetrahydro-2H-pyran-3,4,5-triyltriacetate

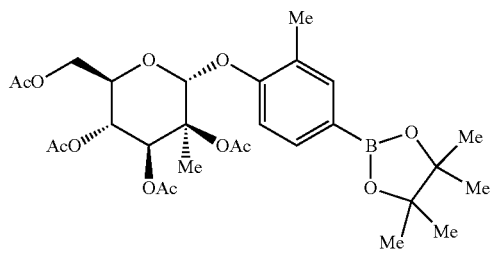 [SMILES: CC(=O)OC[C@H]1O[C@H](Oc2ccc(B3OC(C)(C)C(C)(C)O3)cc2C)[C@@](C)(OC(C)=O)[C@@H](OC(C)=O)[C@@H]1OC(C)=O]

To a degased mixture of INTERMEDIATES M10 (1.00 g, 1.88 mmol), KOAc (369 mg, 3.76 mmol) and Bis(pinacolato)diboron (717 mg, 2.82 mmol) in DMF (10.0 mL) is added PdCl$_2$(dppf)-DCM (77 mg, 0.094 mmol). The reaction is stirred at 80° C. for 21 h, cooled to RT and partitioned between EtOAc and saturated aqueous NH$_4$Cl. The organic layer is separated, filtered on celite, dried over Na$_2$SO$_4$, filtered, concentrated and the residue is purified on Biotage™ SNAP Ultra silica cartridge (25 g) eluting with EtOAc (10-60%) in Hex as gradient to afford the title compound (971 mg, 89%) as a white solid. $^1$H NMR (400 MHz, CDCl$_3$) δ 7.65-7.56 (m, 2H), 7.13 (d, J=8.2 Hz, 1H), 6.31 (s, 1H), 5.59 (d, J=9.7 Hz, 1H), 5.38 (t, J=9.9 Hz, 1H), 4.17 (dd, J=12.2, 5.2 Hz, 1H), 4.08-3.94 (m, 2H), 2.27 (s, 3H), 2.13 (s, 3H), 2.12 (s, 3H), 2.02 (s, 6H), 1.61 (s, 3H), 1.32 (s, 12H).

Step II: Per-acetylated Example 118

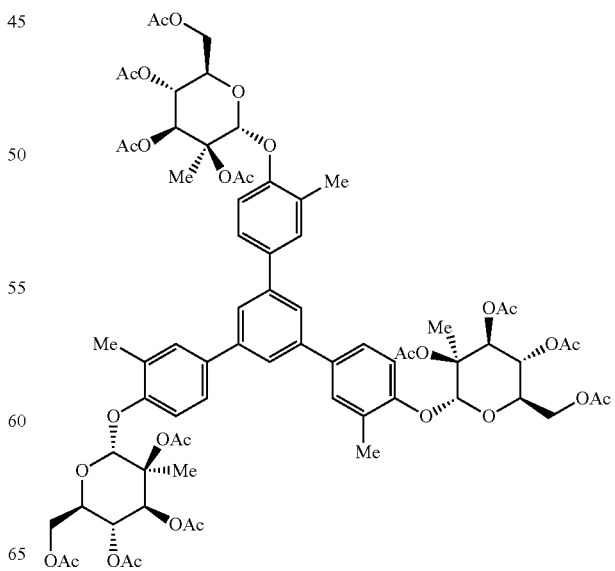

To a degased solution of (2R,3S,4S,5R,6R)-6-(acetoxymethyl)-3-methyl-2-(2-methyl-4-(4,4,5,5-tetramethyl-1,3,2-dioxaborolan-2-yl)phenoxy)tetrahydro-2H-pyran-3,4,5-triyl triacetate from Step I (100 mg, 0.17 mmol), 1,3,5-triiodobenzene (24 mg, 0.052 mmol) in 2-Me THF (3.75 mL) and Water (750 µL) is added K₂CO₃ (36 mg, 0.26 mmol), Pd(OAc)₂ (1.0 mg, 0.0052 mmol) and 3-(2-dicyclohexylphosphanylphenyl)-2,4-dimethoxy-benzenesulfonic acid (Sodium Ion (1)) (5 mg, 0.010 mmol). The reaction mixture is degassed, stirred at 70° C. for 2 h, cooled down to RT and partitioned between EtOAc and water. The organic layer is separated, filtered on celite, dried over Na₂SO₄, filtered, concentrated and purified on Biotage™ SNAP Ultra silica cartridge (12 g) eluting with EtOAc (20-80%) in Hex as gradient to afford the per-acetylated EXAMPLE 118 (50 mg, 61%) as a white solid. ¹H NMR (400 MHz, CD₃OD) δ 7.68 (d, J=1.4 Hz, 3H), 7.58 (d, J=2.4 Hz, 3H), 7.54 (dd, J=8.6, 2.3 Hz, 3H), 7.23 (d, J=8.6 Hz, 3H), 6.35 (s, 3H), 5.64 (d, J=9.7 Hz, 3H), 5.41 (t, J=9.9 Hz, 3H), 4.21 (dd, J=12.2, 4.9 Hz, 3H), 4.12-3.97 (m, 6H), 2.37 (s, 9H), 2.14 (s, 9H), 2.12 (s, 9H), 2.02 (s, 9H), 1.99 (s, 9H), 1.64 (s, 9H).

Step III: Example 118

To a solution of the per-acetylated EXAMPLE 118 from Step II (50 mg, 0.035 mmol) in MeOH (1.0 mL) is added NaOMe (4.0 µL of 25% w/w, 0.018 mmol). The resulting suspension is stirred 2 h at RT followed by addition of Ambilite IR-120 resin until the reaction mixture pH reaches 4. The suspension is diluted with MeOH (10 mL), filtered and concentrated to afford the tittle compound (30 mg, 88%). ¹H NMR (400 MHz, CD₃OD) δ 7.63 (s, 3H), 7.54-7.42 (m, 6H), 7.32 (d, J=8.4 Hz, 3H), 5.28 (s, 3H), 3.82-3.66 (m, 12H), 3.61 (dt, J=6.9, 3.6 Hz, 3H), 2.33 (s, 9H), 1.41 (s, 9H). LCMS m/z (M+H)⁺=925.81

Preparation of Example 119

(2R,3S,4S,5S,6R)-6-(hydroxymethyl)-3-methyl-2-[2-methyl-4-[5-[3-methyl-4-[(2R,3S,4S,5S,6R)-3,4,5-trihydroxy-6-(hydroxymethyl)-3-methyl-tetrahydropyran-2-yl]oxy-phenyl]-3-pyridyl]phenoxy]tetrahydropyran-3,4,5-triol

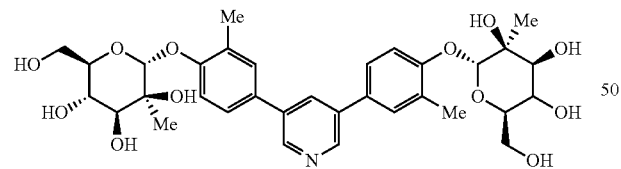

To a degased solution (2R,3S,4S,5R,6R)-6-(acetoxymethyl)-3-methyl-2-(2-methyl-4-(4,4,5,5-tetramethyl-1,3,2-dioxaborolan-2-yl)phenoxy)tetrahydro-2H-pyran-3,4,5-triyl triacetate from EXAMPLE 118 Step I (204 mg, 0.35 mmol), 3-bromo-5-iodo-pyridine (50.0 mg, 0.180 mmol) in 2-MeTHF (1.9 mL) and Water (375 µL) is added K₂CO₃ (74.0 mg, 0.530 mmol), Pd(OAc)₂ (2.0 mg, 0.011 mmol) and 3-(2-dicyclohexylphosphanylphenyl)-2,4-dimethoxy-benzenesulfonic acid (Sodium Ion (1)) (11 mg, 0.021 mmol). The reaction is degassed again, stirred at 70° C. for 16 h and then cooled to RT. The organic layer is separated, dried over Na₂SO₄, filtered on celite, diluted with MeOH (1 mL) and 2-Me THF (2 mL) and treated with NaOMe (352 µL of 0.5 M, 0.18 mmol) for 2 h at room temperature. The reaction mixture is neutralized with AcOH (20 µL, 0.35 mmol), concentrated and purified by reverse phase HPLC to afford the title compound (8 mg, 14%). ¹H NMR (400 MHz, CD₃OD) δ 8.66 (s, 2H), 8.16 (d, J=1.8 Hz, 1H), 7.62-7.42 (m, 4H), 7.36 (d, J=8.5 Hz, 2H), 5.29 (s, 2H), 3.81-3.63 (m, 8H), 3.58 (dt, J=6.8, 3.5 Hz, 2H), 2.33 (s, 6H), 1.40 (s, 6H). LCMS m/z (M+H)⁺=644.38

Preparation of Examples 120, 121 and 122

EXAMPLEs 120 to 122 are prepared according to the procedure described for EXAMPLE 119 using the appropriately substituted commercially available bis-halogenated phenyl or pyridine.

| EX-AM-PLE | Name | ¹H-NMR | LCMS m/z (M + H)⁺ |
|---|---|---|---|
| 120 | (2R,3S,4S,5S,6R)-6-(hydroxymethyl)-3-methyl-2-[2-methyl-4-[3-[3-methyl-4-[(2R,3S,4S,5S,6R)-3,4,5-trihydroxy-6-(hydroxymethyl)-3-methyl-tetrahydropyran-2-yl]oxy-phenyl]phenyl]phenoxy]tetrahydro-pyran-3,4,5-triol | (400 MHz, CD₃OD) δ 7.70 (t, J = 1.8 Hz, 1H), 7.51-7.37 (m, 7H), 7.30 (d, J = 8.3 Hz, 2H), 5.27 (s, 2H), 3.79-3.66 (m, 8H), 3.60 (dp, J = 6.8, 3.2 Hz, 2H), 2.31 (s, 6H), 1.40 (s, 6H). | 644.3 |
| 121 | (2R,3S,4S,5S,6R)-6-(hydroxymethyl)-3-methyl-2-[2-methyl-4-[6-[3-methyl-4-[(2R,3S,4S,5S,6R)-3,4,5-trihydroxy-6-(hydroxymethyl)-3-methyl-tetrahydropyran-2-yl]oxy-phenyl]-2-pyridyl]phenoxy]tetrahydropyran-3,4,5-triol | (400 MHz, CD₃OD) δ 7.95-7.86 (m, 4H), 7.80 (d, J = 7.8 Hz, 1H), 7.66 (d, J = 7.8 Hz, 2H), 7.34 (d, J = 8.4 Hz, 2H), 5.31 (s, 2H), 3.78 – 3.67 (m, 8H), 3.59 (dt, J = 6.9, 3.5 Hz, 2H), 2.34 (s, 6H), 1.41 (s, 6H). | 644.3 |
| 122 | (2R,3S,4S,5S,6R)-6-(hydroxymethyl)-3-methyl-2-[2-methyl-4-[2-[3-methyl-4-[(2R,3S,4S,5S,6R)-3,4,5-trihydroxy-6-(hydroxymethyl)-3-methyl-tetrahydropyran-2-yl]oxy-phenyl]-4-pyridyl]phenoxy]tetrahydropyran-3,4,5-triol | (400 MHz, CD₃OD) δ 8.58-8.46 (m, 1H), 7.96 (dd, J = 1.8, 0.8 Hz, 1H), 7.81-7.76 (m, 2H), 7.67-7.60 (m, 2H), 7.54 (dd, J = 5.4, 1.7 Hz, 1H), 7.36 (dd, J = 8.5, 6.5 Hz, 2H), 5.31 (s, 2H), 3.88-3.62 (m, 8H), 3.58 (ddd, J = 8.3, 6.8, 3.6 Hz, 2H), 2.34 (s, 6H), 1.40 (d, J = 1.0 Hz, 6H). | 645.2 |

Preparation of Example 123

(2R,3S,4S,5S,6R)-6-(hydroxymethyl)-3-methyl-2-[2-methyl-4-[2-[3-methyl-4-[(2R,3S,4S,5S,6R)-3,4,5-trihydroxy-6-(hydroxymethyl)-3-methyl-tetrahydropyran-2-yl]oxy-phenyl]cyclopropyl]phenoxy]tetrahydropyran-3,4,5-triol

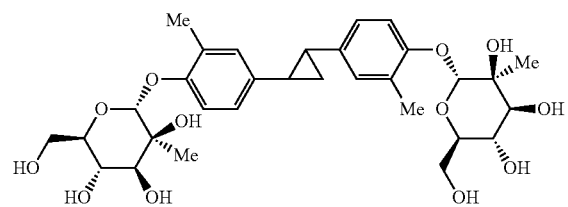 [SMILES: Cc1cc(C2CC2c2ccc(O[C@H]3O[C@H](CO)[C@@H](O)[C@H](O)[C@]3(C)O)c(C)c2)ccc1O[C@H]1O[C@H](CO)[C@@H](O)[C@H](O)[C@]1(C)O]

Step I: (2R,3S,4S,5R,6R)-6-(acetoxymethyl)-3-methyl-2-(2-methyl-4-((E)-2-(6-methyl-4,8-dioxo-1,3,6,2-dioxazaborocan-2-yl)vinyl)phenoxy)tetrahydro-2H-pyran-3,4,5-triyltriacetate

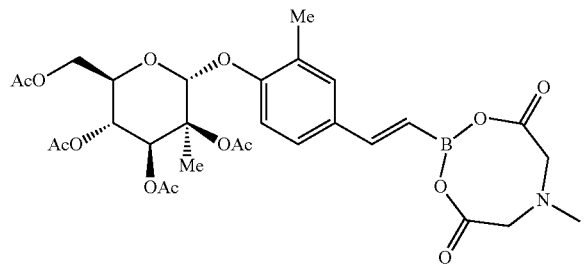 [SMILES: CC(=O)OC[C@H]1O[C@H](Oc2ccc(/C=C/B3OC(=O)CN(C)CC(=O)O3)cc2C)[C@@](C)(OC(C)=O)[C@@H](OC(C)=O)[C@@H]1OC(C)=O]

To a vial containing, 2-[(E)-2-bromovinyl]-6-methyl-1,3,6,2-dioxazaborocane-4,8-dione (95.1 mg, 0.363 mmol), [(2R,3R,4S,5S,6R)-3,4,5-triacetoxy-5-methyl-6-[2-methyl-4-(4,4,5,5-tetramethyl-1,3,2-dioxaborolan-2-yl)phenoxy]tetrahydropyran-2-yl]methyl acetate from EXAMPLE 118 Step I (175 mg, 0.303 mmol) are added under a nitrogen atmosphere PdCl$_2$(dppf). CH$_2$Cl$_2$ (22.1 mg, 0.0303 mmol) and K$_3$PO$_4$ (192.7 mg, 0.908 mmol) in CH$_3$CN (1.2 mL). The vial is sealed and allowed to stir at RT for 3 days. The mixture is filtered on a pad of silica gel and the filtrate is concentrated. The residue is purified on a Biotage™ SNAP silica cartridge eluting with EtOAc in Hex as gradient to afford title compound (107.6 mg, 56%).

Step II: [(2R,3R,4S,5S,6R)-3,4,5-triacetoxy-5-methyl-6-[2-methyl-4-[(E)-2-[3-methyl-4-[(2R,3S,4S,5R,6R)-3,4,5-triacetoxy-6-(acetoxymethyl)-3-methyl-tetrahydropyran-2-yl]oxy-phenyl]vinyl]phenoxy]tetrahydropyran-2-yl]methyl acetate

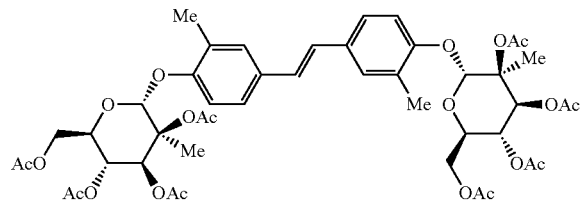 [SMILES: CC(=O)OC[C@H]1O[C@H](Oc2ccc(/C=C/c3ccc(O[C@H]4O[C@H](COC(C)=O)[C@@H](OC(C)=O)[C@H](OC(C)=O)[C@]4(C)OC(C)=O)c(C)c3)cc2C)[C@@](C)(OC(C)=O)[C@@H](OC(C)=O)[C@@H]1OC(C)=O]

To a vial containing INTERMEDIATE M10 (144.4 mg, 0.272 mmol) and (2R,3S,4S,5R,6R)-6-(acetoxymethyl)-3-methyl-2-(2-methyl-4-((E)-2-(6-methyl-4,8-dioxo-1,3,6,2-dioxazaborocan-2-yl)vinyl)phenoxy)tetrahydro-2H-pyran-3,4,5-triyltriacetate (107.6 mg, 0.170 mmol) is added under a nitrogen atmosphere PdCl$_2$(dppf). CH$_2$Cl$_2$ (12.4 mg, 0.0170 mmol) and K$_3$PO$_4$ (108.2 mg, 0.510 mmol) in CH$_3$CN (1.4 mL). The vial is sealed and allowed to stir at 60° C. overnight. The mixture is filtered on a pad of silica gel and the filtrate is concentrated. The residue is purified on a Biotage™ SNAP silica cartridge eluting with EtOAc in Hex to afford title compound (40 mg, 25%).

Step III: [(2R,3R,4S,5S,6R)-3,4,5-triacetoxy-5-methyl-6-[2-methyl-4-[2-[3-methyl-4-[(2R,3S,4S,5R,6R)-3,4,5-triacetoxy-6-(acetoxymethyl)-3-methyl-tetrahydropyran-2-yl]oxy-phenyl]cyclopropyl]phenoxy]tetrahydropyran-2-yl]methyl acetate

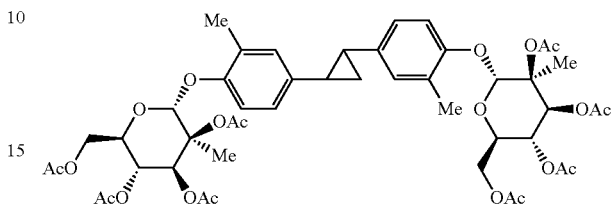

To a solution of [(2R,3R,4S,5S,6R)-3,4,5-triacetoxy-5-methyl-6-[2-methyl-4-[(E)-2-[3-methyl-4-[(2R,3S,4S,5R,6R)-3,4,5-triacetoxy-6-(acetoxymethyl)-3-methyl-tetrahydropyran-2-yl]oxy-phenyl]vinyl]phenoxy]tetrahydropyran-2-yl]methyl acetate from Step II (40 mg, 0.043 mmol) and Pd(OAc)$_2$ (4.8 mg, 0.022 mmol) in CH$_2$CL$_2$ (1.0 mL) at 0° C. is added dropwise a solution of diazomethane (5.4 mL of 0.8 M, 4.3 mmol) and the solution is stirred until complete conversion to desired material (monitored by LCMS). The resulting mixture is filtered over celite and the filtrate is concentrated under reduced pressure to afford a crude mixture (40.6 mg) of the title compound. The latter is used in the next step without further purification.

Step IV: Example 123

A crude mixture of [(2R,3R,4S,5S,6R)-3,4,5-triacetoxy-5-methyl-6-[2-methyl-4-[2-[3-methyl-4-[(2R,3S,4S,5R,6R)-3,4,5-triacetoxy-6-(acetoxymethyl)-3-methyl-tetrahydropyran-2-yl]oxy-phenyl]cyclopropyl]phenoxy]tetrahydropyran-2-yl]methyl acetate from Step III (40.6 mg) is dissolved in MeOH (323 µL) and NaOMe (86 µL, of 0.5 M, 0.043 mmol) is added. The resulting mixture is allowed to stir overnight at RT. AcOH (0.9 µL, 0.015 mmol) is added and the mixture is concentrated. The residue is purified by reverse phase HPLC to afford the Title compound (4.1 mg) as a white solid. $^1$H NMR (400 MHz, CD$_3$OD) δ 7.10 (d, J=8.2 Hz, 3H), 6.96-6.85 (m, J=9.8 Hz, 5H), 5.14 (d, J=6.5 Hz, 2H), 3.76-3.66 (m, J=10.2, 4.1 Hz, 9H), 3.65-3.55 (m, J=4.7 Hz, 3H), 2.19 (s, 6H), 1.96 (t, 2H), 1.37 (s, 6H), 1.27 (t, J=7.1 Hz, 2H). LCMS m/z (M+H)$^+$=607.7

Preparation of Example 124

(2R,3'S,4'S,5'S,6'R)-6'-(hydroxymethyl)spiro[chromane-2,2'-tetrahydropyran]-3',4',5',6-tetrol (VRT-1178998)

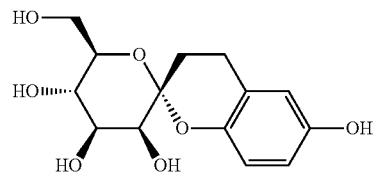 [SMILES: OC[C@H]1O[C@@]2(CCc3cc(O)ccc3O2)[C@@H](O)[C@@H](O)[C@@H]1O]

Step I: (2R,3'S,4'S,5'R,6'R)-3',4',5',6-tetrabenzyloxy-6'-(benzyloxymethyl)spiro[chromane-2,2'-tetrahydropyran]

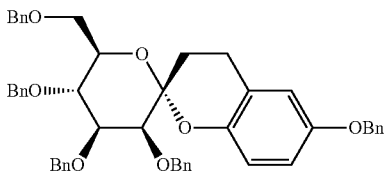 [SMILES: c1ccc(COC[C@H]2O[C@@]3(CCc4cc(OCc5ccccc5)ccc4O3)[C@@H](OCc3ccccc3)[C@@H](OCc3ccccc3)[C@@H]2OCc2ccccc2)cc1]

To a cold (0° C.) solution of INTERMEDIATE M9 (1.99 g, 3.27 mmol) and 4-benzyloxyphenol (1.97 g, 9.84 mmol) in $CH_2Cl_2$ (48 mL) is added $BF_3.OEt_2$ (420 µL, 3.31 mmol). After stirring for 45 min at 0° C., the reaction mixture is quenched with $H_2O$ (25 mL), stirred for 15 min and the layers are separated. The aqueous layer is back extracted with $CH_2Cl_2$ (2×25 mL) and the combined organic extracts are concentrated to about 25 mL. The precipitated unreacted phenol is removed by filtration. The filtrate is purified on a Biotage™ SNAP silica cartridge (100 g) eluting with EtOAc (0 to 20%) in Hex as gradient to afford the title compound (1.56 g, 64% yield) as a colorless gum. $^1$H NMR (400 MHz, $CDCl_3$) δ 7.47-7.05 (m, 25H), 6.81-6.55 (m, 3H), 5.04 (d, J=11.6 Hz, 1H), 4.96 (s, 2H), 4.90 (d, J=10.6 Hz, 1H), 4.84 (s, 2H), 4.72 (d, J=11.6 Hz, 1H), 4.59 (d, J=10.6 Hz, 1H), 4.54 (d, J=11.7 Hz, 1H), 4.41-4.30 (m, 2H), 4.11 (t, J=9.7 Hz, 1H), 3.85 (d, J=2.8 Hz, 1H), 3.82 (ddd, J=10.0, 4.6, 1.6 Hz, 1H), 3.74 (dd, J=11.6, 4.7 Hz, 1H), 3.64 (dd, J=11.5, 1.6 Hz, 1H), 2.95 (ddd, J=16.3, 13.2, 6.4 Hz, 1H), 2.59-2.48 (m, 1H), 2.42 (ddd, J=12.8, 5.9, 1.6 Hz, 1H), 1.50 (dt, J=13.0, 5.8 Hz, 1H).

Step II: Example 124

A pressure vessel is charged with (2R,3'S,4'S,5'R,6'R)-3',4',5',6-tetrabenzyloxy-6'-(benzyloxymethyl)spiro[chromane-2,2'-tetrahydropyran] from Step I (646 mg, 0.863 mmol) in EtOAc (5 mL) and MeOH (10 mL). $Pd(OH)_2$ (31 mg, 0.044 mmol) (slurry in MeOH) is added, followed by acetic acid (245 µL, 4.31 mmol). The reaction mixture is further diluted with MeOH (10 mL) and EtOAc (15 mL). The pressure vessel is filled with $H_2$ and vented (3×), then stirred overnight under 45 psi $H_2$ on a Parr shaker. The reaction mixture is vented under N2, filtered on Celite, and the catalyst is carefully rinsed with portions of MeOH. The combined filtrates are concentrated and coevaporated with heptane. Analysis by NMR showed the reaction is incomplete so the crude mixture is resubmitted to the exact reaction conditions and work-up to provide after co-evaporation with 1,4-dioxane (2×) the title compound (251 mg, 89% yield) as an off-white solid. $^1$H NMR (400 MHz, $CD_3OD$) δ 6.62 (d, J=8.4 Hz, 1H), 6.56-6.47 (m, 2H), 4.06 (dd, J=9.5, 3.4 Hz, 1H), 3.76-3.62 (m, 4H), 3.52 (ddd, J=9.9, 4.5, 2.8 Hz, 1H), 2.96 (ddd, J=16.7, 12.9, 6.2 Hz, 1H), 2.57 (ddd, J=16.4, 6.0, 2.3 Hz, 1H), 2.32 (ddd, J=13.4, 6.1, 2.4 Hz, 1H), 1.69 (td, J=13.1, 6.0 Hz, 1H). LCMS m/z $(M+Na)^+$= 321.29

Preparation of Example 125

(2R,3'S,4'S,5'S,6'R)-6'-(hydroxymethyl)-6-[3-methyl-4-[(2R,3S,4S,5S,6R)-3,4,5-trihydroxy-6-(hydroxymethyl)-3-methyl-tetrahydropyran-2-yl]oxy-phenyl]spiro[chromane-2,2'-tetrahydropyran]-3',4',5'-triol

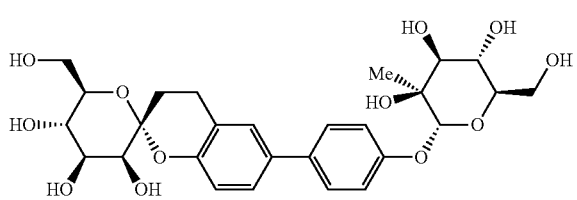 [SMILES: C[C@@]1(O)[C@@H](Oc2ccc(-c3ccc4c(c3)CC[C@]3(O4)O[C@H](CO)[C@@H](O)[C@H](O)[C@@H]3O)cc2)O[C@H](CO)[C@@H](O)[C@@H]1O]

Step I: [(2R,3'S,4'S,5'S,6'R)-3',4',5'-trihydroxy-6'-(hydroxymethyl)spiro[chromane-2,2'-tetrahydropyran]-6-yl]trifluoromethanesulfonate

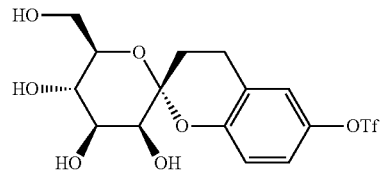 [SMILES: O=S(=O)(Oc1ccc2c(c1)CC[C@]1(O2)O[C@H](CO)[C@@H](O)[C@H](O)[C@@H]1O)C(F)(F)F]

To a solution of EXAMPLE 124 (730 mg, 2.24 mmol) and 1,1,1-trifluoro-N-phenyl-N-(trifluoromethylsulfonyl)methanesulfonamide (962 mg, 2.69 mmol) in DMF (10 mL) is added TEA (625 µL, 4.48 mmol) and the reaction mixture is stirred for 24 h, then concentrated to dryness. The crude product is purified on a Biotage™ SNAP silica cartridge (50 g) eluting with a gradient of MeOH (0-20%) in $CH_2Cl_2$ to afford the title compound (842 mg, 87% yield) as a colorless solid contaminated with TEA. $^1$H NMR (400 MHz, $CD_3OD$) δ 7.14-7.02 (m, 2H), 6.93 (d, J=8.8 Hz, 1H), 4.06 (dd, J=9.5, 3.4 Hz, 1H), 3.79 (d, J=3.4 Hz, 1H), 3.74-3.60 (m, 3H), 3.52 (ddd, J=9.9, 4.6, 3.1 Hz, 1H), 3.15-2.99 (m, 1H), 2.72 (ddd, J=16.6, 5.6, 2.2 Hz, 1H), 2.42 (ddd, J=13.7, 6.1, 2.3 Hz, 1H), 1.74 (td, J=13.3, 5.8 Hz, 1H). LCMS m/z $(M+H)^+$=431.21.

Step II: [(2R,2'R,3'R,4'S,5'S)-3',4',5'-triacetoxy-6-(trifluoromethylsulfonyloxy)spiro[chromane-2,6'-tetrahydropyran]-2'-yl]methyl acetate

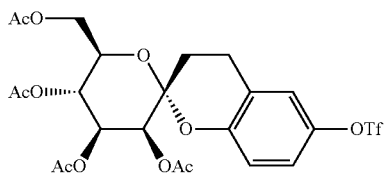 [SMILES: CC(=O)OC[C@H]1O[C@@]2(CCc3cc(OS(=O)(=O)C(F)(F)F)ccc3O2)[C@@H](OC(C)=O)[C@@H](OC(C)=O)[C@@H]1OC(C)=O]

To a vial containing [(2R,3'S,4'S,5'S,6'R)-3',4',5'-trihydroxy-6'-(hydroxymethyl)spiro[chromane-2,2'-tetrahydropyran]-6-yl]trifluoromethanesulfonate from Step I (840 mg, 1.95 mmol) and DMAP (49 mg, 0.401 mmol) is added pyridine (2.8 mL, 34.6 mmol) followed by $Ac_2O$ (3.32 mL, 35.1 mmol). After stirring for 2.5 h, the reaction mixture is diluted with CH$_2$Cl$_2$ (30 mL) and quenched with H$_2$O and 1N HCl (15 mL each). The layers are separated and the aqueous layer is back extracted with CH$_2$Cl$_2$ (2×15 mL). The combined organic extracts are concentrated and coevaporated with CH$_2$Cl$_2$/heptane (3×). The crude residue is purified by flash chromatography on a Biotage™ SNAP silica cartridge (50 g) eluting with a gradient of EtOAc (0-60%) in Hex to afford the title compound (907 mg, 78% yield) as a white crystalline solid. $^1$H NMR (400 MHz, CDCl$_3$) δ 7.07 (dd, J=8.9, 2.9 Hz, 1H), 7.02 (d, J=2.8 Hz, 1H), 6.99 (d, J=8.9 Hz, 1H), 5.65 (dd, J=10.1, 3.5 Hz, 1H), 5.43 (d, J=3.5 Hz, 1H), 5.32 (t, J=10.2 Hz, 1H), 4.23 (dd, J=12.3, 5.8 Hz, 1H), 4.02-3.92 (m, 2H), 2.98 (ddd, J=16.7, 13.1, 6.4 Hz, 1H), 2.69 (ddd, J=6.5, 5.2, 0.8 Hz, 1H), 2.22 (s, 3H), 2.18 (ddd, J=13.5, 6.3, 1.9 Hz, 1H), 2.06 (s, 3H), 2.01 (s, 3H), 1.90 (s, 3H), 1.70 (td, J=13.4, 6.1 Hz, 1H). $^{19}$F NMR (376 MHz, CDCl$_3$) δ −72.88 (s). LCMS m/z (M+H)$^+$= 599.34

Step III: [(2R,3R,4S,5S,6R)-3,4,5-triacetoxy-5-methyl-6-[2-methyl-4-[(2R,3'S,4'S,5'R,6'R)-3',4',5'-triacetoxy-6'-(acetoxymethyl)spiro[chromane-2,2'-tetrahydropyran]-6-yl]phenoxy]tetrahydropyran-2-yl]methyl acetate

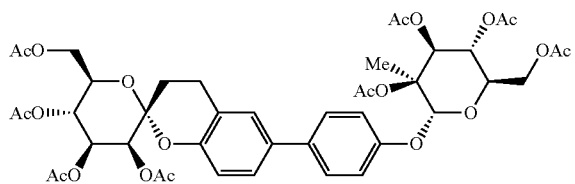 [SMILES: CC(=O)OC[C@H]1O[C@H](Oc2ccc(-c3ccc4c(c3)CC[C@]3(O4)O[C@H](COC(C)=O)[C@@H](OC(C)=O)[C@H](OC(C)=O)[C@@H]3OC(C)=O)cc2)[C@@](C)(OC(C)=O)[C@@H](OC(C)=O)[C@@H]1OC(C)=O]

A pressure tube is charged with [(2R,3R,4S,5S,6R)-3,4,5-triacetoxy-5-methyl-6-[2-methyl-4-(4,4,5,5-tetramethyl-1,3,2-dioxaborolan-2-yl)phenoxy]tetrahydropyran-2-yl]methyl acetate from EXAMPLE 118 Step I (71.0 mg, 0.123 mmol), [(2R,2'R,3'R,4'S,5'S)-3',4',5'-triacetoxy-6-(trifluoromethylsulfonyloxy)spiro[chromane-2,6'-tetrahydropyran]-2'-yl]methyl acetate from Step II (50.0 mg, 0.0835 mmol), K$_2$CO$_3$ (58.0 mg, 0.420 mmol), Pd(OAc)$_2$ (4.9 mg, 0.022 mmol) and [3-(2-dicyclohexylphosphanylphenyl)-2,4-dimethoxy-phenyl]sulfonyloxysodium (V-Phos) (13.6 mg, 0.0265 mmol). The tube is capped and degassed (vacuum then N2, 3×) and 2-methyltetrahydrofuran (1.0 mL) and H$_2$O (200 μL) are added. The tube is degassed again and transferred to a preheated (65° C.) oil bath. After stirring for 2 h, the reaction mixture is cooled down to RT, passed through a small plug of Celite, rinsing with EtOAc (5 mL) and saturated aqueous NH$_4$Cl solution (3 mL). The layer is separated and the aqueous layer is back extracted with EtOAc (2×3 mL). The combined organic extracts are dried over Na$_2$SO$_4$, filtered and concentrated. The crude residue is purified by flash chromatography on a on a Biotage™ SNAP silica cartridge (10 g) eluting with a gradient of EtOAc (20-80%) in Hex to afford the title compound (73 mg) as a colorless solid contaminated with pinacol. $^1$H NMR (400 MHz, CDCl$_3$) δ 7.36-7.33 (m, 1H), 7.31 (dd, J=5.0, 2.2 Hz, 1H), 7.28 (d, J=2.3 Hz, 1H), 7.24 (d, J=1.9 Hz, 1H), 7.20 (d, J=8.5 Hz, 1H), 6.98 (d, J=8.4 Hz, 1H), 6.31 (s, 1H), 5.71 (dd, J=10.1, 3.5 Hz, 1H), 5.62 (d, J=9.7 Hz, 1H), 5.44 (d, J=3.3 Hz, 1H), 5.40 (d, J=9.8 Hz, 1H), 5.35 (t, J=10.1 Hz, 1H), 4.26 (dd, J=12.0, 5.1 Hz, 1H), 4.20 (dd, J=12.2, 5.2 Hz, 1H), 4.16-3.95 (m, 4H), 3.00 (ddd, J=16.4, 13.2, 6.1 Hz, 1H), 2.76-2.64 (m, 1H), 2.34 (s, 3H), 2.25-2.11 (m, 10H), 2.06 (s, 3H), 2.05 (s, 6H), 2.02 (s, 3H), 1.91 (s, 3H), 1.74 (td, J=13.2, 6.0 Hz, 1H), 1.66 (s, 3H). LCMS m/z (M+Na)$^+$=923.71

Step IV: Example 125

To a suspension of [(2R,3R,4S,5S,6R)-3,4,5-triacetoxy-5-methyl-6-[2-methyl-4-[(2R,3'S,4'S,5'R,6'R)-3',4',5'-triacetoxy-6'-(acetoxymethyl)spiro[chromane-2,2'-tetrahydropyran]-6-yl]phenoxy]tetrahydropyran-2-yl]methyl acetate from Step III (66.5 mg, 0.0738 mmol) in MeOH (1.3 mL) is added NaOMe in MeOH (300 μL of 0.5 M, 0.150 mmol After stirring for 3 h, the reaction mixture is diluted with MeOH (2 mL), treated with prewashed Dowex 50WX4-400 resin, filtered and washed with portions of MeOH. The combined filtrates are concentrated and purified on a Biotage™ SNAP C18 cartridge (12 g) eluting with a gradient of CH$_3$CN (10-90%) in H$_2$O. The fractions containing the desired material are combined, concentrated, redissolved in H$_2$O/CH$_3$CN (20%) mixture and freeze-dried to provide the title compound (26.7 mg, 59% yield) as a fluffy white solid. $^1$H NMR (400 MHz, CD$_3$OD) δ 7.38-7.21 (m, 5H), 6.84 (d, J=9.1 Hz, 1H), 5.25 (s, 1H), 4.10 (dd, J=9.5, 3.4 Hz, 1H), 3.80 (d, J=3.4 Hz, 1H), 3.77-3.66 (m, 7H), 3.65-3.52 (m, 2H), 3.08 (ddd, J=16.4, 13.0, 6.2 Hz, 1H), 2.72 (ddd, J=7.3, 5.2, 1.7 Hz, 1H), 2.41 (ddd, J=13.2, 5.8, 2.2 Hz, 1H), 2.29 (s, 3H), 1.77 (td, J=13.2, 5.9 Hz, 1H), 1.41 (s, 3H). LCMS m/z (M+H)$^+$=565.49

Preparation of Example 126

(2R,3'S,4'S,5'S,6'R)-6'-(hydroxymethyl)-6-[(2R,3'S,4'S,5'S,6'R)-3',4',5'-trihydroxy-6'-(hydroxymethyl)spiro[chromane-2,2'-tetrahydropyran]-6-yl]spiro[chromane-2,2'-tetrahydropyran]-3',4',5'-triol

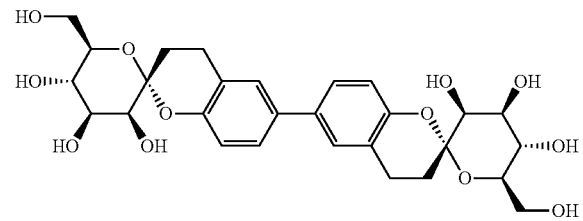 [SMILES: OC[C@H]1O[C@@]2(CCc3cc(-c4ccc5c(c4)CC[C@]4(O5)O[C@H](CO)[C@@H](O)[C@H](O)[C@@H]4O)ccc3O2)[C@@H](O)[C@@H](O)[C@@H]1O]

Step I: [(2R,2'R,3'R,4'S,5'S)-3',4',5'-triacetoxy-6-(4,4,5,5-tetramethyl-1,3,2-dioxaborolan-2-yl)spiro[chromane-2,6'-tetrahydropyran]-2'-yl]methyl acetate

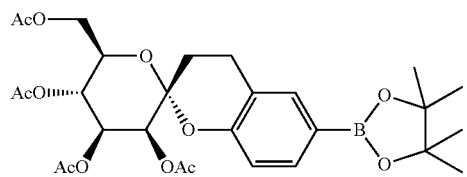 [SMILES: CC(=O)OC[C@H]1O[C@@]2(CCc3cc(B4OC(C)(C)C(C)(C)O4)ccc3O2)[C@@H](OC(C)=O)[C@@H](OC(C)=O)[C@@H]1OC(C)=O]

A pressure tube is charged with [(2R,2'R,3'R,4'S,5'S)-3',4',5'-triacetoxy-6-(trifluoromethylsulfonyloxy)spiro[chromane-2,6'-tetrahydropyran]-2'-yl]methyl acetate from Step II (501 mg, 0.837 mmol), KOAc (170 mg, 1.73 mmol), Bis(pinacolato)diboron (321 mg, 1.26 mmol) and PdCl$_2$(dppf).CH$_2$Cl$_2$ (35 mg, 0.0429 mmol), capped and degassed (vacuum then N2 3×). DMF (5.0 mL) is added, the reaction mixture is degassed again, then heated at 80° C. for 4 h. The reaction mixture is diluted with saturated aqueous NH$_4$Cl solution and EtOAc (15 mL each). The layers are separated and the organic layer is washed with saturated aqueous NH$_4$Cl solution (15 mL), dried over Na$_2$SO$_4$, filtered and concentrated. The crude residue is purified on a Biotage™ SNAP silica cartridge (50 g) eluting with a gradient of EtOAc (0-60%) in Hex to afford the title compound (457 mg, 95% yield) as a white solid. $^1$H NMR (400 MHz, CDCl$_3$) δ 7.61 (d, J=8.0 Hz, 1H), 7.56 (s, 1H), 6.95 (d, J=8.1 Hz, 1H), 5.68 (dd, J=10.1, 3.4 Hz, 1H), 5.42 (d, J=3.4 Hz, 1H), 5.34 (t, J=10.1 Hz, 1H), 4.24 (dd, J=12.1, 4.9 Hz, 1H), 4.01 (ddd, J=9.8, 4.9, 2.3 Hz, 1H), 3.94 (dd, J=12.2, 2.4 Hz, 1H), 3.03-2.86 (m, 1H), 2.75-2.53 (m, 1H), 2.21 (s, 3H), 2.16 (ddd, J=13.2, 5.8, 1.8 Hz, 1H), 2.05 (s, 4H), 2.00 (s, 3H), 1.93 (s, 3H), 1.69 (td, J=13.3, 5.8 Hz, 1H), 1.33 (s, 12H). LCMS m/z (M+Na)$^+$=599.48

Step II: [(2R,2'R,3'R,4'S,5'S)-3',4',5'-triacetoxy-6-[(2R,3'S,4'S,5'R,6'R)-3',4',5'- triacetoxy-6'-(acetoxymethyl)spiro[chromane-2,2'-tetrahydropyran]-6-yl]spiro[chromane-2,6'-tetrahydropyran]-2'-yl]methyl acetate

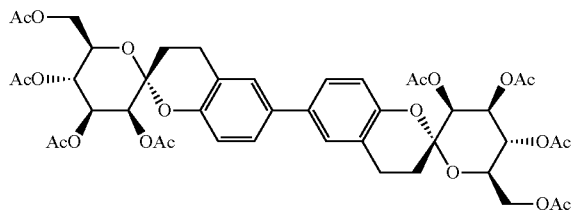 [SMILES: CC(=O)OC[C@H]1O[C@@]2(CCc3cc(-c4ccc5c(c4)CC[C@]4(O5)O[C@H](COC(C)=O)[C@@H](OC(C)=O)[C@H](OC(C)=O)[C@@H]4OC(C)=O)ccc3O2)[C@@H](OC(C)=O)[C@@H](OC(C)=O)[C@@H]1OC(C)=O]

The title compound is prepared according to the procedure described for EXAMPLE 125 Step III using [(2R,2'R,3'R,4'S,5'S)-3',4',5'-triacetoxy-6-(4,4,5,5-tetramethyl-1,3,2-dioxaborolan-2-yl)spiro[chromane-2,6'-tetrahydropyran]-2'-yl]methyl acetate from Step I and [(2R,2'R,3'R,4'S,5'S)-3',4',5'-triacetoxy-6-(trifluoromethylsulfonyloxy)spiro[chromane-2,6'-tetrahydropyran]-2'-yl]methyl acetate from EXAMPLE 125 Step I. The title compound (79% yield) is obtained as a white solid. $^1$H NMR (400 MHz, CDCl$_3$) δ 7.32 (dd, J=8.2, 2.1 Hz, 2H), 7.24 (broad s, 2H), 6.98 (d, J=8.4 Hz, 2H), 5.70 (dd, J=10.1, 3.3 Hz, 2H), 5.44 (d, J=3.3 Hz, 2H), 5.35 (t, J=10.1 Hz, 2H), 4.26 (dd, J=11.9, 4.9 Hz, 2H), 4.10-3.91 (m, 4H), 3.07-2.89 (m, 2H), 2.70 (dd, J=16.9, 5.4 Hz, 2H), 2.27-2.13 (m, 8H), 2.06 (s, 6H), 2.02 (s, 6H), 1.92 (s, 6H), 1.74 (td, J=13.0, 5.7 Hz, 2H). LCMS m/z (M+Na)$^+$=899.72

Step III Example 126

The title compound is prepared according to the procedure described for EXAMPLE 125 Step IV starting with [(2R,2'R,3'R,4'S,5'S)-3',4',5'-triacetoxy-6-[(2R,3'S,4'S,5'R,6'R)-3',4',5'-triacetoxy-6'-(acetoxymethyl)spiro[chromane-2,2'-tetrahydropyran]-6-yl]spiro[chromane-2,6'-tetrahydropyran]-2'-yl]methyl acetate from Step II. $^1$H NMR (400 MHz CD$_3$OD) δ 7.33-7.22 (m, 4H), 6.89-6.78 (m, 2H), 4.10 (dd, J=9.5, 3.4 Hz, 2H), 3.79 (d, J=3.4 Hz, 2H), 3.74 (t, J=9.7 Hz, 2H), 3.71-3.65 (m, 4H), 3.57 (ddd, J=9.9, 4.2, 3.1 Hz, 2H), 3.07 (ddd, J=17.5, 13.0, 6.1 Hz, 2H), 2.77-2.67 (m, 2H), 2.40 (ddd, J=13.3, 5.8, 2.2 Hz, 2H), 1.76 (td, J=13.2, 5.9 Hz, 2H). LCMS m/z (M+H)$^+$=563.49

Preparation of Example 127

(2R,3'S,4'S,5'S,6'R)-6'-(hydroxymethyl)-6-[4-[(2R,3'S,4'S,5'S,6'R)-3',4',5'-trihydroxy-6'-(hydroxymethyl)spiro[chromane-2,2'-tetrahydropyran]-6-yl]phenyl]spiro[chromane-2,2'-tetrahydropyran]-3',4',5'-triol

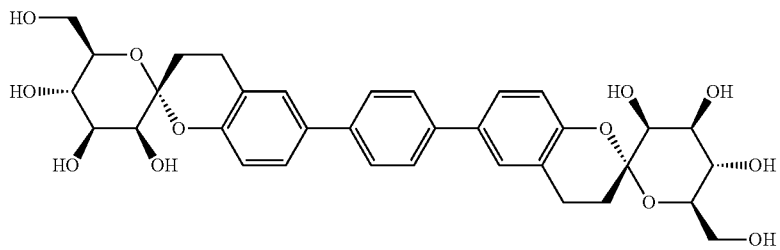 [SMILES: OC[C@H]1O[C@@]2(CCc3cc(-c4ccc(-c5ccc6c(c5)CC[C@]5(O6)O[C@H](CO)[C@@H](O)[C@H](O)[C@@H]5O)cc4)ccc3O2)[C@@H](O)[C@@H](O)[C@@H]1O]

Step I: [(2R,2'R,3'R,4'S,5'S)-3',4',5'-triacetoxy-6-[4-[(2R,3'S,4'S,5'R,6'R)-3',4',5'-triacetoxy-6'-(acetoxymethyl)spiro[chromane-2,2'-tetrahydropyran]-6-yl]phenyl]spiro[chromane-2,6'-tetrahydropyran]-2'-yl]methyl acetate 6.93-6.85 (m, 2H), 4.11 (dd, J=9.5, 3.4 Hz, 2H), 3.81 (d, J=3.4 Hz, 2H), 3.79-3.67 (m, 6H), 3.59 (dt, J=9.9, 3.7 Hz, 2H), 3.11 (ddd, J=16.7, 12.9, 6.0 Hz, 2H), 2.75 (ddd, J=16.2, 5.5, 2.0 Hz, 2H), 2.43 (ddd, J=13.4, 6.0, 2.4 Hz, 2H), 1.79 (td, J=13.3, 5.8 Hz, 2H). LCMS m/z (M+H)+=639.49

Step II: Example 127

The title compound is prepared according to the procedure described for EXAMPLE 125 Step IV starting with [(2R,2'R,3'R,4'S,5'S)-3',4',5'-triacetoxy-6-[4-[(2R,3'S,4'S,5'R,6'R)-3',4',5'-triacetoxy-6'-(acetoxymethyl)spiro[chromane-2,2'-tetrahydropyran]-6-yl]phenyl]spiro[chromane-2,6'-tetrahydropyran]-2'-yl]methyl acetate from Step I. ¹H NMR (400 MHz, CD₃OD) δ 7.60 (s, 4H), 7.44-7.34 (m, 4H),

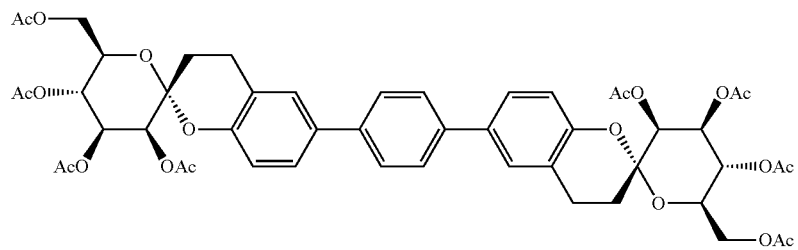 [SMILES: CC(=O)OC[C@H]1O[C@@]2(CCc3cc(-c4ccc(-c5ccc6c(c5)CC[C@]5(O6)O[C@H](COC(C)=O)[C@@H](OC(C)=O)[C@H](OC(C)=O)[C@@H]5OC(C)=O)cc4)ccc3O2)[C@@H](OC(C)=O)[C@@H](OC(C)=O)[C@@H]1OC(C)=O]

A pressure tube is charged with [(2R,2'R,3'R,4'S,5'S)-3',4',5'-triacetoxy-6-(4,4,5,5-tetramethyl-1,3,2-dioxaborolan-2-yl)spiro[chromane-2,6'-tetrahydropyran]-2'-yl]methyl acetate from EXAMPLE 126 Step I (105 mg, 0.182 mmol), 1,4-dibromobenzene (20 mg, 0.0845 mmol), K₂CO₃ (64 mg, 0.463 mmol), Pd(OAc)₂ (2.6 mg, 0.0116 mmol) and [3-(2-dicyclohexylphosphanylphenyl)-2,4-dimethoxy-phenyl]sulfonyloxysodium (V-Phos) (9 mg, 0.0176 mmol). The tube is capped and degassed (vacuum then N2, 3×) and 2-methyltetrahydrofuran (400 µL) and H₂O (80 µL) are added, the tube is degassed again and transferred to a preheated (65° C.) oil bath. After stirring for 2 h, the reaction mixture is cooled down to RT, diluted with CH₂Cl₂ (3 mL) and H₂O (2 mL). The layers are separated and the aqueous layer is back extracted with CH₂Cl₂ (2×1 mL). The combined organic extracts are concentrated. The crude residue is purified on a Biotage™ SNAP silica cartridge (10 g) eluting with a gradient of EtOAc (50-100%) in Hex to afford the title compound (71 mg) as a white solid contaminated with pinacol. ¹H NMR (400 MHz, CDCl₃) δ 7.59 (s, 4H), 7.43 (dd, J=8.4, 2.2 Hz, 2H), 7.35 (d, J=2.1 Hz, 2H), 7.02 (d, J=8.4 Hz, 2H), 5.72 (dd, J=10.1, 3.5 Hz, 2H), 5.46 (d, J=3.5 Hz, 2H), 5.35 (t, J=10.1 Hz, 2H), 4.27 (dd, J=12.1, 5.1 Hz, 2H), 4.05 (ddd, J=10.1, 5.2, 2.5 Hz, 2H), 4.00 (dd, J=12.0, 2.5 Hz, 2H), 3.03 (ddd, J=15.9, 12.9, 5.8 Hz, 2H), 2.79-2.65 (m, 2H), 2.29-2.14 (m, 8H), 2.07 (s, 6H), 2.02 (s, 6H), 1.92 (s, 6H), 1.76 (dt, J=13.2, 5.9 Hz, 2H). LCMS m/z (M+H)+= 975.72.

Preparation of Example 128
(2R,3'S,4'S,5'S,6'R)-6'-(hydroxymethyl)-6-[3-[(2R,3'S,4'S,5'S,6'R)-3',4',5'-trihydroxy-6'-(hydroxymethyl)spiro[chromane-2,2'-tetrahydropyran]-6-yl]phenyl]spiro[chromane-2,2'-tetrahydropyran]-3',4',5'-triol

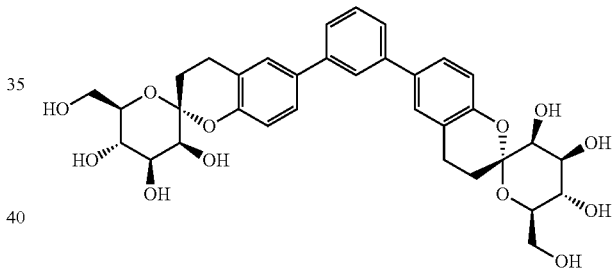

The title compound is prepared in two steps according to the procedure described for EXAMPLE 127 but using 1,3-dibromobenzene in the first Step. ¹H NMR (400 MHz, CD₃OD+DMSO-D₆) δ 7.80-7.65 (m, 1H), 7.57-7.37 (m, 7H), 6.97-6.88 (m, 2H), 4.10 (dd, J=9.5, 3.4 Hz, 2H), 3.82 (d, J=3.4 Hz, 2H), 3.78-3.67 (m, 6H), 3.58 (dt, J=9.9, 3.7 Hz, 2H), 3.11 (ddd, J=16.4, 12.9, 6.1 Hz, 2H), 2.79 (ddd, J=7.8, 5.3, 2.1 Hz, 2H), 2.43 (ddd, J=13.4, 5.9, 2.4 Hz, 2H), 1.80 (td, J=13.2, 5.8 Hz, 2H). LCMS m/z (M+H)+=639.49

Preparation of Example 129
(2R,3'S,4'S,5'S,6'R)-6'-(hydroxymethyl)-6-[5-[(2R,3'S,4'S,5'S,6'R)-3',4',5'-trihydroxy-6'-(hydroxymethyl)spiro[chromane-2,2'-tetrahydropyran]-6-yl]-3-pyridyl]spiro[chromane-2,2'-tetrahydropyran]-3',4',5'-triol

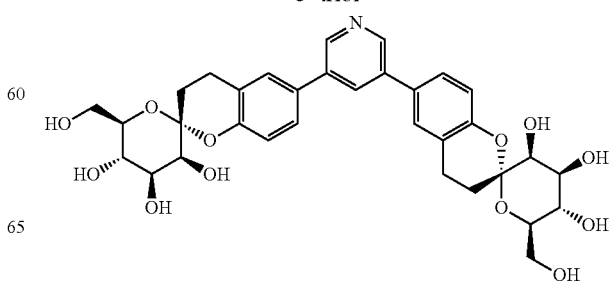

The title compound is prepared in two steps according to the procedure described for EXAMPLE 127 but using 3,5-dibromopyridine in the first Step. $^1$H NMR (400 MHz, CD$_3$OD) δ 8.63 (broad s, 2H), 8.13 (s, 1H), 7.51-7.36 (m, 4H), 7.01-6.86 (m, 2H), 4.09 (dd, J=9.5, 3.4 Hz, 2H), 3.80 (d, J=3.4 Hz, 2H), 3.76-3.63 (m, 6H), 3.56 (ddd, J=9.9, 4.2, 3.2 Hz, 2H), 3.18-2.97 (m, 2H), 2.76 (ddd, J=16.5, 5.5, 2.1 Hz, 2H), 2.42 (ddd, J=13.4, 5.9, 2.3 Hz, 2H), 1.77 (td, J=13.3, 5.8 Hz, 2H). LCMS m/z (M+H)$^+$=640.47

Thermal Shift Assay

The carbohydrate recognition domain of the protein FimH (M1-T179) with an uncleavable C-terminus 6-His tag is cloned in a pET21b plasmid and expressed in *E. coli* and purified to homogeneity. The thermal stabilization of the protein upon ligand binding is measured in a 96-well format on a ViiA™ 7 (Life Technologies, Carlsbad, Calif.) RT-PCR instrument. The assay is conducted in duplicate in 20 mM Tris pH 7.4 and 150 mM NaCl at a final concentration of 5.6 μM and 56 μM for protein and ligand, respectively. An environmentally-sensitive dye (Applied Biosystems Protein Thermal Shift™ Dye (P/N 4461141)) is added to each well to a final ratio of 1:1000. Plates are spun at 1000×g for 1 minute and incubated at room temperature for 10 minutes. Thermal stability of protein with and without ligand is measured from 45° C. to 85° C. at a scan rate of 0.05° C./sec. The resulting data is analyzed using Protein Thermal Shift™ Software (version 1.1) with DMSO control used as reference. Table 2 below provides the delta thermal melt for compounds 1-129 in the thermal shift assay.

TABLE 2

| COMPOUND # | *Delta Thermal melt (° C.) |
|---|---|
| 1 | 3 (1) |
| 2 | 6.01 (1) |
| 3 | 3.2 (1) |
| 4 | 5.6 (1) |
| 5 | 1.8 (1) |
| 6 | 4.905 ± 0.195 (2) |
| 7 | 3.86 ± 0.09 (2) |
| 8 | 4 (1) |
| 9 | 4.39 ± 0.11 (2) |
| 10 | 3.405 ± 0.105 (2) |
| 11 | 2.6 (1) |
| 12 | 0.06 ± 0.11 (2) |
| 13 | 10.71 ± 0 (2) |
| 25 | 7.9 ± 0 (4) |
| 26 | 5.405 ± 0.005 (2) |
| 27 | 3.7 ± 0.041 (4) |
| 28 | 4.2 ± 0.058 (4) |
| 29 | 1.7 ± 0 (2) |
| 32 | 8 ± 0.058 (4) |
| 33 | 8.9 ± 0.115 (4) |
| 35 | 5.6 ± (1) |

*Delta Thermal melt ± Standard error of the mean (number of repeats)

Bacterial Binding Assay

The purpose of the Bacterial Binding Assay (BBA) is to determine the inhibition activity of selective FimH antagonists on the bacterial strain LF82 binding to the glycoprotein BSA-(Mannose)$_3$.

Below is a list of the Materials used to run the BBA are described below.
1. LB broth: Supplier: Gibco, #10855
2. D-PBS: Supplier: Wisent, #311-425-CL
3. LB agar plates
4. 96-well black plate (high binding): Supplier: Costar, #3925
5. TopSeal™-A adhesive sealing films; Supplier PerkinElmer, #6005185
6. Carbonate-bicarbonate buffer pH 9.6 tablets, Supplier: Medicago, #09-8922-24
7. Water, Supplier: Gibco, #15230-162
8. Bovine serum albumin (BSA): Supplier: Sigma, #A-7888
9. (Man)-3-BSA (α1-3, α1-6 Mannotriose-BSA, 1 mg), V-Labs, #NGP1336, lot#HGDX37-169-1
10. Tween 20: Supplier: Sigma, #P9416
11. Bright-Glo Luciferase Assay System: Supplier: Promega, #E2610
12. LF82/Luciferase strain: Invasive ability of an *Escherichia coli* strain isolated from the ileal mucosa of a patient with Crohn's disease. Boudeau J, Glasser A L, Masseret E, Joly B, Darfeuille-Michaud A, *Infect Immun.* 1999, 67(9), 4499-509

Solutions and buffers used to run the BBA are described below.
1. 0.04M carbonate-bicarbonate buffer (coating buffer)
2. 40 ng/mL BSA-(Man)$_3$: Dissolve 1 mg of (Man)-3-BSA in 25 mL of water.
3. 4000 ng/mL BSA
4. 40 ng/mL BSA
5. 1 μg/mL BSA-(Man)$_3$: 150 μL of 40 ng/mL BSA-(Man)$_3$+5.85 mL of 40 ng/mL BSA
6. 0.5 μg/mL BSA-(Man)$_3$ in 0.02M carbonate-bicarbonate buffer.
7. 20 ng/mL BSA in 0.02M carbonate-bicarbonate buffer
8. Blocking buffer (2% BSA/DPBS): 1 g of BSA in 50 mL D-PBS
9. 2× binding buffer (0.2% BSA/D-PBS): 5 mL of blocking buffer+45 mL D-PBS.
10. Washing buffer (D-PBS/0.01% Tween 20): 10 μL of Tween 20 in 100 mL D-PBS.
11. 1× Bright-Glo Luciferase substrate:Dilute 1:1 the Bright-Glo Luciferase Assay System with D-PBS The experimental protocol to run the BBA is described below.

Overnight culture of LF82/Luciferase strain: Into two Falcon 50 mL tubes, add 20 mL of LB+20 μL of 50 mg/mL Kanamycin and inoculate with a loop from glycerol stock of the LF82/Luciferase strain. Incubate overnight at 37° C. with no shaking.

Glycoprotein coating of 96-well plates: Add 100 μL/well of 0.5-2 μg/mL BSA-(Man)$_3$. 20 μg/mL BSA is used as the control background. Seal plate using an adhesive sealing film and incubate overnight at room temperature. Wash the 96-well plate three times with 150 μL/well of D-PBS, add 170 μL/well of blocking solution and incubate 45 min (minimum) at room temperature.

Preparation of bacterial suspension: Mix the two cultures tubes (40 mL) and perform a 1:10 dilution in LB (900 μl LB+100 μl culture. Measure optical density (OD) of the bacterial cultures. OD1 ~5×10$^8$ cells/mL. Centrifuge LF82 culture for 20 min at 3500 rpm at room temperature. Re-suspend bacterial pellet in D-PBS and centrifuge again for 20 min at 3500 rpm. Re-suspend bacterial pellet in D-PBS to obtain a bacterial concentration of 2×10$^9$ bacteria/mL. Dilute ⅒ in D-PBS to obtain a final bacterial concentration of 2×10$^8$ bacteria/mL (=107 bacteria/50 μL). Perform ⅒ serial dilutions in LB of each bacterial suspension, plate 10 μL of dilutions on LB agar plates (final dilutions of 10$^{-7}$) and incubate overnight at 37° C. and count CFUs to determine the actual bacteria density in the assay.

Bacterial binding assay: Add 147 μL 2× binding buffer to compound plate (containing 3 μL of compound). After blocking step is performed (at least 45 min), wash plates three times with 200 μL/well of D-PBS. With a 100 μL multichannel manual pipettor, add 50 µL/well of compound diluted in 2× binding buffer. With a 100 µL multichannel manual pipettor, add 50 µL/well of bacterial suspension. Agitate at slow speed for 1 min and incubate 40-75 min at room temperature. Wash 5 times with 150 µL/well of washing buffer and then once with D-PBS. Add 100 µL/well of 1× Bright-Glo Luciferase substrate. Read luminescence by using the Analyst HT plate reader or the Trilux 1450 microbeta plate reader. Table 3 below provides IC50 data for compounds 1-129 in the bacterial binding assay.

TABLE 3

| Compound | Bacterial Binding Assay $IC_{50}$ (mM) |
|---|---|
| 1 | N/A |
| 2 | 1.15 ± 0.35 (2) |
| 3 | N/A |
| 4 | 0.47 ± 0.032 (3) |
| 5 | N/A |
| 6 | 0.75 ± 0.141 (4) |
| 7 | 8.62 ± 1.298 (5) |
| 8 | 5.4 ± 0.2 (2) |
| 9 | N/A |
| 10 | N/A |
| 11 | 14 ± 0 (2) |
| 12 | N/A |
| 13 | 0.015 ± 0.002 (20) |
| 14 | 0.132 ± 0.044 (4) |
| 15 | 0.013 ± 0.002 (4) |
| 16 | 0.067 ± 0.018 (4) |
| 17 | 0.027 ± 0.008 (4) |
| 18 | 0.013 ± 0.003 (4) |
| 19 | 0.013 ± 0.006 (4) |
| 20 | 0.02 ± 0 (2) |
| 21 | 0.112 ± 0.037 (6) |
| 22 | 0.015 ± 0.004 (6) |
| 23 | 0.115 ± 0.025 (2) |
| 24 | 0.019 ± 0.003 (7) |
| 25 | 0.068 ± 0.018 (4) |
| 26 | 2.372 ± 0.544 (6) |
| 27 | 0.165 ± 0.049 (3) |
| 28 | 1.3 ± 0 (2) |
| 29 | >10 ± 0 (2) |
| 30 | >10 ± 0 (2) |
| 31 | >10 ± 0 (2) |
| 32 | 0.333 ± 0.1 (3) |
| 33 | 0.027 ± 0.008 (3) |
| 34 | 0.079 ± 0.031 (2) |
| 35 | 1.8 ± 0.3 (2) |
| 36 | N/A |
| 37 | >10 ± 0 (2) |
| 38 | 0.105 ± 0.005 (2) |
| 39 | 0.265 ± 0.135 (2) |
| 40 | 0.22 ± 0.11 (2) |
| 41 | 0.22 ± 0.11 (2) |
| 42 | 0.375 ± 0.255 (2) |
| 43 | 0.785 ± 0.474 (4) |
| 44 | 0.043 ± 0.012 (4) |
| 45 | 0.116 ± 0.034 (2) |
| 46 | 0.126 ± 0.038 (4) |
| 47 | 0.055 ± 0.029 (4) |
| 48 | 0.605 ± 0.215 (2) |
| 49 | 0.28 ± 0.02 (2) |
| 50 | 0.83 ± 0.17 (2) |
| 51 | 7.15 ± 0.05 (2) |
| 52 | 0.048 ± 0.01 (2) |
| 53 | 0.024 ± 0.006 (3) |
| 54 | 0.042 ± 0.007 (2) |
| 55 | 0.02 ± 0.0005 (2) |
| 56 | 0.024 ± 0.0005 (2) |
| 57 | 0.017 ± 0.004 (2) |
| 58 | 0.013 ± 0.001 (6) |
| 59 | 0.02 ± 0.004 (2) |
| 60 | 0.016 ± 0.0005 (2) |
| 61 | 0.022 ± 0.006 (2) |
| 62 | 0.009 ± 0.003 (2) |
| 63 | 0.012 ± 0.003 (2) |
| 64 | 0.02 ± 0.0005 (2) |
| 65 | 0.02 ± 0.008 (2) |
| 66 | 0.011 ± 0.003 (2) |
| 67 | 0.015 ± 0.006 (2) |
| 68 | 0.026 ± 0.004 (2) |
| 69 | 0.03 ± 0.012 (3) |
| 70 | 0.03 ± 0.001 (2) |
| 71 | 0.008 ± 0.002 (2) |
| 72 | 0.036 ± 0.009 (2) |
| 73 | 0.016 ± 0.005 (2) |
| 74 | 0.18 ± 0.04 (2) |
| 75 | 0.038 ± 0.018 (2) |
| 76 | 0.024 ± 0.003 (2) |
| 77 | 0.15 ± 0 (2) |
| 78 | 0.094 ± 0.006 (2) |
| 79 | 0.02 ± 0.005 (2) |
| 80 | 0.055 ± 0.015 (2) |
| 81 | 0.185 ± 0.015 (2) |
| 82 | 0.11 ± 0.031 (2) |
| 83 | 0.019 ± 0.006 (2) |
| 84 | 0.01 ± 0.002 (2) |
| 85 | 0.03 ± 0.008 (2) |
| 86 | 0.026 ± 0.008 (2) |
| 87 | 0.087 ± 0.033 (2) |
| 88 | 2.95 ± 0.15 (2) |
| 89 | 0.455 ± 0.095 (2) |
| 90 | 0.083 ± 0.003 (2) |
| 91 | 0.092 ± 0.027 (2) |
| 92 | 0.082 ± 0.015 (2) |
| 93 | 0.215 ± 0.005 (2) |
| 94 | 0.016 ± 0.006 (2) |
| 95 | 0.024 ± 0.012 (2) |
| 96 | 0.02 ± 0.009 (2) |
| 97 | 0.11 ± 0.02 (2) |
| 98 | 0.016 ± 0.007 (3) |
| 99 | 0.038 ± 0.008 (2) |
| 100 | 0.155 ± 0.025 (2) |
| 101 | 1.185 ± 0.215 (2) |
| 102 | 0.024 ± 0.005 (2) |
| 103 | 0.018 ± 0.008 (2) |
| 104 | 0.069 ± 0.023 (3) |
| 105 | 0.006 ± 0.002 (13) |
| 106 | 0.435 ± 0.115 (2) |
| 107 | 0.005 ± 0.001 (7) |
| 108 | 0.158 ± 0.061 (2) |
| 109 | 0.008 ± 0.004 (3) |
| 110 | 0.003 ± 0.001 (3) |
| 111 | 0.006 ± 0.002 (4) |
| 112 | 0.068 ± 0.011 (2) |
| 113 | 0.015 ± 0.011 (3) |
| 114 | 0.001 ± 0.001 (4) |
| 115 | 0.004 ± 0.0006 (2) |
| 116 | 0.03 ± 0.013 (3) |
| 117 | 0.015 ± 0.008 (3) |
| 118 | 0.002 ± 0.0007 (4) |
| 119 | 0.0006 ± 0.0002 (3) |
| 120 | 0.003 ± 0.002 (2) |
| 121 | 0.006 ± 0.0008 (2) |
| 122 | 0.0006 ± 0.0003 (2) |
| 123 | 0.001 ± 0.0005 (2) |
| 124 | 0.65 ± 0.55 (2) |
| 125 | 0.011 ± 0.011 (4) |
| 126 | 0.008 ± 0 (2) |
| 127 | N/A |
| 128 | N/A |
| 129 | 0.011 ± 0.006 (3) |

N/A = not available

Competitive Binding Assay

The first 177 amino acids of the FimH protein can be expressed as a fusion protein with thrombin in a pET21b plasmid in bacteria. This FimH protein sequence contains the carbohydrate recognition domain (CRD) and shall be termed FimH-CRD. Following bacterial expression of the protein, the FimH-CRD protein is purified to homogeneity and the thrombin tag removed by protease cleavage. A competitive binding assay by fluorescence polarization is performed using 5 nM of the Alexa 647 mannoside probe and 60 nM of the FimH-CRD. The samples are assayed in a low volume 384 well microtiter plate in a final volume of 20 µl. The final assay buffer conditions are the following, 50 mM Tris-Cl, ph 7.0, 100 mM NaCl, 1 mM EDTA, 5 mM β-mercaptoethanol, 0.05% BSA and 2.5% DMSO. Two assays are performed for FimH, termed assay 1 or assay 2. The assay conditions are the same for both assays except the following: assay 1 has compounds prepared by manual dilution in a serial dilution factor with 12-point dose response while assay 2 has compounds prepared by a robotics system also through a serial dilution factor (12 point dose response) and initially prepared in duplicate in 384 well-Corning polypropylene round bottom plates. The assay 2 plates have compound which is then frozen and must be thawed prior to use. Initially the Alexa 647 probe and the FimH-CRD are added to the assay buffer and then 0.5 µl of test compound (assay 1 or 2) between 0.4 nM to 75 µM final concentration are added (12 point titration with 3-fold serial dilution). Control wells for the Alexa 647 probe are prepared with the same conditions except for the addition of the FimH-CRD protein. Plates are then incubated for 5 hrs at room temperature in the dark and under humid conditions to prevent drying. Plates are read using the SpectraMax Paradigm multi-mode plate reader and the appropriate fluorescent polarization detection cartridge (Alexa-647).

Alexa 647 mannoside probe is prepared using the similar procedure reported for FAM mannoside (Han, Z. et. al., 2010, J. Med. Chem., 53, 4779) and is described in the scheme below.

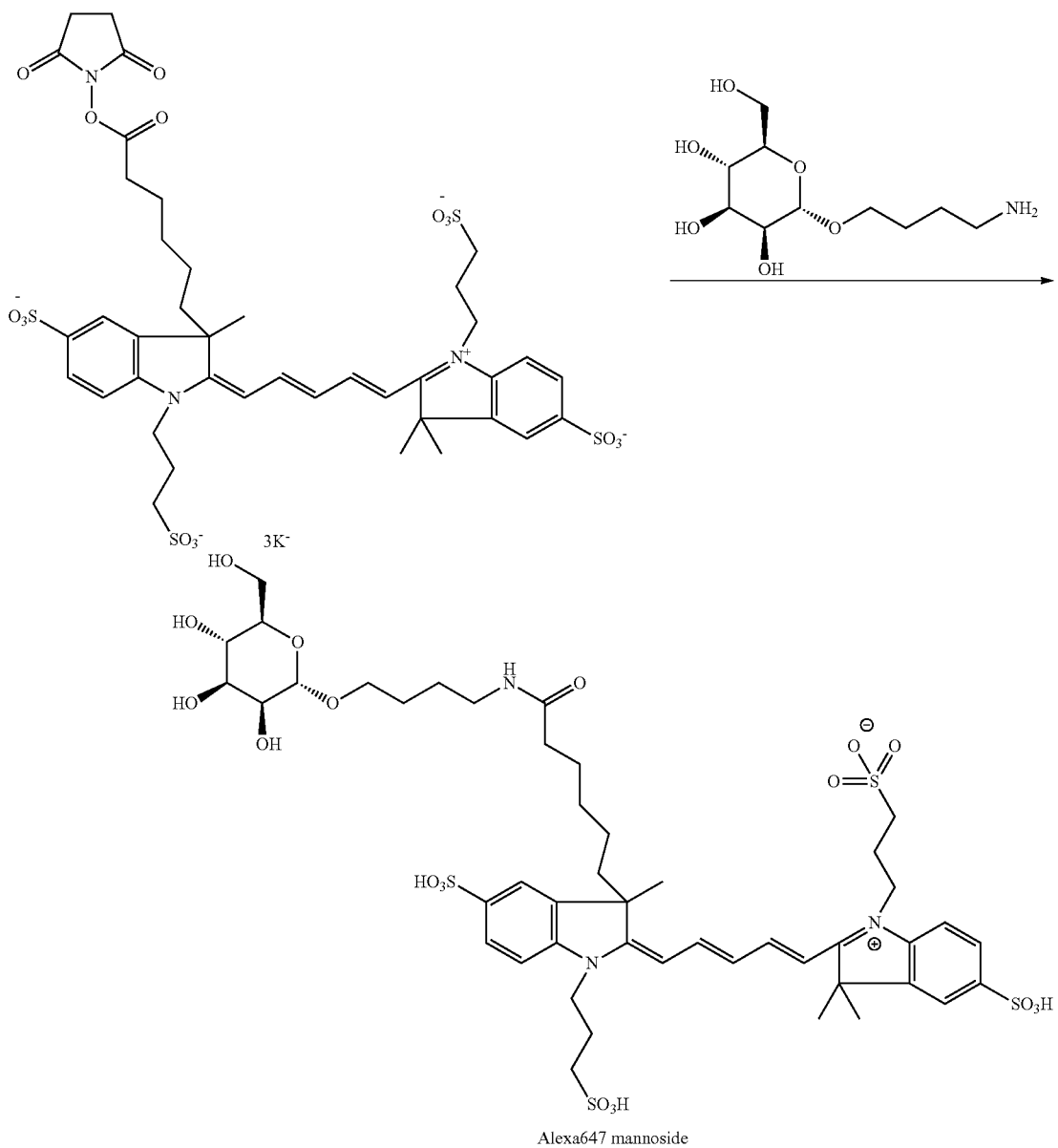

Alexa647 mannoside

To a blue colored stirred solution of (2S,3S,4S,5S,6R)-2-(4-aminobutoxy)-6-(hydroxymethyl)tetrahydropyran-3,4,5-triol (2.21 mg, 0.009 mmol) and the (2E)-2-[(2E,4E)-5-[3,3-dimethyl-5-sulfonato-1-(3-sulfonatopropyl)indol-1-ium-2-yl]penta-2,4-dienylidene]-3-[6-(2,5-dioxopyrrolidin-1-yl)

oxy-6-oxo-hexyl]-3-methyl-1-(3-sulfonatopropyl)indoline-5-sulfonate (Potassium Ion (3)) (4.9 mg, 0.0044 mmol) in DMF (44 µL) is added Et₃N (5.4 mg, 7.0 µL, 0.053 mmol) at RT. The solution is stirred at room temperature over night, concentrated, dissolved in water and purified on 12 g C-18 silica gel cartridge on Isolera system using acetonitrile in water (0 to 40%, 10 CV) and followed by lyophilization to afford Alexa 647 mannoside probe (3.3 mg, 34%) as deep blue solid.

The $K_d$ values of the compounds are determined from dose response curves using twelve concentrations per compound in duplicate. Curves are fitted to data points using Fluorescence Polarization competitive displacement analysis, and Kds are interpolated from the resulting curves using GraphPad Prism software, version 50.4 (GraphPad software Inc., San Diego, Calif., USA).

Mouse Feces Stability Assay

The mouse feces stability assay can be used to measure the stability of FimH antagonists in an environment that mimics the gut. Fresh mouse feces samples from a number of animals (at least 4) are homogenized with 10 volumes (w/v) of 100 mM potassium phosphate buffer (pH 6.5) using a Stomacher device. The feces mixture is then centrifuged 5 min at 2000 g and the supernatant is collected for incubation. Compounds to be tested are spiked at 100 uM in the feces supernatant and incubated at 37° C. up to 6 hours. The enzymatic reaction is stopped by adding 9 volumes of acetonitrile containing 0.1% formic acid and an internal standard. The mixture is centrifuged and the supernatants are analyzed by HPLC-MS/MS to assess percentage of parent remaining relative to a control sample. The compounds of the present invention are unexpectedly and surprisingly stable compared to similar compounds where the mannose moiety is not modified (see Compound A).

| Compound | Structure | In vitro mice feces stability - % Parent remaining at 6 h |
|---|---|---|
| A | 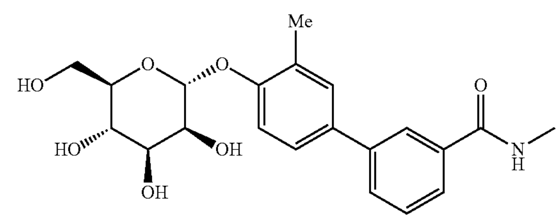 [SMILES: CNC(=O)c1cccc(-c2ccc(O[C@H]3O[C@H](CO)[C@@H](O)[C@H](O)[C@@H]3O)c(C)c2)c1] | 0 |
| 4 | 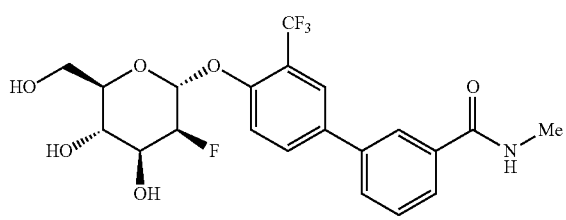 [SMILES: CNC(=O)c1cccc(-c2ccc(O[C@H]3O[C@H](CO)[C@@H](O)[C@H](O)[C@@H]3F)c(C(F)(F)F)c2)c1] | 108 |
| 6 | 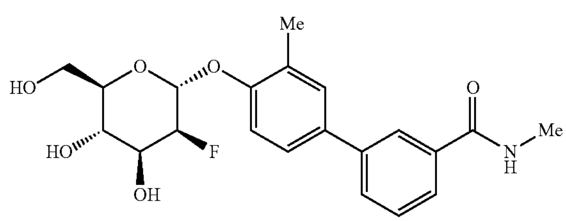 [SMILES: CNC(=O)c1cccc(-c2ccc(O[C@H]3O[C@H](CO)[C@@H](O)[C@H](O)[C@@H]3F)c(C)c2)c1] | 108 |
| 12 | 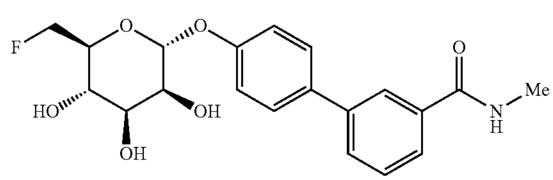 [SMILES: CNC(=O)c1cccc(-c2ccc(O[C@H]3O[C@H](CF)[C@@H](O)[C@H](O)[C@@H]3O)cc2)c1] | 118 |
| 26 | 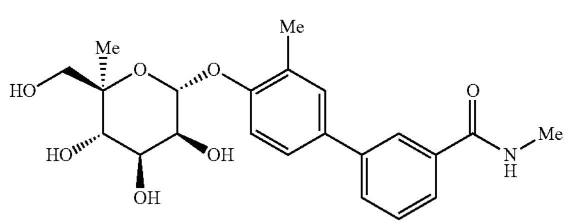 [SMILES: CNC(=O)c1cccc(-c2ccc(O[C@H]3O[C@](C)(CO)[C@@H](O)[C@H](O)[C@@H]3O)c(C)c2)c1] | 101 |

| Compound | Structure | In vitro mice feces stability - % Parent remaining at 6 h |
|---|---|---|
| 27 | 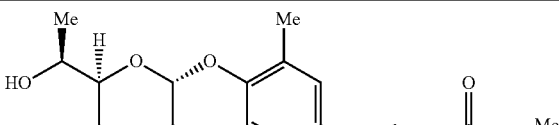 | 93 |
| 36 | 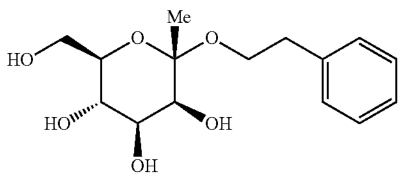 [SMILES: C[C@]1(OCCc2ccccc2)O[C@H](CO)[C@@H](O)[C@H](O)[C@@H]1O] | 81 |

Human Feces Stability Assay

The human feces stability assay ca be used to measure the stability of FimH antagonists in an environment that mimics the gut. Fresh human feces samples from 3 donors are homogenized with 10 volumes (w/v) of 100 mM potassium phosphate buffer (pH 6.5) using a Stomacher device. The feces mixture is then centrifuged 5 min at 2000 g and supernatant is collected for incubations. Compounds to be tested are spiked at 100 uM in feces supernatant and incubated at 37° C. up to 24 hours. The enzymatic reaction is stopped by adding 9 volumes of acetonitrile containing 0.1% formic acid and internal standard. The mixture is centrifuged and the supernatants are analysed by HPLC-MS/MS to assess percentage of parent remaining relative to a control sample. The compounds of the present invention are unexpectedly and surprisingly stable compared to similar compounds where the mannose moiety is not modified (see Compound A).

| Compound | Structure | In vitro human feces stability - % Parent remaining at 24 h |
|---|---|---|
| A | 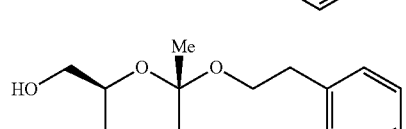 | 35% |
| 25 | 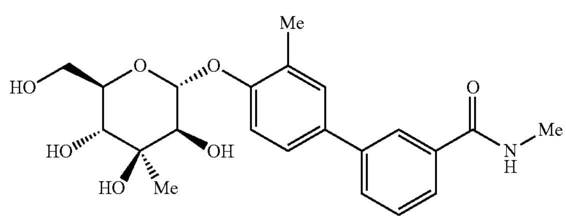 [SMILES: CNC(=O)c1cccc(-c2ccc(O[C@H]3O[C@H](CO)[C@@H](O)[C@](C)(O)[C@@H]3O)c(C)c2)c1] | 107% |
| 33 | 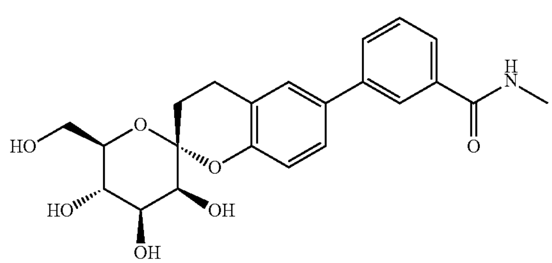 [SMILES: CNC(=O)c1cccc(-c2ccc3c(c2)CC[C@]2(O3)O[C@H](CO)[C@@H](O)[C@H](O)[C@@H]2O)c1] | 105% |

| Compound | Structure | In vitro human feces stability - % Parent remaining at 24 h |
|---|---|---|
| 36 | (structure of 2-C-methyl mannose phenethyl glycoside) | 99% |

Mouse Excretion Study Following FimH Antagonist Oral Dosing

Mice are dosed 10 mg/kg orally (10 mL/kg; 0.5% methocel) with FimH antagonists and urine and feces are collected on ice up to 72 h in excretion cages. Post-collection, feces samples are diluted with 10 volumes of water and homogenized using a Stomacher device. Feces mixture and urine samples are then quenched with acetonitrile containing an internal standard, centrifuged, and the supernatants are then diluted with 1 volume of water prior to analysis by HPLC-MS/MS in SRM mode. The compounds of the present invention are unexpectedly and surprisingly stable compared to similar compounds where the mannose moiety is not modified (see Compound A).

While we have described a number of embodiments of this invention, it is apparent that our basic examples may be altered to provide other embodiments that utilize the compounds, methods, and processes of this invention. Therefore, it will be appreciated that the scope of this invention is to be defined by the appended claims rather than by the specific embodiments that have been represented by way of example herein.

| Compound Number | Structure | % Oral dose recovered intact in mice feces | % Oral dose recovered intact in mice urine |
|---|---|---|---|
| A | (biphenyl methylamide mannoside structure) | 8.4% | 0.20% |
| 36 | 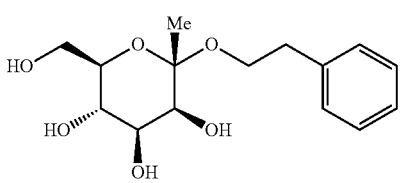 [SMILES: C[C@]1(OCCc2ccccc2)O[C@H](CO)[C@@H](O)[C@H](O)[C@@H]1O] | 108% | 0.90% |

The invention claimed is:

1. A compound of Formula I

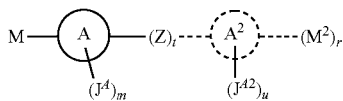

or a pharmaceutically acceptable salt thereof, wherein each M and M² is independently

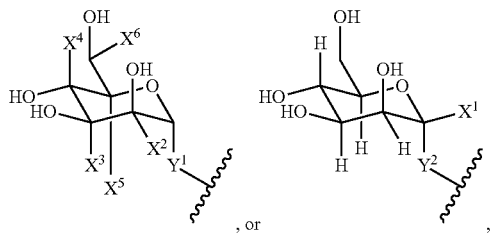

wherein:
$Y^1$ is —O—, —O($C_1$-$C_4$ aliphatic)-, —O(halo$C_1$-$C_4$ aliphatic)-, —S—, —S($C_1$-$C_4$ aliphatic)-, —S(O)$_p$—, —S(O)$_p$($C_1$-$C_4$ aliphatic)-, or —($C_1$-$C_6$)aliphatic;

$Y^2$ is —O($C_1$-$C_4$ aliphatic)-, —O(halo$C_1$-$C_4$ aliphatic)-, —S($C_1$-$C_4$ aliphatic)-, —SO$_2$($C_1$-$C_4$ aliphatic)-, or —($C_1$-$C_6$) aliphatic;

$X^1$ is methyl or —$U^1$—$V^1$; $X^1$ is optionally substituted with 1-4 occurrences of halo;

$U^1$ is —(CH$_2$)$_q$— or —C(O)—;

$V^1$ is a $C_1$-$C_{10}$ aliphatic wherein up to four methylene units can be optionally replaced with —O—, —NR²—, —S—, —C(O)—, —S(O)—, —S(O)$_2$—, or P(O);

$X^2$ is H, $C_1$-$C_{10}$ aliphatic, —$U^2$—$V^2$, or —$U^2$—$V^2$-Q;

$U^2$ is —(CH$_2$)$_q$— or —C(O)—;

$V^2$ is a $C_1$-$C_{10}$ aliphatic wherein up to four methylene units can be optionally replaced with —O—, —NR²—, —S—, —C(O)—, —S(O)—, —S(O)$_2$—, or P(O);

Q is a 3-8 membered saturated, partially unsaturated, or aromatic ring having 0-4 heteratoms selected from oxygen, nitrogen, or sulfur;

wherein $X^2$ is optionally substituted with 1-4 occurrences of halo, CN, NO$_2$, or $C_1$-$C_{10}$aliphatic wherein up to three methylene units of the $C_1$-$C_{10}$aliphatic can be optionally replaced with —NR—, —O—, —S—, —C(O)—, or —S(O)—, or —S(O)$_2$—;

each $X^3$, $X^4$, $X^5$, and $X^6$ is independently H or $C_{1-3}$alkyl; provided that only one of $X^2$, $X^3$, $X^4$, $X^5$, and $X^6$ is not H;

Ring A is $C_3$-$C_{10}$ cycloalkyl, 3-12 membered heterocyclyl, $C_{6-10}$ aryl, or 5-14 membered heteroaryl; wherein the heterocyclyl or heteroaryl independently has 1-6 heteroatoms selected from oxygen, nitrogen, or sulfur;

Ring $A^2$ is optionally absent, $C_3$-$C_{10}$ cycloalkyl, 3-12 membered heterocyclyl, $C_{6-10}$ aryl, or 5-14 membered heteroaryl;

Z is —CH=CH—, —C≡C—, or Ring B substituted by $(J^B)_n$;

Ring B is $C_3$-$C_{10}$ cycloalkyl, 3-12 membered heterocyclyl, $C_{6-10}$ aryl, or 5-14 membered heteroaryl; wherein said heterocyclyl or heterocyclyl independently has 1-6 heteroatoms selected from oxygen, nitrogen, or sulfur;

each $J^A$, $J^{A2}$, and $J^B$ is independently halogen, CN, NO$_2$, oxo, $C_{3-8}$ cycloalkyl, 3-8 membered heterocyclyl, $C_{6-10}$ aryl, 5-10 membered heteroaryl, ($C_{6-10}$ aryl)-($C_1$-$C_6$alkyl)-, (5-10 membered heteroaryl)-($C_1$-$C_6$alkyl)-, ($C_{3-8}$ cycloalkyl)-($C_1$-$C_6$alkyl)-, (3-8 membered heterocyclyl)-($C_1$-$C_6$alkyl)-, or a $C_1$-$C_{12}$ aliphatic; wherein up to four methylene units of the $C_1$-$C_{12}$ aliphatic or up to three methylene units of the $C_1$-$C_6$alkyl can be optionally replaced with —NR, —O—, —S—, —C(O)—, —S(O)—, —S(O)$_2$—, or P(O); each $J^A$, $J^{A2}$, and $J^B$ is independently and optionally substituted with 1-5 occurrences of halo, CN, NO$_2$, or $C_1$-$C_{10}$aliphatic wherein up to three methylene units of the $C_1$-$C_{10}$aliphatic can be optionally replaced with —NR—, —O—, —S—, —C(O)—, or —S(O)—, or —S(O)$_2$—;

R and R² are each independently H, $C_1$-$C_6$ aliphatic, or $C_{3-6}$cycloalkyl;

each m, n, and u is independently 0, 1, 2, 3, or 4;

each t and r is independently 0 or 1; and each p and q is independently 1 or 2.

2. The compound of claim 1, wherein Ring $A^2$ is absent; r and q are 0; t is 1; and Z is Ring B as shown in Formula Ia:

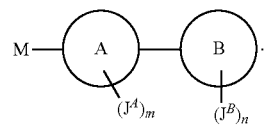

3. The compound of claim 2, as represented in Formula II:

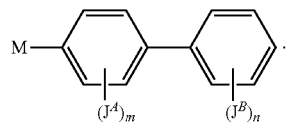

4. The compound of claim 1, wherein M is

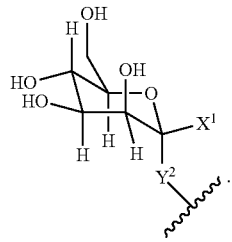

5. The compound of claim 1, as represented by formula A:

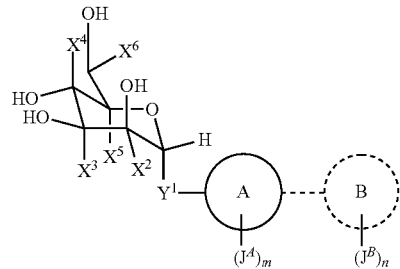

wherein
Y$^1$ is —O—, —O(C$_1$-C$_4$alkyl)-, —S—, —S(C$_1$-C$_4$alkyl)-, —S(O)$_p$—, —SO$_p$(C$_1$-C$_4$alkyl)-, or —(C$_1$-C$_6$)aliphatic;

X$^2$ is H, C$_1$-C$_{10}$ aliphatic, —U$^2$—V$^2$, or —U$^2$—V$^2$-Q;

U$^2$ is —(CH$_2$)$_q$— or —C(O)—;

V$^2$ is a C$_1$-C$_{10}$ aliphatic wherein up to four methylene units can be optionally replaced with —O—, —NR$^2$—, —S—, —C(O)—, —S(O)—, —S(O)$_2$—, or P(O);

Q is a 3-8 membered saturated, partially unsaturated, or aromatic ring having 0-4 heteratoms selected from oxygen, nitrogen, or sulfur;

wherein X$^2$ is optionally substituted with 1-4 occurrences of halo, CN, NO$_2$, or C$_1$-C$_{10}$ aliphatic wherein up to three methylene units of the C$_1$-C$_{10}$aliphatic can be optionally replaced with —NR—, —O—, —S—, —C(O)—, or —S(O)—, or —S(O)$_2$—;

R$^2$ is H, C$_1$-C$_6$ aliphatic, or C$_{3-6}$cycloalkyl;

each X$^3$, X$^4$, and X$^6$ is independently H or C$_{1-3}$alkyl;

X$^5$ is H;

provided that only one of X$^2$, X$^3$, X$^4$, and X$^6$ is not H;

Ring A is C$_3$-C$_{10}$ cycloalkyl, 3-12 membered heterocyclyl, C$_{6-10}$ aryl, or 5-14 membered heteroaryl; wherein the heterocyclyl or heteroaryl independently has 1-6 heteroatoms selected from oxygen, nitrogen, or sulfur; Ring A is optionally bonded to Ring B;

Ring B is absent, C$_3$-C$_{10}$ cycloalkyl, 3-12 membered heterocyclyl, C$_{6-10}$ aryl, or 5-14 membered heteroaryl; wherein said heterocyclyl or heterocyclyl independently has 1-6 heteroatoms selected from oxygen, nitrogen, or sulfur;

each J$^A$ and J$^B$ is independently halogen, CN, NO$_2$, C$_{3-8}$ cycloalkyl, 3-8 membered heterocyclyl, C$_{6-10}$ aryl, 5-10 membered heteroaryl, (C$_{6-10}$ aryl)-(C$_1$-C$_6$alkyl)-, (5-10 membered heteroaryl)-(C$_1$-C$_6$alkyl)-, or a C$_1$-C$_{12}$ aliphatic wherein up to four methylene units of the C$_1$-C$_{10}$ aliphatic can be optionally replaced with —NR, —O—, —S—, —C(O)—, —S(O)—, —SO$_2$—, or P(O); each J$^A$ and J$^B$ is independently and optionally substituted with 1-5 occurrences of halo, CN, or NO$_2$;

R is H, C$_1$-C$_6$ aliphatic, C$_{3-6}$cycloalkyl, C(O)OH, C(O)O(C$_{1-4}$alkyl), or C(O)(C$_{1-4}$alkyl);

each m and n is independently 0, 1, 2, 3, or 4;

each p and q is independently 1 or 2.

6. The compound of claim 1, as represented by formula B:

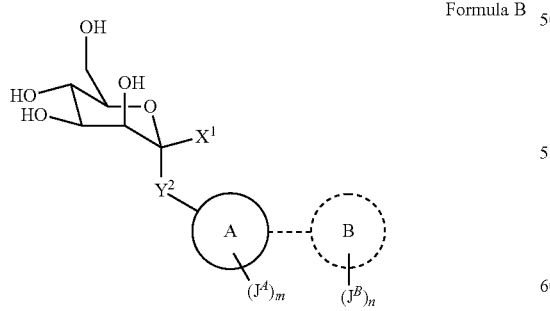

Formula B wherein
Y$^2$ is —O(C$_1$-C$_4$alkyl)-, —S(C$_1$-C$_4$alkyl)-, —S(O)—, —SO$_2$(C$_1$-C$_4$alkyl)-, or —(C$_1$-C$_6$)alkyl;

X$^1$ is methyl or —U$^1$—V$^1$; X$^1$ is optionally substituted with 1-4 occurrences of halo;

U$^1$ is —(CH$_2$)$_q$— or —C(O)—;

V$^1$ is a C$_1$-C$_{10}$ aliphatic wherein up to four methylene units can be optionally replaced with —O—, —NR$^2$—, —S—, —C(O)—, —S(O)—, —S(O)$_2$—, or P(O);

Ring A is C$_3$-C$_{10}$ cycloalkyl, 3-12 membered heterocyclyl, C$_{6-10}$ aryl, or 5-14 membered heteroaryl; wherein the heterocyclyl or heteroaryl independently has 1-6 heteroatoms selected from oxygen, nitrogen, or sulfur; Ring A is optionally bonded to Ring B;

Ring B is absent, C$_3$-C$_{10}$ cycloalkyl, 3-12 membered heterocyclyl, C$_{6-10}$ aryl, or 5-14 membered heteroaryl; wherein said heterocyclyl or heterocyclyl independently has 1-6 heteroatoms selected from oxygen, nitrogen, or sulfur;

each J$^A$ and J$^B$ is independently halogen, CN, NO$_2$, C$_{3-8}$ cycloalkyl, 3-8 membered heterocyclyl, C$_{6-10}$ aryl, 5-10 membered heteroaryl, (C$_{6-10}$ aryl)-(C$_1$-C$_6$alkyl)-, (5-10 membered heteroaryl)-(C$_1$-C$_6$alkyl)-, or a C$_1$-C$_{12}$ aliphatic wherein up to four methylene units of the C$_1$-C$_{10}$ aliphatic can be optionally replaced with —NR, —O—, —S—, —C(O)—, —S(O)—, —SO$_2$—, or P(O); each J$^A$ and J$^B$ is independently and optionally substituted with 1-5 occurrences of halo, CN, or NO$_2$;

R is H, C$_1$-C$_6$ aliphatic, C$_{3-6}$cycloalkyl, C(O)OH, C(O)O(C$_{1-4}$alkyl), or C(O)(C$_{1-4}$alkyl);

each m and n is independently 0, 1, 2, 3, or 4;

each p and q is independently 1 or 2.

7. The compound of claim 1, as represented by formula III:

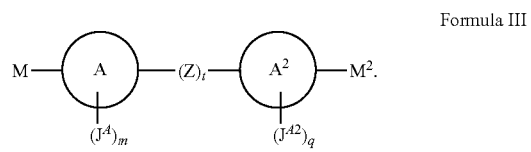

Formula III

8. The compound of claim 1, as represented by formula E:

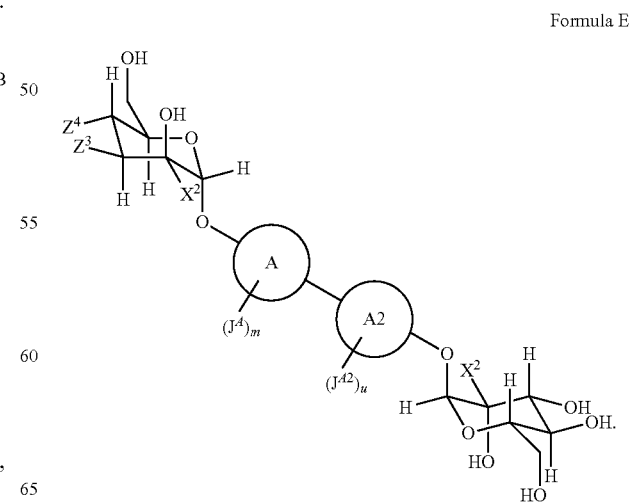

Formula E

9. The compound of claim 1, as represented by formula F:
10. The compound of claim 1, as represented by formula G:
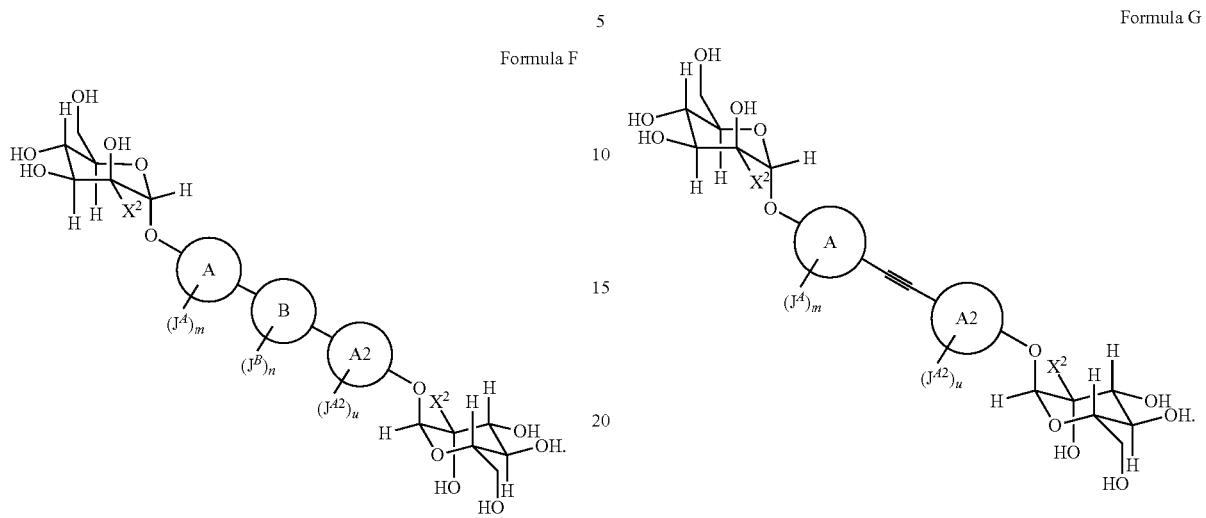
11. The compound of claim 1, wherein the compound is selected from one of the following:
| Compound No. | Structure |
|---|---|
| 13 | 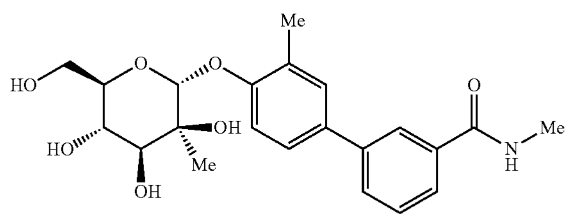 [SMILES: CNC(=O)c1cccc(-c2ccc(O[C@H]3O[C@H](CO)[C@@H](O)[C@H](O)[C@]3(C)O)c(C)c2)c1] |
| 14 | 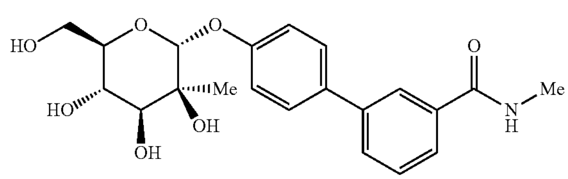 [SMILES: CNC(=O)c1cccc(-c2ccc(O[C@H]3O[C@H](CO)[C@@H](O)[C@H](O)[C@]3(C)O)cc2)c1] |
| 15 | 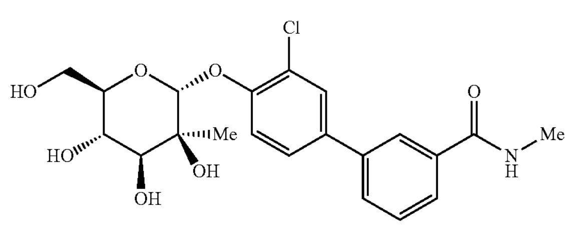 |
| 16 | 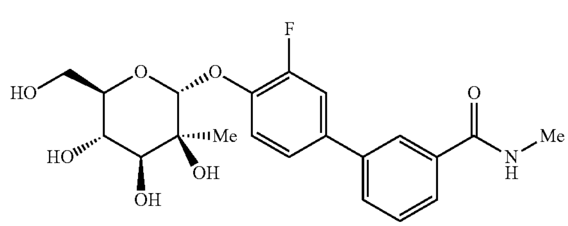 |

| Compound No. | Structure |
|---|---|
| 17 | 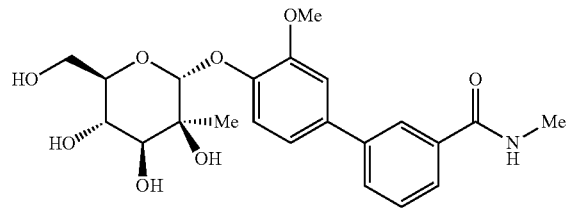 [SMILES: CNC(=O)c1cccc(-c2ccc(O[C@H]3O[C@H](CO)[C@@H](O)[C@H](O)[C@]3(C)O)c(OC)c2)c1] |
| 18 | 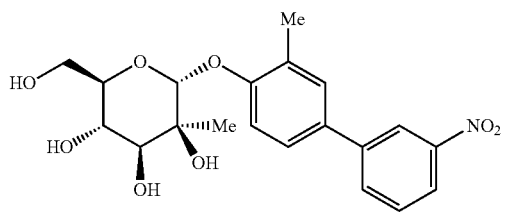 [SMILES: Cc1cc(-c2cccc([N+](=O)[O-])c2)ccc1O[C@H]1O[C@H](CO)[C@@H](O)[C@H](O)[C@]1(C)O] |
| 19 | 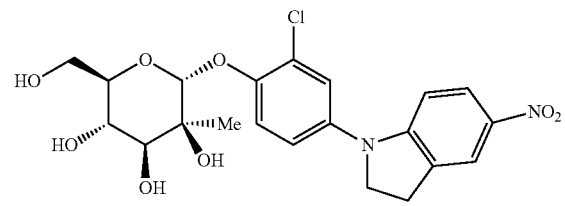 [SMILES: C[C@@]1(O)[C@@H](Oc2ccc(N3CCc4cc([N+](=O)[O-])ccc43)cc2Cl)O[C@H](CO)[C@@H](O)[C@@H]1O] |
| 20 | 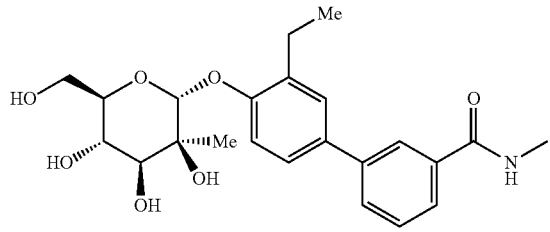 [SMILES: CCc1cc(-c2cccc(C(=O)NC)c2)ccc1O[C@H]1O[C@H](CO)[C@@H](O)[C@H](O)[C@]1(C)O] |
| 21 | 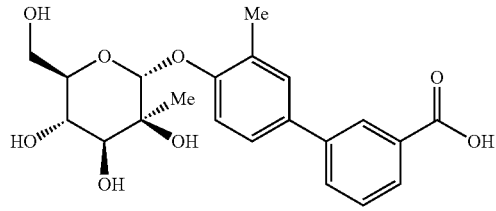 [SMILES: Cc1cc(-c2cccc(C(=O)O)c2)ccc1O[C@H]1O[C@H](CO)[C@@H](O)[C@H](O)[C@]1(C)O] |
| 22 | 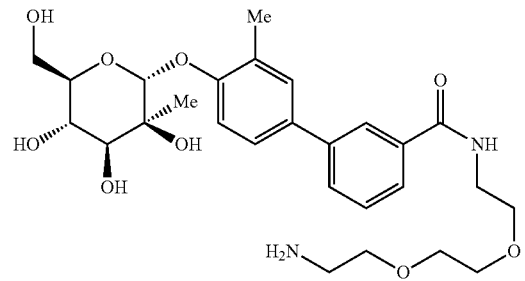 [SMILES: Cc1cc(-c2cccc(C(=O)NCCOCCOCCN)c2)ccc1O[C@H]1O[C@H](CO)[C@@H](O)[C@H](O)[C@]1(C)O] |

-continued

| Compound No. | Structure |
|---|---|
| 23 | 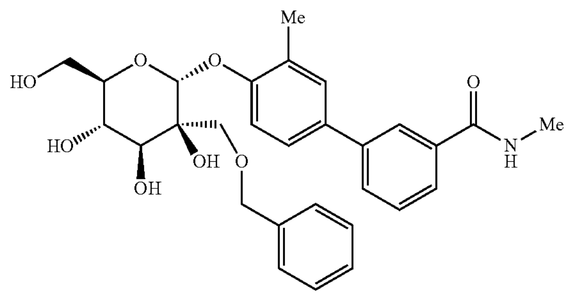 [SMILES: CNC(=O)c1cccc(-c2ccc(O[C@H]3O[C@H](CO)[C@@H](O)[C@H](O)[C@@]3(O)COCc3ccccc3)c(C)c2)c1] |
| 24 | 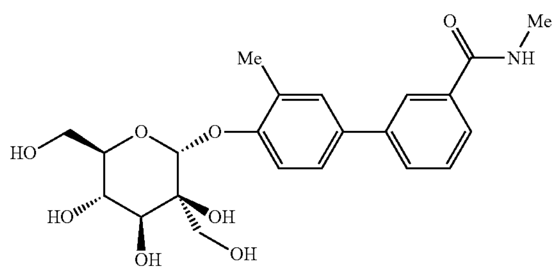 [SMILES: CNC(=O)c1cccc(-c2ccc(O[C@H]3O[C@H](CO)[C@@H](O)[C@H](O)[C@@]3(O)CO)c(C)c2)c1] |
| 25 | 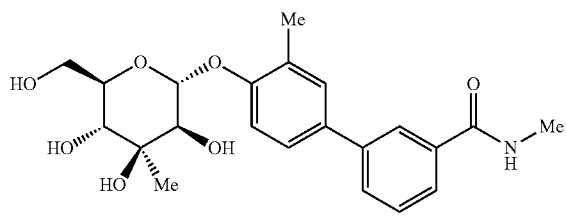 [SMILES: CNC(=O)c1cccc(-c2ccc(O[C@H]3O[C@H](CO)[C@@H](O)[C@](C)(O)[C@@H]3O)c(C)c2)c1] |
| 26 | 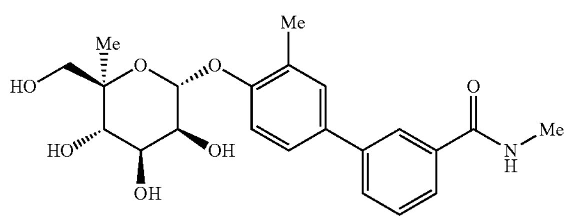 [SMILES: CNC(=O)c1cccc(-c2ccc(O[C@H]3O[C@](C)(CO)[C@@H](O)[C@H](O)[C@@H]3O)c(C)c2)c1] |
| 27 | 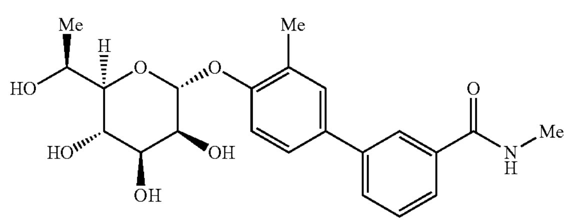 [SMILES: CNC(=O)c1cccc(-c2ccc(O[C@H]3O[C@H]([C@H](C)O)[C@@H](O)[C@H](O)[C@@H]3O)c(C)c2)c1] |
| 28 | 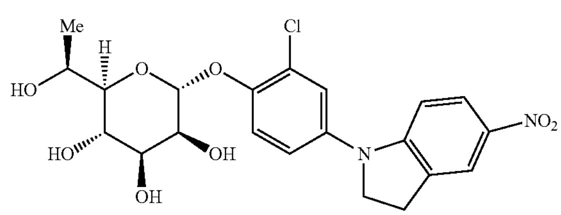 [SMILES: C[C@H](O)[C@H]1O[C@H](Oc2ccc(N3CCc4cc([N+](=O)[O-])ccc43)cc2Cl)[C@@H](O)[C@@H](O)[C@@H]1O] |

-continued
| Compound No. | Structure |
|---|---|
| 29 | 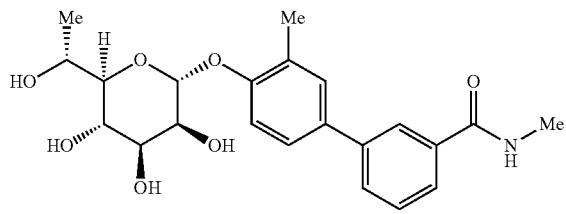 [SMILES: CNC(=O)c1cccc(-c2ccc(O[C@H]3O[C@H]([C@@H](C)O)[C@@H](O)[C@H](O)[C@@H]3O)c(C)c2)c1] |
| 30 | 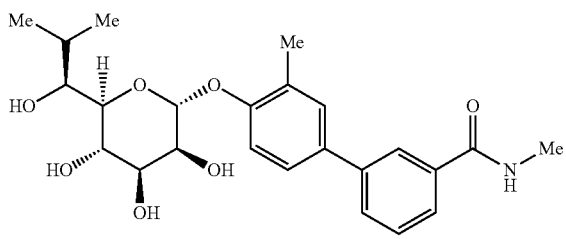 [SMILES: CNC(=O)c1cccc(-c2ccc(O[C@H]3O[C@H]([C@@H](O)C(C)C)[C@@H](O)[C@H](O)[C@@H]3O)c(C)c2)c1] |
| 31 | 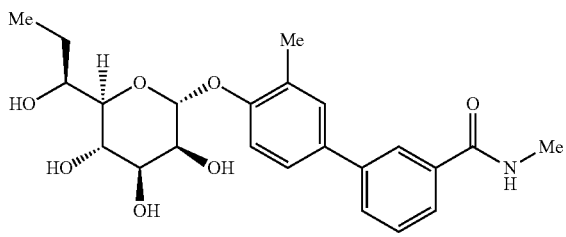 [SMILES: CC[C@H](O)[C@H]1O[C@H](Oc2ccc(-c3cccc(C(=O)NC)c3)cc2C)[C@@H](O)[C@@H](O)[C@@H]1O] |
| 35 | 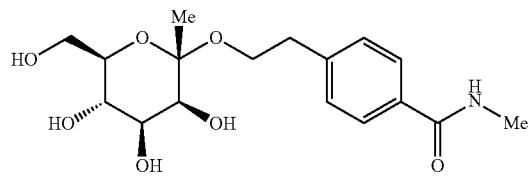 [SMILES: CNC(=O)c1ccc(CCO[C@@]2(C)O[C@H](CO)[C@@H](O)[C@H](O)[C@@H]2O)cc1] |
| 36 | 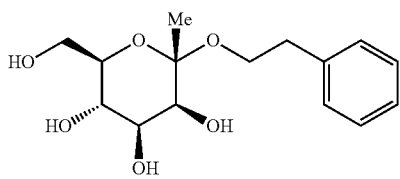 |
| 37 | 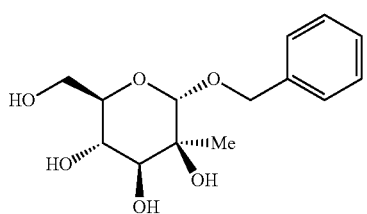 [SMILES: C[C@@]1(O)[C@@H](OCc2ccccc2)O[C@H](CO)[C@@H](O)[C@@H]1O] |
| 38 | 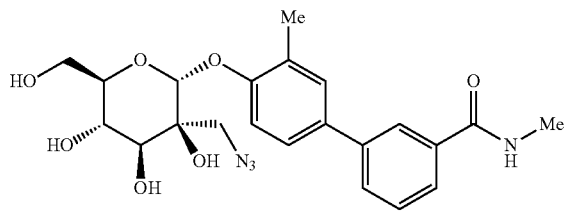 |

-continued
| Compound No. | Structure |
|---|---|
| 39 | 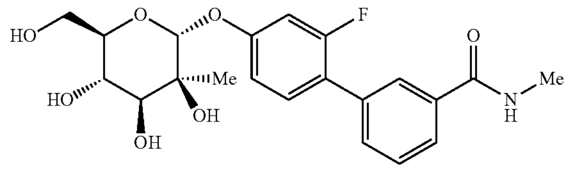 [SMILES: CNC(=O)c1cccc(-c2ccc(O[C@H]3O[C@H](CO)[C@@H](O)[C@H](O)[C@]3(C)O)cc2F)c1] |
| 40 | 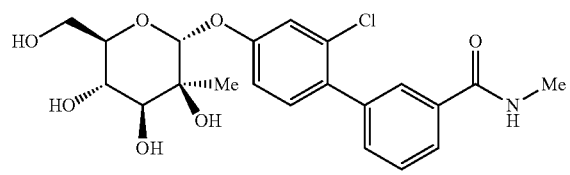 |
| 41 | 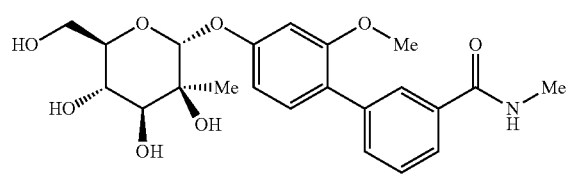 |
| 42 | 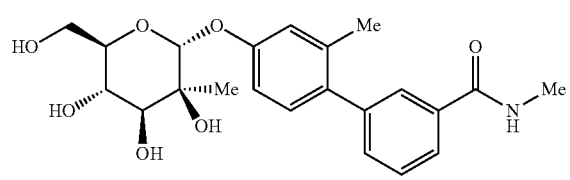 |
| 43 | 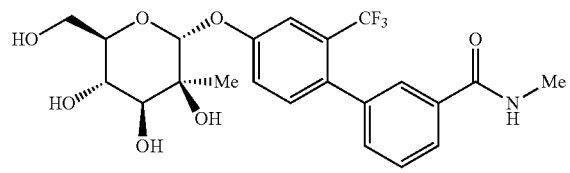 |
| 44 | 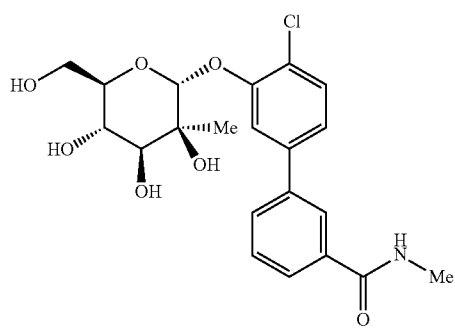 [SMILES: CNC(=O)c1cccc(-c2ccc(Cl)c(O[C@H]3O[C@H](CO)[C@@H](O)[C@H](O)[C@]3(C)O)c2)c1] |
| 45 | 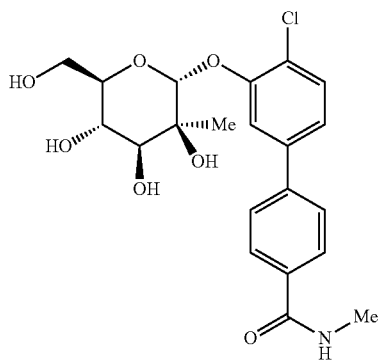 [SMILES: CNC(=O)c1ccc(-c2ccc(Cl)c(O[C@H]3O[C@H](CO)[C@@H](O)[C@H](O)[C@]3(C)O)c2)cc1] |

| Compound No. | Structure |
|---|---|
| 46 | 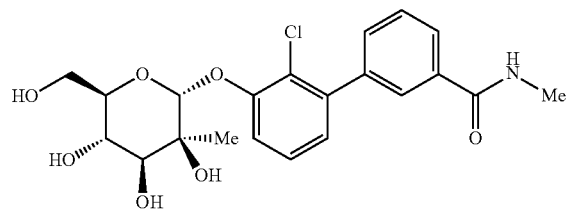 [SMILES: CNC(=O)c1cccc(-c2cccc(O[C@H]3O[C@H](CO)[C@@H](O)[C@H](O)[C@]3(C)O)c2Cl)c1] |
| 47 | 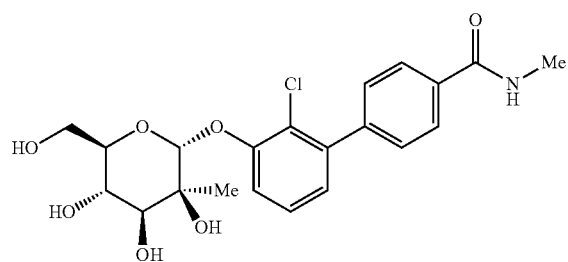 [SMILES: CNC(=O)c1ccc(-c2cccc(O[C@H]3O[C@H](CO)[C@@H](O)[C@H](O)[C@]3(C)O)c2Cl)cc1] |
| 48 | 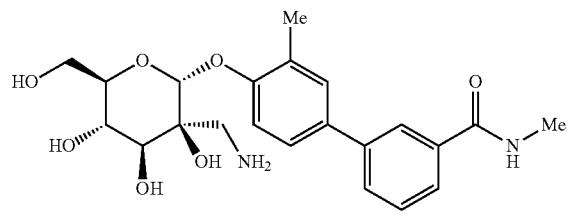 |
| 49 | 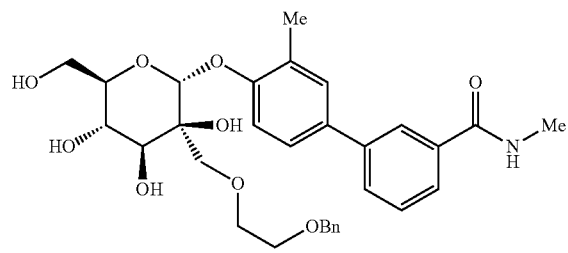 |
| 50 | 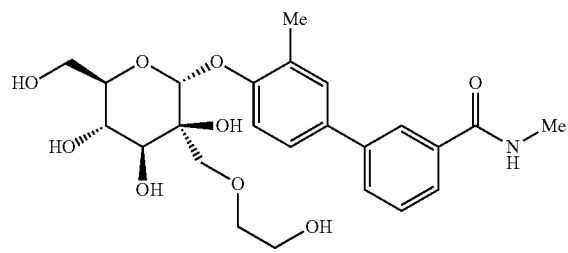 [SMILES: CNC(=O)c1cccc(-c2ccc(O[C@H]3O[C@H](CO)[C@@H](O)[C@H](O)[C@@]3(O)COCCO)c(C)c2)c1] |
| 51 | 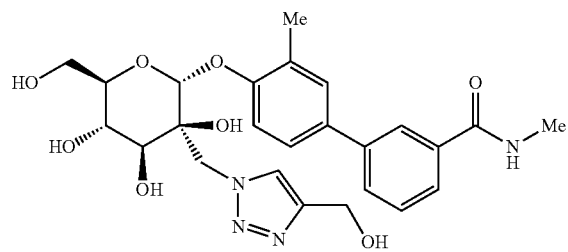 [SMILES: CNC(=O)c1cccc(-c2ccc(O[C@H]3O[C@H](CO)[C@@H](O)[C@H](O)[C@@]3(O)Cn3cc(CO)nn3)c(C)c2)c1] |

-continued
| Compound No. | Structure |
|---|---|
| 52 | 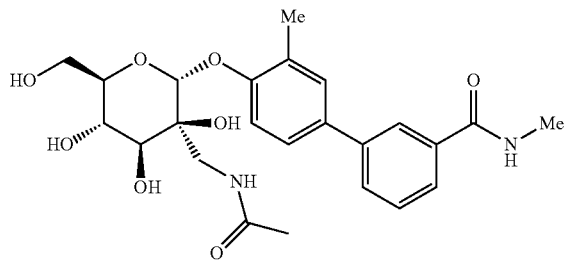 [SMILES: CNC(=O)c1cccc(-c2ccc(O[C@H]3O[C@H](CO)[C@@H](O)[C@H](O)[C@@]3(O)CNC(C)=O)c(C)c2)c1] |
| 53 | 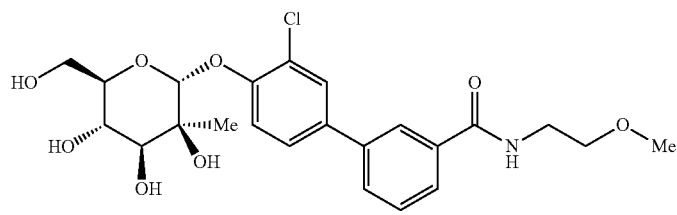 [SMILES: COCCNC(=O)c1cccc(-c2ccc(O[C@H]3O[C@H](CO)[C@@H](O)[C@H](O)[C@]3(C)O)c(Cl)c2)c1] |
| 54 | 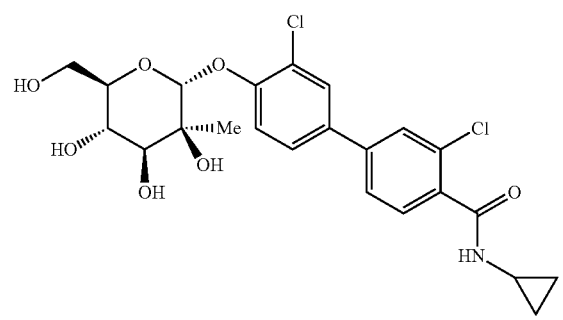 [SMILES: C[C@@]1(O)[C@@H](Oc2ccc(-c3ccc(C(=O)NC4CC4)c(Cl)c3)cc2Cl)O[C@H](CO)[C@@H](O)[C@@H]1O] |
| 55 | 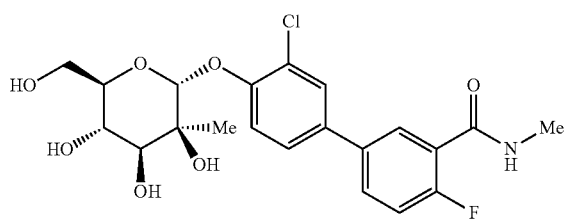 [SMILES: CNC(=O)c1cc(-c2ccc(O[C@H]3O[C@H](CO)[C@@H](O)[C@H](O)[C@]3(C)O)c(Cl)c2)ccc1F] |
| 56 | 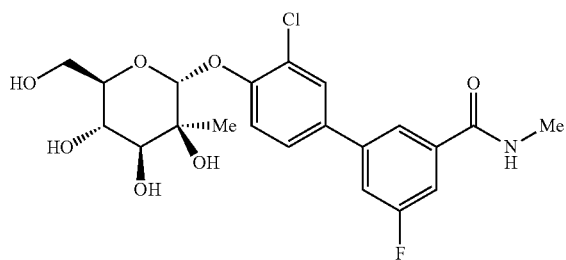 |
| 57 | 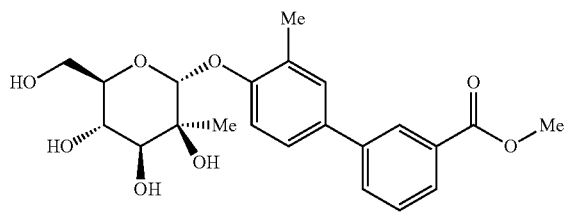 [SMILES: COC(=O)c1cccc(-c2ccc(O[C@H]3O[C@H](CO)[C@@H](O)[C@H](O)[C@]3(C)O)c(C)c2)c1] |

-continued
| Compound No. | Structure |
|---|---|
| 58 | 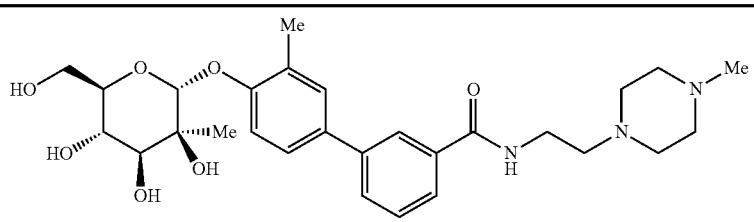 |
| 59 | 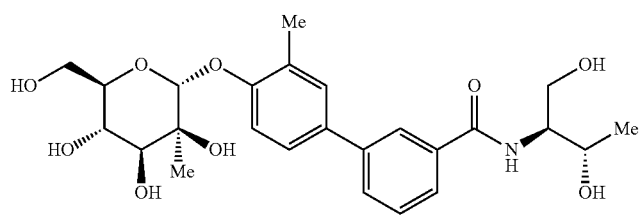 [SMILES: Cc1cc(-c2cccc(C(=O)N[C@@H](CO)[C@H](C)O)c2)ccc1O[C@H]1O[C@H](CO)[C@@H](O)[C@H](O)[C@]1(C)O] |
| 60 | 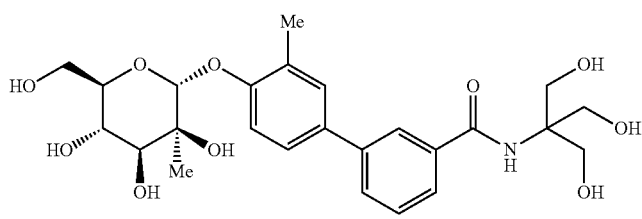 [SMILES: Cc1cc(-c2cccc(C(=O)NC(CO)(CO)CO)c2)ccc1O[C@H]1O[C@H](CO)[C@@H](O)[C@H](O)[C@]1(C)O] |
| 61 | 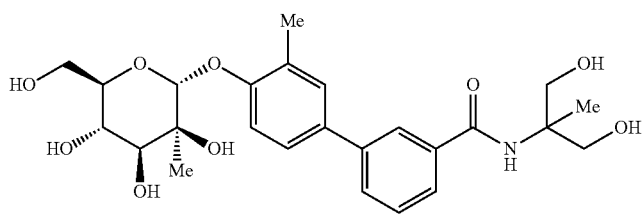 [SMILES: Cc1cc(-c2cccc(C(=O)NC(C)(CO)CO)c2)ccc1O[C@H]1O[C@H](CO)[C@@H](O)[C@H](O)[C@]1(C)O] |
| 62 | 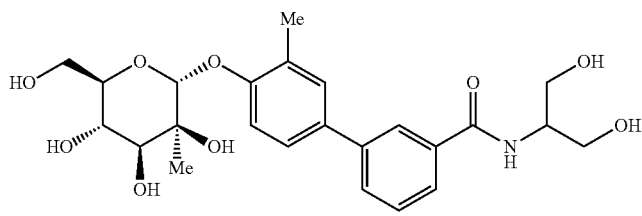 [SMILES: Cc1cc(-c2cccc(C(=O)NC(CO)CO)c2)ccc1O[C@H]1O[C@H](CO)[C@@H](O)[C@H](O)[C@]1(C)O] |
| 63 | 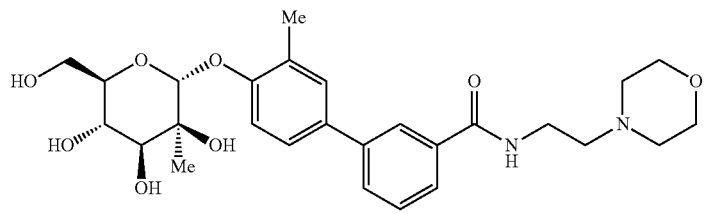 [SMILES: Cc1cc(-c2cccc(C(=O)NCCN3CCOCC3)c2)ccc1O[C@H]1O[C@H](CO)[C@@H](O)[C@H](O)[C@]1(C)O] |
| 64 | 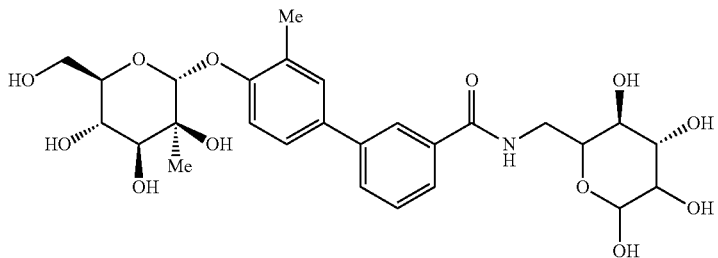 [SMILES: Cc1cc(-c2cccc(C(=O)NCC3OC(O)C(O)[C@@H](O)[C@@H]3O)c2)ccc1O[C@H]1O[C@H](CO)[C@@H](O)[C@H](O)[C@]1(C)O] |

-continued
| Compound No. | Structure |
|---|---|
| 65 | 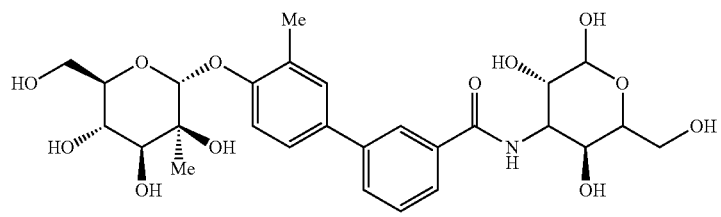 [SMILES: Cc1cc(-c2cccc(C(=O)NC3[C@H](O)C(O)OC(CO)[C@H]3O)c2)ccc1O[C@H]1O[C@H](CO)[C@@H](O)[C@H](O)[C@]1(C)O] |
| 66 | 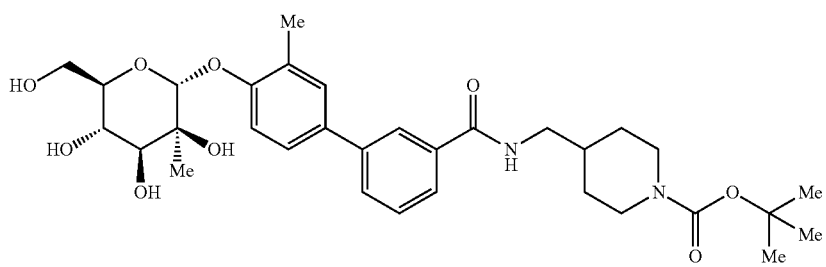 [SMILES: Cc1cc(-c2cccc(C(=O)NCC3CCN(C(=O)OC(C)(C)C)CC3)c2)ccc1O[C@H]1O[C@H](CO)[C@@H](O)[C@H](O)[C@]1(C)O] |
| 67 | 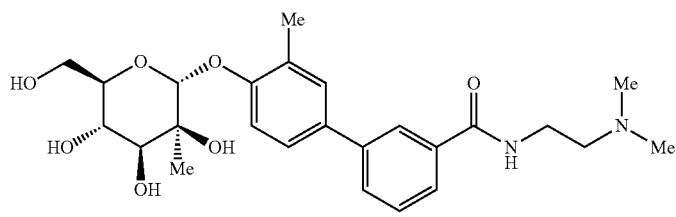 [SMILES: Cc1cc(-c2cccc(C(=O)NCCN(C)C)c2)ccc1O[C@H]1O[C@H](CO)[C@@H](O)[C@H](O)[C@]1(C)O] |
| 68 | 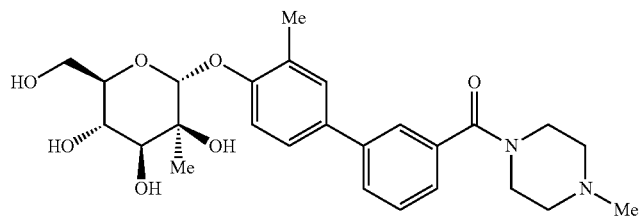 [SMILES: Cc1cc(-c2cccc(C(=O)N3CCN(C)CC3)c2)ccc1O[C@H]1O[C@H](CO)[C@@H](O)[C@H](O)[C@]1(C)O] |
| 69 | 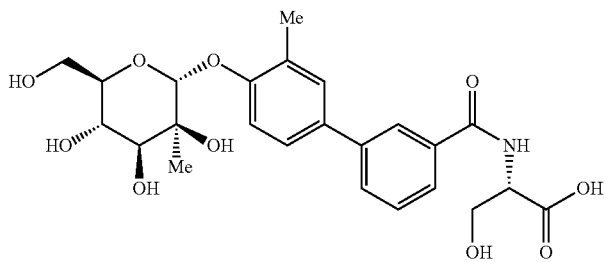 [SMILES: Cc1cc(-c2cccc(C(=O)N[C@@H](CO)C(=O)O)c2)ccc1O[C@H]1O[C@H](CO)[C@@H](O)[C@H](O)[C@]1(C)O] |
| 70 | 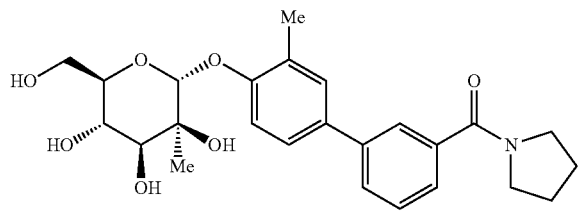 [SMILES: Cc1cc(-c2cccc(C(=O)N3CCCC3)c2)ccc1O[C@H]1O[C@H](CO)[C@@H](O)[C@H](O)[C@]1(C)O] |

| Compound No. | Structure |
|---|---|
| 71 | 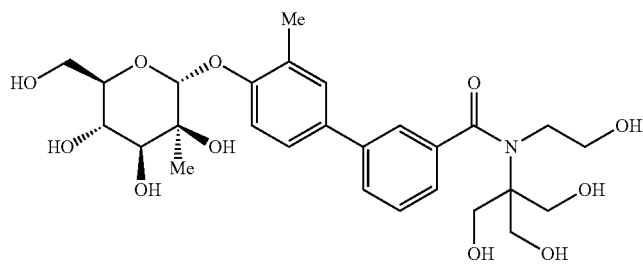 [SMILES: Cc1cc(-c2cccc(C(=O)N(CCO)C(CO)(CO)CO)c2)ccc1O[C@H]1O[C@H](CO)[C@@H](O)[C@H](O)[C@]1(C)O] |
| 72 | 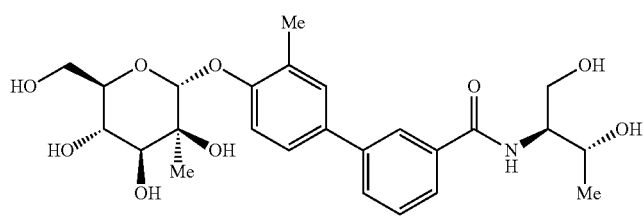 [SMILES: Cc1cc(-c2cccc(C(=O)N[C@@H](CO)[C@@H](C)O)c2)ccc1O[C@H]1O[C@H](CO)[C@@H](O)[C@H](O)[C@]1(C)O] |
| 73 | 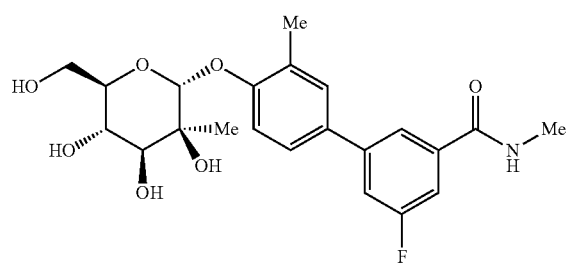 |
| 74 | 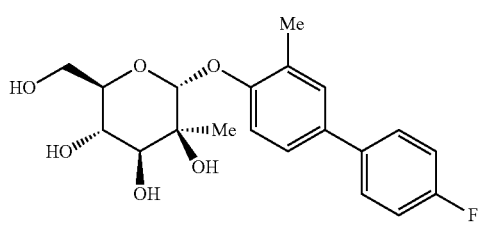 [SMILES: Cc1cc(-c2ccc(F)cc2)ccc1O[C@H]1O[C@H](CO)[C@@H](O)[C@H](O)[C@]1(C)O] |
| 75 | 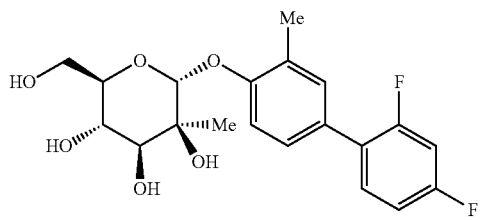 |
| 76 | 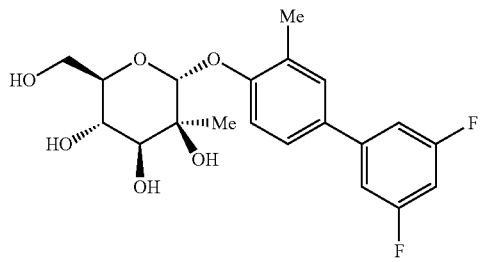 |

| Compound No. | Structure |
|---|---|
| 77 | 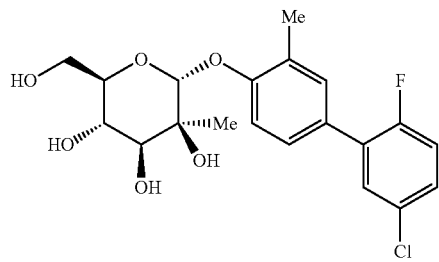 [SMILES: Cc1cc(-c2cc(Cl)ccc2F)ccc1O[C@H]1O[C@H](CO)[C@@H](O)[C@H](O)[C@]1(C)O] |
| 78 | 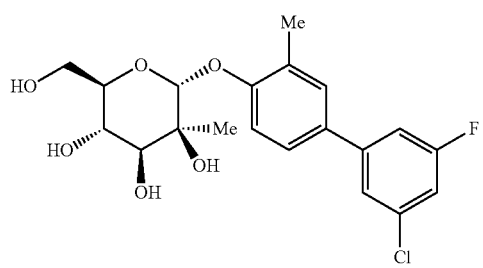 |
| 79 | 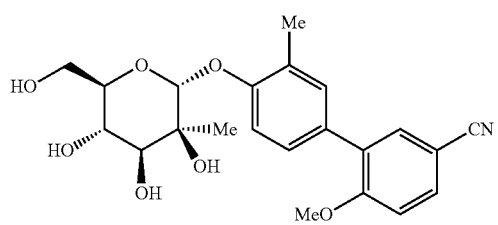 [SMILES: COc1ccc(C#N)cc1-c1ccc(O[C@H]2O[C@H](CO)[C@@H](O)[C@H](O)[C@]2(C)O)c(C)c1] |
| 80 | 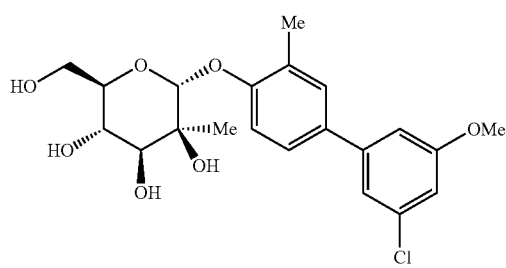 [SMILES: COc1cc(Cl)cc(-c2ccc(O[C@H]3O[C@H](CO)[C@@H](O)[C@H](O)[C@]3(C)O)c(C)c2)c1] |
| 81 | 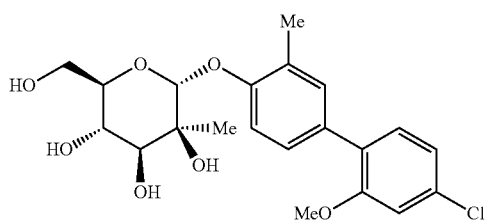 [SMILES: COc1cc(Cl)ccc1-c1ccc(O[C@H]2O[C@H](CO)[C@@H](O)[C@H](O)[C@]2(C)O)c(C)c1] |
| 82 | 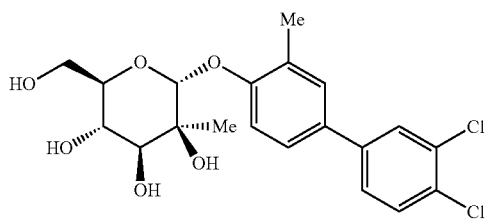 |

-continued
| Compound No. | Structure |
|---|---|
| 83 | 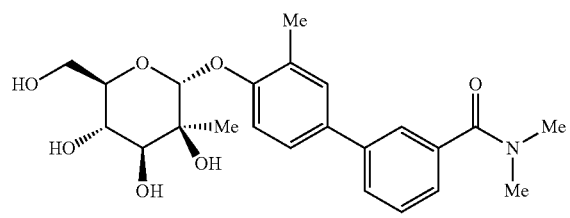 [SMILES: Cc1cc(-c2cccc(C(=O)N(C)C)c2)ccc1O[C@H]1O[C@H](CO)[C@@H](O)[C@H](O)[C@]1(C)O] |
| 84 | 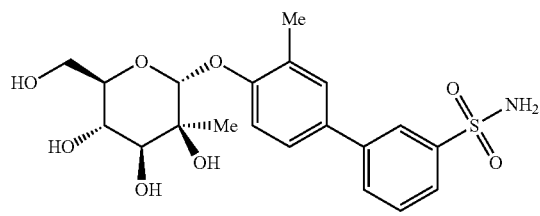 [SMILES: Cc1cc(-c2cccc(S(N)(=O)=O)c2)ccc1O[C@H]1O[C@H](CO)[C@@H](O)[C@H](O)[C@]1(C)O] |
| 85 | 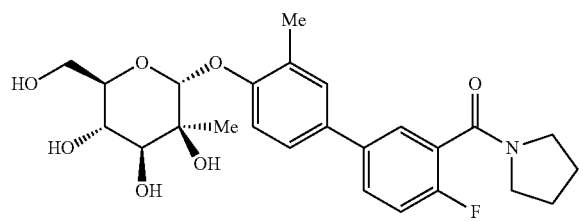 [SMILES: Cc1cc(-c2ccc(F)c(C(=O)N3CCCC3)c2)ccc1O[C@H]1O[C@H](CO)[C@@H](O)[C@H](O)[C@]1(C)O] |
| 86 | 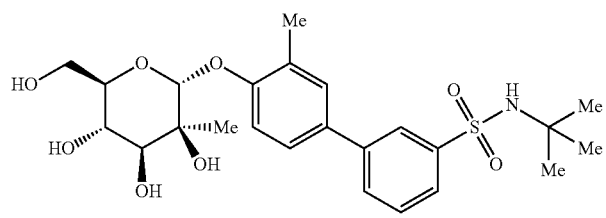 [SMILES: Cc1cc(-c2cccc(S(=O)(=O)NC(C)(C)C)c2)ccc1O[C@H]1O[C@H](CO)[C@@H](O)[C@H](O)[C@]1(C)O] |
| 87 | 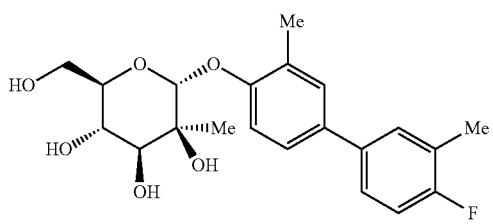 [SMILES: Cc1cc(-c2ccc(O[C@H]3O[C@H](CO)[C@@H](O)[C@H](O)[C@]3(C)O)c(C)c2)ccc1F] |
| 88 | 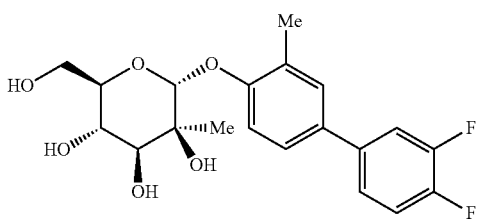 |
| 89 | 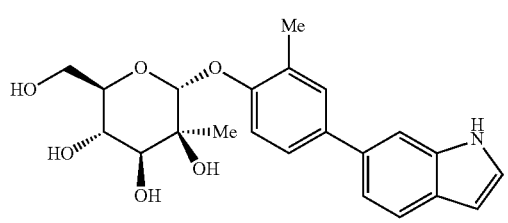 [SMILES: Cc1cc(-c2ccc3cc[nH]c3c2)ccc1O[C@H]1O[C@H](CO)[C@@H](O)[C@H](O)[C@]1(C)O] |

| Compound No. | Structure |
|---|---|
| 90 | 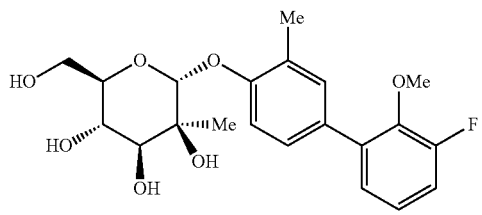 [SMILES: COc1c(F)cccc1-c1ccc(O[C@H]2O[C@H](CO)[C@@H](O)[C@H](O)[C@]2(C)O)c(C)c1] |
| 91 | 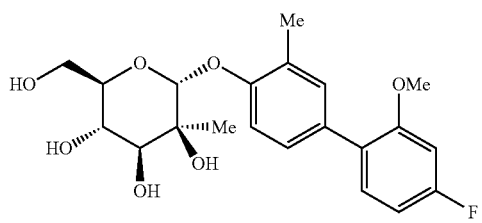 [SMILES: COc1cc(F)ccc1-c1ccc(O[C@H]2O[C@H](CO)[C@@H](O)[C@H](O)[C@]2(C)O)c(C)c1] |
| 92 | 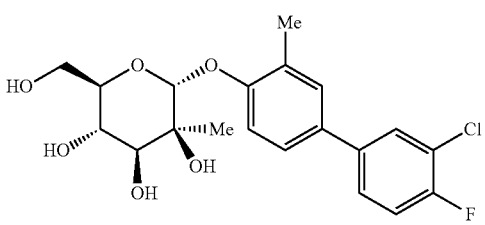 |
| 93 | 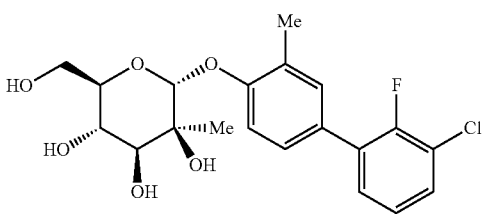 [SMILES: Cc1cc(-c2cccc(Cl)c2F)ccc1O[C@H]1O[C@H](CO)[C@@H](O)[C@H](O)[C@]1(C)O] |
| 94 | 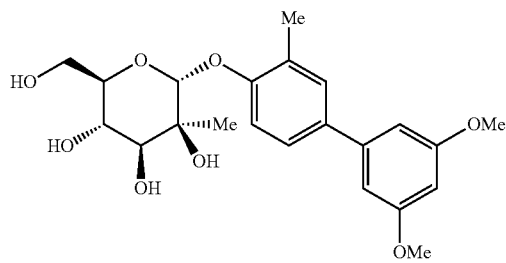 |
| 95 | 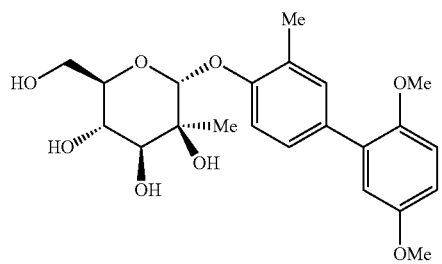 [SMILES: COc1ccc(OC)c(-c2ccc(O[C@H]3O[C@H](CO)[C@@H](O)[C@H](O)[C@]3(C)O)c(C)c2)c1] |

-continued
| Compound No. | Structure |
|---|---|
| 96 | 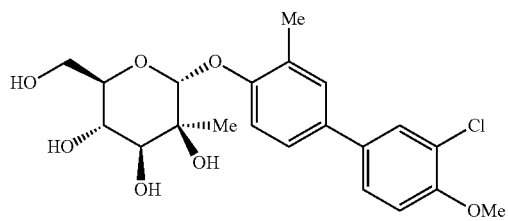 [SMILES: COc1ccc(-c2ccc(O[C@H]3O[C@H](CO)[C@@H](O)[C@H](O)[C@]3(C)O)c(C)c2)cc1Cl] |
| 97 | 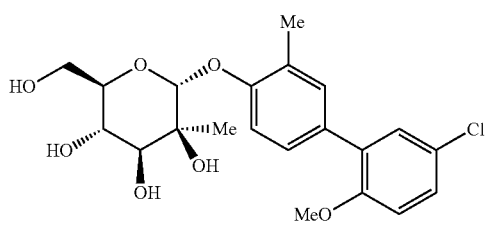 |
| 98 | 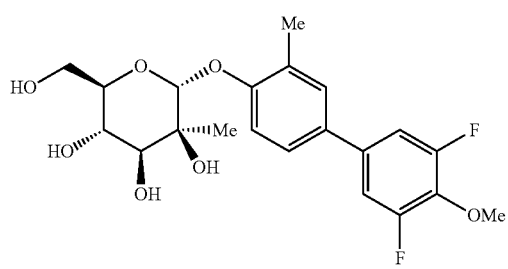 [SMILES: COc1c(F)cc(-c2ccc(O[C@H]3O[C@H](CO)[C@@H](O)[C@H](O)[C@]3(C)O)c(C)c2)cc1F] |
| 99 | 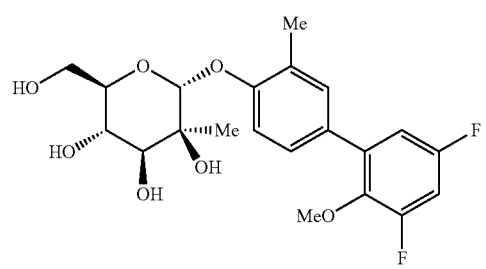 [SMILES: COc1c(F)cc(F)cc1-c1ccc(O[C@H]2O[C@H](CO)[C@@H](O)[C@H](O)[C@]2(C)O)c(C)c1] |
| 100 | 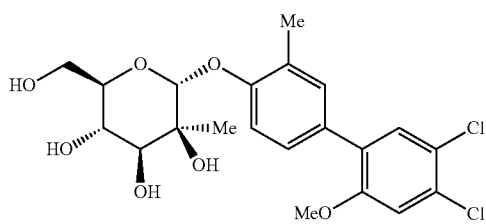 [SMILES: COc1cc(Cl)c(Cl)cc1-c1ccc(O[C@H]2O[C@H](CO)[C@@H](O)[C@H](O)[C@]2(C)O)c(C)c1] |
| 101 | 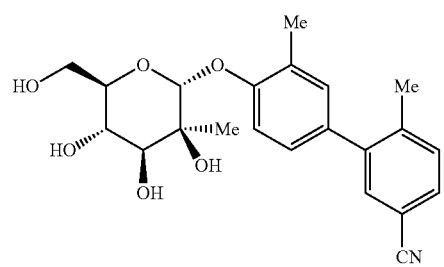 [SMILES: Cc1cc(-c2cc(C#N)ccc2C)ccc1O[C@H]1O[C@H](CO)[C@@H](O)[C@H](O)[C@]1(C)O] |

-continued
| Compound No. | Structure |
|---|---|
| 102 | 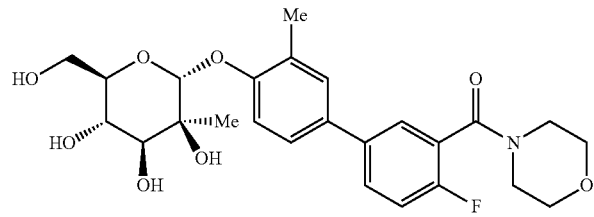 [SMILES: Cc1cc(-c2ccc(F)c(C(=O)N3CCOCC3)c2)ccc1O[C@H]1O[C@H](CO)[C@@H](O)[C@H](O)[C@]1(C)O] |
| 103 | 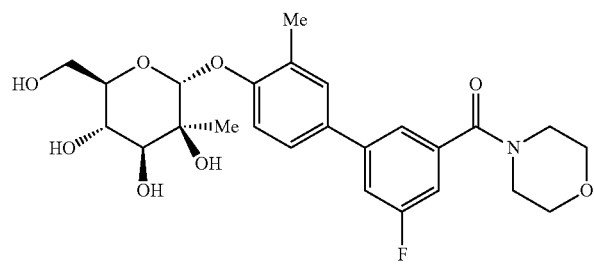 [SMILES: Cc1cc(-c2cc(F)cc(C(=O)N3CCOCC3)c2)ccc1O[C@H]1O[C@H](CO)[C@@H](O)[C@H](O)[C@]1(C)O] |
| 104 | 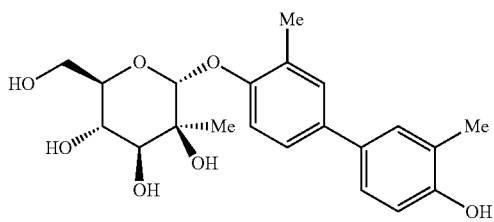 [SMILES: Cc1cc(-c2ccc(O[C@H]3O[C@H](CO)[C@@H](O)[C@H](O)[C@]3(C)O)c(C)c2)ccc1O] |
| 105 | 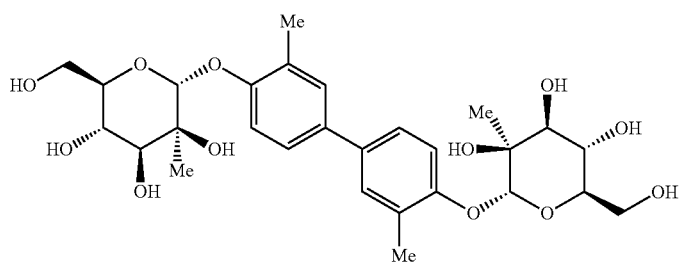 [SMILES: Cc1cc(-c2ccc(O[C@H]3O[C@H](CO)[C@@H](O)[C@H](O)[C@]3(C)O)c(C)c2)ccc1O[C@H]1O[C@H](CO)[C@@H](O)[C@H](O)[C@]1(C)O] |
| 106 | 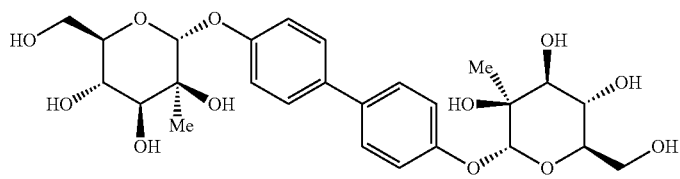 [SMILES: C[C@@]1(O)[C@@H](Oc2ccc(-c3ccc(O[C@H]4O[C@H](CO)[C@@H](O)[C@H](O)[C@]4(C)O)cc3)cc2)O[C@H](CO)[C@@H](O)[C@@H]1O] |
| 107 | 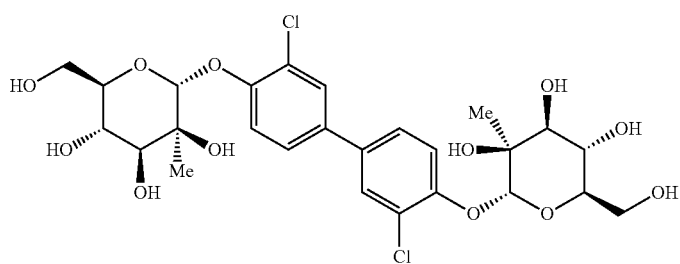 [SMILES: C[C@@]1(O)[C@@H](Oc2ccc(-c3ccc(O[C@H]4O[C@H](CO)[C@@H](O)[C@H](O)[C@]4(C)O)c(Cl)c3)cc2Cl)O[C@H](CO)[C@@H](O)[C@@H]1O] |

| Compound No. | Structure |
|---|---|
| 108 | 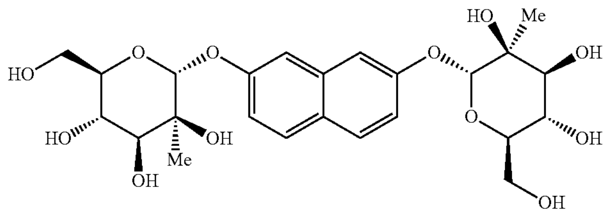 [SMILES: C[C@@]1(O)[C@@H](Oc2ccc3ccc(O[C@H]4O[C@H](CO)[C@@H](O)[C@H](O)[C@]4(C)O)cc3c2)O[C@H](CO)[C@@H](O)[C@@H]1O] |
| 109 | 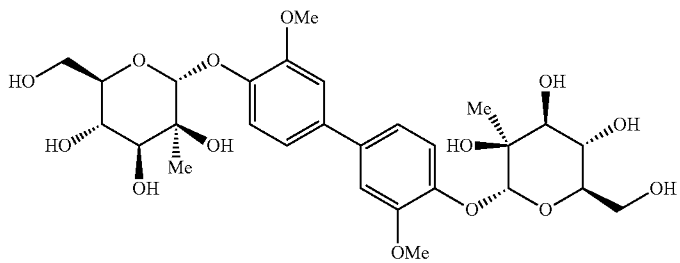 [SMILES: COc1cc(-c2ccc(O[C@H]3O[C@H](CO)[C@@H](O)[C@H](O)[C@]3(C)O)c(OC)c2)ccc1O[C@H]1O[C@H](CO)[C@@H](O)[C@H](O)[C@]1(C)O] |
| 110 | 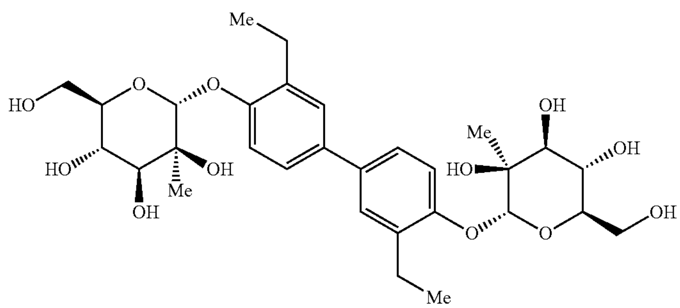 [SMILES: CCc1cc(-c2ccc(O[C@H]3O[C@H](CO)[C@@H](O)[C@H](O)[C@]3(C)O)c(CC)c2)ccc1O[C@H]1O[C@H](CO)[C@@H](O)[C@H](O)[C@]1(C)O] |
| 111 | 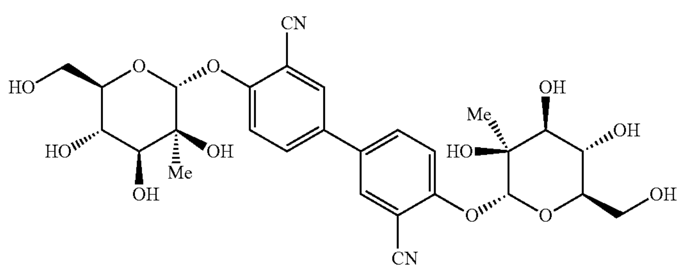 [SMILES: C[C@@]1(O)[C@@H](Oc2ccc(-c3ccc(O[C@H]4O[C@H](CO)[C@@H](O)[C@H](O)[C@]4(C)O)c(C#N)c3)cc2C#N)O[C@H](CO)[C@@H](O)[C@@H]1O] |
| 112 | 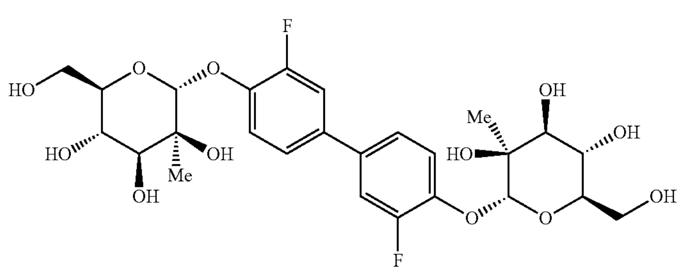 |

| Compound No. | Structure |
|---|---|
| 113 | 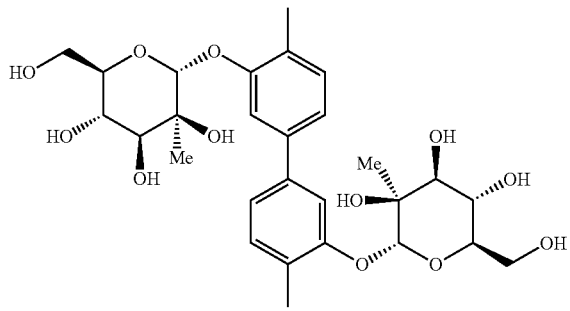 [SMILES: Cc1ccc(-c2ccc(C)c(O[C@H]3O[C@H](CO)[C@@H](O)[C@H](O)[C@]3(C)O)c2)cc1O[C@H]1O[C@H](CO)[C@@H](O)[C@H](O)[C@]1(C)O] |
| 114 | 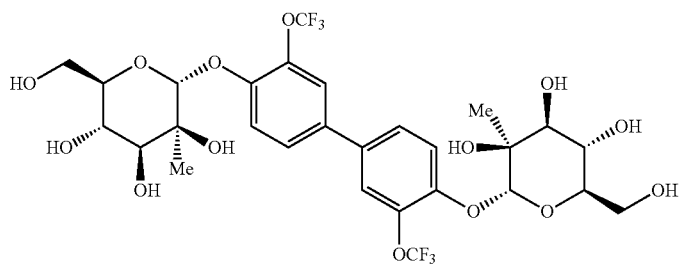 [SMILES: C[C@@]1(O)[C@@H](Oc2ccc(-c3ccc(O[C@H]4O[C@H](CO)[C@@H](O)[C@H](O)[C@]4(C)O)c(OC(F)(F)F)c3)cc2OC(F)(F)F)O[C@H](CO)[C@@H](O)[C@@H]1O] |
| 115 | 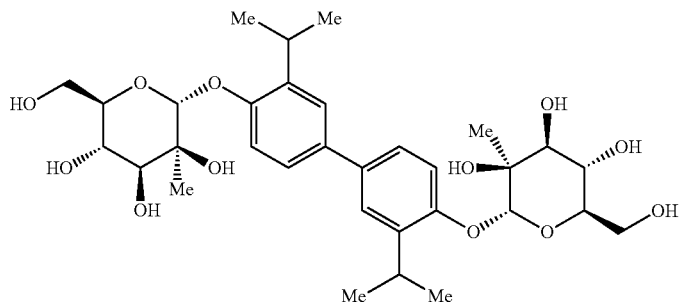 [SMILES: CC(C)c1cc(-c2ccc(O[C@H]3O[C@H](CO)[C@@H](O)[C@H](O)[C@]3(C)O)c(C(C)C)c2)ccc1O[C@H]1O[C@H](CO)[C@@H](O)[C@H](O)[C@]1(C)O] |
| 116 | 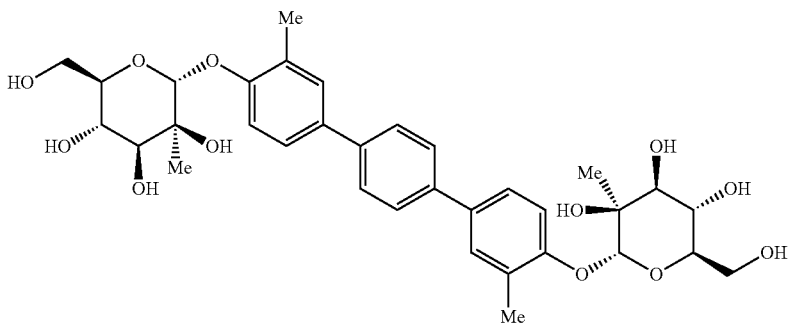 [SMILES: Cc1cc(-c2ccc(-c3ccc(O[C@H]4O[C@H](CO)[C@@H](O)[C@H](O)[C@]4(C)O)c(C)c3)cc2)ccc1O[C@H]1O[C@H](CO)[C@@H](O)[C@H](O)[C@]1(C)O] |
| 117 | 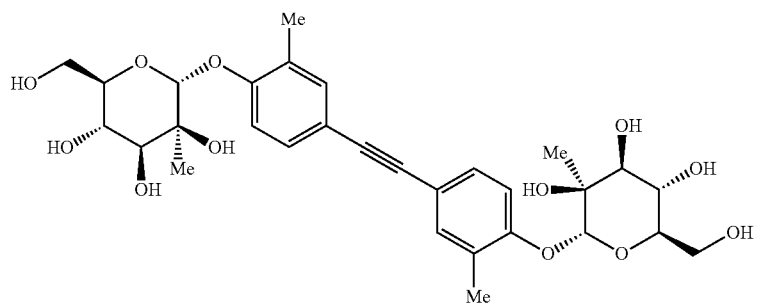 [SMILES: Cc1cc(C#Cc2ccc(O[C@H]3O[C@H](CO)[C@@H](O)[C@H](O)[C@]3(C)O)c(C)c2)ccc1O[C@H]1O[C@H](CO)[C@@H](O)[C@H](O)[C@]1(C)O] |

| Compound No. | Structure |
|---|---|
| 119 | 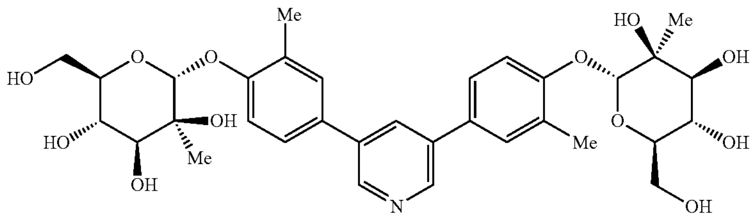 |
| 120 | 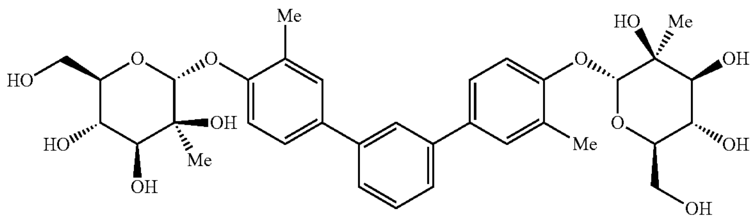 |
| 121 | 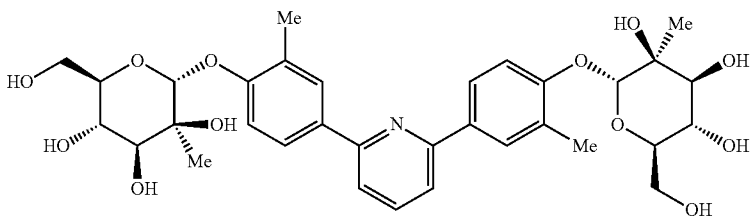 [SMILES: Cc1cc(-c2cccc(-c3ccc(O[C@H]4O[C@H](CO)[C@@H](O)[C@H](O)[C@]4(C)O)c(C)c3)c2)ccc1O[C@H]1O[C@H](CO)[C@@H](O)[C@H](O)[C@]1(C)O] |
| 122 | 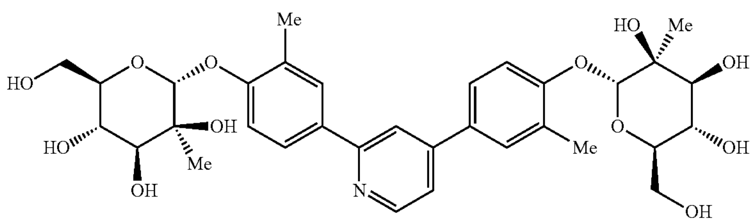 |
| 123 | 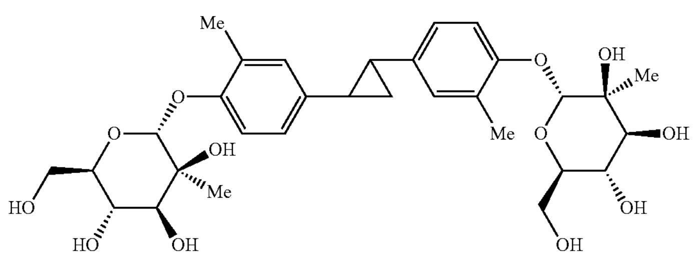 [SMILES: Cc1cc(C2CC2c2ccc(O[C@H]3O[C@H](CO)[C@@H](O)[C@H](O)[C@]3(C)O)c(C)c2)ccc1O[C@H]1O[C@H](CO)[C@@H](O)[C@H](O)[C@]1(C)O] |
12. The compound of claim 1 having the formula
13. A composition comprising the compound of claim 1, or a pharmaceutically acceptable salt thereof, and a pharmaceutically acceptable carrier, adjuvant, or vehicle.
14. The composition of claim 13 comprising the compound of formula
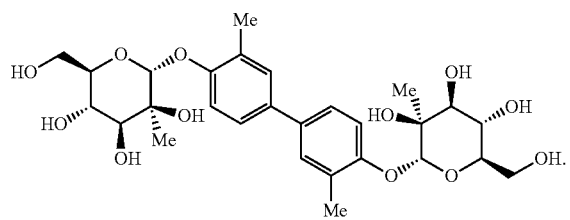 [SMILES: Cc1cc(-c2ccc(O[C@H]3O[C@H](CO)[C@@H](O)[C@H](O)[C@]3(C)O)c(C)c2)ccc1O[C@H]1O[C@H](CO)[C@@H](O)[C@H](O)[C@]1(C)O]
or a pharmaceutically acceptable salt thereof.

15. A method of treating a bacterial infection in a subject, comprising administering to the subject an effective amount of the compound of claim 1 or a pharmaceutically acceptable salt thereof.

16. The method of claim 15 comprising administering to the subject an effective amount of the compound of formula

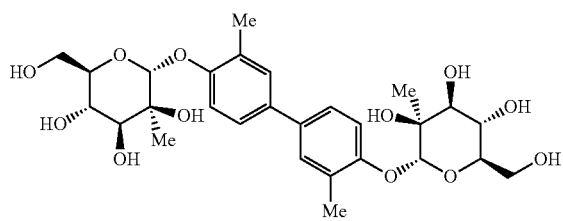 [SMILES: Cc1cc(-c2ccc(O[C@H]3O[C@H](CO)[C@@H](O)[C@H](O)[C@]3(C)O)c(C)c2)ccc1O[C@H]1O[C@H](CO)[C@@H](O)[C@H](O)[C@]1(C)O]

or a pharmaceutically acceptable salt thereof.

17. A method of inhibiting FimH in a subject, comprising administering to the subject an effective amount of the compound of claim 1 or a pharmaceutically acceptable salt thereof.

18. The method of claim 17, comprising administering to the subject an effective amount of the compound of formula

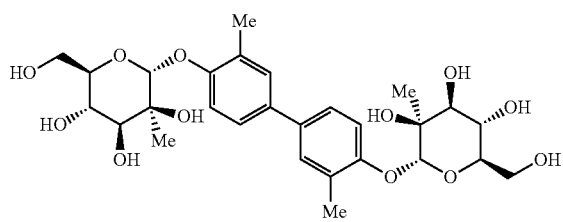 [SMILES: Cc1cc(-c2ccc(O[C@H]3O[C@H](CO)[C@@H](O)[C@H](O)[C@]3(C)O)c(C)c2)ccc1O[C@H]1O[C@H](CO)[C@@H](O)[C@H](O)[C@]1(C)O]

or a pharmaceutically acceptable salt thereof.

19. A method of inhibiting adhesion of *e. coli* in a subject, comprising administering to the subject an effective amount of the compound of claim 1 or a pharmaceutically acceptable salt thereof.

20. The method of claim 19, comprising administering to the subject an effective amount of the compound of formula

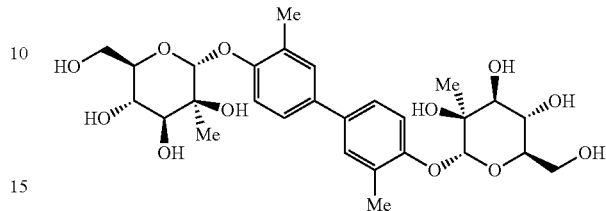

or a pharmaceutically acceptable salt thereof.

21. A method of blocking the interaction between type 1 pili and CEACAM6 in a subject, comprising administering to the subject an effective amount of the compound of claim 1 or a pharmaceutically acceptable salt thereof.

22. The method of claim 21, comprising administering to the subject an effective amount of the compound of formula

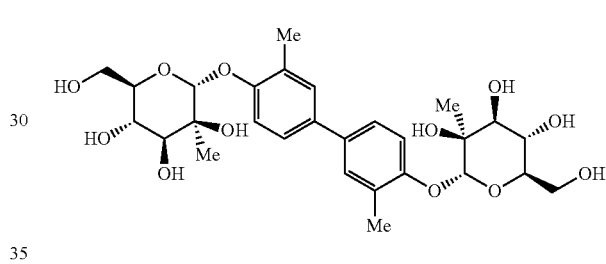

or a pharmaceutically acceptable salt thereof.

* * * * *